(12) United States Patent
Malito et al.

(10) Patent No.: US 11,932,669 B2
(45) Date of Patent: Mar. 19, 2024

(54) MODIFIED CYTOMEGALOVIRUS PROTEINS AND STABILIZED COMPLEXES

(71) Applicant: GLAXOSMITHKLINE BIOLOGICALS SA, Rixensart (BE)

(72) Inventors: Enrico Malito, Rockville, MD (US); Matthew James Bottomley, Rockville, MD (US); Andrea Carfi, Cambridge, MA (US); Sumana Chandramouli, Rockville, MD (US); Kate Luisi, Rockville, MD (US)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 188 days.

(21) Appl. No.: 17/223,207

(22) Filed: Apr. 6, 2021

(65) Prior Publication Data

US 2021/0277067 A1    Sep. 9, 2021

Related U.S. Application Data

(63) Continuation of application No. PCT/IB2019/058777, filed on Oct. 15, 2019.

(60) Provisional application No. 62/746,804, filed on Oct. 17, 2018.

(51) Int. Cl.
  *C07K 14/045* (2006.01)
  *A61K 38/00* (2006.01)
  *A61K 39/245* (2006.01)

(52) U.S. Cl.
  CPC .......... *C07K 14/045* (2013.01); *A61K 39/245* (2013.01); *A61K 38/00* (2013.01)

(58) Field of Classification Search
  CPC .. C07K 14/045; C07K 14/005; A61K 39/245; A61K 38/00; A61K 39/12; C12N 2710/16122; C12N 2710/16134
  See application file for complete search history.

(56) References Cited

U.S. PATENT DOCUMENTS

| | | | |
|---|---|---|---|
| 9,683,022 B2 * | 6/2017 | Carfi | A61P 31/22 |
| 10,064,935 B2 * | 9/2018 | Ciaramella | A61K 31/7115 |
| 10,111,945 B2 * | 10/2018 | Orlinger | A61P 31/22 |

FOREIGN PATENT DOCUMENTS

| | | |
|---|---|---|
| JP | 2003509013 A | 3/2003 |
| WO | 01/00648 A1 | 6/2000 |
| WO | 2015181142 A1 | 12/2015 |
| WO | 2016116904 A1 | 7/2016 |
| WO | 2018182983 A1 | 10/2018 |

OTHER PUBLICATIONS

Chandramouli S, Malito E, Nguyen T, Luisi K, Donnarumma D, Xing Y, Norais N, Yu D, Carfi A. Structural basis for potent antibody-mediated neutralization of human cytomegalovirus. Sci Immunol. Jun. 30, 2017;2(12):eaan1457. (Year: 2017).*
International Search Report and Written Opinion for corresponding International Application No. PCT/IB2019/058777, dated Dec. 10, 2019 (11 pages).
Saito et al., J. Phys. Chem. Part B., 104(15): 3705-3711 (2000).
Davey et al., Structure, 23(11): 2011-2021 (2015).
Sung et al., Expert Rev. Vaccines, 9(11): 1303-1314 (2010).
Office Action in corresponding Japanese Patent Application No. 2021-521000, dated Oct. 3, 2023 (2 pages).

* cited by examiner

*Primary Examiner* — Rachel B Gill

(57) ABSTRACT

Described are mutant human cytomegalovirus (HCMV) pentamer complex polypeptides, methods of making them, and their use in HCMV protein complexes and compositions. In particular, the use of the modified HCMV polypeptides to stabilize HCMV complexes or unmask a pentamer epitope is described.

18 Claims, 24 Drawing Sheets

Specification includes a Sequence Listing.

gH-gL-ULs INTERFACE

SEQUENCE LISTING

```
<160> NUMBER OF SEQ ID NOS: 83

<210> SEQ ID NO 1
<211> LENGTH: 742
<212> TYPE: PRT
<213> ORGANISM: Artificial Sequence
<220> FEATURE:
<223> OTHER INFORMATION: HCMV Merlin strain, full length gH

<400> SEQUENCE: 1

Met Arg Pro Gly Leu Pro Ser Tyr Leu Ile Ile Leu Ala Val Cys Leu
1               5                   10                  15

Phe Ser His Leu Leu Ser Ser Arg Tyr Gly Ala Glu Ala Val Ser Glu
            20                  25                  30

Pro Leu Asp Lys Ala Phe His Leu Leu Leu Asn Thr Tyr Gly Arg Pro
        35                  40                  45
```

-continued

```
Ile Arg Phe Leu Arg Glu Asn Thr Thr Gln Cys Thr Tyr Asn Ser Ser
 50                  55                  60

Leu Arg Asn Ser Thr Val Val Arg Glu Asn Ala Ile Ser Phe Asn Phe
 65                  70                  75                  80

Phe Gln Ser Tyr Asn Gln Tyr Tyr Val Phe His Met Pro Arg Cys Leu
                 85                  90                  95

Phe Ala Gly Pro Leu Ala Glu Gln Phe Leu Asn Gln Val Asp Leu Thr
                100                 105                 110

Glu Thr Leu Glu Arg Tyr Gln Gln Arg Leu Asn Thr Tyr Ala Leu Val
            115                 120                 125

Ser Lys Asp Leu Ala Ser Tyr Arg Ser Phe Ser Gln Gln Leu Lys Ala
130                 135                 140

Gln Asp Ser Leu Gly Glu Gln Pro Thr Val Pro Pro Ile Asp
145                 150                 155                 160

Leu Ser Ile Pro His Val Trp Met Pro Pro Gln Thr Thr Pro His Gly
                165                 170                 175

Trp Thr Glu Ser His Thr Thr Ser Gly Leu His Arg Pro His Phe Asn
                180                 185                 190

Gln Thr Cys Ile Leu Phe Asp Gly His Asp Leu Leu Phe Ser Thr Val
            195                 200                 205

Thr Pro Cys Leu His Gln Gly Phe Tyr Leu Ile Asp Glu Leu Arg Tyr
210                 215                 220

Val Lys Ile Thr Leu Thr Glu Asp Phe Phe Val Val Thr Val Ser Ile
225                 230                 235                 240

Asp Asp Asp Thr Pro Met Leu Leu Ile Phe Gly His Leu Pro Arg Val
                245                 250                 255

Leu Phe Lys Ala Pro Tyr Gln Arg Asp Asn Phe Ile Leu Arg Gln Thr
                260                 265                 270

Glu Lys His Glu Leu Leu Val Leu Val Lys Lys Asp Gln Leu Asn Arg
            275                 280                 285

His Ser Tyr Leu Lys Asp Pro Asp Phe Leu Asp Ala Ala Leu Asp Phe
290                 295                 300

Asn Tyr Leu Asp Leu Ser Ala Leu Leu Arg Asn Ser Phe His Arg Tyr
305                 310                 315                 320

Ala Val Asp Val Leu Lys Ser Gly Arg Cys Gln Met Leu Asp Arg Arg
                325                 330                 335

Thr Val Glu Met Ala Phe Ala Tyr Ala Leu Ala Leu Phe Ala Ala Ala
                340                 345                 350

Arg Gln Glu Glu Ala Gly Ala Gln Val Ser Val Pro Arg Ala Leu Asp
            355                 360                 365

Arg Gln Ala Ala Leu Leu Gln Ile Gln Glu Phe Met Ile Thr Cys Leu
370                 375                 380

Ser Gln Thr Pro Pro Arg Thr Thr Leu Leu Tyr Pro Thr Ala Val
385                 390                 395                 400

Asp Leu Ala Lys Arg Ala Leu Trp Thr Pro Asn Gln Ile Thr Asp Ile
                405                 410                 415

Thr Ser Leu Val Arg Leu Val Tyr Ile Leu Ser Lys Gln Asn Gln Gln
                420                 425                 430

His Leu Ile Pro Gln Trp Ala Leu Arg Gln Ile Ala Asp Phe Ala Leu
            435                 440                 445

Lys Leu His Lys Thr His Leu Ala Ser Phe Leu Ser Ala Phe Ala Arg
450                 455                 460
```

```
Gln Glu Leu Tyr Leu Met Gly Ser Leu Val His Ser Met Leu Val His
465                 470                 475                 480

Thr Thr Glu Arg Arg Glu Ile Phe Ile Val Glu Thr Gly Leu Cys Ser
                485                 490                 495

Leu Ala Glu Leu Ser His Phe Thr Gln Leu Leu Ala His Pro His His
            500                 505                 510

Glu Tyr Leu Ser Asp Leu Tyr Thr Pro Cys Ser Ser Gly Arg Arg
        515                 520                 525

Asp His Ser Leu Glu Arg Leu Thr Arg Leu Phe Pro Asp Ala Thr Val
    530                 535                 540

Pro Ala Thr Val Pro Ala Ala Leu Ser Ile Leu Ser Thr Met Gln Pro
545                 550                 555                 560

Ser Thr Leu Glu Thr Phe Pro Asp Leu Phe Cys Leu Pro Leu Gly Glu
                565                 570                 575

Ser Phe Ser Ala Leu Thr Val Ser Glu His Val Ser Tyr Ile Val Thr
            580                 585                 590

Asn Gln Tyr Leu Ile Lys Gly Ile Ser Tyr Pro Val Ser Thr Thr Val
        595                 600                 605

Val Gly Gln Ser Leu Ile Ile Thr Gln Thr Asp Ser Gln Thr Lys Cys
610                 615                 620

Glu Leu Thr Arg Asn Met His Thr Thr His Ser Ile Thr Val Ala Leu
625                 630                 635                 640

Asn Ile Ser Leu Glu Asn Cys Ala Phe Cys Gln Ser Ala Leu Leu Glu
                645                 650                 655

Tyr Asp Asp Thr Gln Gly Val Ile Asn Ile Met Tyr Met His Asp Ser
            660                 665                 670

Asp Asp Val Leu Phe Ala Leu Asp Pro Tyr Asn Glu Val Val Val Ser
        675                 680                 685

Ser Pro Arg Thr His Tyr Leu Met Leu Leu Lys Asn Gly Thr Val Leu
    690                 695                 700

Glu Val Thr Asp Val Val Val Asp Ala Thr Asp Ser Arg Leu Leu Met
705                 710                 715                 720

Met Ser Val Tyr Ala Leu Ser Ala Ile Ile Gly Ile Tyr Leu Leu Tyr
                725                 730                 735

Arg Met Leu Lys Thr Cys
            740

<210> SEQ ID NO 2
<211> LENGTH: 719
<212> TYPE: PRT
<213> ORGANISM: Artificial Sequence
<220> FEATURE:
<223> OTHER INFORMATION: HCMV Merlin strain, mature gH

<400> SEQUENCE: 2

Arg Tyr Gly Ala Glu Ala Val Ser Glu Pro Leu Asp Lys Ala Phe His
1               5                   10                  15

Leu Leu Leu Asn Thr Tyr Gly Arg Pro Ile Arg Phe Leu Arg Glu Asn
                20                  25                  30

Thr Thr Gln Cys Thr Tyr Asn Ser Ser Leu Arg Asn Ser Thr Val Val
            35                  40                  45

Arg Glu Asn Ala Ile Ser Phe Asn Phe Phe Gln Ser Tyr Asn Gln Tyr
        50                  55                  60

Tyr Val Phe His Met Pro Arg Cys Leu Phe Ala Gly Pro Leu Ala Glu
65                  70                  75                  80
```

```
Gln Phe Leu Asn Gln Val Asp Leu Thr Glu Thr Leu Glu Arg Tyr Gln
             85                  90                  95

Gln Arg Leu Asn Thr Tyr Ala Leu Val Ser Lys Asp Leu Ala Ser Tyr
        100                 105                 110

Arg Ser Phe Ser Gln Gln Leu Lys Ala Gln Asp Ser Leu Gly Glu Gln
            115                 120                 125

Pro Thr Thr Val Pro Pro Ile Asp Leu Ser Ile Pro His Val Trp
        130                 135             140

Met Pro Pro Gln Thr Thr Pro His Gly Trp Thr Glu Ser His Thr Thr
145                 150                 155                 160

Ser Gly Leu His Arg Pro His Phe Asn Gln Thr Cys Ile Leu Phe Asp
            165                 170                 175

Gly His Asp Leu Leu Phe Ser Thr Val Thr Pro Cys Leu His Gln Gly
            180                 185                 190

Phe Tyr Leu Ile Asp Glu Leu Arg Tyr Val Lys Ile Thr Leu Thr Glu
            195                 200                 205

Asp Phe Phe Val Val Thr Val Ser Ile Asp Asp Thr Pro Met Leu
            210                 215                 220

Leu Ile Phe Gly His Leu Pro Arg Val Leu Phe Lys Ala Pro Tyr Gln
225                 230                 235                 240

Arg Asp Asn Phe Ile Leu Arg Gln Thr Glu Lys His Glu Leu Leu Val
                245                 250                 255

Leu Val Lys Lys Asp Gln Leu Asn Arg His Ser Tyr Leu Lys Asp Pro
            260                 265                 270

Asp Phe Leu Asp Ala Ala Leu Asp Phe Asn Tyr Leu Asp Leu Ser Ala
            275                 280                 285

Leu Leu Arg Asn Ser Phe His Arg Tyr Ala Val Asp Val Leu Lys Ser
            290                 295                 300

Gly Arg Cys Gln Met Leu Asp Arg Arg Thr Val Glu Met Ala Phe Ala
305                 310                 315                 320

Tyr Ala Leu Ala Leu Phe Ala Ala Ala Arg Gln Glu Glu Ala Gly Ala
                325                 330                 335

Gln Val Ser Val Pro Arg Ala Leu Asp Arg Gln Ala Ala Leu Leu Gln
            340                 345                 350

Ile Gln Glu Phe Met Ile Thr Cys Leu Ser Gln Thr Pro Pro Arg Thr
            355                 360                 365

Thr Leu Leu Leu Tyr Pro Thr Ala Val Asp Leu Ala Lys Arg Ala Leu
            370                 375                 380

Trp Thr Pro Asn Gln Ile Thr Asp Ile Thr Ser Leu Val Arg Leu Val
385                 390                 395                 400

Tyr Ile Leu Ser Lys Gln Asn Gln Gln His Leu Ile Pro Gln Trp Ala
                405                 410                 415

Leu Arg Gln Ile Ala Asp Phe Ala Leu Lys Leu His Lys Thr His Leu
            420                 425                 430

Ala Ser Phe Leu Ser Ala Phe Ala Arg Gln Glu Leu Tyr Leu Met Gly
            435                 440                 445

Ser Leu Val His Ser Met Leu Val His Thr Thr Glu Arg Arg Glu Ile
            450                 455                 460

Phe Ile Val Glu Thr Gly Leu Cys Ser Leu Ala Glu Leu Ser His Phe
465                 470                 475                 480

Thr Gln Leu Leu Ala His Pro His His Glu Tyr Leu Ser Asp Leu Tyr
                485                 490                 495

Thr Pro Cys Ser Ser Ser Gly Arg Arg Asp His Ser Leu Glu Arg Leu
```

```
                500                 505                 510
Thr Arg Leu Phe Pro Asp Ala Thr Val Pro Ala Thr Val Pro Ala Ala
            515                 520                 525

Leu Ser Ile Leu Ser Thr Met Gln Pro Ser Thr Leu Glu Thr Phe Pro
530                 535                 540

Asp Leu Phe Cys Leu Pro Leu Gly Glu Ser Phe Ser Ala Leu Thr Val
545                 550                 555                 560

Ser Glu His Val Ser Tyr Ile Val Thr Asn Gln Tyr Leu Ile Lys Gly
                565                 570                 575

Ile Ser Tyr Pro Val Ser Thr Thr Val Val Gly Gln Ser Leu Ile Ile
            580                 585                 590

Thr Gln Thr Asp Ser Gln Thr Lys Cys Glu Leu Thr Arg Asn Met His
            595                 600                 605

Thr Thr His Ser Ile Thr Val Ala Leu Asn Ile Ser Leu Glu Asn Cys
            610                 615                 620

Ala Phe Cys Gln Ser Ala Leu Leu Glu Tyr Asp Asp Thr Gln Gly Val
625                 630                 635                 640

Ile Asn Ile Met Tyr Met His Asp Ser Asp Val Leu Phe Ala Leu
                645                 650                 655

Asp Pro Tyr Asn Glu Val Val Ser Ser Pro Arg Thr His Tyr Leu
                660                 665                 670

Met Leu Leu Lys Asn Gly Thr Val Leu Glu Val Thr Asp Val Val Val
                675                 680                 685

Asp Ala Thr Asp Ser Arg Leu Leu Met Met Ser Val Tyr Ala Leu Ser
            690                 695                 700

Ala Ile Ile Gly Ile Tyr Leu Leu Tyr Arg Met Leu Lys Thr Cys
705                 710                 715

<210> SEQ ID NO 3
<211> LENGTH: 715
<212> TYPE: PRT
<213> ORGANISM: Artificial Sequence
<220> FEATURE:
<223> OTHER INFORMATION: HCMV Truncated gH, residues 1 to 715 of SEQ ID
      NO: 1

<400> SEQUENCE: 3

Met Arg Pro Gly Leu Pro Ser Tyr Leu Ile Ile Leu Ala Val Cys Leu
1               5                   10                  15

Phe Ser His Leu Leu Ser Ser Arg Tyr Gly Ala Glu Ala Val Ser Glu
                20                  25                  30

Pro Leu Asp Lys Ala Phe His Leu Leu Leu Asn Thr Tyr Gly Arg Pro
            35                  40                  45

Ile Arg Phe Leu Arg Glu Asn Thr Thr Gln Cys Thr Tyr Asn Ser Ser
50                  55                  60

Leu Arg Asn Ser Thr Val Val Arg Glu Asn Ala Ile Ser Phe Asn Phe
65                  70                  75                  80

Phe Gln Ser Tyr Asn Gln Tyr Tyr Val Phe His Met Pro Arg Cys Leu
                85                  90                  95

Phe Ala Gly Pro Leu Ala Glu Gln Phe Leu Asn Gln Val Asp Leu Thr
            100                 105                 110

Glu Thr Leu Glu Arg Tyr Gln Gln Arg Leu Asn Thr Tyr Ala Leu Val
            115                 120                 125

Ser Lys Asp Leu Ala Ser Tyr Arg Ser Phe Ser Gln Gln Leu Lys Ala
            130                 135                 140
```

```
Gln Asp Ser Leu Gly Glu Gln Pro Thr Thr Val Pro Pro Ile Asp
145                 150                 155                 160

Leu Ser Ile Pro His Val Trp Met Pro Pro Gln Thr Thr Pro His Gly
                165                 170                 175

Trp Thr Glu Ser His Thr Thr Ser Gly Leu His Arg Pro His Phe Asn
            180                 185                 190

Gln Thr Cys Ile Leu Phe Asp Gly His Asp Leu Leu Phe Ser Thr Val
        195                 200                 205

Thr Pro Cys Leu His Gln Gly Phe Tyr Leu Ile Asp Glu Leu Arg Tyr
    210                 215                 220

Val Lys Ile Thr Leu Thr Glu Asp Phe Phe Val Val Thr Val Ser Ile
225                 230                 235                 240

Asp Asp Asp Thr Pro Met Leu Leu Ile Phe Gly His Leu Pro Arg Val
                245                 250                 255

Leu Phe Lys Ala Pro Tyr Gln Arg Asp Asn Phe Ile Leu Arg Gln Thr
            260                 265                 270

Glu Lys His Glu Leu Leu Val Leu Val Lys Lys Asp Gln Leu Asn Arg
        275                 280                 285

His Ser Tyr Leu Lys Asp Pro Asp Phe Leu Asp Ala Ala Leu Asp Phe
    290                 295                 300

Asn Tyr Leu Asp Leu Ser Ala Leu Leu Arg Asn Ser Phe His Arg Tyr
305                 310                 315                 320

Ala Val Asp Val Leu Lys Ser Gly Arg Cys Gln Met Leu Asp Arg Arg
                325                 330                 335

Thr Val Glu Met Ala Phe Ala Tyr Ala Leu Ala Leu Phe Ala Ala Ala
            340                 345                 350

Arg Gln Glu Glu Ala Gly Ala Gln Val Ser Val Pro Arg Ala Leu Asp
        355                 360                 365

Arg Gln Ala Ala Leu Leu Gln Ile Gln Glu Phe Met Ile Thr Cys Leu
    370                 375                 380

Ser Gln Thr Pro Pro Arg Thr Thr Leu Leu Leu Tyr Pro Thr Ala Val
385                 390                 395                 400

Asp Leu Ala Lys Arg Ala Leu Trp Thr Pro Asn Gln Ile Thr Asp Ile
                405                 410                 415

Thr Ser Leu Val Arg Leu Val Tyr Ile Leu Ser Lys Gln Asn Gln Gln
            420                 425                 430

His Leu Ile Pro Gln Trp Ala Leu Arg Gln Ile Ala Asp Phe Ala Leu
        435                 440                 445

Lys Leu His Lys Thr His Leu Ala Ser Phe Leu Ser Ala Phe Ala Arg
    450                 455                 460

Gln Glu Leu Tyr Leu Met Gly Ser Leu Val His Ser Met Leu Val His
465                 470                 475                 480

Thr Thr Glu Arg Arg Glu Ile Phe Ile Val Glu Thr Gly Leu Cys Ser
                485                 490                 495

Leu Ala Glu Leu Ser His Phe Thr Gln Leu Leu Ala His Pro His His
            500                 505                 510

Glu Tyr Leu Ser Asp Leu Tyr Thr Pro Cys Ser Ser Gly Arg Arg
        515                 520                 525

Asp His Ser Leu Glu Arg Leu Thr Arg Leu Phe Pro Asp Ala Thr Val
    530                 535                 540

Pro Ala Thr Val Pro Ala Ala Leu Ser Ile Leu Ser Thr Met Gln Pro
545                 550                 555                 560

Ser Thr Leu Glu Thr Phe Pro Asp Leu Phe Cys Leu Pro Leu Gly Glu
```

```
                      565                 570                 575

Ser Phe Ser Ala Leu Thr Val Ser Glu His Val Ser Tyr Ile Val Thr
                580                 585                 590

Asn Gln Tyr Leu Ile Lys Gly Ile Ser Tyr Pro Val Ser Thr Thr Val
                595                 600                 605

Val Gly Gln Ser Leu Ile Ile Thr Gln Thr Asp Ser Gln Thr Lys Cys
                610                 615                 620

Glu Leu Thr Arg Asn Met His Thr Thr His Ser Ile Thr Val Ala Leu
625                 630                 635                 640

Asn Ile Ser Leu Glu Asn Cys Ala Phe Cys Gln Ser Ala Leu Leu Glu
                645                 650                 655

Tyr Asp Asp Thr Gln Gly Val Ile Asn Ile Met Tyr Met His Asp Ser
                660                 665                 670

Asp Asp Val Leu Phe Ala Leu Asp Pro Tyr Asn Glu Val Val Val Ser
                675                 680                 685

Ser Pro Arg Thr His Tyr Leu Met Leu Leu Lys Asn Gly Thr Val Leu
                690                 695                 700

Glu Val Thr Asp Val Val Val Asp Ala Thr Asp
705                 710                 715

<210> SEQ ID NO 4
<211> LENGTH: 692
<212> TYPE: PRT
<213> ORGANISM: Artificial Sequence
<220> FEATURE:
<223> OTHER INFORMATION: HCMV mature truncated gH, residues 24 to 715 of
      SEQ ID NO: 1

<400> SEQUENCE: 4

Arg Tyr Gly Ala Glu Ala Val Ser Glu Pro Leu Asp Lys Ala Phe His
1               5                   10                  15

Leu Leu Leu Asn Thr Tyr Gly Arg Pro Ile Arg Phe Leu Arg Glu Asn
                20                  25                  30

Thr Thr Gln Cys Thr Tyr Asn Ser Ser Leu Arg Asn Ser Thr Val Val
                35                  40                  45

Arg Glu Asn Ala Ile Ser Phe Asn Phe Phe Gln Ser Tyr Asn Gln Tyr
            50                  55                  60

Tyr Val Phe His Met Pro Arg Cys Leu Phe Ala Gly Pro Leu Ala Glu
65              70                  75                  80

Gln Phe Leu Asn Gln Val Asp Leu Thr Glu Thr Leu Glu Arg Tyr Gln
                85                  90                  95

Gln Arg Leu Asn Thr Tyr Ala Leu Val Ser Lys Asp Leu Ala Ser Tyr
                100                 105                 110

Arg Ser Phe Ser Gln Gln Leu Lys Ala Gln Asp Ser Leu Gly Glu Gln
            115                 120                 125

Pro Thr Thr Val Pro Pro Ile Asp Leu Ser Ile Pro His Val Trp
130                 135                 140

Met Pro Pro Gln Thr Thr Pro His Gly Trp Thr Glu Ser His Thr Thr
145                 150                 155                 160

Ser Gly Leu His Arg Pro His Phe Asn Gln Thr Cys Ile Leu Phe Asp
                165                 170                 175

Gly His Asp Leu Leu Phe Ser Thr Val Thr Pro Cys Leu His Gln Gly
            180                 185                 190

Phe Tyr Leu Ile Asp Glu Leu Arg Tyr Val Lys Ile Thr Leu Thr Glu
                195                 200                 205
```

```
Asp Phe Phe Val Val Thr Val Ser Ile Asp Asp Thr Pro Met Leu
    210                 215                 220

Leu Ile Phe Gly His Leu Pro Arg Val Leu Phe Lys Ala Pro Tyr Gln
225                 230                 235                 240

Arg Asp Asn Phe Ile Leu Arg Gln Thr Glu Lys His Glu Leu Leu Val
                245                 250                 255

Leu Val Lys Lys Asp Gln Leu Asn Arg His Ser Tyr Leu Lys Asp Pro
            260                 265                 270

Asp Phe Leu Asp Ala Ala Leu Asp Phe Asn Tyr Leu Asp Leu Ser Ala
        275                 280                 285

Leu Leu Arg Asn Ser Phe His Arg Tyr Ala Val Asp Val Leu Lys Ser
290                 295                 300

Gly Arg Cys Gln Met Leu Asp Arg Arg Thr Val Glu Met Ala Phe Ala
305                 310                 315                 320

Tyr Ala Leu Ala Leu Phe Ala Ala Ala Arg Gln Glu Glu Ala Gly Ala
                325                 330                 335

Gln Val Ser Val Pro Arg Ala Leu Asp Arg Gln Ala Ala Leu Leu Gln
            340                 345                 350

Ile Gln Glu Phe Met Ile Thr Cys Leu Ser Gln Thr Pro Pro Arg Thr
        355                 360                 365

Thr Leu Leu Leu Tyr Pro Thr Ala Val Asp Leu Ala Lys Arg Ala Leu
370                 375                 380

Trp Thr Pro Asn Gln Ile Thr Asp Ile Thr Ser Leu Val Arg Leu Val
385                 390                 395                 400

Tyr Ile Leu Ser Lys Gln Asn Gln Gln His Leu Ile Pro Gln Trp Ala
                405                 410                 415

Leu Arg Gln Ile Ala Asp Phe Ala Leu Lys Leu His Lys Thr His Leu
            420                 425                 430

Ala Ser Phe Leu Ser Ala Phe Ala Arg Gln Glu Leu Tyr Leu Met Gly
        435                 440                 445

Ser Leu Val His Ser Met Leu Val His Thr Thr Glu Arg Arg Glu Ile
450                 455                 460

Phe Ile Val Glu Thr Gly Leu Cys Ser Leu Ala Glu Leu Ser His Phe
465                 470                 475                 480

Thr Gln Leu Leu Ala His Pro His His Glu Tyr Leu Ser Asp Leu Tyr
                485                 490                 495

Thr Pro Cys Ser Ser Gly Arg Arg Asp His Ser Leu Glu Arg Leu
            500                 505                 510

Thr Arg Leu Phe Pro Asp Ala Thr Val Pro Ala Thr Val Pro Ala Ala
        515                 520                 525

Leu Ser Ile Leu Ser Thr Met Gln Pro Ser Thr Leu Glu Thr Phe Pro
530                 535                 540

Asp Leu Phe Cys Leu Pro Leu Gly Glu Ser Phe Ser Ala Leu Thr Val
545                 550                 555                 560

Ser Glu His Val Ser Tyr Ile Val Thr Asn Gln Tyr Leu Ile Lys Gly
                565                 570                 575

Ile Ser Tyr Pro Val Ser Thr Val Val Gly Gln Ser Leu Ile Ile
            580                 585                 590

Thr Gln Thr Asp Ser Gln Thr Lys Cys Glu Leu Thr Arg Asn Met His
        595                 600                 605

Thr Thr His Ser Ile Thr Val Ala Leu Asn Ile Ser Leu Glu Asn Cys
610                 615                 620

Ala Phe Cys Gln Ser Ala Leu Leu Glu Tyr Asp Asp Thr Gln Gly Val
```

-continued

```
                625                 630                 635                 640
        Ile Asn Ile Met Tyr Met His Asp Ser Asp Asp Val Leu Phe Ala Leu
                            645                 650                 655

Asp Pro Tyr Asn Glu Val Val Ser Ser Pro Arg Thr His Tyr Leu
                        660                 665                 670

Met Leu Leu Lys Asn Gly Thr Val Leu Glu Val Thr Asp Val Val Val
                    675                 680                 685

Asp Ala Thr Asp
                690

<210> SEQ ID NO 5
<211> LENGTH: 742
<212> TYPE: PRT
<213> ORGANISM: Artificial Sequence
<220> FEATURE:
<223> OTHER INFORMATION: HCMV Towne strain, full length gH

<400> SEQUENCE: 5

Met Arg Pro Gly Leu Pro Ser Tyr Leu Ile Val Leu Ala Val Cys Leu
1               5                   10                  15

Leu Ser His Leu Leu Ser Ser Arg Tyr Gly Ala Glu Ala Ile Ser Glu
                20                  25                  30

Pro Leu Asp Lys Ala Phe His Leu Leu Leu Asn Thr Tyr Gly Arg Pro
            35                  40                  45

Ile Arg Phe Leu Arg Glu Asn Thr Thr Gln Cys Thr Tyr Asn Ser Ser
        50                  55                  60

Leu Arg Asn Ser Thr Val Val Arg Glu Asn Ala Ile Ser Phe Asn Phe
65                  70                  75                  80

Phe Gln Ser Tyr Asn Gln Tyr Tyr Val Phe His Met Pro Arg Cys Leu
                85                  90                  95

Phe Ala Gly Pro Leu Ala Glu Gln Phe Leu Asn Gln Val Asp Leu Thr
            100                 105                 110

Glu Thr Leu Glu Arg Tyr Gln Gln Arg Leu Asn Thr Tyr Ala Leu Val
        115                 120                 125

Ser Lys Asp Leu Ala Ser Tyr Arg Ser Phe Ser Gln Gln Leu Lys Ala
    130                 135                 140

Gln Asp Ser Leu Gly Glu Gln Pro Thr Thr Val Pro Pro Pro Ile Asp
145                 150                 155                 160

Leu Ser Ile Pro His Val Trp Met Pro Pro Gln Thr Thr Pro His Gly
                165                 170                 175

Trp Thr Glu Ser His Thr Thr Ser Gly Leu His Arg Pro His Phe Asn
            180                 185                 190

Gln Thr Cys Ile Leu Phe Asp Gly His Asp Leu Leu Phe Ser Thr Val
        195                 200                 205

Thr Pro Cys Leu His Gln Gly Phe Tyr Leu Ile Asp Glu Leu Arg Tyr
    210                 215                 220

Val Lys Ile Thr Leu Thr Glu Asp Phe Phe Val Val Thr Val Ser Ile
225                 230                 235                 240

Asp Asp Asp Thr Pro Met Leu Leu Ile Phe Gly His Leu Pro Arg Val
                245                 250                 255

Leu Phe Lys Ala Pro Tyr Gln Arg Asp Asn Phe Ile Leu Arg Gln Thr
            260                 265                 270

Glu Lys His Glu Leu Leu Val Leu Val Lys Lys Asp Gln Leu Asn Arg
        275                 280                 285

His Ser Tyr Leu Lys Asp Pro Asp Phe Leu Asp Ala Ala Leu Asp Phe
```

```
                290                 295                 300
Asn Tyr Leu Asp Leu Ser Ala Leu Leu Arg Asn Ser Phe His Arg Tyr
305                 310                 315                 320

Ala Val Asp Val Leu Lys Ser Gly Arg Cys Gln Met Leu Asp Arg Arg
                325                 330                 335

Thr Val Glu Met Ala Phe Ala Tyr Ala Leu Ala Leu Phe Ala Ala Ala
                340                 345                 350

Arg Gln Glu Glu Ala Gly Ala Gln Val Ser Val Pro Arg Ala Leu Asp
                355                 360                 365

Arg Gln Ala Ala Leu Leu Gln Ile Gln Glu Phe Met Ile Thr Cys Leu
                370                 375                 380

Ser Gln Thr Pro Pro Arg Thr Thr Leu Leu Leu Tyr Pro Thr Ala Val
385                 390                 395                 400

Asp Leu Ala Lys Arg Ala Leu Trp Thr Pro Asn Gln Ile Thr Asp Ile
                405                 410                 415

Thr Ser Leu Val Arg Leu Val Tyr Ile Leu Ser Lys Gln Asn Gln Gln
                420                 425                 430

His Leu Ile Pro Gln Trp Ala Leu Arg Gln Ile Ala Asp Phe Ala Leu
                435                 440                 445

Lys Leu His Lys Thr His Leu Ala Ser Phe Leu Ser Ala Phe Ala Arg
                450                 455                 460

Gln Glu Leu Tyr Leu Met Gly Ser Leu Val His Ser Met Leu Val His
465                 470                 475                 480

Thr Thr Glu Arg Arg Glu Ile Phe Ile Val Glu Thr Gly Leu Cys Ser
                485                 490                 495

Leu Ala Glu Leu Ser His Phe Thr Gln Leu Leu Ala His Pro His His
                500                 505                 510

Glu Tyr Leu Ser Asp Leu Tyr Thr Pro Cys Ser Ser Gly Arg Arg
                515                 520                 525

Asp His Ser Leu Glu Arg Leu Thr Arg Leu Phe Pro Asp Ala Thr Val
                530                 535                 540

Pro Thr Thr Val Pro Ala Ala Leu Ser Ile Leu Ser Thr Met Gln Pro
545                 550                 555                 560

Ser Thr Leu Glu Thr Phe Pro Asp Leu Phe Cys Leu Pro Leu Gly Glu
                565                 570                 575

Ser Phe Ser Ala Leu Thr Val Ser Glu His Val Ser Tyr Val Val Thr
                580                 585                 590

Asn Gln Tyr Leu Ile Lys Gly Ile Ser Tyr Pro Val Ser Thr Thr Val
                595                 600                 605

Val Gly Gln Ser Leu Ile Ile Thr Gln Thr Asp Ser Gln Thr Lys Cys
                610                 615                 620

Glu Leu Thr Arg Asn Met His Thr Thr His Ser Ile Thr Ala Ala Leu
625                 630                 635                 640

Asn Ile Ser Leu Glu Asn Cys Ala Phe Cys Gln Ser Ala Leu Leu Glu
                645                 650                 655

Tyr Asp Asp Thr Gln Gly Val Ile Asn Ile Met Tyr Met His Asp Ser
                660                 665                 670

Asp Asp Val Leu Phe Ala Leu Asp Pro Tyr Asn Glu Val Val Ser
                675                 680                 685

Ser Pro Arg Thr His Tyr Leu Met Leu Leu Lys Asn Gly Thr Val Leu
                690                 695                 700

Glu Val Thr Asp Val Val Asp Ala Thr Asp Ser Arg Leu Leu Met
705                 710                 715                 720
```

```
Met Ser Val Tyr Ala Leu Ser Ala Ile Ile Gly Ile Tyr Leu Leu Tyr
            725                 730                 735

Arg Met Leu Lys Thr Cys
            740

<210> SEQ ID NO 6
<211> LENGTH: 743
<212> TYPE: PRT
<213> ORGANISM: Artificial Sequence
<220> FEATURE:
<223> OTHER INFORMATION: HCMV AD169 strain, full length gH

<400> SEQUENCE: 6

Met Arg Pro Gly Leu Pro Pro Tyr Leu Thr Val Phe Thr Val Tyr Leu
1               5                   10                  15

Leu Ser His Leu Pro Ser Gln Arg Tyr Gly Ala Asp Ala Ala Ser Glu
            20                  25                  30

Ala Leu Asp Pro His Ala Phe His Leu Leu Asn Thr Tyr Gly Arg
        35                  40                  45

Pro Ile Arg Phe Leu Arg Glu Asn Thr Thr Gln Cys Thr Tyr Asn Ser
    50                  55                  60

Ser Leu Arg Asn Ser Thr Val Val Arg Glu Asn Ala Ile Ser Phe Asn
65                  70                  75                  80

Phe Phe Gln Ser Tyr Asn Gln Tyr Tyr Val Phe His Met Pro Arg Cys
                85                  90                  95

Leu Phe Ala Gly Pro Leu Ala Glu Gln Phe Leu Asn Gln Val Asp Leu
            100                 105                 110

Thr Glu Thr Leu Glu Arg Tyr Gln Gln Arg Leu Asn Thr Tyr Ala Leu
        115                 120                 125

Val Ser Lys Asp Leu Ala Ser Tyr Arg Ser Phe Ser Gln Gln Leu Lys
    130                 135                 140

Ala Gln Asp Ser Leu Gly Gln Gln Pro Thr Thr Val Pro Pro Pro Ile
145                 150                 155                 160

Asp Leu Ser Ile Pro His Val Trp Met Pro Pro Gln Thr Thr Pro His
                165                 170                 175

Asp Trp Lys Gly Ser His Thr Thr Ser Gly Leu His Arg Pro His Phe
            180                 185                 190

Asn Gln Thr Cys Ile Leu Phe Asp Gly His Asp Leu Leu Phe Ser Thr
        195                 200                 205

Val Thr Pro Cys Leu His Gln Gly Phe Tyr Leu Met Asp Glu Leu Arg
    210                 215                 220

Tyr Val Lys Ile Thr Leu Thr Glu Asp Phe Phe Val Val Thr Val Ser
225                 230                 235                 240

Ile Asp Asp Asp Thr Pro Met Leu Leu Ile Phe Gly His Leu Pro Arg
                245                 250                 255

Val Leu Phe Lys Ala Pro Tyr Gln Arg Asp Asn Phe Ile Leu Arg Gln
            260                 265                 270

Thr Glu Lys His Glu Leu Leu Val Leu Val Lys Lys Ala Gln Leu Asn
        275                 280                 285

Arg His Ser Tyr Leu Lys Asp Ser Asp Phe Leu Asp Ala Ala Leu Asp
    290                 295                 300

Phe Asn Tyr Leu Asp Leu Ser Ala Leu Leu Arg Asn Ser Phe His Arg
305                 310                 315                 320

Tyr Ala Val Asp Val Leu Lys Ser Gly Arg Cys Gln Met Leu Asp Arg
                325                 330                 335
```

```
Arg Thr Val Glu Met Ala Phe Ala Tyr Ala Leu Ala Leu Phe Ala Ala
                340                 345                 350

Ala Arg Gln Glu Glu Ala Gly Thr Glu Ile Ser Ile Pro Arg Ala Leu
            355                 360                 365

Asp Arg Gln Ala Ala Leu Leu Gln Ile Gln Glu Phe Met Ile Thr Cys
        370                 375                 380

Leu Ser Gln Thr Pro Pro Arg Thr Thr Leu Leu Leu Tyr Pro Thr Ala
385                 390                 395                 400

Val Asp Leu Ala Lys Arg Ala Leu Trp Thr Pro Asp Gln Ile Thr Asp
                405                 410                 415

Ile Thr Ser Leu Val Arg Leu Val Tyr Ile Leu Ser Lys Gln Asn Gln
            420                 425                 430

Gln His Leu Ile Pro Gln Trp Ala Leu Arg Gln Ile Ala Asp Phe Ala
        435                 440                 445

Leu Gln Leu His Lys Thr His Leu Ala Ser Phe Leu Ser Ala Phe Ala
    450                 455                 460

Arg Gln Glu Leu Tyr Leu Met Gly Ser Leu Val His Ser Met Leu Val
465                 470                 475                 480

His Thr Thr Glu Arg Arg Glu Ile Phe Ile Val Glu Thr Gly Leu Cys
                485                 490                 495

Ser Leu Ala Glu Leu Ser His Phe Thr Gln Leu Leu Ala His Pro His
            500                 505                 510

His Glu Tyr Leu Ser Asp Leu Tyr Thr Pro Cys Ser Ser Ser Gly Arg
        515                 520                 525

Arg Asp His Ser Leu Glu Arg Leu Thr Arg Leu Phe Pro Asp Ala Thr
    530                 535                 540

Val Pro Ala Thr Val Pro Ala Ala Leu Ser Ile Leu Ser Thr Met Gln
545                 550                 555                 560

Pro Ser Thr Leu Glu Thr Phe Pro Asp Leu Phe Cys Leu Pro Leu Gly
                565                 570                 575

Glu Ser Phe Ser Ala Leu Thr Val Ser Glu His Val Ser Tyr Val Val
            580                 585                 590

Thr Asn Gln Tyr Leu Ile Lys Gly Ile Ser Tyr Pro Val Ser Thr Thr
        595                 600                 605

Val Val Gly Gln Ser Leu Ile Ile Thr Gln Thr Asp Ser Gln Thr Lys
    610                 615                 620

Cys Glu Leu Thr Arg Asn Met His Thr Thr His Ser Ile Thr Ala Ala
625                 630                 635                 640

Leu Asn Ile Ser Leu Glu Asn Cys Ala Phe Cys Gln Ser Ala Leu Leu
                645                 650                 655

Glu Tyr Asp Asp Thr Gln Gly Val Ile Asn Ile Met Tyr Met His Asp
            660                 665                 670

Ser Asp Asp Val Leu Phe Ala Leu Asp Pro Tyr Asn Glu Val Val Val
        675                 680                 685

Ser Ser Pro Arg Thr His Tyr Leu Met Leu Leu Lys Asn Gly Thr Val
    690                 695                 700

Leu Glu Val Thr Asp Val Val Val Asp Ala Thr Asp Ser Arg Leu Leu
705                 710                 715                 720

Met Met Ser Val Tyr Ala Leu Ser Ala Ile Ile Gly Ile Tyr Leu Leu
                725                 730                 735

Tyr Arg Met Leu Lys Thr Cys
            740
```

```
<210> SEQ ID NO 7
<211> LENGTH: 278
<212> TYPE: PRT
<213> ORGANISM: Artificial Sequence
<220> FEATURE:
<223> OTHER INFORMATION: HCMV Merlin strain, full length gL

<400> SEQUENCE: 7

Met Cys Arg Arg Pro Asp Cys Gly Phe Ser Phe Ser Pro Gly Pro Val
1               5                   10                  15

Ile Leu Leu Trp Cys Cys Leu Leu Pro Ile Val Ser Ser Ala Ala
            20                  25                  30

Val Ser Val Ala Pro Thr Ala Ala Glu Lys Val Pro Ala Glu Cys Pro
            35                  40                  45

Glu Leu Thr Arg Arg Cys Leu Leu Gly Glu Val Phe Glu Gly Asp Lys
        50                  55                  60

Tyr Glu Ser Trp Leu Arg Pro Leu Val Asn Val Thr Gly Arg Asp Gly
65                  70                  75                  80

Pro Leu Ser Gln Leu Ile Arg Tyr Arg Pro Val Thr Pro Glu Ala Ala
                85                  90                  95

Asn Ser Val Leu Leu Asp Glu Ala Phe Leu Asp Thr Leu Ala Leu Leu
            100                 105                 110

Tyr Asn Asn Pro Asp Gln Leu Arg Ala Leu Leu Thr Leu Leu Ser Ser
        115                 120                 125

Asp Thr Ala Pro Arg Trp Met Thr Val Met Arg Gly Tyr Ser Glu Cys
130                 135                 140

Gly Asp Gly Ser Pro Ala Val Tyr Thr Cys Val Asp Asp Leu Cys Arg
145                 150                 155                 160

Gly Tyr Asp Leu Thr Arg Leu Ser Tyr Gly Arg Ser Ile Phe Thr Glu
                165                 170                 175

His Val Leu Gly Phe Glu Leu Val Pro Pro Ser Leu Phe Asn Val Val
            180                 185                 190

Val Ala Ile Arg Asn Glu Ala Thr Arg Thr Asn Arg Ala Val Arg Leu
        195                 200                 205

Pro Val Ser Thr Ala Ala Ala Pro Glu Gly Ile Thr Leu Phe Tyr Gly
    210                 215                 220

Leu Tyr Asn Ala Val Lys Glu Phe Cys Leu Arg His Gln Leu Asp Pro
225                 230                 235                 240

Pro Leu Leu Arg His Leu Asp Lys Tyr Tyr Ala Gly Leu Pro Pro Glu
                245                 250                 255

Leu Lys Gln Thr Arg Val Asn Leu Pro Ala His Ser Arg Tyr Gly Pro
            260                 265                 270

Gln Ala Val Asp Ala Arg
        275

<210> SEQ ID NO 8
<211> LENGTH: 248
<212> TYPE: PRT
<213> ORGANISM: Artificial Sequence
<220> FEATURE:
<223> OTHER INFORMATION: HCMV Merlin strain, mature full length gL

<400> SEQUENCE: 8

Ala Ala Val Ser Val Ala Pro Thr Ala Ala Glu Lys Val Pro Ala Glu
1               5                   10                  15

Cys Pro Glu Leu Thr Arg Arg Cys Leu Leu Gly Glu Val Phe Glu Gly
            20                  25                  30
```

```
Asp Lys Tyr Glu Ser Trp Leu Arg Pro Leu Val Asn Val Thr Gly Arg
            35                  40                  45

Asp Gly Pro Leu Ser Gln Leu Ile Arg Tyr Arg Pro Val Thr Pro Glu
 50                  55                  60

Ala Ala Asn Ser Val Leu Leu Asp Glu Ala Phe Leu Asp Thr Leu Ala
 65                  70                  75                  80

Leu Leu Tyr Asn Asn Pro Asp Gln Leu Arg Ala Leu Leu Thr Leu Leu
                85                  90                  95

Ser Ser Asp Thr Ala Pro Arg Trp Met Thr Val Met Arg Gly Tyr Ser
            100                 105                 110

Glu Cys Gly Asp Gly Ser Pro Ala Val Tyr Thr Cys Val Asp Asp Leu
        115                 120                 125

Cys Arg Gly Tyr Asp Leu Thr Arg Leu Ser Tyr Gly Arg Ser Ile Phe
    130                 135                 140

Thr Glu His Val Leu Gly Phe Glu Leu Val Pro Pro Ser Leu Phe Asn
145                 150                 155                 160

Val Val Val Ala Ile Arg Asn Glu Ala Thr Arg Thr Asn Arg Ala Val
                165                 170                 175

Arg Leu Pro Val Ser Thr Ala Ala Ala Pro Glu Gly Ile Thr Leu Phe
            180                 185                 190

Tyr Gly Leu Tyr Asn Ala Val Lys Glu Phe Cys Leu Arg His Gln Leu
        195                 200                 205

Asp Pro Pro Leu Leu Arg His Leu Asp Lys Tyr Tyr Ala Gly Leu Pro
    210                 215                 220

Pro Glu Leu Lys Gln Thr Arg Val Asn Leu Pro Ala His Ser Arg Tyr
225                 230                 235                 240

Gly Pro Gln Ala Val Asp Ala Arg
                245

<210> SEQ ID NO 9
<211> LENGTH: 278
<212> TYPE: PRT
<213> ORGANISM: Artificial Sequence
<220> FEATURE:
<223> OTHER INFORMATION: HCMV Merlin strain, full length LSG gL

<400> SEQUENCE: 9

Met Cys Arg Arg Pro Asp Cys Gly Phe Ser Phe Ser Pro Gly Pro Val
 1               5                  10                  15

Ile Leu Leu Trp Cys Cys Leu Leu Leu Pro Ile Val Ser Ser Ala Ala
            20                  25                  30

Val Ser Val Ala Pro Thr Ala Ala Glu Lys Val Pro Ala Glu Cys Pro
        35                  40                  45

Glu Leu Thr Arg Arg Cys Leu Leu Gly Glu Val Phe Glu Gly Asp Lys
    50                  55                  60

Tyr Glu Ser Trp Leu Arg Pro Leu Val Asn Val Thr Gly Arg Asp Gly
 65                  70                  75                  80

Pro Leu Ser Gln Leu Ile Arg Tyr Arg Pro Val Thr Pro Glu Ala Leu
                85                  90                  95

Ser Gly Val Leu Leu Asp Glu Ala Phe Leu Asp Thr Leu Ala Leu Leu
            100                 105                 110

Tyr Asn Asn Pro Asp Gln Leu Arg Ala Leu Leu Thr Leu Leu Ser Ser
        115                 120                 125

Asp Thr Ala Pro Arg Trp Met Thr Val Met Arg Gly Tyr Ser Glu Cys
    130                 135                 140
```

```
Gly Asp Gly Ser Pro Ala Val Tyr Thr Cys Val Asp Leu Cys Arg
145                 150                 155                 160

Gly Tyr Asp Leu Thr Arg Leu Ser Tyr Gly Arg Ser Ile Phe Thr Glu
                165                 170                 175

His Val Leu Gly Phe Glu Leu Val Pro Pro Ser Leu Phe Asn Val Val
            180                 185                 190

Val Ala Ile Arg Asn Glu Ala Thr Arg Thr Asn Arg Ala Val Arg Leu
        195                 200                 205

Pro Val Ser Thr Ala Ala Pro Glu Gly Ile Thr Leu Phe Tyr Gly
    210                 215                 220

Leu Tyr Asn Ala Val Lys Glu Phe Cys Leu Arg His Gln Leu Asp Pro
225                 230                 235                 240

Pro Leu Arg His Leu Asp Lys Tyr Tyr Ala Gly Leu Pro Pro Glu
                245                 250                 255

Leu Lys Gln Thr Arg Val Asn Leu Pro Ala His Ser Arg Tyr Gly Pro
                260                 265                 270

Gln Ala Val Asp Ala Arg
            275
```

<210> SEQ ID NO 10
<211> LENGTH: 248
<212> TYPE: PRT
<213> ORGANISM: Artificial Sequence
<220> FEATURE:
<223> OTHER INFORMATION: HCMV Merlin strain, mature LSG gL, residues 31 to 278 of SEQ ID NO: 9

<400> SEQUENCE: 10

```
Ala Ala Val Ser Val Ala Pro Thr Ala Ala Glu Lys Val Pro Ala Glu
1               5                   10                  15

Cys Pro Glu Leu Thr Arg Arg Cys Leu Leu Gly Glu Val Phe Glu Gly
                20                  25                  30

Asp Lys Tyr Glu Ser Trp Leu Arg Pro Leu Val Asn Val Thr Gly Arg
            35                  40                  45

Asp Gly Pro Leu Ser Gln Leu Ile Arg Tyr Arg Pro Val Thr Pro Glu
50                  55                  60

Ala Leu Ser Gly Val Leu Leu Asp Glu Ala Phe Leu Asp Thr Leu Ala
65                  70                  75                  80

Leu Leu Tyr Asn Asn Pro Asp Gln Leu Arg Ala Leu Leu Thr Leu Leu
                85                  90                  95

Ser Ser Asp Thr Ala Pro Arg Trp Met Thr Val Met Arg Gly Tyr Ser
                100                 105                 110

Glu Cys Gly Asp Gly Ser Pro Ala Val Tyr Thr Cys Val Asp Asp Leu
            115                 120                 125

Cys Arg Gly Tyr Asp Leu Thr Arg Leu Ser Tyr Gly Arg Ser Ile Phe
130                 135                 140

Thr Glu His Val Leu Gly Phe Glu Leu Val Pro Pro Ser Leu Phe Asn
145                 150                 155                 160

Val Val Val Ala Ile Arg Asn Glu Ala Thr Arg Thr Asn Arg Ala Val
                165                 170                 175

Arg Leu Pro Val Ser Thr Ala Ala Pro Glu Gly Ile Thr Leu Phe
            180                 185                 190

Tyr Gly Leu Tyr Asn Ala Val Lys Glu Phe Cys Leu Arg His Gln Leu
        195                 200                 205

Asp Pro Pro Leu Leu Arg His Leu Asp Lys Tyr Tyr Ala Gly Leu Pro
```

Pro Glu Leu Lys Gln Thr Arg Val Asn Leu Pro Ala His Ser Arg Tyr
225                 230                 235                 240

Gly Pro Gln Ala Val Asp Ala Arg
                245

<210> SEQ ID NO 11
<211> LENGTH: 278
<212> TYPE: PRT
<213> ORGANISM: Artificial Sequence
<220> FEATURE:
<223> OTHER INFORMATION: HCMV Towne strain, full length gL

<400> SEQUENCE: 11

Met Cys Arg Arg Pro Asp Cys Gly Phe Ser Phe Ser Pro Gly Pro Val
1               5                   10                  15

Ala Leu Leu Trp Cys Cys Leu Leu Leu Pro Ile Val Ser Ser Ala Thr
                20                  25                  30

Val Ser Val Ala Pro Thr Val Ala Glu Lys Val Pro Ala Glu Cys Pro
            35                  40                  45

Glu Leu Thr Arg Arg Cys Leu Leu Gly Glu Val Phe Gln Gly Asp Lys
        50                  55                  60

Tyr Glu Ser Trp Leu Arg Pro Leu Val Asn Val Thr Arg Arg Asp Gly
65                  70                  75                  80

Pro Leu Ser Gln Leu Ile Arg Tyr Arg Pro Val Thr Pro Glu Ala Ala
                85                  90                  95

Asn Ser Val Leu Leu Asp Asp Ala Phe Leu Asp Thr Leu Ala Leu Leu
            100                 105                 110

Tyr Asn Asn Pro Asp Gln Leu Arg Ala Leu Leu Thr Leu Leu Ser Ser
        115                 120                 125

Asp Thr Ala Pro Arg Trp Met Thr Val Met Arg Gly Tyr Ser Glu Cys
130                 135                 140

Gly Asp Gly Ser Pro Ala Val Tyr Thr Cys Val Asp Asp Leu Cys Arg
145                 150                 155                 160

Gly Tyr Asp Leu Thr Arg Leu Ser Tyr Gly Arg Ser Ile Phe Thr Glu
                165                 170                 175

His Val Leu Gly Phe Glu Leu Val Pro Pro Ser Leu Phe Asn Val Val
            180                 185                 190

Val Ala Ile Arg Asn Glu Ala Thr Arg Thr Asn Arg Ala Val Arg Leu
        195                 200                 205

Pro Val Ser Thr Ala Ala Ala Pro Glu Gly Ile Thr Leu Phe Tyr Gly
210                 215                 220

Leu Tyr Asn Ala Val Lys Glu Phe Cys Leu Arg His Gln Leu Asp Pro
225                 230                 235                 240

Pro Leu Leu Arg His Leu Asp Lys Tyr Tyr Ala Gly Leu Pro Pro Glu
                245                 250                 255

Leu Lys Gln Thr Arg Val Asn Leu Pro Ala His Ser Arg Tyr Gly Pro
            260                 265                 270

Gln Ala Val Asp Ala Arg
        275

<210> SEQ ID NO 12
<211> LENGTH: 278
<212> TYPE: PRT
<213> ORGANISM: Artificial Sequence
<220> FEATURE:
<223> OTHER INFORMATION: HCMV AD169 strain, full length gL

```
<400> SEQUENCE: 12

Met Cys Arg Arg Pro Asp Cys Gly Phe Ser Phe Ser Pro Gly Pro Val
1               5                   10                  15

Val Leu Leu Trp Cys Cys Leu Leu Pro Ile Val Ser Ser Val Ala
                20                  25                  30

Val Ser Val Ala Pro Thr Ala Ala Glu Lys Val Pro Ala Glu Cys Pro
            35                  40                  45

Glu Leu Thr Arg Arg Cys Leu Leu Gly Glu Val Phe Gln Gly Asp Lys
        50                  55                  60

Tyr Glu Ser Trp Leu Arg Pro Leu Val Asn Val Thr Arg Arg Asp Gly
65                  70                  75                  80

Pro Leu Ser Gln Leu Ile Arg Tyr Arg Pro Val Thr Pro Glu Ala Ala
                85                  90                  95

Asn Ser Val Leu Leu Asp Asp Ala Phe Leu Asp Thr Leu Ala Leu Leu
            100                 105                 110

Tyr Asn Asn Pro Asp Gln Leu Arg Ala Leu Leu Thr Leu Leu Ser Ser
        115                 120                 125

Asp Thr Ala Pro Arg Trp Met Thr Val Met Arg Gly Tyr Ser Glu Cys
130                 135                 140

Gly Asp Gly Ser Pro Ala Val Tyr Thr Cys Val Asp Asp Leu Cys Arg
145                 150                 155                 160

Gly Tyr Asp Leu Thr Arg Leu Ser Tyr Gly Arg Ser Ile Phe Thr Glu
                165                 170                 175

His Val Leu Gly Phe Glu Leu Val Pro Pro Ser Leu Phe Asn Val Val
            180                 185                 190

Val Ala Ile Arg Asn Glu Ala Thr Arg Thr Asn Arg Ala Val Arg Leu
        195                 200                 205

Pro Val Ser Thr Ala Ala Ala Pro Glu Gly Ile Thr Leu Phe Tyr Gly
        210                 215                 220

Leu Tyr Asn Ala Val Lys Glu Phe Cys Leu Arg His Gln Leu Asp Pro
225                 230                 235                 240

Pro Leu Leu Arg His Leu Asp Lys Tyr Tyr Ala Gly Leu Pro Pro Glu
                245                 250                 255

Leu Lys Gln Thr Arg Val Asn Leu Pro Ala His Ser Arg Tyr Gly Pro
            260                 265                 270

Gln Ala Val Asp Ala Arg
        275

<210> SEQ ID NO 13
<211> LENGTH: 171
<212> TYPE: PRT
<213> ORGANISM: Artificial Sequence
<220> FEATURE:
<223> OTHER INFORMATION: HCMV Merlin strain, full length pUL128

<400> SEQUENCE: 13

Met Ser Pro Lys Asp Leu Thr Pro Phe Leu Thr Ala Leu Trp Leu Leu
1               5                   10                  15

Leu Gly His Ser Arg Val Pro Arg Val Arg Ala Glu Glu Cys Cys Glu
                20                  25                  30

Phe Ile Asn Val Asn His Pro Pro Glu Arg Cys Tyr Asp Phe Lys Met
            35                  40                  45

Cys Asn Arg Phe Thr Val Ala Leu Arg Cys Pro Asp Gly Glu Val Cys
        50                  55                  60
```

Tyr Ser Pro Glu Lys Thr Ala Glu Ile Arg Gly Ile Val Thr Thr Met
65                  70                  75                  80

Thr His Ser Leu Thr Arg Gln Val Val His Asn Lys Leu Thr Ser Cys
            85                  90                  95

Asn Tyr Asn Pro Leu Tyr Leu Glu Ala Asp Gly Arg Ile Arg Cys Gly
            100                 105                 110

Lys Val Asn Asp Lys Ala Gln Tyr Leu Leu Gly Ala Ala Gly Ser Val
        115                 120                 125

Pro Tyr Arg Trp Ile Asn Leu Glu Tyr Asp Lys Ile Thr Arg Ile Val
        130                 135                 140

Gly Leu Asp Gln Tyr Leu Glu Ser Val Lys Lys His Lys Arg Leu Asp
145                 150                 155                 160

Val Cys Arg Ala Lys Met Gly Tyr Met Leu Gln
                165                 170

<210> SEQ ID NO 14
<211> LENGTH: 144
<212> TYPE: PRT
<213> ORGANISM: Artificial Sequence
<220> FEATURE:
<223> OTHER INFORMATION: HCMV Merlin strain, mature pUL128, residues 28
      to 171 of SEQ ID NO: 13

<400> SEQUENCE: 14

Glu Glu Cys Cys Glu Phe Ile Asn Val Asn His Pro Pro Glu Arg Cys
1               5                   10                  15

Tyr Asp Phe Lys Met Cys Asn Arg Phe Thr Val Ala Leu Arg Cys Pro
            20                  25                  30

Asp Gly Glu Val Cys Tyr Ser Pro Glu Lys Thr Ala Glu Ile Arg Gly
        35                  40                  45

Ile Val Thr Thr Met Thr His Ser Leu Thr Arg Gln Val Val His Asn
    50                  55                  60

Lys Leu Thr Ser Cys Asn Tyr Asn Pro Leu Tyr Leu Glu Ala Asp Gly
65                  70                  75                  80

Arg Ile Arg Cys Gly Lys Val Asn Asp Lys Ala Gln Tyr Leu Leu Gly
                85                  90                  95

Ala Ala Gly Ser Val Pro Tyr Arg Trp Ile Asn Leu Glu Tyr Asp Lys
            100                 105                 110

Ile Thr Arg Ile Val Gly Leu Asp Gln Tyr Leu Glu Ser Val Lys Lys
        115                 120                 125

His Lys Arg Leu Asp Val Cys Arg Ala Lys Met Gly Tyr Met Leu Gln
    130                 135                 140

<210> SEQ ID NO 15
<211> LENGTH: 171
<212> TYPE: PRT
<213> ORGANISM: Artificial Sequence
<220> FEATURE:
<223> OTHER INFORMATION: HCMV Towne strain, full length pUL128

<400> SEQUENCE: 15

Met Ser Pro Lys Asn Leu Thr Pro Phe Leu Thr Ala Leu Trp Leu Leu
1               5                   10                  15

Leu Gly His Ser Arg Val Pro Arg Val Arg Ala Glu Glu Cys Cys Glu
            20                  25                  30

Phe Ile Asn Val Asn His Pro Pro Glu Arg Cys Tyr Asp Phe Lys Met
        35                  40                  45

Cys Asn Arg Phe Thr Val Ala Leu Arg Cys Pro Asp Gly Glu Val Cys

```
                 50                  55                  60

Tyr Ser Pro Glu Lys Thr Ala Glu Ile Arg Gly Ile Val Thr Thr Met
 65                  70                  75                  80

Thr His Ser Leu Thr Arg Gln Val Val His Asn Lys Leu Thr Ser Cys
                     85                  90                  95

Asn Tyr Asn Pro Leu Tyr Leu Glu Ala Asp Gly Arg Ile Arg Cys Gly
                    100                 105                 110

Lys Val Asn Asp Lys Ala Gln Tyr Leu Leu Gly Ala Ala Gly Ser Val
                115                 120                 125

Pro Tyr Arg Trp Ile Asn Leu Glu Tyr Asp Lys Ile Thr Arg Ile Val
            130                 135                 140

Gly Leu Asp Gln Tyr Leu Glu Ser Val Lys Lys His Lys Arg Leu Asp
145                 150                 155                 160

Val Cys Arg Ala Lys Met Gly Tyr Met Leu Gln
                165                 170

<210> SEQ ID NO 16
<211> LENGTH: 171
<212> TYPE: PRT
<213> ORGANISM: Artificial Sequence
<220> FEATURE:
<223> OTHER INFORMATION: HCMV AD169 strain, full length pUL128

<400> SEQUENCE: 16

Met Ser Pro Lys Asp Leu Thr Pro Phe Leu Thr Thr Leu Trp Leu Leu
 1               5                  10                  15

Leu Gly His Ser Arg Val Pro Arg Val Arg Ala Glu Glu Cys Cys Glu
                 20                  25                  30

Phe Ile Asn Val Asn His Pro Pro Glu Arg Cys Tyr Asp Phe Lys Met
             35                  40                  45

Cys Asn Arg Phe Thr Val Ala Leu Arg Cys Pro Asp Gly Glu Val Cys
         50                  55                  60

Tyr Ser Pro Glu Lys Thr Ala Glu Ile Arg Gly Ile Val Thr Thr Met
 65                  70                  75                  80

Thr His Ser Leu Thr Arg Gln Val Val His Asn Lys Leu Thr Ser Cys
                     85                  90                  95

Asn Tyr Asn Pro Leu Tyr Leu Glu Ala Asp Gly Arg Ile Arg Cys Gly
                    100                 105                 110

Lys Val Asn Asp Lys Ala Gln Tyr Leu Leu Gly Ala Ala Gly Ser Val
                115                 120                 125

Pro Tyr Arg Trp Ile Asn Leu Glu Tyr Asp Lys Ile Thr Arg Ile Val
            130                 135                 140

Gly Leu Asp Gln Tyr Leu Glu Ser Val Lys Lys His Lys Arg Leu Asp
145                 150                 155                 160

Val Cys Arg Ala Lys Met Gly Tyr Met Leu Gln
                165                 170

<210> SEQ ID NO 17
<211> LENGTH: 214
<212> TYPE: PRT
<213> ORGANISM: Artificial Sequence
<220> FEATURE:
<223> OTHER INFORMATION: HCMV Merlin strain, full length pUL130

<400> SEQUENCE: 17

Met Leu Arg Leu Leu Leu Arg His His Phe His Cys Leu Leu Leu Cys
 1               5                  10                  15
```

```
Ala Val Trp Ala Thr Pro Cys Leu Ala Ser Pro Trp Ser Thr Leu Thr
            20                  25                  30

Ala Asn Gln Asn Pro Ser Pro Pro Trp Ser Lys Leu Thr Tyr Ser Lys
        35                  40                  45

Pro His Asp Ala Ala Thr Phe Tyr Cys Pro Phe Leu Tyr Pro Ser Pro
50                  55                  60

Pro Arg Ser Pro Leu Gln Phe Ser Gly Phe Gln Arg Val Ser Thr Gly
65                  70                  75                  80

Pro Glu Cys Arg Asn Glu Thr Leu Tyr Leu Tyr Asn Arg Glu Gly
                85                  90                  95

Gln Thr Leu Val Glu Arg Ser Ser Thr Trp Val Lys Lys Val Ile Trp
            100                 105                 110

Tyr Leu Ser Gly Arg Asn Gln Thr Ile Leu Gln Arg Met Pro Arg Thr
            115                 120                 125

Ala Ser Lys Pro Ser Asp Gly Asn Val Gln Ile Ser Val Glu Asp Ala
        130                 135                 140

Lys Ile Phe Gly Ala His Met Val Pro Lys Gln Thr Lys Leu Leu Arg
145                 150                 155                 160

Phe Val Val Asn Asp Gly Thr Arg Tyr Gln Met Cys Val Met Lys Leu
                165                 170                 175

Glu Ser Trp Ala His Val Phe Arg Asp Tyr Ser Val Ser Phe Gln Val
            180                 185                 190

Arg Leu Thr Phe Thr Glu Ala Asn Asn Gln Thr Tyr Thr Phe Cys Thr
            195                 200                 205

His Pro Asn Leu Ile Val
        210

<210> SEQ ID NO 18
<211> LENGTH: 189
<212> TYPE: PRT
<213> ORGANISM: Artificial Sequence
<220> FEATURE:
<223> OTHER INFORMATION: HCMV Merlin strain, mature pUL130, residues 26
      to 214 of SEQ ID NO: 17

<400> SEQUENCE: 18

Ser Pro Trp Ser Thr Leu Thr Ala Asn Gln Asn Pro Ser Pro Pro Trp
1               5                   10                  15

Ser Lys Leu Thr Tyr Ser Lys Pro His Asp Ala Ala Thr Phe Tyr Cys
            20                  25                  30

Pro Phe Leu Tyr Pro Ser Pro Pro Arg Ser Pro Leu Gln Phe Ser Gly
        35                  40                  45

Phe Gln Arg Val Ser Thr Gly Pro Glu Cys Arg Asn Glu Thr Leu Tyr
50                  55                  60

Leu Leu Tyr Asn Arg Glu Gly Gln Thr Leu Val Glu Arg Ser Ser Thr
65                  70                  75                  80

Trp Val Lys Lys Val Ile Trp Tyr Leu Ser Gly Arg Asn Gln Thr Ile
                85                  90                  95

Leu Gln Arg Met Pro Arg Thr Ala Ser Lys Pro Ser Asp Gly Asn Val
            100                 105                 110

Gln Ile Ser Val Glu Asp Ala Lys Ile Phe Gly Ala His Met Val Pro
        115                 120                 125

Lys Gln Thr Lys Leu Leu Arg Phe Val Val Asn Asp Gly Thr Arg Tyr
    130                 135                 140

Gln Met Cys Val Met Lys Leu Glu Ser Trp Ala His Val Phe Arg Asp
145                 150                 155                 160
```

-continued

```
Tyr Ser Val Ser Phe Gln Val Arg Leu Thr Phe Thr Glu Ala Asn Asn
                165                 170                 175

Gln Thr Tyr Thr Phe Cys Thr His Pro Asn Leu Ile Val
            180                 185
```

<210> SEQ ID NO 19
<211> LENGTH: 229
<212> TYPE: PRT
<213> ORGANISM: Artificial Sequence
<220> FEATURE:
<223> OTHER INFORMATION: HCMV Towne strain, full length pUL130

<400> SEQUENCE: 19

```
Met Leu Arg Leu Leu Arg His His Phe His Cys Leu Leu Leu Cys
1               5                   10                  15

Ala Val Trp Ala Thr Pro Cys Leu Ala Ser Pro Trp Ser Thr Leu Thr
                20                  25                  30

Ala Asn Gln Asn Pro Ser Pro Pro Trp Ser Lys Leu Thr Tyr Ser Lys
            35                  40                  45

Pro His Asp Ala Ala Thr Phe Tyr Cys Pro Phe Leu Tyr Pro Ser Pro
        50                  55                  60

Pro Arg Ser Pro Leu Gln Phe Ser Gly Phe Gln Arg Val Leu Thr Gly
65                  70                  75                  80

Pro Glu Cys Arg Asn Glu Thr Leu Tyr Leu Leu Tyr Asn Arg Glu Gly
                85                  90                  95

Gln Thr Leu Val Glu Arg Ser Ser Thr Trp Val Lys Lys Val Ile Trp
            100                 105                 110

Tyr Leu Ser Gly Arg Asn Gln Thr Ile Leu Gln Arg Met Pro Arg Thr
        115                 120                 125

Ala Ser Lys Pro Ser Asp Gly Asn Val Gln Ile Ser Val Glu Asp Ala
    130                 135                 140

Lys Ile Phe Gly Ala His Met Val Pro Lys Gln Thr Lys Leu Leu Arg
145                 150                 155                 160

Phe Val Val Asn Asp Gly Thr Arg Tyr Gln Met Cys Val Met Lys Leu
                165                 170                 175

Glu Ser Trp Ala His Val Phe Arg Asp Tyr Ser Val Ser Phe Gln Val
            180                 185                 190

Arg Leu Thr Phe Thr Glu Ala Asn Asn Gln Thr Phe Thr Pro Ser Ala
        195                 200                 205

Pro Ile Pro Ile Ser Ser Phe Glu Pro Val Ala Arg Ala Gly Asn Phe
    210                 215                 220

Glu Asn Arg Ala Ser
225
```

<210> SEQ ID NO 20
<211> LENGTH: 214
<212> TYPE: PRT
<213> ORGANISM: Artificial Sequence
<220> FEATURE:
<223> OTHER INFORMATION: HCMV AD169 strain, full length pUL130

<400> SEQUENCE: 20

```
Met Leu Arg Leu Leu Arg His His Phe His Cys Leu Leu Leu Cys
1               5                   10                  15

Ala Val Trp Ala Thr Pro Cys Leu Ala Ser Pro Trp Ser Thr Leu Thr
                20                  25                  30

Ala Asn Gln Asn Pro Ser Pro Pro Trp Ser Lys Leu Thr Tyr Ser Lys
```

```
                35                  40                  45
Pro His Asp Ala Ala Thr Phe Tyr Cys Pro Phe Leu Tyr Pro Ser Pro
 50                  55                  60
Pro Arg Ser Pro Leu Gln Phe Ser Gly Phe Gln Gln Val Ser Thr Gly
 65                  70                  75                  80
Pro Glu Cys Arg Asn Glu Thr Leu Tyr Leu Leu Tyr Asn Arg Glu Gly
                 85                  90                  95
Gln Thr Leu Val Glu Arg Ser Ser Thr Trp Val Lys Lys Val Ile Trp
                100                 105                 110
Tyr Leu Ser Gly Arg Asn Gln Thr Ile Leu Gln Arg Met Pro Gln Thr
                115                 120                 125
Ala Ser Lys Pro Ser Asp Gly Asn Val Gln Ile Ser Val Glu Asp Ala
130                 135                 140
Lys Ile Phe Gly Ala His Met Val Pro Lys Gln Thr Lys Leu Leu Arg
145                 150                 155                 160
Phe Val Val Asn Asp Gly Thr Arg Tyr Gln Met Cys Val Met Lys Leu
                165                 170                 175
Glu Ser Trp Ala His Val Phe Arg Asp Tyr Ser Val Ser Phe Gln Val
                180                 185                 190
Arg Leu Thr Phe Thr Glu Ala Asn Asn Gln Thr Tyr Thr Phe Cys Thr
                195                 200                 205
His Pro Asn Leu Ile Val
    210

<210> SEQ ID NO 21
<211> LENGTH: 129
<212> TYPE: PRT
<213> ORGANISM: Artificial Sequence
<220> FEATURE:
<223> OTHER INFORMATION: HCMV Merlin strain, full length pUL131A

<400> SEQUENCE: 21

Met Arg Leu Cys Arg Val Trp Leu Ser Val Cys Leu Cys Ala Val Val
 1               5                  10                  15
Leu Gly Gln Cys Gln Arg Glu Thr Ala Glu Lys Asn Asp Tyr Tyr Arg
                20                  25                  30
Val Pro His Tyr Trp Asp Ala Cys Ser Arg Ala Leu Pro Asp Gln Thr
                35                  40                  45
Arg Tyr Lys Tyr Val Glu Gln Leu Val Asp Leu Thr Leu Asn Tyr His
 50                  55                  60
Tyr Asp Ala Ser His Gly Leu Asp Asn Phe Asp Val Leu Lys Arg Ile
 65                  70                  75                  80
Asn Val Thr Glu Val Ser Leu Leu Ile Ser Asp Phe Arg Arg Gln Asn
                 85                  90                  95
Arg Arg Gly Gly Thr Asn Lys Arg Thr Thr Phe Asn Ala Ala Gly Ser
                100                 105                 110
Leu Ala Pro His Ala Arg Ser Leu Glu Phe Ser Val Arg Leu Phe Ala
                115                 120                 125
Asn

<210> SEQ ID NO 22
<211> LENGTH: 111
<212> TYPE: PRT
<213> ORGANISM: Artificial Sequence
<220> FEATURE:
<223> OTHER INFORMATION: HCMV Merlin strain, mature pUL131A, residues 19
      to 129 of SEQ ID NO: 21
```

<400> SEQUENCE: 22

Gln Cys Gln Arg Glu Thr Ala Glu Lys Asn Asp Tyr Tyr Arg Val Pro
1               5                   10                  15

His Tyr Trp Asp Ala Cys Ser Arg Ala Leu Pro Asp Gln Thr Arg Tyr
20 25 30

Lys Tyr Val Glu Gln Leu Val Asp Leu Thr Leu Asn Tyr His Tyr Asp
35 40 45

Ala Ser His Gly Leu Asp Asn Phe Asp Val Leu Lys Arg Ile Asn Val
50 55 60

Thr Glu Val Ser Leu Leu Ile Ser Asp Phe Arg Arg Gln Asn Arg Arg
65 70 75 80

Gly Gly Thr Asn Lys Arg Thr Thr Phe Asn Ala Ala Gly Ser Leu Ala
85 90 95

Pro His Ala Arg Ser Leu Glu Phe Ser Val Arg Leu Phe Ala Asn
100 105 110

<210> SEQ ID NO 23
<211> LENGTH: 129
<212> TYPE: PRT
<213> ORGANISM: Artificial Sequence
<220> FEATURE:
<223> OTHER INFORMATION: HCMV Towne strain, full length pUL131A

<400> SEQUENCE: 23

Met Arg Leu Cys Arg Val Trp Leu Ser Val Cys Leu Cys Ala Val Val
1 5 10 15

Leu Gly Gln Cys Gln Arg Glu Thr Ala Glu Lys Asn Asp Tyr Tyr Arg
20 25 30

Val Pro His Tyr Trp Asp Ala Cys Ser Arg Ala Leu Pro Asp Gln Thr
35 40 45

Arg Tyr Lys Tyr Val Glu Gln Leu Val Asp Leu Thr Leu Asn Tyr His
50 55 60

Tyr Asp Ala Ser His Gly Leu Asp Asn Phe Asp Val Leu Lys Arg Ile
65 70 75 80

Asn Val Thr Glu Val Ser Leu Leu Ile Ser Asp Phe Arg Arg Gln Asn
85 90 95

Arg Arg Gly Gly Thr Asn Lys Arg Thr Thr Phe Asn Ala Ala Gly Ser
100 105 110

Leu Ala Pro His Ala Arg Ser Leu Glu Phe Ser Val Arg Leu Phe Ala
115 120 125

Asn

<210> SEQ ID NO 24
<211> LENGTH: 74
<212> TYPE: PRT
<213> ORGANISM: Artificial Sequence
<220> FEATURE:
<223> OTHER INFORMATION: HCMV AD169 strain, full length pUL131A

<400> SEQUENCE: 24

Met Arg Leu Cys Arg Val Trp Leu Ser Val Cys Leu Cys Ala Val Val
1 5 10 15

Leu Gly Gln Cys Gln Arg Glu Thr Ala Glu Lys Lys Arg Leu Leu Pro
20 25 30

Ser Thr Ala Leu Leu Gly Arg Val Leu Ser Arg Ala Ala Arg Pro Asn
35 40 45

```
Pro Leu Gln Val Cys Gly Thr Ala Arg Gly Pro His Val Glu Leu Pro
        50                  55                  60

Leu Arg Cys Glu Pro Arg Leu Gly Gln Leu
 65                  70

<210> SEQ ID NO 25
<211> LENGTH: 472
<212> TYPE: PRT
<213> ORGANISM: Artificial Sequence
<220> FEATURE:
<223> OTHER INFORMATION: HCMV Merlin strain, full length gO

<400> SEQUENCE: 25

Met Gly Lys Lys Glu Met Ile Met Val Lys Gly Ile Pro Lys Ile Met
 1               5                  10                  15

Leu Leu Ile Ser Ile Thr Phe Leu Leu Leu Ser Leu Ile Asn Cys Asn
                20                  25                  30

Val Leu Val Asn Ser Arg Gly Thr Arg Arg Ser Trp Pro Tyr Thr Val
            35                  40                  45

Leu Ser Tyr Arg Gly Lys Glu Ile Leu Lys Lys Gln Lys Glu Asp Ile
        50                  55                  60

Leu Lys Arg Leu Met Ser Thr Ser Ser Asp Gly Tyr Arg Phe Leu Met
 65                  70                  75                  80

Tyr Pro Ser Gln Gln Lys Phe His Ala Ile Val Ile Ser Met Asp Lys
                 85                  90                  95

Phe Pro Gln Asp Tyr Ile Leu Ala Gly Pro Ile Arg Asn Asp Ser Ile
            100                 105                 110

Thr His Met Trp Phe Asp Phe Tyr Ser Thr Gln Leu Arg Lys Pro Ala
        115                 120                 125

Lys Tyr Val Tyr Ser Glu Tyr Asn His Thr Ala His Lys Ile Thr Leu
130                 135                 140

Arg Pro Pro Pro Cys Gly Thr Val Pro Ser Met Asn Cys Leu Ser Glu
145                 150                 155                 160

Met Leu Asn Val Ser Lys Arg Asn Asp Thr Gly Glu Lys Gly Cys Gly
                165                 170                 175

Asn Phe Thr Thr Phe Asn Pro Met Phe Phe Asn Val Pro Arg Trp Asn
            180                 185                 190

Thr Lys Leu Tyr Ile Gly Ser Asn Lys Val Asn Val Asp Ser Gln Thr
        195                 200                 205

Ile Tyr Phe Leu Gly Leu Thr Ala Leu Leu Leu Arg Tyr Ala Gln Arg
    210                 215                 220

Asn Cys Thr Arg Ser Phe Tyr Leu Val Asn Ala Met Ser Arg Asn Leu
225                 230                 235                 240

Phe Arg Val Pro Lys Tyr Ile Asn Gly Thr Lys Leu Lys Asn Thr Met
                245                 250                 255

Arg Lys Leu Lys Arg Lys Gln Ala Leu Val Lys Glu Gln Pro Gln Lys
            260                 265                 270

Lys Asn Lys Lys Ser Gln Ser Thr Thr Thr Pro Tyr Leu Ser Tyr Thr
        275                 280                 285

Thr Ser Thr Ala Phe Asn Val Thr Thr Asn Val Thr Tyr Ser Ala Thr
    290                 295                 300

Ala Ala Val Thr Arg Val Ala Thr Ser Thr Thr Gly Tyr Arg Pro Asp
305                 310                 315                 320

Ser Asn Phe Met Lys Ser Ile Met Ala Thr Gln Leu Arg Asp Leu Ala
                325                 330                 335
```

```
Thr Trp Val Tyr Thr Thr Leu Arg Tyr Arg Asn Glu Pro Phe Cys Lys
            340                 345                 350

Pro Asp Arg Asn Arg Thr Ala Val Ser Glu Phe Met Lys Asn Thr His
        355                 360                 365

Val Leu Ile Arg Asn Glu Thr Pro Tyr Thr Ile Tyr Gly Thr Leu Asp
    370                 375                 380

Met Ser Ser Leu Tyr Tyr Asn Glu Thr Met Ser Val Glu Asn Glu Thr
385                 390                 395                 400

Ala Ser Asp Asn Asn Glu Thr Thr Pro Thr Ser Pro Ser Thr Arg Phe
                405                 410                 415

Gln Arg Thr Phe Ile Asp Pro Leu Trp Asp Tyr Leu Asp Ser Leu Leu
        420                 425                 430

Phe Leu Asp Lys Ile Arg Asn Phe Ser Leu Gln Leu Pro Ala Tyr Gly
            435                 440                 445

Asn Leu Thr Pro Pro Glu His Arg Arg Ala Ala Asn Leu Ser Thr Leu
    450                 455                 460

Asn Ser Leu Trp Trp Trp Ser Gln
465                 470

<210> SEQ ID NO 26
<211> LENGTH: 442
<212> TYPE: PRT
<213> ORGANISM: Artificial Sequence
<220> FEATURE:
<223> OTHER INFORMATION: HCMV Merlin strain, mature gO, residues 31 to
      472 of SEQ ID NO: 25

<400> SEQUENCE: 26

Cys Asn Val Leu Val Asn Ser Arg Gly Thr Arg Arg Ser Trp Pro Tyr
1               5                   10                  15

Thr Val Leu Ser Tyr Arg Gly Lys Glu Ile Leu Lys Lys Gln Lys Glu
            20                  25                  30

Asp Ile Leu Lys Arg Leu Met Ser Thr Ser Ser Asp Gly Tyr Arg Phe
        35                  40                  45

Leu Met Tyr Pro Ser Gln Gln Lys Phe His Ala Ile Val Ile Ser Met
    50                  55                  60

Asp Lys Phe Pro Gln Asp Tyr Ile Leu Ala Gly Pro Ile Arg Asn Asp
65                  70                  75                  80

Ser Ile Thr His Met Trp Phe Asp Phe Tyr Ser Thr Gln Leu Arg Lys
                85                  90                  95

Pro Ala Lys Tyr Val Tyr Ser Glu Tyr Asn His Thr Ala His Lys Ile
            100                 105                 110

Thr Leu Arg Pro Pro Pro Cys Gly Thr Val Pro Ser Met Asn Cys Leu
        115                 120                 125

Ser Glu Met Leu Asn Val Ser Lys Arg Asn Asp Thr Gly Glu Lys Gly
    130                 135                 140

Cys Gly Asn Phe Thr Thr Phe Asn Pro Met Phe Phe Asn Val Pro Arg
145                 150                 155                 160

Trp Asn Thr Lys Leu Tyr Ile Gly Ser Asn Lys Val Asn Val Asp Ser
                165                 170                 175

Gln Thr Ile Tyr Phe Leu Gly Leu Thr Ala Leu Leu Leu Arg Tyr Ala
            180                 185                 190

Gln Arg Asn Cys Thr Arg Ser Phe Tyr Leu Val Asn Ala Met Ser Arg
        195                 200                 205

Asn Leu Phe Arg Val Pro Lys Tyr Ile Asn Gly Thr Lys Leu Lys Asn
    210                 215                 220
```

```
Thr Met Arg Lys Leu Lys Arg Lys Gln Ala Leu Val Lys Glu Gln Pro
225                 230                 235                 240

Gln Lys Lys Asn Lys Ser Gln Ser Thr Thr Pro Tyr Leu Ser
            245                 250                 255

Tyr Thr Thr Ser Thr Ala Phe Asn Val Thr Asn Val Thr Tyr Ser
        260                 265                 270

Ala Thr Ala Ala Val Thr Arg Val Ala Thr Ser Thr Gly Tyr Arg
        275                 280                 285

Pro Asp Ser Asn Phe Met Lys Ser Ile Met Ala Thr Gln Leu Arg Asp
    290                 295                 300

Leu Ala Thr Trp Val Tyr Thr Thr Leu Arg Tyr Arg Asn Glu Pro Phe
305                 310                 315                 320

Cys Lys Pro Asp Arg Asn Arg Thr Ala Val Ser Glu Phe Met Lys Asn
                325                 330                 335

Thr His Val Leu Ile Arg Asn Glu Thr Pro Tyr Thr Ile Tyr Gly Thr
            340                 345                 350

Leu Asp Met Ser Ser Leu Tyr Tyr Asn Glu Thr Met Ser Val Glu Asn
            355                 360                 365

Glu Thr Ala Ser Asp Asn Asn Glu Thr Thr Pro Thr Ser Pro Ser Thr
370                 375                 380

Arg Phe Gln Arg Thr Phe Ile Asp Pro Leu Trp Asp Tyr Leu Asp Ser
385                 390                 395                 400

Leu Leu Phe Leu Asp Lys Ile Arg Asn Phe Ser Leu Gln Leu Pro Ala
                405                 410                 415

Tyr Gly Asn Leu Thr Pro Pro Glu His Arg Arg Ala Ala Asn Leu Ser
            420                 425                 430

Thr Leu Asn Ser Leu Trp Trp Trp Ser Gln
            435                 440

<210> SEQ ID NO 27
<211> LENGTH: 457
<212> TYPE: PRT
<213> ORGANISM: Artificial Sequence
<220> FEATURE:
<223> OTHER INFORMATION: HCMV Towne strain, full length gO

<400> SEQUENCE: 27

Met Gly Arg Lys Gly Glu Met Arg Gly Val Phe Asn Leu Phe Phe Leu
1               5                   10                  15

Met Ser Leu Thr Phe Leu Leu Phe Ser Phe Ile Asn Cys Lys Ile Ala
            20                  25                  30

Val Ala Arg Phe Arg Val Lys Ser Gln Lys Ala Lys Glu Glu Glu Arg
        35                  40                  45

Gln Leu Lys Leu Arg Ile Leu Gln Glu Leu Ala Ser Lys Thr Gly Asp
    50                  55                  60

Tyr Tyr Lys Phe Phe Thr Phe Pro Ser Gln Gln Lys Leu Tyr Asn Ile
65                  70                  75                  80

Thr Val Glu Met Lys Gln Phe Pro Pro Asn Ser Ile Leu Ala Gly Pro
                85                  90                  95

Ile Arg Asn His Ser Ile Thr His Leu Trp Phe Asp Phe His Thr Thr
            100                 105                 110

Gln Leu Arg Lys Pro Ala Lys Tyr Val Tyr Ser Glu Tyr Asn His Thr
        115                 120                 125

Gly Gln Lys Ile Thr Phe Arg Pro Pro Ser Cys Gly Thr Ile Pro Ser
    130                 135                 140
```

```
Met Thr Cys Leu Ser Glu Met Leu Asn Val Ser Arg Arg Asn Asn Thr
145                 150                 155                 160

Gly Glu Glu Asn Cys Gly Asn Phe Thr Thr Phe Asn Pro Met Phe Phe
            165                 170                 175

Asn Val Pro Arg Trp Asn Thr Lys Leu Tyr Val Gly Pro Ser Lys Val
        180                 185                 190

Asn Val Asp Ser Gln Thr Ile Tyr Phe Leu Gly Leu Ala Ala Leu Leu
    195                 200                 205

Leu Arg Tyr Ala Gln Arg Asn Cys Thr Arg Ser Phe Tyr Leu Val Asn
210                 215                 220

Ala Met Ser Arg Asn Ile Phe Arg Val Pro Lys Tyr Ile Asn Ser Thr
225                 230                 235                 240

Lys Leu Lys Asn Thr Met Arg Lys Leu Lys Arg Lys Gln Ala Pro Val
                245                 250                 255

Lys Ser Ile Ser Lys Lys Ser Arg Val Ser Thr Thr Pro Tyr Ser
            260                 265                 270

Ser Tyr Thr Ser Thr Ile Phe Asn Val Ser Thr Asn Val Thr Tyr Ser
    275                 280                 285

Pro Ile Val Pro Thr Arg Ile Pro Thr Ser Thr Ile Gly Tyr Arg Pro
290                 295                 300

Asp Glu Asn Phe Met Lys Ser Ile Leu Thr Thr Gln Leu Lys Asp Leu
305                 310                 315                 320

Ala Thr Trp Val Tyr Thr Thr Leu Arg Tyr Arg Asp Glu Pro Phe Cys
            325                 330                 335

Lys Pro Asn Arg Asn Arg Thr Ala Val Ser Glu Phe Met Lys Asn Thr
            340                 345                 350

His Val Leu Ile Arg Asn Glu Thr Pro Tyr Thr Ile Tyr Gly Thr Leu
        355                 360                 365

Asp Met Ser Ser Leu Tyr Tyr Asn Asp Thr Met Pro Val Glu Asn Glu
370                 375                 380

Thr Ala Ser Asp Asn Asn Lys Thr Thr Pro Thr Ser Pro Ser Thr Arg
385                 390                 395                 400

Phe Gln Arg Thr Phe Ile Asp Pro Met Trp Asp Tyr Leu Asp Ser Leu
            405                 410                 415

Leu Phe Leu Ser Glu Ile Arg Asn Phe Ser Leu Gln Ser Ser Thr Tyr
            420                 425                 430

Gly Asn Leu Thr Pro Pro Glu His Arg Arg Ala Val Asn Leu Ser Thr
        435                 440                 445

Leu Asn Ser Leu Trp Trp Trp Leu Gln
    450                 455

<210> SEQ ID NO 28
<211> LENGTH: 466
<212> TYPE: PRT
<213> ORGANISM: Artificial Sequence
<220> FEATURE:
<223> OTHER INFORMATION: HCMV AD169 strain, full length gO

<400> SEQUENCE: 28

Met Gly Arg Lys Glu Met Met Val Arg Asp Val Pro Lys Met Val Phe
1               5                   10                  15

Leu Ile Ser Ile Ser Phe Leu Leu Val Ser Phe Ile Asn Cys Lys Val
            20                  25                  30

Met Ser Lys Ala Leu Tyr Asn Arg Pro Trp Arg Gly Leu Val Leu Ser
        35                  40                  45
```

```
Lys Ile Gly Lys Tyr Lys Leu Asp Gln Leu Lys Leu Glu Ile Leu Arg
     50                  55                  60

Gln Leu Glu Thr Thr Ile Ser Thr Lys Tyr Asn Val Ser Lys Gln Pro
 65                  70                  75                  80

Val Lys Asn Leu Thr Met Asn Met Thr Glu Phe Pro Gln Tyr Tyr Ile
                     85                  90                  95

Leu Ala Gly Pro Ile Gln Asn Tyr Ser Ile Thr Tyr Leu Trp Phe Asp
                100                 105                 110

Phe Tyr Ser Thr Gln Leu Arg Lys Pro Ala Lys Tyr Val Tyr Ser Gln
            115                 120                 125

Tyr Asn His Thr Ala Lys Thr Ile Thr Phe Arg Pro Pro Cys Gly
        130                 135                 140

Thr Val Pro Ser Met Thr Cys Leu Ser Glu Met Leu Asn Val Ser Lys
145                 150                 155                 160

Arg Asn Asp Thr Gly Glu Gln Gly Cys Gly Asn Phe Thr Thr Phe Asn
                165                 170                 175

Pro Met Phe Phe Asn Val Pro Arg Trp Asn Thr Lys Leu Tyr Val Gly
                180                 185                 190

Pro Thr Lys Val Asn Val Asp Ser Gln Thr Ile Tyr Phe Leu Gly Leu
            195                 200                 205

Thr Ala Leu Leu Leu Arg Tyr Ala Gln Arg Asn Cys Thr His Ser Phe
        210                 215                 220

Tyr Leu Val Asn Ala Met Ser Arg Asn Leu Phe Arg Val Pro Lys Tyr
225                 230                 235                 240

Ile Asn Gly Thr Lys Leu Lys Asn Thr Met Arg Lys Leu Lys Arg Lys
                245                 250                 255

Gln Ala Pro Val Lys Glu Gln Phe Glu Lys Lys Ala Lys Lys Thr Gln
                260                 265                 270

Ser Thr Thr Thr Pro Tyr Phe Ser Tyr Thr Thr Ser Ala Ala Leu Asn
            275                 280                 285

Val Thr Thr Asn Val Thr Tyr Ser Ile Thr Thr Ala Ala Arg Arg Val
        290                 295                 300

Ser Thr Ser Thr Ile Ala Tyr Arg Pro Asp Ser Ser Phe Met Lys Ser
305                 310                 315                 320

Ile Met Ala Thr Gln Leu Arg Asp Leu Ala Thr Trp Val Tyr Thr Thr
                325                 330                 335

Leu Arg Tyr Arg Gln Asn Pro Phe Cys Glu Pro Ser Arg Asn Arg Thr
            340                 345                 350

Ala Val Ser Glu Phe Met Lys Asn Thr His Val Leu Ile Arg Asn Glu
        355                 360                 365

Thr Pro Tyr Thr Ile Tyr Gly Thr Leu Asp Met Ser Ser Leu Tyr Tyr
    370                 375                 380

Asn Glu Thr Met Phe Val Glu Asn Lys Thr Ala Ser Asp Ser Asn Lys
385                 390                 395                 400

Thr Thr Pro Thr Ser Pro Ser Met Gly Phe Gln Arg Thr Phe Ile Asp
                405                 410                 415

Pro Leu Trp Asp Tyr Leu Asp Ser Leu Leu Phe Leu Asp Glu Ile Arg
            420                 425                 430

Asn Phe Ser Leu Arg Ser Pro Thr Tyr Val Asn Leu Thr Pro Pro Glu
        435                 440                 445

His Arg Arg Ala Val Asn Leu Ser Thr Leu Asn Ser Leu Trp Trp Trp
    450                 455                 460
```

Leu Gln
465

<210> SEQ ID NO 29
<211> LENGTH: 278
<212> TYPE: PRT
<213> ORGANISM: Artificial Sequence
<220> FEATURE:
<223> OTHER INFORMATION: HCMV Merlin strain, full length IDG gL

<400> SEQUENCE: 29

Met Cys Arg Arg Pro Asp Cys Gly Phe Ser Phe Ser Pro Gly Pro Val
1               5                   10                  15

Ile Leu Leu Trp Cys Cys Leu Leu Leu Pro Ile Val Ser Ser Ala Ala
            20                  25                  30

Val Ser Val Ala Pro Thr Ala Ala Glu Lys Val Pro Ala Glu Cys Pro
        35                  40                  45

Glu Leu Thr Arg Arg Cys Leu Leu Gly Glu Val Phe Glu Gly Asp Lys
    50                  55                  60

Tyr Glu Ser Trp Leu Arg Pro Leu Val Asn Val Thr Gly Arg Asp Gly
65                  70                  75                  80

Pro Leu Ser Gln Leu Ile Arg Tyr Arg Pro Val Thr Pro Glu Ala Ile
                85                  90                  95

Asp Gly Val Leu Leu Asp Glu Ala Phe Leu Asp Thr Leu Ala Leu Leu
            100                 105                 110

Tyr Asn Asn Pro Asp Gln Leu Arg Ala Leu Leu Thr Leu Leu Ser Ser
        115                 120                 125

Asp Thr Ala Pro Arg Trp Met Thr Val Met Arg Gly Tyr Ser Glu Cys
    130                 135                 140

Gly Asp Gly Ser Pro Ala Val Tyr Thr Cys Val Asp Asp Leu Cys Arg
145                 150                 155                 160

Gly Tyr Asp Leu Thr Arg Leu Ser Tyr Gly Arg Ser Ile Phe Thr Glu
                165                 170                 175

His Val Leu Gly Phe Glu Leu Val Pro Pro Ser Leu Phe Asn Val Val
            180                 185                 190

Val Ala Ile Arg Asn Glu Ala Thr Arg Thr Asn Arg Ala Val Arg Leu
        195                 200                 205

Pro Val Ser Thr Ala Ala Ala Pro Glu Gly Ile Thr Leu Phe Tyr Gly
    210                 215                 220

Leu Tyr Asn Ala Val Lys Glu Phe Cys Leu Arg His Gln Leu Asp Pro
225                 230                 235                 240

Pro Leu Leu Arg His Leu Asp Lys Tyr Tyr Ala Gly Leu Pro Pro Glu
                245                 250                 255

Leu Lys Gln Thr Arg Val Asn Leu Pro Ala His Ser Arg Tyr Gly Pro
            260                 265                 270

Gln Ala Val Asp Ala Arg
        275

<210> SEQ ID NO 30
<211> LENGTH: 248
<212> TYPE: PRT
<213> ORGANISM: Artificial Sequence
<220> FEATURE:
<223> OTHER INFORMATION: HCMV Merlin strain, mature IDG gL, residues 31
      to 278 of SEQ ID NO: 29

<400> SEQUENCE: 30

Ala Ala Val Ser Val Ala Pro Thr Ala Ala Glu Lys Val Pro Ala Glu

```
                1               5                  10                 15
            Cys Pro Glu Leu Thr Arg Arg Cys Leu Leu Gly Glu Val Phe Glu Gly
                           20                  25                 30

Asp Lys Tyr Glu Ser Trp Leu Arg Pro Leu Val Asn Val Thr Gly Arg
                       35                  40                 45

Asp Gly Pro Leu Ser Gln Leu Ile Arg Tyr Arg Pro Val Thr Pro Glu
                   50                  55                 60

Ala Ile Asp Gly Val Leu Leu Asp Glu Ala Phe Leu Asp Thr Leu Ala
            65                  70                  75                 80

Leu Leu Tyr Asn Asn Pro Asp Gln Leu Arg Ala Leu Leu Thr Leu Leu
                           85                  90                 95

Ser Ser Asp Thr Ala Pro Arg Trp Met Thr Val Met Arg Gly Tyr Ser
                       100                 105                110

Glu Cys Gly Asp Gly Ser Pro Ala Val Tyr Thr Cys Val Asp Asp Leu
                   115                 120                125

Cys Arg Gly Tyr Asp Leu Thr Arg Leu Ser Tyr Gly Arg Ser Ile Phe
                   130                 135                140

Thr Glu His Val Leu Gly Phe Glu Leu Val Pro Pro Ser Leu Phe Asn
            145                 150                 155                160

Val Val Val Ala Ile Arg Asn Glu Ala Thr Arg Thr Asn Arg Ala Val
                           165                 170                175

Arg Leu Pro Val Ser Thr Ala Ala Pro Glu Gly Ile Thr Leu Phe
                       180                 185                190

Tyr Gly Leu Tyr Asn Ala Val Lys Glu Phe Cys Leu Arg His Gln Leu
                   195                 200                205

Asp Pro Pro Leu Leu Arg His Leu Asp Lys Tyr Tyr Ala Gly Leu Pro
                   210                 215                220

Pro Glu Leu Lys Gln Thr Arg Val Asn Leu Pro Ala His Ser Arg Tyr
            225                 230                 235                240

Gly Pro Gln Ala Val Asp Ala Arg
                       245

<210> SEQ ID NO 31
<211> LENGTH: 2229
<212> TYPE: DNA
<213> ORGANISM: Artificial Sequence
<220> FEATURE:
<223> OTHER INFORMATION: Encodes full length gH sequence SEQ ID NO: 1

<400> SEQUENCE: 31
atgcggccag gcctcccctc ctacctcatc atcctcgccg tctgtctctt cagccaccta    60
ctttcgtcac gatatggcgc agaagccgta tccgaaccgc tggacaaagc gtttcaccta   120
ctgctcaaca cctacgggag acccatccgc ttcctgcgtg aaaataccac ccagtgtacc   180
tacaacagca gcctccgtaa cagcacggtc gtcagggaaa acgccatcag tttcaacttt   240
ttccaaagct ataatcaata ctatgtattc catatgcctc gatgtctttt tgcgggtcct   300
ctggcggagc agtttctgaa ccaggtagat ctgaccgaaa ccctggaaag ataccaacag   360
agacttaaca cttacgcgct ggtatccaaa gacctggcca gctaccgatc ttttcgcag   420 cagctaaagg cacaagacag cctaggtgaa cagcccacca ctgtgccacc gcccattgac   480
ctgtcaatac ctcacgtttg atgccaccg caaaccactc acacggctg acagaatca   540 cataccacct caggactaca ccgaccacac tttaaccaga cctgtatcct ctttgatgga   600
cacgatctac tattcagcac cgtcacacct tgtttgcacc aaggctttta cctcatcgac   660
```

| | |
|---|---|
| gaactacgtt acgttaaaat aacactgacc gaggacttct tcgtagttac ggtgtccata | 720 |
| gacgacgaca cacccatgct gcttatcttc ggccatcttc cacgcgtact tttcaaagcg | 780 |
| ccctatcaac gcgacaactt tatactacga caaactgaaa aacacgagct cctggtgcta | 840 |
| gttaagaaag atcaactgaa ccgtcactct tatctcaaag acccggactt tcttgacgcc | 900 |
| gcacttgact tcaactacct agacctcagc gcactactac gtaacagctt tcaccgttac | 960 |
| gccgtggatg tactcaagag cggtcgatgt cagatgctgg accgccgcac ggtagaaatg | 1020 |
| gccttcgcct acgcattagc actgttcgca gcagcccgac aagaagaggc cggcgcccaa | 1080 |
| gtctccgtcc cacgggccct agaccgccag gccgcactct acaaatacaa gaatttatg | 1140 |
| atcacctgcc tctcacaaac accaccacgc accacgttgc tgctgtatcc cacggccgtg | 1200 |
| gacctggcca acgagcccct ttggacaccg aatcagatca ccgacatcac cagcctcgta | 1260 |
| cgcctggtct acatactctc taaacagaat cagcaacatc tcatccccca tgggcacta | 1320 |
| cgacagatcg ccgactttgc cctaaaacta cacaaaacgc acctggcctc ttttctttca | 1380 |
| gccttcgcac gccaagaact ctacctcatg ggcagcctcg tccactccat gctggtacat | 1440 |
| acgacggaga gacgcgaaat cttcatcgta gaaacgggcc tctgttcatt ggccgagcta | 1500 |
| tcacacttta cgcagttgtt agctcatcca caccacgaat acctcagcga cctgtacaca | 1560 |
| ccctgttcca gtagcgggcg acgcgatcac tcgctcgaac gcctcacgcg tctcttcccc | 1620 |
| gatgccaccg tccccgctac cgttcccgcc gccctctcca tcctatctac catgcaacca | 1680 |
| agcacgctgg aaaccttccc cgacctgttt tgcttgccgc tcggcgaatc cttctccgcg | 1740 |
| ctgaccgtct ccgaacacgt cagtatatc gtaacaaacc agtacctgat caaaggtatc | 1800 |
| tcctaccctg tctccaccac cgtcgtaggc cagagcctca tcatcaccca cggacagt | 1860 |
| caaactaaat gcgaactgac gcgcaacatg cataccacac acagcatcac agtggcgctc | 1920 |
| aacatttcgc tagaaaactg cgccttttgc caaagcgccc tgctagaata cgacgacacg | 1980 |
| caaggcgtca tcaacatcat gtacatgcac gactcggacg acgtcctttt cgccctggat | 2040 |
| ccctacaacg aagtggtggt ctcatctccg cgaactcact acctcatgct tttgaaaaac | 2100 |
| ggtacggtac tagaagtaac tgacgtcgtc gtggacgcca ccgacagtcg tctcctcatg | 2160 |
| atgtccgtct acgcgctatc ggccatcatc ggcatctatc tgctctaccg catgctcaag | 2220 |
| acatgctga | 2229 |

<210> SEQ ID NO 32
<211> LENGTH: 2145
<212> TYPE: DNA
<213> ORGANISM: Artificial Sequence
<220> FEATURE:
<223> OTHER INFORMATION: Encodes truncated gH sequence SEQ ID NO: 3, is
      codon optimized for mammal

<400> SEQUENCE: 32

| | |
|---|---|
| atgaggcctg gcctgccctc ctacctgatc atcctggccg tgtgcctgtt cagccacctg | 60 |
| ctgtccagca gatacggcgc cgaggccgtg agcgagcccc tggacaaggc tttccacctg | 120 |
| ctgctgaaca cctacggcag acccatccgg tttctgcggg agaacaccac ccagtgcacc | 180 |
| tacaacagca gcctgcggaa cagcaccgtc gtgagagaga cgccatcag cttcaacttt | 240 |
| ttccagagct acaaccagta ctacgtgttc cacatgccca gatgcctgtt tgccggccct | 300 |
| ctggccgagc agttcctgaa ccaggtggac ctgaccgaga cactggaaag ataccagcag | 360 |
| cggctgaata cctacgccct ggtgtccaag gacctggcca gctaccggtc ctttagccag | 420 |

```
cagctcaagg ctcaggatag cctcggcgag cagcctacca ccgtgccccc tcccatcgac    480
ctgagcatcc cccacgtgtg gatgcctccc cagaccaccc ctcacggctg gaccgagagc    540
cacaccacct ccggcctgca cagaccccac ttcaaccaga cctgcatcct gttcgacggc    600
cacgacctgc tgtttagcac cgtgaccccc tgcctgcacc agggcttcta cctgatcgac    660
gagctgagat acgtgaagat caccctgacc gaggatttct tcgtggtcac cgtgtccatc    720
gacgacgaca cccccatgct gctgatcttc ggccacctgc cagagtgctg gttcaaggcc    780
ccctaccagc gggacaactt catcctgcgg cagaccgaga agcacgagct gctggtgctg    840
gtcaagaagg accagctgaa ccggcactcc tacctgaagg accccgactt cctggacgcc    900
gccctggact tcaactacct ggacctgagc gccctgctga aaacagctt ccacagatac    960 gccgtggacg tgctgaagtc cggacggtgc cagatgctcg atcggcggac cgtggagatg   1020
gccttcgcct atgccctcgc cctgttcgcc gctgccagac aggaagaggc tggcgcccag   1080
gtgtcagtgc ccagagccct ggatagacag gccgccctgc tgcagatcca ggaattcatg   1140
atcacctgcc tgagccagac ccccctaga accaccctg tgctgtaccc cacagccgtg   1200
gatctggcca agagggccct gtggaccccc aaccagatca ccgacatcac aagcctcgtg   1260
cggctcgtgt acatcctgag caagcagaac cagcagcacc tgatccccca gtgggccctg   1320
agacagatcg ccgacttcgc cctgaagctg cacaagaccc atctggccag ctttctgagc   1380
gccttcgcca ggcaggaact gtacctgatg gcagcctgg tccacagcat gctggtgcat   1440
accaccgagc ggcgggagat cttcatcgtg gagacaggcc tgtgtagcct ggccgagctg   1500
tcccacttta cccagctgct ggcccacccct caccacgagt acctgagcga cctgtacacc   1560
ccctgcagca gcagcggcag acgggaccac agcctggaac ggctgaccag actgttcccc   1620
gatgccaccg tgcctgctac agtgcctgcc gccctgtcca tcctgtccac catgcagccc   1680
agcaccctgg aaaccttccc cgacctgttc tgcctgcccc tgggcgagag ctttagcgcc   1740
ctgaccgtgt ccgagcacgt gtcctacatc gtgaccaatc agtacctgat caagggcatc   1800
agctaccccg tgtccaccac agtcgtgggc cagagcctga tcatcaccca gaccgacagc   1860
cagaccaagt gcgagctgac ccggaacatg cacaccacac acagcatcac cgtggccctg   1920
aacatcagcc tggaaaactg cgctttctgt cagtctgccc tgctggaata cgacgatacc   1980
cagggcgtga tcaacatcat gtacatgcac gacagcgacg acgtgctgtt cgccctggac   2040
ccctacaacg aggtggtggt gtccagcccc cggacccact acctgatgct gctgaagaac   2100
ggcaccgtgc tggaagtgac cgacgtggtg gtggacgcca ccgac               2145
```

<210> SEQ ID NO 33
<211> LENGTH: 834
<212> TYPE: DNA
<213> ORGANISM: Artificial Sequence
<220> FEATURE:
<223> OTHER INFORMATION: Encodes full length gL sequence SEQ ID NO: 7

<400> SEQUENCE: 33

```
atgtgcagac ggcccgactg cggcttcagc ttctcccctg acccgtgat cctgctgtgg     60 tgctgcctgc tgctgcctat cgtgtcctct gccgccgtgt ccgtggcccc taccgctgct    120
gagaaggtgc ccgccgagtg ccctgagctg accagacgct gtctgctggg cgaggtgttc    180
gagggcgata agtacgagtc ctggctgcgg ccccggtga acgtgaccgg cagagatggc    240
cccctgtccc agctgatccg gtacagacct gtgacccccg aggccgccaa ctccgtgctg    300
ctggacgagg cctttctgga caccctggcc ctgctgtaca caaccccga ccagctgcgg    360
```

```
gccctgctga ccctgctgtc tagcgacacc gcccctcggt ggatgaccgt gatgcggggc      420
tactctgagt gcggcgacgg ctcccctgcc gtgtacacct gtgtggacga cctgtgccgg      480
ggctacgacc tgaccagact gtcctacggc cggtctatct tcacagagca cgtgctgggc      540
ttcgagctgg tgcccccctc cctgttcaat gtggtggtgg ctatccggaa cgaggccacc      600
cggaccaata gagccgtgcg gctgcctgtg tctaccgccg ctgctcctga gggaatcacc      660
ctgttctacg gcctgtacaa cgccgtgaaa gagttctgcc tgagacacca gctggacccc      720
cctctgctgc ggcacctgga caagtactac gccggcctgc ccccgagct gaagcagacc       780 agagtgaacc tgcccgccca cagcagatac ggcccccagg ctgtggacgc cagg            834

<210> SEQ ID NO 34
<211> LENGTH: 834
<212> TYPE: DNA
<213> ORGANISM: Artificial Sequence
<220> FEATURE:
<223> OTHER INFORMATION: Encodes full length LSG gL sequence SEQ ID NO:
      9

<400> SEQUENCE: 34
atgtgcagac ggcccgactg cggcttcagc ttctcccctg acccgtgat cctgctgtgg       60 tgctgcctgc tgctgcctat cgtgtcctct gccgccgtgt ccgtggcccc taccgctgct      120
gagaaggtgc ccgccgagtg ccctgagctg accagacgct gtctgctggg cgaggtgttc      180
gagggcgata agtacgagtc ctggctgcgg cccctggtga acgtgaccgg cagagatggc      240
cccctgtccc agctgatccg gtacagacct gtgaccccg aggccctgag cggcgtgctg       300
ctggacgagg cctttctgga caccctggcc ctgctgtaca acaaccccga ccagctgcgg     360
gccctgctga ccctgctgtc tagcgacacc gcccctcggt ggatgaccgt gatgcggggc      420
tactctgagt gcggcgacgg ctcccctgcc gtgtacacct gtgtggacga cctgtgccgg      480
ggctacgacc tgaccagact gtcctacggc cggtctatct tcacagagca cgtgctgggc      540
ttcgagctgg tgcccccctc cctgttcaat gtggtggtgg ctatccggaa cgaggccacc      600
cggaccaata gagccgtgcg gctgcctgtg tctaccgccg ctgctcctga gggaatcacc      660
ctgttctacg gcctgtacaa cgccgtgaaa gagttctgcc tgagacacca gctggacccc      720
cctctgctgc ggcacctgga caagtactac gccggcctgc ccccgagct gaagcagacc       780 agagtgaacc tgcccgccca cagcagatac ggcccccagg ctgtggacgc cagg            834

<210> SEQ ID NO 35
<211> LENGTH: 834
<212> TYPE: DNA
<213> ORGANISM: Artificial Sequence
<220> FEATURE:
<223> OTHER INFORMATION: Encodes full length IDG gL sequence SEQ ID NO:
      29

<400> SEQUENCE: 35
atgtgcagac ggcccgactg cggcttcagc ttctcccctg acccgtgat cctgctgtgg       60 tgctgcctgc tgctgcctat cgtgtcctct gccgccgtgt ccgtggcccc taccgctgct      120
gagaaggtgc ccgccgagtg ccctgagctg accagacgct gtctgctggg cgaggtgttc      180
gagggcgata agtacgagtc ctggctgcgg cccctggtga acgtgaccgg cagagatggc      240
cccctgtccc agctgatccg gtacagacct gtgaccccg aggccatcga tggcgtgctg       300
ctggacgagg cctttctgga caccctggcc ctgctgtaca acaaccccga ccagctgcgg     360
```

```
gccctgctga cccctgctgtc tagcgacacc gccctcggt ggatgaccgt gatgcgggc     420 tactctgagt gcggcgacgg ctcccctgcc gtgtacacct gtgtggacga cctgtgccgg     480
ggctacgacc tgaccagact gtcctacggc cggtctatct tcacagagca cgtgctgggc    540
ttcgagctgg tgccccctc cctgttcaat gtggtggtgg ctatccggaa cgaggccacc     600
cggaccaata gagccgtgcg gctgcctgtg tctaccgccg ctgctcctga gggaatcacc    660
ctgttctacg gcctgtacaa cgccgtgaaa gagttctgcc tgagacacca gctggacccc    720
cctctgctgc ggcacctgga caagtactac gccggcctgc ccccgagct gaagcagacc    780 agagtgaacc tgcccgccca cagcagatac ggcccccagg ctgtggacgc cagg          834
```

<210> SEQ ID NO 36
<211> LENGTH: 513
<212> TYPE: DNA
<213> ORGANISM: Artificial Sequence
<220> FEATURE:
<223> OTHER INFORMATION: Encodes full length pUL128 sequence SEQ ID NO: 13

<400> SEQUENCE: 36

```
atgtccccca aggacctgac ccccttcctg accaccctgt ggctgctgct gggccactct    60
agggtgccca gagtgcgggc cgaagagtgc tgcgagttta tcaacgtgaa ccaccccccc    120
gagcggtgct acgacttcaa gatgtgcaac cggttcaccg tggccctgcg gtgccctgac    180
ggcgaagtgt gctactcccc cgaaaagacc gccgagatcc ggggaatcgt gaccacaatg    240
acccactccc tgaccagaca ggtggtgcac aacaagctga ccagctgcaa ctacaacccc    300
ctgtacctgg aagccgacgg ccggatccgc tgcggcaaag tgaacgacaa ggcccagtac    360
ctgctgggcg ctgccggctc tgtgccctac cggtggatca acctggaata cgacaagatc    420 accoggatcg tgggcctgga ccagtacctg gaatccgtga agaagcacaa gcggctggac    480
gtgtgccggg ccaagatggg ctatatgctg cag                                  513
```

<210> SEQ ID NO 37
<211> LENGTH: 642
<212> TYPE: DNA
<213> ORGANISM: Artificial Sequence
<220> FEATURE:
<223> OTHER INFORMATION: Encodes full length pUL130 sequence SEQ ID NO: 17

<400> SEQUENCE: 37

```
atgctgcggc tgctgctgcg gcaccacttc cactgcctgc tgctgtgtgc cgtgtgggcc    60 acccccttgtc tggcctcccc gtggtccacc ctgaccgcca accagaaccc cagccccccc    120
tggtccaagc tgacctactc caagcctcac gacgccgcta ccttctactg ccccttcctg    180
taccctcccc caccccggtc cccactgcag ttctccggct tccagagagt gtccaccggc    240
cctgagtgcc ggaacgagac actgtacctg ctgtacaacc gcgagggcca gaccctggtg    300
gaacggtcct ccacctgggt gaaaaaagtg atctggtatc tgtccggccg gaaccagaca    360
atcctgcagc ggatgcctcg gaccgcctcc aagccttccg acggcaacgt gcagatctcc    420
gtggaagatg ccaagatctt cggcgcccac atggtgccca gcagaccaa gctgctgaga    480 ttcgtggtga acgacggcac ccgctaccag atgtgcgtga tgaagctgga atcctgggcc    540
cacgtgttcc gggactactc agtgagcttc aagtccgac tgaccttcac cgaggccaac    600
aaccagacct acaccttctg cacccacccc aacctgatcg tg                        642
```

```
<210> SEQ ID NO 38
<211> LENGTH: 387
<212> TYPE: DNA
<213> ORGANISM: Artificial Sequence
<220> FEATURE:
<223> OTHER INFORMATION: Encodes full length pUL131A sequence SEQ ID NO:
      21

<400> SEQUENCE: 38
atgcggctgt gcagagtgtg gctgtccgtg tgcctgtgcg ccgtggtgct gggccagtgc      60
cagagagaga cagccgagaa gaacgactac taccgggtgc cccactactg ggacgcctgc     120
tccagagccc tgcccgacca gacccggtac aaatacgtgg aacagctggt ggacctgacc     180
ctgaactacc actacgacgc ctcccacggc ctggacaact cgacgtgct gaagcggatc      240 aacgtgaccg aggtgtccct gctgatctcc gacttccggc ggcagaacag aagaggcggc     300
accaacaagc ggaccacctt caacgccgct ggctccctgg cccctcacgc ccggtccctg     360
gaattctctg tgcggctgtt cgccaac                                         387

<210> SEQ ID NO 39
<211> LENGTH: 1395
<212> TYPE: DNA
<213> ORGANISM: Artificial Sequence
<220> FEATURE:
<223> OTHER INFORMATION: Encoding full length gO sequence SEQ ID NO: 25

<400> SEQUENCE: 39
atggggaaaa aagagatgat aatggtgaaa ggcattccta aaattatgct cctgatctct      60
ataacgttct tgctcctttc cctcataaat tgtaatgtat tggtaaactc agaggaaca      120 agacgttcct ggccgtatac cgtgctatct tatcgaggta aagagattct gaagaaacag     180
aaggaagata tcttaaaacg attgatgtct acatcatctg acggataccg gttttttaatg   240 tacccccagtc agcaaaaatt tcatgccatc gttattagca tggataaatt tcctcaagac    300
tacattttag cgggtcccat tagaaatgat agcattaccc atatgtggtt tgactttac    360 agtactcaac tccgaaaacc agccaagtac gtatattccg aatataatca cacggcccac    420
aaaataacgt tacgaccccc accttgcggc acagtgcctt ctatgaactg cctatccgaa   480
atgttaaatg tttccaaacg caatgatacc ggcgaaaaag gttgcggtaa tttcaccacg    540
tttaatccta tgttttttcaa cgtaccacgt tggaacacaa aactgtacat aggttccaac   600
aaagtcaacg tggatagtca gacaatctac ttttttgggcc taaccgccct acttttacga    660
tacgcgcaac gtaactgcac tcgcagtttc tacctggtta acgccatgag ccgaaattta    720
ttccgcgttc ccaagtatat taacggcacc aagttgaaaa acactatgcg aaaactcaaa    780
cgtaaacaag cgcttgtcaa agaacaacca caaaaaaaga ataagaaatc tcaaagtact    840
actacgccat atctttccta taacgtctct accgctttca acgtcaccac taacgtgact    900
tatagtgcta ccgctgctgt aacgcgggtt gccacatcta cgacaggtta tcgtcctgat    960 agtaaccttta tgaaatccat tatggccacg cagttaagag atctcgcaac atgggtatat    1020
actactctgc ggtatcggaa tgaacccttt tgtaaaccag accgtaaccg taccgccgtg    1080
tcagaattta tgaaaacac gcacgtactg attcgtaacg aaacgccgta cactatttat    1140
ggcactcttg acatgagctc cttatattac aacgaaacca tgtccgtgga aaacgaaacg    1200
gcttccgata taacgaaac tacacctacg tcaccatcga cgaggtttca gagaacgttc    1260
atagatcccc tatgggacta tctagactcg ctgctgtttc tagataaaat ccgtaacttt    1320
agcctccagt tacccgcgta tggaaatctt accccgccgg aacaccgccg ggctgcaaat    1380
```
ctatccaccc tcaat                                                          1395

<210> SEQ ID NO 40
<211> LENGTH: 715
<212> TYPE: PRT
<213> ORGANISM: Artificial Sequence
<220> FEATURE:
<223> OTHER INFORMATION: gH G358R mutant

<400> SEQUENCE: 40

Met Arg Pro Gly Leu Pro Ser Tyr Leu Ile Ile Leu Ala Val Cys Leu
1               5                   10                  15

Phe Ser His Leu Leu Ser Ser Arg Tyr Gly Ala Glu Ala Val Ser Glu
            20                  25                  30

Pro Leu Asp Lys Ala Phe His Leu Leu Leu Asn Thr Tyr Gly Arg Pro
        35                  40                  45

Ile Arg Phe Leu Arg Glu Asn Thr Thr Gln Cys Thr Tyr Asn Ser Ser
    50                  55                  60

Leu Arg Asn Ser Thr Val Val Arg Glu Asn Ala Ile Ser Phe Asn Phe
65                  70                  75                  80

Phe Gln Ser Tyr Asn Gln Tyr Tyr Val Phe His Met Pro Arg Cys Leu
                85                  90                  95

Phe Ala Gly Pro Leu Ala Glu Gln Phe Leu Asn Gln Val Asp Leu Thr
            100                 105                 110

Glu Thr Leu Glu Arg Tyr Gln Gln Arg Leu Asn Thr Tyr Ala Leu Val
        115                 120                 125

Ser Lys Asp Leu Ala Ser Tyr Arg Ser Phe Ser Gln Gln Leu Lys Ala
    130                 135                 140

Gln Asp Ser Leu Gly Glu Gln Pro Thr Thr Val Pro Pro Pro Ile Asp
145                 150                 155                 160

Leu Ser Ile Pro His Val Trp Met Pro Pro Gln Thr Thr Pro His Gly
                165                 170                 175

Trp Thr Glu Ser His Thr Thr Ser Gly Leu His Arg Pro His Phe Asn
            180                 185                 190

Gln Thr Cys Ile Leu Phe Asp Gly His Asp Leu Leu Phe Ser Thr Val
        195                 200                 205

Thr Pro Cys Leu His Gln Gly Phe Tyr Leu Ile Asp Glu Leu Arg Tyr
    210                 215                 220

Val Lys Ile Thr Leu Thr Glu Asp Phe Phe Val Val Thr Val Ser Ile
225                 230                 235                 240

Asp Asp Asp Thr Pro Met Leu Leu Ile Phe Gly His Leu Pro Arg Val
                245                 250                 255

Leu Phe Lys Ala Pro Tyr Gln Arg Asp Asn Phe Ile Leu Arg Gln Thr
            260                 265                 270

Glu Lys His Glu Leu Leu Val Leu Val Lys Lys Asp Gln Leu Asn Arg
        275                 280                 285

His Ser Tyr Leu Lys Asp Pro Asp Phe Leu Asp Ala Ala Leu Asp Phe
    290                 295                 300

Asn Tyr Leu Asp Leu Ser Ala Leu Leu Arg Asn Ser Phe His Arg Tyr
305                 310                 315                 320

Ala Val Asp Val Leu Lys Ser Gly Arg Cys Gln Met Leu Asp Arg Arg
                325                 330                 335

Thr Val Glu Met Ala Phe Ala Tyr Ala Leu Ala Leu Phe Ala Ala Ala
            340                 345                 350

Arg Gln Glu Glu Ala Arg Ala Gln Val Ser Val Pro Arg Ala Leu Asp
355                 360                 365

Arg Gln Ala Ala Leu Leu Gln Ile Gln Glu Phe Met Ile Thr Cys Leu
370                 375                 380

Ser Gln Thr Pro Pro Arg Thr Thr Leu Leu Leu Tyr Pro Thr Ala Val
385                 390                 395                 400

Asp Leu Ala Lys Arg Ala Leu Trp Thr Pro Asn Gln Ile Thr Asp Ile
                405                 410                 415

Thr Ser Leu Val Arg Leu Val Tyr Ile Leu Ser Lys Gln Asn Gln Gln
                420                 425                 430

His Leu Ile Pro Gln Trp Ala Leu Arg Gln Ile Ala Asp Phe Ala Leu
                435                 440                 445

Lys Leu His Lys Thr His Leu Ala Ser Phe Leu Ser Ala Phe Ala Arg
450                 455                 460

Gln Glu Leu Tyr Leu Met Gly Ser Leu Val His Ser Met Leu Val His
465                 470                 475                 480

Thr Thr Glu Arg Arg Glu Ile Phe Ile Val Glu Thr Gly Leu Cys Ser
                485                 490                 495

Leu Ala Glu Leu Ser His Phe Thr Gln Leu Leu Ala His Pro His His
                500                 505                 510

Glu Tyr Leu Ser Asp Leu Tyr Thr Pro Cys Ser Ser Gly Arg Arg
                515                 520                 525

Asp His Ser Leu Glu Arg Leu Thr Arg Leu Phe Pro Asp Ala Thr Val
                530                 535                 540

Pro Ala Thr Val Pro Ala Ala Leu Ser Ile Leu Ser Thr Met Gln Pro
545                 550                 555                 560

Ser Thr Leu Glu Thr Phe Pro Asp Leu Phe Cys Leu Pro Leu Gly Glu
                565                 570                 575

Ser Phe Ser Ala Leu Thr Val Ser Glu His Val Ser Tyr Ile Val Thr
                580                 585                 590

Asn Gln Tyr Leu Ile Lys Gly Ile Ser Tyr Pro Val Ser Thr Thr Val
                595                 600                 605

Val Gly Gln Ser Leu Ile Ile Thr Gln Thr Asp Ser Gln Thr Lys Cys
610                 615                 620

Glu Leu Thr Arg Asn Met His Thr Thr His Ser Ile Thr Val Ala Leu
625                 630                 635                 640

Asn Ile Ser Leu Glu Asn Cys Ala Phe Cys Gln Ser Ala Leu Leu Glu
                645                 650                 655

Tyr Asp Asp Thr Gln Gly Val Ile Asn Ile Met Tyr Met His Asp Ser
                660                 665                 670

Asp Asp Val Leu Phe Ala Leu Asp Pro Tyr Asn Glu Val Val Val Ser
                675                 680                 685

Ser Pro Arg Thr His Tyr Leu Met Leu Leu Lys Asn Gly Thr Val Leu
690                 695                 700

Glu Val Thr Asp Val Val Asp Ala Thr Asp
705                 710                 715

<210> SEQ ID NO 41
<211> LENGTH: 692
<212> TYPE: PRT
<213> ORGANISM: Artificial Sequence
<220> FEATURE:
<223> OTHER INFORMATION: mature gH G358R mutant

<400> SEQUENCE: 41

```
Arg Tyr Gly Ala Glu Ala Val Ser Glu Pro Leu Asp Lys Ala Phe His
 1               5                  10                  15

Leu Leu Leu Asn Thr Tyr Gly Arg Pro Ile Arg Phe Leu Arg Glu Asn
             20                  25                  30

Thr Thr Gln Cys Thr Tyr Asn Ser Ser Leu Arg Asn Ser Thr Val Val
         35                  40                  45

Arg Glu Asn Ala Ile Ser Phe Asn Phe Phe Gln Ser Tyr Asn Gln Tyr
     50                  55                  60

Tyr Val Phe His Met Pro Arg Cys Leu Phe Ala Gly Pro Leu Ala Glu
 65                  70                  75                  80

Gln Phe Leu Asn Gln Val Asp Leu Thr Glu Thr Leu Glu Arg Tyr Gln
                 85                  90                  95

Gln Arg Leu Asn Thr Tyr Ala Leu Val Ser Lys Asp Leu Ala Ser Tyr
                100                 105                 110

Arg Ser Phe Ser Gln Gln Leu Lys Ala Gln Asp Ser Leu Gly Glu Gln
            115                 120                 125

Pro Thr Thr Val Pro Pro Ile Asp Leu Ser Ile Pro His Val Trp
        130                 135                 140

Met Pro Pro Gln Thr Thr Pro His Gly Trp Thr Glu Ser His Thr Thr
145                 150                 155                 160

Ser Gly Leu His Arg Pro His Phe Asn Gln Thr Cys Ile Leu Phe Asp
                165                 170                 175

Gly His Asp Leu Leu Phe Ser Thr Val Thr Pro Cys Leu His Gln Gly
            180                 185                 190

Phe Tyr Leu Ile Asp Glu Leu Arg Tyr Val Lys Ile Thr Leu Thr Glu
        195                 200                 205

Asp Phe Phe Val Val Thr Val Ser Ile Asp Asp Thr Pro Met Leu
210                 215                 220

Leu Ile Phe Gly His Leu Pro Arg Val Leu Phe Lys Ala Pro Tyr Gln
225                 230                 235                 240

Arg Asp Asn Phe Ile Leu Arg Gln Thr Glu Lys His Glu Leu Leu Val
                245                 250                 255

Leu Val Lys Lys Asp Gln Leu Asn Arg His Ser Tyr Leu Lys Asp Pro
            260                 265                 270

Asp Phe Leu Asp Ala Ala Leu Asp Phe Asn Tyr Leu Asp Leu Ser Ala
        275                 280                 285

Leu Leu Arg Asn Ser Phe His Arg Tyr Ala Val Asp Val Leu Lys Ser
            290                 295                 300

Gly Arg Cys Gln Met Leu Asp Arg Arg Thr Val Glu Met Ala Phe Ala
305                 310                 315                 320

Tyr Ala Leu Ala Leu Phe Ala Ala Ala Arg Gln Glu Glu Ala Arg Ala
                325                 330                 335

Gln Val Ser Val Pro Arg Ala Leu Asp Arg Gln Ala Ala Leu Leu Gln
            340                 345                 350

Ile Gln Glu Phe Met Ile Thr Cys Leu Ser Gln Thr Pro Pro Arg Thr
        355                 360                 365

Thr Leu Leu Leu Tyr Pro Thr Ala Val Asp Leu Ala Lys Arg Ala Leu
    370                 375                 380

Trp Thr Pro Asn Gln Ile Thr Asp Ile Thr Ser Leu Val Arg Leu Val
385                 390                 395                 400

Tyr Ile Leu Ser Lys Gln Asn Gln Gln His Leu Ile Pro Gln Trp Ala
                405                 410                 415

Leu Arg Gln Ile Ala Asp Phe Ala Leu Lys Leu His Lys Thr His Leu
```

|   |   | 420 |   |   |   | 425 |   |   |   | 430 |   |   |
|---|---|---|---|---|---|---|---|---|---|---|---|---|

Ala Ser Phe Leu Ser Ala Phe Ala Arg Gln Glu Leu Tyr Leu Met Gly
                435                     440                     445

Ser Leu Val His Ser Met Leu Val His Thr Thr Glu Arg Arg Glu Ile
   450                           455                     460

Phe Ile Val Glu Thr Gly Leu Cys Ser Leu Ala Glu Leu Ser His Phe
465                       470                     475                     480

Thr Gln Leu Leu Ala His Pro His His Glu Tyr Leu Ser Asp Leu Tyr
                485                     490                     495

Thr Pro Cys Ser Ser Ser Gly Arg Arg Asp His Ser Leu Glu Arg Leu
   500                           505                     510

Thr Arg Leu Phe Pro Asp Ala Thr Val Pro Ala Thr Val Pro Ala Ala
                515                     520                     525

Leu Ser Ile Leu Ser Thr Met Gln Pro Ser Thr Leu Glu Thr Phe Pro
   530                           535                     540

Asp Leu Phe Cys Leu Pro Leu Gly Glu Ser Phe Ser Ala Leu Thr Val
545                       550                     555                     560

Ser Glu His Val Ser Tyr Ile Val Thr Asn Gln Tyr Leu Ile Lys Gly
                565                     570                     575

Ile Ser Tyr Pro Val Ser Thr Thr Val Val Gly Gln Ser Leu Ile Ile
            580                     585                     590

Thr Gln Thr Asp Ser Gln Thr Lys Cys Glu Leu Thr Arg Asn Met His
       595                        600                     605

Thr Thr His Ser Ile Thr Val Ala Leu Asn Ile Ser Leu Glu Asn Cys
   610                           615                     620

Ala Phe Cys Gln Ser Ala Leu Leu Glu Tyr Asp Asp Thr Gln Gly Val
625                       630                     635                     640

Ile Asn Ile Met Tyr Met His Asp Ser Asp Asp Val Leu Phe Ala Leu
                645                     650                     655

Asp Pro Tyr Asn Glu Val Val Val Ser Ser Pro Arg Thr His Tyr Leu
            660                     665                     670

Met Leu Leu Lys Asn Gly Thr Val Leu Glu Val Thr Asp Val Val Val
       675                        680                     685

Asp Ala Thr Asp
   690

<210> SEQ ID NO 42
<211> LENGTH: 278
<212> TYPE: PRT
<213> ORGANISM: Artificial Sequence
<220> FEATURE:
<223> OTHER INFORMATION: gL N74Q mutant

<400> SEQUENCE: 42

Met Cys Arg Arg Pro Asp Cys Gly Phe Ser Phe Ser Pro Gly Pro Val
1                  5                     10                     15

Ile Leu Leu Trp Cys Cys Leu Leu Leu Pro Ile Val Ser Ser Ala Ala
                20                     25                     30

Val Ser Val Ala Pro Thr Ala Ala Glu Lys Val Pro Ala Glu Cys Pro
             35                     40                     45

Glu Leu Thr Arg Arg Cys Leu Leu Gly Glu Val Phe Glu Gly Asp Lys
       50                        55                     60

Tyr Glu Ser Trp Leu Arg Pro Leu Val Gln Val Thr Gly Arg Asp Gly
65                       70                     75                     80

Pro Leu Ser Gln Leu Ile Arg Tyr Arg Pro Val Thr Pro Glu Ala Leu

```
              85                  90                  95
Ser Gly Val Leu Leu Asp Glu Ala Phe Leu Asp Thr Leu Ala Leu Leu
            100                 105                 110
Tyr Asn Asn Pro Asp Gln Leu Arg Ala Leu Leu Thr Leu Leu Ser Ser
            115                 120                 125
Asp Thr Ala Pro Arg Trp Met Thr Val Met Arg Gly Tyr Ser Glu Cys
            130                 135                 140
Gly Asp Gly Ser Pro Ala Val Tyr Thr Cys Val Asp Asp Leu Cys Arg
145                 150                 155                 160
Gly Tyr Asp Leu Thr Arg Leu Ser Tyr Gly Arg Ser Ile Phe Thr Glu
            165                 170                 175
His Val Leu Gly Phe Glu Leu Val Pro Pro Ser Leu Phe Asn Val Val
            180                 185                 190
Val Ala Ile Arg Asn Glu Ala Thr Arg Thr Asn Arg Ala Val Arg Leu
            195                 200                 205
Pro Val Ser Thr Ala Ala Pro Glu Gly Ile Thr Leu Phe Tyr Gly
            210                 215                 220
Leu Tyr Asn Ala Val Lys Glu Phe Cys Leu Arg His Gln Leu Asp Pro
225                 230                 235                 240
Pro Leu Leu Arg His Leu Asp Lys Tyr Tyr Ala Gly Leu Pro Pro Glu
            245                 250                 255
Leu Lys Gln Thr Arg Val Asn Leu Pro Ala His Ser Arg Tyr Gly Pro
            260                 265                 270
Gln Ala Val Asp Ala Arg
            275

<210> SEQ ID NO 43
<211> LENGTH: 248
<212> TYPE: PRT
<213> ORGANISM: Artificial Sequence
<220> FEATURE:
<223> OTHER INFORMATION: mature gL N74Q mutant

<400> SEQUENCE: 43

Ala Ala Val Ser Val Ala Pro Thr Ala Ala Glu Lys Val Pro Ala Glu
1               5                   10                  15
Cys Pro Glu Leu Thr Arg Arg Cys Leu Leu Gly Glu Val Phe Glu Gly
            20                  25                  30
Asp Lys Tyr Glu Ser Trp Leu Arg Pro Leu Val Gln Val Thr Gly Arg
            35                  40                  45
Asp Gly Pro Leu Ser Gln Leu Ile Arg Tyr Arg Pro Val Thr Pro Glu
        50                  55                  60
Ala Leu Ser Gly Val Leu Leu Asp Glu Ala Phe Leu Asp Thr Leu Ala
65                  70                  75                  80
Leu Leu Tyr Asn Asn Pro Asp Gln Leu Arg Ala Leu Leu Thr Leu Leu
                85                  90                  95
Ser Ser Asp Thr Ala Pro Arg Trp Met Thr Val Met Arg Gly Tyr Ser
            100                 105                 110
Glu Cys Gly Asp Gly Ser Pro Ala Val Tyr Thr Cys Val Asp Asp Leu
            115                 120                 125
Cys Arg Gly Tyr Asp Leu Thr Arg Leu Ser Tyr Gly Arg Ser Ile Phe
            130                 135                 140
Thr Glu His Val Leu Gly Phe Glu Leu Val Pro Pro Ser Leu Phe Asn
145                 150                 155                 160
Val Val Val Ala Ile Arg Asn Glu Ala Thr Arg Thr Asn Arg Ala Val
```

```
                165                 170                 175
Arg Leu Pro Val Ser Thr Ala Ala Pro Glu Gly Ile Thr Leu Phe
            180                 185                 190

Tyr Gly Leu Tyr Asn Ala Val Lys Glu Phe Cys Leu Arg His Gln Leu
            195                 200                 205

Asp Pro Pro Leu Leu Arg His Leu Asp Lys Tyr Tyr Ala Gly Leu Pro
210                 215                 220

Pro Glu Leu Lys Gln Thr Arg Val Asn Leu Pro Ala His Ser Arg Tyr
225                 230                 235                 240

Gly Pro Gln Ala Val Asp Ala Arg
                245

<210> SEQ ID NO 44
<211> LENGTH: 278
<212> TYPE: PRT
<213> ORGANISM: Artificial Sequence
<220> FEATURE:
<223> OTHER INFORMATION: gL G140F mutant

<400> SEQUENCE: 44

Met Cys Arg Arg Pro Asp Cys Gly Phe Ser Phe Ser Pro Gly Pro Val
1               5                   10                  15

Ile Leu Leu Trp Cys Cys Leu Leu Pro Ile Val Ser Ser Ala Ala
            20                  25                  30

Val Ser Val Ala Pro Thr Ala Ala Glu Lys Val Pro Ala Glu Cys Pro
            35                  40                  45

Glu Leu Thr Arg Arg Cys Leu Leu Gly Glu Val Phe Glu Gly Asp Lys
50                  55                  60

Tyr Glu Ser Trp Leu Arg Pro Leu Val Asn Val Thr Gly Arg Asp Gly
65                  70                  75                  80

Pro Leu Ser Gln Leu Ile Arg Tyr Arg Pro Val Thr Pro Glu Ala Leu
            85                  90                  95

Ser Gly Val Leu Leu Asp Glu Ala Phe Leu Asp Thr Leu Ala Leu Leu
            100                 105                 110

Tyr Asn Asn Pro Asp Gln Leu Arg Ala Leu Leu Thr Leu Leu Ser Ser
            115                 120                 125

Asp Thr Ala Pro Arg Trp Met Thr Val Met Arg Phe Tyr Ser Glu Cys
130                 135                 140

Gly Asp Gly Ser Pro Ala Val Tyr Thr Cys Val Asp Asp Leu Cys Arg
145                 150                 155                 160

Gly Tyr Asp Leu Thr Arg Leu Ser Tyr Gly Arg Ser Ile Phe Thr Glu
            165                 170                 175

His Val Leu Gly Phe Glu Leu Val Pro Pro Ser Leu Phe Asn Val Val
            180                 185                 190

Val Ala Ile Arg Asn Glu Ala Thr Arg Thr Asn Arg Ala Val Arg Leu
            195                 200                 205

Pro Val Ser Thr Ala Ala Pro Glu Gly Ile Thr Leu Phe Tyr Gly
210                 215                 220

Leu Tyr Asn Ala Val Lys Glu Phe Cys Leu Arg His Gln Leu Asp Pro
225                 230                 235                 240

Pro Leu Leu Arg His Leu Asp Lys Tyr Tyr Ala Gly Leu Pro Pro Glu
            245                 250                 255

Leu Lys Gln Thr Arg Val Asn Leu Pro Ala His Ser Arg Tyr Gly Pro
            260                 265                 270

Gln Ala Val Asp Ala Arg
```

-continued

```
                            275

<210> SEQ ID NO 45
<211> LENGTH: 248
<212> TYPE: PRT
<213> ORGANISM: Artificial Sequence
<220> FEATURE:
<223> OTHER INFORMATION: mature gL G140F mutant

<400> SEQUENCE: 45

Ala Ala Val Ser Val Ala Pro Thr Ala Ala Glu Lys Val Pro Ala Glu
1               5                   10                  15

Cys Pro Glu Leu Thr Arg Arg Cys Leu Leu Gly Glu Val Phe Glu Gly
            20                  25                  30

Asp Lys Tyr Glu Ser Trp Leu Arg Pro Leu Val Asn Val Thr Gly Arg
        35                  40                  45

Asp Gly Pro Leu Ser Gln Leu Ile Arg Tyr Arg Pro Val Thr Pro Glu
    50                  55                  60

Ala Leu Ser Gly Val Leu Leu Asp Glu Ala Phe Leu Asp Thr Leu Ala
65                  70                  75                  80

Leu Leu Tyr Asn Asn Pro Asp Gln Leu Arg Ala Leu Leu Thr Leu Leu
                85                  90                  95

Ser Ser Asp Thr Ala Pro Arg Trp Met Thr Val Met Arg Phe Tyr Ser
            100                 105                 110

Glu Cys Gly Asp Gly Ser Pro Ala Val Tyr Thr Cys Val Asp Asp Leu
        115                 120                 125

Cys Arg Gly Tyr Asp Leu Thr Arg Leu Ser Tyr Gly Arg Ser Ile Phe
    130                 135                 140

Thr Glu His Val Leu Gly Phe Glu Leu Val Pro Pro Ser Leu Phe Asn
145                 150                 155                 160

Val Val Val Ala Ile Arg Asn Glu Ala Thr Arg Thr Asn Arg Ala Val
                165                 170                 175

Arg Leu Pro Val Ser Thr Ala Ala Pro Glu Gly Ile Thr Leu Phe
            180                 185                 190

Tyr Gly Leu Tyr Asn Ala Val Lys Glu Phe Cys Leu Arg His Gln Leu
        195                 200                 205

Asp Pro Pro Leu Leu Arg His Leu Asp Lys Tyr Tyr Ala Gly Leu Pro
    210                 215                 220

Pro Glu Leu Lys Gln Thr Arg Val Asn Leu Pro Ala His Ser Arg Tyr
225                 230                 235                 240

Gly Pro Gln Ala Val Asp Ala Arg
                245

<210> SEQ ID NO 46
<211> LENGTH: 278
<212> TYPE: PRT
<213> ORGANISM: Artificial Sequence
<220> FEATURE:
<223> OTHER INFORMATION: gL G145L mutant

<400> SEQUENCE: 46

Met Cys Arg Arg Pro Asp Cys Gly Phe Ser Phe Ser Pro Gly Pro Val
1               5                   10                  15

Ile Leu Leu Trp Cys Cys Leu Leu Leu Pro Ile Val Ser Ser Ala Ala
            20                  25                  30

Val Ser Val Ala Pro Thr Ala Ala Glu Lys Val Pro Ala Glu Cys Pro
        35                  40                  45
```

```
Glu Leu Thr Arg Arg Cys Leu Leu Gly Glu Val Phe Glu Gly Asp Lys
 50                  55                  60

Tyr Glu Ser Trp Leu Arg Pro Leu Val Asn Val Thr Gly Arg Asp Gly
 65                  70                  75                  80

Pro Leu Ser Gln Leu Ile Arg Tyr Arg Pro Val Thr Pro Glu Ala Leu
                 85                  90                  95

Ser Gly Val Leu Leu Asp Glu Ala Phe Leu Asp Thr Leu Ala Leu Leu
            100                 105                 110

Tyr Asn Asn Pro Asp Gln Leu Arg Ala Leu Leu Thr Leu Leu Ser Ser
        115                 120                 125

Asp Thr Ala Pro Arg Trp Met Thr Val Met Arg Gly Tyr Ser Glu Cys
130                 135                 140

Leu Asp Gly Ser Pro Ala Val Tyr Thr Cys Val Asp Leu Cys Arg
145                 150                 155                 160

Gly Tyr Asp Leu Thr Arg Leu Ser Tyr Gly Arg Ser Ile Phe Thr Glu
                165                 170                 175

His Val Leu Gly Phe Glu Leu Val Pro Pro Ser Leu Phe Asn Val Val
            180                 185                 190

Val Ala Ile Arg Asn Glu Ala Thr Arg Thr Asn Arg Ala Val Arg Leu
        195                 200                 205

Pro Val Ser Thr Ala Ala Ala Pro Glu Gly Ile Thr Leu Phe Tyr Gly
210                 215                 220

Leu Tyr Asn Ala Val Lys Glu Phe Cys Leu Arg His Gln Leu Asp Pro
225                 230                 235                 240

Pro Leu Leu Arg His Leu Asp Lys Tyr Tyr Ala Gly Leu Pro Pro Glu
                245                 250                 255

Leu Lys Gln Thr Arg Val Asn Leu Pro Ala His Ser Arg Tyr Gly Pro
            260                 265                 270

Gln Ala Val Asp Ala Arg
        275

<210> SEQ ID NO 47
<211> LENGTH: 248
<212> TYPE: PRT
<213> ORGANISM: Artificial Sequence
<220> FEATURE:
<223> OTHER INFORMATION: mature gL G145L mutant

<400> SEQUENCE: 47

Ala Ala Val Ser Val Ala Pro Thr Ala Ala Glu Lys Val Pro Ala Glu
  1               5                  10                  15

Cys Pro Glu Leu Thr Arg Arg Cys Leu Leu Gly Glu Val Phe Glu Gly
                 20                  25                  30

Asp Lys Tyr Glu Ser Trp Leu Arg Pro Leu Val Asn Val Thr Gly Arg
             35                  40                  45

Asp Gly Pro Leu Ser Gln Leu Ile Arg Tyr Arg Pro Val Thr Pro Glu
 50                  55                  60

Ala Leu Ser Gly Val Leu Leu Asp Glu Ala Phe Leu Asp Thr Leu Ala
 65                  70                  75                  80

Leu Leu Tyr Asn Asn Pro Asp Gln Leu Arg Ala Leu Leu Thr Leu Leu
                 85                  90                  95

Ser Ser Asp Thr Ala Pro Arg Trp Met Thr Val Met Arg Gly Tyr Ser
            100                 105                 110

Glu Cys Leu Asp Gly Ser Pro Ala Val Tyr Thr Cys Val Asp Leu
        115                 120                 125
```

```
Cys Arg Gly Tyr Asp Leu Thr Arg Leu Ser Tyr Gly Arg Ser Ile Phe
130                 135                 140

Thr Glu His Val Leu Gly Phe Glu Leu Val Pro Pro Ser Leu Phe Asn
145                 150                 155                 160

Val Val Val Ala Ile Arg Asn Glu Ala Thr Arg Thr Asn Arg Ala Val
                165                 170                 175

Arg Leu Pro Val Ser Thr Ala Ala Pro Glu Gly Ile Thr Leu Phe
                180                 185                 190

Tyr Gly Leu Tyr Asn Ala Val Lys Glu Phe Cys Leu Arg His Gln Leu
                195                 200                 205

Asp Pro Pro Leu Leu Arg His Leu Asp Lys Tyr Ala Gly Leu Pro
210                 215                 220

Pro Glu Leu Lys Gln Thr Arg Val Asn Leu Pro Ala His Ser Arg Tyr
225                 230                 235                 240

Gly Pro Gln Ala Val Asp Ala Arg
                245
```

<210> SEQ ID NO 48
<211> LENGTH: 278
<212> TYPE: PRT
<213> ORGANISM: Artificial Sequence
<220> FEATURE:
<223> OTHER INFORMATION: gL A150C mutant

<400> SEQUENCE: 48

```
Met Cys Arg Arg Pro Asp Cys Gly Phe Ser Phe Ser Pro Gly Pro Val
1               5                   10                  15

Ile Leu Leu Trp Cys Cys Leu Leu Pro Ile Val Ser Ser Ala Ala
                20                  25                  30

Val Ser Val Ala Pro Thr Ala Ala Glu Lys Val Pro Ala Glu Cys Pro
                35                  40                  45

Glu Leu Thr Arg Arg Cys Leu Leu Gly Glu Val Phe Glu Gly Asp Lys
50                  55                  60

Tyr Glu Ser Trp Leu Arg Pro Leu Val Asn Val Thr Gly Arg Asp Gly
65                  70                  75                  80

Pro Leu Ser Gln Leu Ile Arg Tyr Arg Pro Val Thr Pro Glu Ala Leu
                85                  90                  95

Ser Gly Val Leu Leu Asp Glu Ala Phe Leu Asp Thr Leu Ala Leu Leu
                100                 105                 110

Tyr Asn Asn Pro Asp Gln Leu Arg Ala Leu Leu Thr Leu Leu Ser Ser
                115                 120                 125

Asp Thr Ala Pro Arg Trp Met Thr Val Met Arg Gly Tyr Ser Glu Cys
130                 135                 140

Gly Asp Gly Ser Pro Cys Val Tyr Thr Cys Val Asp Asp Leu Cys Arg
145                 150                 155                 160

Gly Tyr Asp Leu Thr Arg Leu Ser Tyr Gly Arg Ser Ile Phe Thr Glu
                165                 170                 175

His Val Leu Gly Phe Glu Leu Val Pro Pro Ser Leu Phe Asn Val Val
                180                 185                 190

Val Ala Ile Arg Asn Glu Ala Thr Arg Thr Asn Arg Ala Val Arg Leu
                195                 200                 205

Pro Val Ser Thr Ala Ala Pro Glu Gly Ile Thr Leu Phe Tyr Gly
                210                 215                 220

Leu Tyr Asn Ala Val Lys Glu Phe Cys Leu Arg His Gln Leu Asp Pro
225                 230                 235                 240
```

```
Pro Leu Leu Arg His Leu Asp Lys Tyr Tyr Ala Gly Leu Pro Pro Glu
                245                 250                 255

Leu Lys Gln Thr Arg Val Asn Leu Pro Ala His Ser Arg Tyr Gly Pro
            260                 265                 270

Gln Ala Val Asp Ala Arg
        275

<210> SEQ ID NO 49
<211> LENGTH: 248
<212> TYPE: PRT
<213> ORGANISM: Artificial Sequence
<220> FEATURE:
<223> OTHER INFORMATION: mature gL A150C mutant

<400> SEQUENCE: 49

Ala Ala Val Ser Val Ala Pro Thr Ala Ala Glu Lys Val Pro Ala Glu
1               5                   10                  15

Cys Pro Glu Leu Thr Arg Arg Cys Leu Leu Gly Glu Val Phe Glu Gly
            20                  25                  30

Asp Lys Tyr Glu Ser Trp Leu Arg Pro Leu Val Asn Val Thr Gly Arg
        35                  40                  45

Asp Gly Pro Leu Ser Gln Leu Ile Arg Tyr Arg Pro Val Thr Pro Glu
    50                  55                  60

Ala Leu Ser Gly Val Leu Leu Asp Glu Ala Phe Leu Asp Thr Leu Ala
65                  70                  75                  80

Leu Leu Tyr Asn Asn Pro Asp Gln Leu Arg Ala Leu Leu Thr Leu Leu
                85                  90                  95

Ser Ser Asp Thr Ala Pro Arg Trp Met Thr Val Met Arg Gly Tyr Ser
            100                 105                 110

Glu Cys Gly Asp Gly Ser Pro Cys Val Tyr Thr Cys Val Asp Asp Leu
        115                 120                 125

Cys Arg Gly Tyr Asp Leu Thr Arg Leu Ser Tyr Gly Arg Ser Ile Phe
130                 135                 140

Thr Glu His Val Leu Gly Phe Glu Leu Val Pro Pro Ser Leu Phe Asn
145                 150                 155                 160

Val Val Val Ala Ile Arg Asn Glu Ala Thr Arg Thr Asn Arg Ala Val
                165                 170                 175

Arg Leu Pro Val Ser Thr Ala Ala Pro Glu Gly Ile Thr Leu Phe
            180                 185                 190

Tyr Gly Leu Tyr Asn Ala Val Lys Glu Phe Cys Leu Arg His Gln Leu
        195                 200                 205

Asp Pro Pro Leu Leu Arg His Leu Asp Lys Tyr Tyr Ala Gly Leu Pro
    210                 215                 220

Pro Glu Leu Lys Gln Thr Arg Val Asn Leu Pro Ala His Ser Arg Tyr
225                 230                 235                 240

Gly Pro Gln Ala Val Asp Ala Arg
                245

<210> SEQ ID NO 50
<211> LENGTH: 278
<212> TYPE: PRT
<213> ORGANISM: Artificial Sequence
<220> FEATURE:
<223> OTHER INFORMATION: gL R160C mutant

<400> SEQU

Ile Leu Leu Trp Cys Cys Leu Leu Pro Ile Val Ser Ser Ala Ala
            20                  25                  30

Val Ser Val Ala Pro Thr Ala Ala Glu Lys Val Pro Ala Glu Cys Pro
        35                  40                  45

Glu Leu Thr Arg Arg Cys Leu Leu Gly Glu Val Phe Glu Gly Asp Lys
50                  55                  60

Tyr Glu Ser Trp Leu Arg Pro Leu Val Asn Val Thr Gly Arg Asp Gly
65                  70                  75                  80

Pro Leu Ser Gln Leu Ile Arg Tyr Arg Pro Val Thr Pro Glu Ala Leu
                85                  90                  95

Ser Gly Val Leu Leu Asp Glu Ala Phe Leu Asp Thr Leu Ala Leu Leu
            100                 105                 110

Tyr Asn Asn Pro Asp Gln Leu Arg Ala Leu Leu Thr Leu Leu Ser Ser
            115                 120                 125

Asp Thr Ala Pro Arg Trp Met Thr Val Met Arg Gly Tyr Ser Glu Cys
130                 135                 140

Gly Asp Gly Ser Pro Ala Val Tyr Thr Cys Val Asp Asp Leu Cys Cys
145                 150                 155                 160

Gly Tyr Asp Leu Thr Arg Leu Ser Tyr Gly Arg Ser Ile Phe Thr Glu
                165                 170                 175

His Val Leu Gly Phe Glu Leu Val Pro Pro Ser Leu Phe Asn Val Val
            180                 185                 190

Val Ala Ile Arg Asn Glu Ala Thr Arg Thr Asn Arg Ala Val Arg Leu
            195                 200                 205

Pro Val Ser Thr Ala Ala Ala Pro Glu Gly Ile Thr Leu Phe Tyr Gly
        210                 215                 220

Leu Tyr Asn Ala Val Lys Glu Phe Cys Leu Arg His Gln Leu Asp Pro
225                 230                 235                 240

Pro Leu Leu Arg His Leu Asp Lys Tyr Tyr Ala Gly Leu Pro Pro Glu
                245                 250                 255

Leu Lys Gln Thr Arg Val Asn Leu Pro Ala His Ser Arg Tyr Gly Pro
            260                 265                 270

Gln Ala Val Asp Ala Arg
            275

<210> SEQ ID NO 51
<211> LENGTH: 248
<212> TYPE: PRT
<213> ORGANISM: Artificial Sequence
<220> FEATURE:
<223> OTHER INFORMATION: mature gL R160C mutant

<400> SEQUENCE: 51

Ala Ala Val Ser Val Ala Pro Thr Ala Ala Glu Lys Val Pro Ala Glu
1               5                   10                  15

Cys Pro Glu Leu Thr Arg Arg Cys Leu Leu Gly Glu Val Phe Glu Gly
            20                  25                  30

Asp Lys Tyr Glu Ser Trp Leu Arg Pro Leu Val Asn Val Thr Gly Arg
        35                  40                  45

Asp Gly Pro Leu Ser Gln Leu Ile Arg Tyr Arg Pro Val Thr Pro Glu
50                  55                  60

Ala Leu Ser Gly Val Leu Leu Asp Glu Ala Phe Leu Asp Thr Leu Ala
65                  70                  75                  80

Leu Leu Tyr Asn Asn Pro Asp Gln Leu Arg Ala Leu Leu Thr Leu Leu
                85                  90                  95

```
Ser Ser Asp Thr Ala Pro Arg Trp Met Thr Val Met Arg Gly Tyr Ser
            100                 105                 110

Glu Cys Gly Asp Gly Ser Pro Ala Val Tyr Thr Cys Val Asp Asp Leu
            115                 120                 125

Cys Cys Gly Tyr Asp Leu Thr Arg Leu Ser Tyr Gly Arg Ser Ile Phe
130                 135                 140

Thr Glu His Val Leu Gly Phe Glu Leu Val Pro Pro Ser Leu Phe Asn
145                 150                 155                 160

Val Val Val Ala Ile Arg Asn Glu Ala Thr Arg Thr Asn Arg Ala Val
                165                 170                 175

Arg Leu Pro Val Ser Thr Ala Ala Pro Glu Gly Ile Thr Leu Phe
            180                 185                 190

Tyr Gly Leu Tyr Asn Ala Val Lys Glu Phe Cys Leu Arg His Gln Leu
            195                 200                 205

Asp Pro Pro Leu Leu Arg His Leu Asp Lys Tyr Tyr Ala Gly Leu Pro
            210                 215                 220

Pro Glu Leu Lys Gln Thr Arg Val Asn Leu Pro Ala His Ser Arg Tyr
225                 230                 235                 240

Gly Pro Gln Ala Val Asp Ala Arg
                245

<210> SEQ ID NO 52
<211> LENGTH: 278
<212> TYPE: PRT
<213> ORGANISM: Artificial Sequence
<220> FEATURE:
<223> OTHER INFORMATION: gL R166C mutant

<400> SEQUENCE: 52

Met Cys Arg Arg Pro Asp Cys Gly Phe Ser Phe Ser Pro Gly Pro Val
1               5                   10                  15

Ile Leu Leu Trp Cys Cys Leu Leu Leu Pro Ile Val Ser Ser Ala Ala
            20                  25                  30

Val Ser Val Ala Pro Thr Ala Ala Glu Lys Val Pro Ala Glu Cys Pro
            35                  40                  45

Glu Leu Thr Arg Arg Cys Leu Leu Gly Glu Val Phe Glu Gly Asp Lys
        50                  55                  60

Tyr Glu Ser Trp Leu Arg Pro Leu Val Asn Val Thr Gly Arg Asp Gly
65                  70                  75                  80

Pro Leu Ser Gln Leu Ile Arg Tyr Arg Pro Val Thr Pro Glu Ala Leu
                85                  90                  95

Ser Gly Val Leu Leu Asp Glu Ala Phe Leu Asp Thr Leu Ala Leu Leu
            100                 105                 110

Tyr Asn Asn Pro Asp Gln Leu Arg Ala Leu Leu Thr Leu Leu Ser Ser
            115                 120                 125

Asp Thr Ala Pro Arg Trp Met Thr Val Met Arg Gly Tyr Ser Glu Cys
130                 135                 140

Gly Asp Gly Ser Pro Ala Val Tyr Thr Cys Val Asp Asp Leu Cys Arg
145                 150                 155                 160

Gly Tyr Asp Leu Thr Cys Leu Ser Tyr Gly Arg Ser Ile Phe Thr Glu
                165                 170                 175

His Val Leu Gly Phe Glu Leu Val Pro Pro Ser Leu Phe Asn Val Val
            180                 185                 190

Val Ala Ile Arg Asn Glu Ala Thr Arg Thr Asn Arg Ala Val Arg Leu
            195                 200                 205
```

Pro Val Ser Thr Ala Ala Pro Glu Gly Ile Thr Leu Phe Tyr Gly
          210                 215                 220

Leu Tyr Asn Ala Val Lys Glu Phe Cys Leu Arg His Gln Leu Asp Pro
225                 230                 235                 240

Pro Leu Leu Arg His Leu Asp Lys Tyr Tyr Ala Gly Leu Pro Pro Glu
              245                 250                 255

Leu Lys Gln Thr Arg Val Asn Leu Pro Ala His Ser Arg Tyr Gly Pro
          260                 265                 270

Gln Ala Val Asp Ala Arg
          275

<210> SEQ ID NO 53
<211> LENGTH: 248
<212> TYPE: PRT
<213> ORGANISM: Artificial Sequence
<220> FEATURE:
<223> OTHER INFORMATION: mature gL R166C mutant

<400> SEQUENCE: 53

Ala Ala Val Ser Val Ala Pro Thr Ala Ala Glu Lys Val Pro Ala Glu
1               5                   10                  15

Cys Pro Glu Leu Thr Arg Arg Cys Leu Leu Gly Glu Val Phe Glu Gly
            20                  25                  30

Asp Lys Tyr Glu Ser Trp Leu Arg Pro Leu Val Asn Val Thr Gly Arg
        35                  40                  45

Asp Gly Pro Leu Ser Gln Leu Ile Arg Tyr Arg Pro Val Thr Pro Glu
    50                  55                  60

Ala Leu Ser Gly Val Leu Leu Asp Glu Ala Phe Leu Asp Thr Leu Ala
65                  70                  75                  80

Leu Leu Tyr Asn Asn Pro Asp Gln Leu Arg Ala Leu Leu Thr Leu Leu
                85                  90                  95

Ser Ser Asp Thr Ala Pro Arg Trp Met Thr Val Met Arg Gly Tyr Ser
            100                 105                 110

Glu Cys Gly Asp Gly Ser Pro Ala Val Tyr Thr Cys Val Asp Asp Leu
        115                 120                 125

Cys Arg Gly Tyr Asp Leu Thr Cys Leu Ser Tyr Gly Arg Ser Ile Phe
    130                 135                 140

Thr Glu His Val Leu Gly Phe Glu Leu Val Pro Pro Ser Leu Phe Asn
145                 150                 155                 160

Val Val Val Ala Ile Arg Asn Glu Ala Thr Arg Thr Asn Arg Ala Val
                165                 170                 175

Arg Leu Pro Val Ser Thr Ala Ala Pro Glu Gly Ile Thr Leu Phe
            180                 185                 190

Tyr Gly Leu Tyr Asn Ala Val Lys Glu Phe Cys Leu Arg His Gln Leu
        195                 200                 205

Asp Pro Pro Leu Leu Arg His Leu Asp Lys Tyr Tyr Ala Gly Leu Pro
    210                 215                 220

Pro Glu Leu Lys Gln Thr Arg Val Asn Leu Pro Ala His Ser Arg Tyr
225                 230                 235                 240

Gly Pro Gln Ala Val Asp Ala Arg
                245

<210> SEQ ID NO 54
<211> LENGTH: 278
<212> TYPE: PRT
<213> ORGANISM: Artificial Sequence
<220> FEATURE:
<223> OTHER INFORMATION: gL C233V mutant

<400> SEQUENCE: 54

Met Cys Arg Arg Pro Asp Cys Gly Phe Ser Phe Ser Pro Gly Pro Val
1               5                   10                  15

Ile Leu Leu Trp Cys Cys Leu Leu Pro Ile Val Ser Ser Ala Ala
            20                  25                  30

Val Ser Val Ala Pro Thr Ala Ala Glu Lys Val Pro Ala Glu Cys Pro
        35                  40                  45

Glu Leu Thr Arg Arg Cys Leu Leu Gly Glu Val Phe Glu Gly Asp Lys
    50                  55                  60

Tyr Glu Ser Trp Leu Arg Pro Leu Val Asn Val Thr Gly Arg Asp Gly
65              70                  75                  80

Pro Leu Ser Gln Leu Ile Arg Tyr Arg Pro Val Thr Pro Glu Ala Leu
                85                  90                  95

Ser Gly Val Leu Leu Asp Glu Ala Phe Leu Asp Thr Leu Ala Leu Leu
            100                 105                 110

Tyr Asn Asn Pro Asp Gln Leu Arg Ala Leu Leu Thr Leu Leu Ser Ser
        115                 120                 125

Asp Thr Ala Pro Arg Trp Met Thr Val Met Arg Gly Tyr Ser Glu Cys
    130                 135                 140

Gly Asp Gly Ser Pro Ala Val Tyr Thr Cys Val Asp Asp Leu Cys Arg
145             150                 155                 160

Gly Tyr Asp Leu Thr Arg Leu Ser Tyr Gly Arg Ser Ile Phe Thr Glu
                165                 170                 175

His Val Leu Gly Phe Glu Leu Val Pro Pro Ser Leu Phe Asn Val Val
            180                 185                 190

Val Ala Ile Arg Asn Glu Ala Thr Arg Thr Asn Arg Ala Val Arg Leu
        195                 200                 205

Pro Val Ser Thr Ala Ala Ala Pro Glu Gly Ile Thr Leu Phe Tyr Gly
    210                 215                 220

Leu Tyr Asn Ala Val Lys Glu Phe Val Leu Arg His Gln Leu Asp Pro
225             230                 235                 240

Pro Leu Leu Arg His Leu Asp Lys Tyr Tyr Ala Gly Leu Pro Pro Glu
                245                 250                 255

Leu Lys Gln Thr Arg Val Asn Leu Pro Ala His Ser Arg Tyr Gly Pro
            260                 265                 270

Gln Ala Val Asp Ala Arg
        275

<210> SEQ ID NO 55
<211> LENGTH: 248
<212> TYPE: PRT
<213> ORGANISM: Artificial Sequence
<220> FEATURE:
<223> OTHER INFORMATION: mature gL C233V mutant

<400> SEQUENCE: 55

Ala Ala Val Ser Val Ala Pro Thr Ala Ala Glu Lys Val Pro Ala Glu
1               5                   10                  15

Cys Pro Glu Leu Thr Arg Arg Cys Leu Leu Gly Glu Val Phe Glu Gly
            20                  25                  30

Asp Lys Tyr Glu Ser Trp Leu Arg Pro Leu Val Asn Val Thr Gly Arg
        35                  40                  45

Asp Gly Pro Leu Ser Gln Leu Ile Arg Tyr Arg Pro Val Thr Pro Glu

```
                50                  55                  60
Ala Leu Ser Gly Val Leu Leu Asp Glu Ala Phe Leu Asp Thr Leu Ala
 65                  70                  75                  80

Leu Leu Tyr Asn Asn Pro Asp Gln Leu Arg Ala Leu Leu Thr Leu Leu
                 85                  90                  95

Ser Ser Asp Thr Ala Pro Arg Trp Met Thr Val Met Arg Gly Tyr Ser
                100                 105                 110

Glu Cys Gly Asp Gly Ser Pro Ala Val Tyr Thr Cys Val Asp Asp Leu
                115                 120                 125

Cys Arg Gly Tyr Asp Leu Thr Arg Leu Ser Tyr Gly Arg Ser Ile Phe
            130                 135                 140

Thr Glu His Val Leu Gly Phe Glu Leu Val Pro Pro Ser Leu Phe Asn
145                 150                 155                 160

Val Val Val Ala Ile Arg Asn Glu Ala Thr Arg Thr Asn Arg Ala Val
                165                 170                 175

Arg Leu Pro Val Ser Thr Ala Ala Pro Glu Gly Ile Thr Leu Phe
                180                 185                 190

Tyr Gly Leu Tyr Asn Ala Val Lys Glu Phe Val Leu Arg His Gln Leu
            195                 200                 205

Asp Pro Pro Leu Leu Arg His Leu Asp Lys Tyr Tyr Ala Gly Leu Pro
210                 215                 220

Pro Glu Leu Lys Gln Thr Arg Val Asn Leu Pro Ala His Ser Arg Tyr
225                 230                 235                 240

Gly Pro Gln Ala Val Asp Ala Arg
                245

<210> SEQ ID NO 56
<211> LENGTH: 171
<212> TYPE: PRT
<213> ORGANISM: Artificial Sequence
<220> FEATURE:
<223> OTHER INFORMATION: pUL128 M48C and G107C mutant

<400> SEQUENCE: 56

Met Ser Pro Lys Asp Leu Thr Pro Phe Leu Thr Thr Leu Trp Leu Leu
 1               5                  10                  15

Leu Gly His Ser Arg Val Pro Arg Val Arg Ala Glu Glu Cys Cys Glu
                20                  25                  30

Phe Ile Asn Val Asn His Pro Pro Glu Arg Cys Tyr Asp Phe Lys Cys
            35                  40                  45

Cys Asn Arg Phe Thr Val Ala Leu Arg Cys Pro Asp Gly Glu Val Cys
 50                  55                  60

Tyr Ser Pro Glu Lys Thr Ala Glu Ile Arg Gly Ile Val Thr Thr Met
 65                  70                  75                  80

Thr His Ser Leu Thr Arg Gln Val Val His Asn Lys Leu Thr Ser Cys
                85                  90                  95

Asn Tyr Asn Pro Leu Tyr Leu Glu Ala Asp Cys Arg Ile Arg Cys Gly
            100                 105                 110

Lys Val Asn Asp Lys Ala Gln Tyr Leu Leu Gly Ala Ala Gly Ser Val
            115                 120                 125

Pro Tyr Arg Trp Ile Asn Leu Glu Tyr Asp Lys Ile Thr Arg Ile Val
            130                 135                 140

Gly Leu Asp Gln Tyr Leu Glu Ser Val Lys Lys His Lys Arg Leu Asp
145                 150                 155                 160

Val Cys Arg Ala Lys Met Gly Tyr Met Leu Gln
```

<210> SEQ ID NO 57
<211> LENGTH: 144
<212> TYPE: PRT
<213> ORGANISM: Artificial Sequence
<220> FEATURE:
<223> OTHER INFORMATION: mature pUL128 M48C and G107C mutant

<400> SEQUENCE: 57

```
Glu Glu Cys Cys Glu Phe Ile Asn Val Asn His Pro Pro Glu Arg Cys
1               5                   10                  15

Tyr Asp Phe Lys Cys Cys Asn Arg Phe Thr Val Ala Leu Arg Cys Pro
            20                  25                  30

Asp Gly Glu Val Cys Tyr Ser Pro Glu Lys Thr Ala Glu Ile Arg Gly
        35                  40                  45

Ile Val Thr Thr Met Thr His Ser Leu Thr Arg Gln Val Val His Asn
    50                  55                  60

Lys Leu Thr Ser Cys Asn Tyr Asn Pro Leu Tyr Leu Glu Ala Asp Cys
65                  70                  75                  80

Arg Ile Arg Cys Gly Lys Val Asn Asp Lys Ala Gln Tyr Leu Leu Gly
                85                  90                  95

Ala Ala Gly Ser Val Pro Tyr Arg Trp Ile Asn Leu Glu Tyr Asp Lys
            100                 105                 110

Ile Thr Arg Ile Val Gly Leu Asp Gln Tyr Leu Glu Ser Val Lys Lys
        115                 120                 125

His Lys Arg Leu Asp Val Cys Arg Ala Lys Met Gly Tyr Met Leu Gln
    130                 135                 140
```

<210> SEQ ID NO 58
<211> LENGTH: 171
<212> TYPE: PRT
<213> ORGANISM: Artificial Sequence
<220> FEATURE:
<223> OTHER INFORMATION: pUL128 V77I mutant

<400> SEQUENCE: 58

```
Met Ser Pro Lys Asp Leu Thr Pro Phe Leu Thr Thr Leu Trp Leu Leu
1               5                   10                  15

Leu Gly His Ser Arg Val Pro Arg Val Arg Ala Glu Glu Cys Cys Glu
            20                  25                  30

Phe Ile Asn Val Asn His Pro Pro Glu Arg Cys Tyr Asp Phe Lys Met
        35                  40                  45

Cys Asn Arg Phe Thr Val Ala Leu Arg Cys Pro Asp Gly Glu Val Cys
    50                  55                  60

Tyr Ser Pro Glu Lys Thr Ala Glu Ile Arg Gly Ile Ile Thr Met
65                  70                  75                  80

Thr His Ser Leu Thr Arg Gln Val Val His Asn Lys Leu Thr Ser Cys
                85                  90                  95

Asn Tyr Asn Pro Leu Tyr Leu Glu Ala Asp Gly Arg Ile Arg Cys Gly
            100                 105                 110

Lys Val Asn Asp Lys Ala Gln Tyr Leu Leu Gly Ala Ala Gly Ser Val
        115                 120                 125

Pro Tyr Arg Trp Ile Asn Leu Glu Tyr Asp Lys Ile Thr Arg Ile Val
    130                 135                 140

Gly Leu Asp Gln Tyr Leu Glu Ser Val Lys Lys His Lys Arg Leu Asp
145                 150                 155                 160
```

-continued

Val Cys Arg Ala Lys Met Gly Tyr Met Leu Gln
             165                 170

<210> SEQ ID NO 59
<211> LENGTH: 144
<212> TYPE: PRT
<213> ORGANISM: Artificial Sequence
<220> FEATURE:
<223> OTHER INFORMATION: mature pUL128 V77I mutant

<400> SEQUENCE: 59

Glu Glu Cys Cys Glu Phe Ile Asn Val Asn His Pro Pro Glu Arg Cys
1               5                   10                  15

Tyr Asp Phe Lys Met Cys Asn Arg Phe Thr Val Ala Leu Arg Cys Pro
            20                  25                  30

Asp Gly Glu Val Cys Tyr Ser Pro Glu Lys Thr Ala Glu Ile Arg Gly
        35                  40                  45

Ile Ile Thr Thr Met Thr His Ser Leu Thr Arg Gln Val Val His Asn
    50                  55                  60

Lys Leu Thr Ser Cys Asn Tyr Asn Pro Leu Tyr Leu Glu Ala Asp Gly
65                  70                  75                  80

Arg Ile Arg Cys Gly Lys Val Asn Asp Lys Ala Gln Tyr Leu Leu Gly
                85                  90                  95

Ala Ala Gly Ser Val Pro Tyr Arg Trp Ile Asn Leu Glu Tyr Asp Lys
            100                 105                 110

Ile Thr Arg Ile Val Gly Leu Asp Gln Tyr Leu Glu Ser Val Lys Lys
        115                 120                 125

His Lys Arg Leu Asp Val Cys Arg Ala Lys Met Gly Tyr Met Leu Gln
    130                 135                 140

<210> SEQ ID NO 60
<211> LENGTH: 171
<212> TYPE: PRT
<213> ORGANISM: Artificial Sequence
<220> FEATURE:
<223> OTHER INFORMATION: pUL128 S83C mutant

<400> SEQUENCE: 60

Met Ser Pro Lys Asp Leu Thr Pro Phe Leu Thr Thr Leu Trp Leu Leu
1               5                   10                  15

Leu Gly His Ser Arg Val Pro Arg Val Arg Ala Glu Glu Cys Cys Glu
            20                  25                  30

Phe Ile Asn Val Asn His Pro Pro Glu Arg Cys Tyr Asp Phe Lys Met
        35                  40                  45

Cys Asn Arg Phe Thr Val Ala Leu Arg Cys Pro Asp Gly Glu Val Cys
    50                  55                  60

Tyr Ser Pro Glu Lys Thr Ala Glu Ile Arg Gly Ile Val Thr Thr Met
65                  70                  75                  80

Thr His Cys Leu Thr Arg Gln Val Val His Asn Lys Leu Thr Ser Cys
                85                  90                  95

Asn Tyr Asn Pro Leu Tyr Leu Glu Ala Asp Gly Arg Ile Arg Cys Gly
            100                 105                 110

Lys Val Asn Asp Lys Ala Gln Tyr Leu Leu Gly Ala Ala Gly Ser Val
        115                 120                 125

Pro Tyr Arg Trp Ile Asn Leu Glu Tyr Asp Lys Ile Thr Arg Ile Val
    130                 135                 140

Gly Leu Asp Gln Tyr Leu Glu Ser Val Lys Lys His Lys Arg Leu Asp
145                 150                 155                 160

Val Cys Arg Ala Lys Met Gly Tyr Met Leu Gln
            165                 170

<210> SEQ ID NO 61
<211> LENGTH: 144
<212> TYPE: PRT
<213> ORGANISM: Artificial Sequence
<220> FEATURE:
<223> OTHER INFORMATION: mature pUL128 S83C mutant

<400> SEQUENCE: 61

Glu Glu Cys Cys Glu Phe Ile Asn Val Asn His Pro Pro Glu Arg Cys
1               5                   10                  15

Tyr Asp Phe Lys Met Cys Asn Arg Phe Thr Val Ala Leu Arg Cys Pro
                20                  25                  30

Asp Gly Glu Val Cys Tyr Ser Pro Glu Lys Thr Ala Glu Ile Arg Gly
            35                  40                  45

Ile Val Thr Thr Met Thr His Cys Leu Thr Arg Gln Val Val His Asn
        50                  55                  60

Lys Leu Thr Ser Cys Asn Tyr Asn Pro Leu Tyr Leu Glu Ala Asp Gly
65                  70                  75                  80

Arg Ile Arg Cys Gly Lys Val Asn Asp Lys Ala Gln Tyr Leu Leu Gly
                85                  90                  95

Ala Ala Gly Ser Val Pro Tyr Arg Trp Ile Asn Leu Glu Tyr Asp Lys
            100                 105                 110

Ile Thr Arg Ile Val Gly Leu Asp Gln Tyr Leu Glu Ser Val Lys Lys
        115                 120                 125

His Lys Arg Leu Asp Val Cys Arg Ala Lys Met Gly Tyr Met Leu Gln
130                 135                 140

<210> SEQ ID NO 62
<211> LENGTH: 171
<212> TYPE: PRT
<213> ORGANISM: Artificial Sequence
<220> FEATURE:
<223> OTHER INFORMATION: pUL128 Y98C mutant

<400> SEQUENCE: 62

Met Ser Pro Lys Asp Leu Thr Pro Phe Leu Thr Thr Leu Trp Leu Leu
1               5                   10                  15

Leu Gly His Ser Arg Val Pro Arg Val Arg Ala Glu Glu Cys Cys Glu
                20                  25                  30

Phe Ile Asn Val Asn His Pro Pro Glu Arg Cys Tyr Asp Phe Lys Met
            35                  40                  45

Cys Asn Arg Phe Thr Val Ala Leu Arg Cys Pro Asp Gly Glu Val Cys
        50                  55                  60

Tyr Ser Pro Glu Lys Thr Ala Glu Ile Arg Gly Ile Val Thr Thr Met
65                  70                  75                  80

Thr His Ser Leu Thr Arg Gln Val Val His Asn Lys Leu Thr Ser Cys
                85                  90                  95

Asn Cys Asn Pro Leu Tyr Leu Glu Ala Asp Gly Arg Ile Arg Cys Gly
            100                 105                 110

Lys Val Asn Asp Lys Ala Gln Tyr Leu Leu Gly Ala Ala Gly Ser Val
        115                 120                 125

Pro Tyr Arg Trp Ile Asn Leu Glu Tyr Asp Lys Ile Thr Arg Ile Val
            130                 135                 140

Gly Leu Asp Gln Tyr Leu Glu Ser Val Lys Lys His Lys Arg Leu Asp

```
                    145                 150                 155                 160
Val Cys Arg Ala Lys Met Gly Tyr Met Leu Gln
            165                 170

<210> SEQ ID NO 63
<211> LENGTH: 144
<212> TYPE: PRT
<213> ORGANISM: Artificial Sequence
<220> FEATURE:
<223> OTHER INFORMATION: mature pUL128 Y98C mutant

<400> SEQUENCE: 63

Glu Glu Cys Cys Glu Phe Ile Asn Val Asn His Pro Pro Glu Arg Cys
1               5                   10                  15

Tyr Asp Phe Lys Met Cys Asn Arg Phe Thr Val Ala Leu Arg Cys Pro
            20                  25                  30

Asp Gly Glu Val Cys Tyr Ser Pro Glu Lys Thr Ala Glu Ile Arg Gly
        35                  40                  45

Ile Val Thr Thr Met Thr His Ser Leu Thr Arg Gln Val Val His Asn
    50                  55                  60

Lys Leu Thr Ser Cys Asn Cys Asn Pro Leu Tyr Leu Glu Ala Asp Gly
65                  70                  75                  80

Arg Ile Arg Cys Gly Lys Val Asn Asp Lys Ala Gln Tyr Leu Leu Gly
                85                  90                  95

Ala Ala Gly Ser Val Pro Tyr Arg Trp Ile Asn Leu Glu Tyr Asp Lys
            100                 105                 110

Ile Thr Arg Ile Val Gly Leu Asp Gln Tyr Leu Glu Ser Val Lys Lys
        115                 120                 125

His Lys Arg Leu Asp Val Cys Arg Ala Lys Met Gly Tyr Met Leu Gln
    130                 135                 140

<210> SEQ ID NO 64
<211> LENGTH: 171
<212> TYPE: PRT
<213> ORGANISM: Artificial Sequence
<220> FEATURE:
<223> OTHER INFORMATION: pUL128 L103I mutant

<400> SEQUENCE: 64

Met Ser Pro Lys Asp Leu Thr Pro Phe Leu Thr Thr Leu Trp Leu Leu
1               5                   10                  15

Leu Gly His Ser Arg Val Pro Arg Val Arg Ala Glu Glu Cys Cys Glu
            20                  25                  30

Phe Ile Asn Val Asn His Pro Pro Glu Arg Cys Tyr Asp Phe Lys Met
        35                  40                  45

Cys Asn Arg Phe Thr Val Ala Leu Arg Cys Pro Asp Gly Glu Val Cys
    50                  55                  60

Tyr Ser Pro Glu Lys Thr Ala Glu Ile Arg Gly Ile Val Thr Thr Met
65                  70                  75                  80

Thr His Ser Leu Thr Arg Gln Val Val His Asn Lys Leu Thr Ser Cys
                85                  90                  95

Asn Tyr Asn Pro Leu Tyr Ile Glu Ala Asp Gly Arg Ile Arg Cys Gly
            100                 105                 110

Lys Val Asn Asp Lys Ala Gln Tyr Leu Leu Gly Ala Ala Gly Ser Val
        115                 120                 125

Pro Tyr Arg Trp Ile Asn Leu Glu Tyr Asp Lys Ile Thr Arg Ile Val
    130                 135                 140
```

```
Gly Leu Asp Gln Tyr Leu Glu Ser Val Lys Lys His Lys Arg Leu Asp
145                 150                 155                 160

Val Cys Arg Ala Lys Met Gly Tyr Met Leu Gln
                165                 170
```

<210> SEQ ID NO 65
<211> LENGTH: 144
<212> TYPE: PRT
<213> ORGANISM: Artificial Sequence
<220> FEATURE:
<223> OTHER INFORMATION: mature pUL128 L103I mutant

<400> SEQUENCE: 65

```
Glu Glu Cys Cys Glu Phe Ile Asn Val Asn His Pro Pro Glu Arg Cys
1               5                   10                  15

Tyr Asp Phe Lys Met Cys Asn Arg Phe Thr Val Ala Leu Arg Cys Pro
                20                  25                  30

Asp Gly Glu Val Cys Tyr Ser Pro Glu Lys Thr Ala Glu Ile Arg Gly
            35                  40                  45

Ile Val Thr Thr Met Thr His Ser Leu Thr Arg Gln Val Val His Asn
        50                  55                  60

Lys Leu Thr Ser Cys Asn Tyr Asn Pro Leu Tyr Ile Glu Ala Asp Gly
65                  70                  75                  80

Arg Ile Arg Cys Gly Lys Val Asn Asp Lys Ala Gln Tyr Leu Leu Gly
                85                  90                  95

Ala Ala Gly Ser Val Pro Tyr Arg Trp Ile Asn Leu Glu Tyr Asp Lys
            100                 105                 110

Ile Thr Arg Ile Val Gly Leu Asp Gln Tyr Leu Glu Ser Val Lys Lys
        115                 120                 125

His Lys Arg Leu Asp Val Cys Arg Ala Lys Met Gly Tyr Met Leu Gln
130                 135                 140
```

<210> SEQ ID NO 66
<211> LENGTH: 171
<212> TYPE: PRT
<213> ORGANISM: Artificial Sequence
<220> FEATURE:
<223> OTHER INFORMATION: pUL128 R142C mutant

<400> SEQUENCE: 66

```
Met Ser Pro Lys Asp Leu Thr Pro Phe Leu Thr Thr Leu Trp Leu Leu
1               5                   10                  15

Leu Gly His Ser Arg Val Pro Arg Val Arg Ala Glu Glu Cys Cys Glu
                20                  25                  30

Phe Ile Asn Val Asn His Pro Pro Glu Arg Cys Tyr Asp Phe Lys Met
            35                  40                  45

Cys Asn Arg Phe Thr Val Ala Leu Arg Cys Pro Asp Gly Glu Val Cys
        50                  55                  60

Tyr Ser Pro Glu Lys Thr Ala Glu Ile Arg Gly Ile Val Thr Thr Met
65                  70                  75                  80

Thr His Ser Leu Thr Arg Gln Val Val His Asn Lys Leu Thr Ser Cys
                85                  90                  95

Asn Tyr Asn Pro Leu Tyr Leu Glu Ala Asp Gly Arg Ile Arg Cys Gly
            100                 105                 110

Lys Val Asn Asp Lys Ala Gln Tyr Leu Leu Gly Ala Ala Gly Ser Val
        115                 120                 125

Pro Tyr Arg Trp Ile Asn Leu Glu Tyr Asp Lys Ile Thr Cys Ile Val
130                 135                 140
```

```
Gly Leu Asp Gln Tyr Leu Glu Ser Val Lys Lys His Lys Arg Leu Asp
145                 150                 155                 160

Val Cys Arg Ala Lys Met Gly Tyr Met Leu Gln
                165                 170
```

<210> SEQ ID NO 67
<211> LENGTH: 144
<212> TYPE: PRT
<213> ORGANISM: Artificial Sequence
<220> FEATURE:
<223> OTHER INFORMATION: mature pUL128 R142C mutant

<400> SEQUENCE: 67

```
Glu Glu Cys Cys Glu Phe Ile Asn Val Asn His Pro Pro Glu Arg Cys
1               5                   10                  15

Tyr Asp Phe Lys Met Cys Asn Arg Phe Thr Val Ala Leu Arg Cys Pro
                20                  25                  30

Asp Gly Glu Val Cys Tyr Ser Pro Glu Lys Thr Ala Glu Ile Arg Gly
            35                  40                  45

Ile Val Thr Thr Met Thr His Ser Leu Thr Arg Gln Val Val His Asn
        50                  55                  60

Lys Leu Thr Ser Cys Asn Tyr Asn Pro Leu Tyr Leu Glu Ala Asp Gly
65                  70                  75                  80

Arg Ile Arg Cys Gly Lys Val Asn Asp Lys Ala Gln Tyr Leu Leu Gly
                85                  90                  95

Ala Ala Gly Ser Val Pro Tyr Arg Trp Ile Asn Leu Glu Tyr Asp Lys
            100                 105                 110

Ile Thr Cys Ile Val Gly Leu Asp Gln Tyr Leu Glu Ser Val Lys Lys
        115                 120                 125

His Lys Arg Leu Asp Val Cys Arg Ala Lys Met Gly Tyr Met Leu Gln
    130                 135                 140
```

<210> SEQ ID NO 68
<211> LENGTH: 214
<212> TYPE: PRT
<213> ORGANISM: Artificial Sequence
<220> FEATURE:
<223> OTHER INFORMATION: pUL130 Y56C mutant

<400> SEQUENCE: 68

```
Met Leu Arg Leu Leu Leu Arg His His Phe His Cys Leu Leu Leu Cys
1               5                   10                  15

Ala Val Trp Ala Thr Pro Cys Leu Ala Ser Pro Trp Ser Thr Leu Thr
                20                  25                  30

Ala Asn Gln Asn Pro Ser Pro Pro Trp Ser Lys Leu Thr Tyr Ser Lys
            35                  40                  45

Pro His Asp Ala Ala Thr Phe Cys Cys Pro Phe Leu Tyr Pro Ser Pro
        50                  55                  60

Pro Arg Ser Pro Leu Gln Phe Ser Gly Phe Gln Arg Val Ser Thr Gly
65                  70                  75                  80

Pro Glu Cys Arg Asn Glu Thr Leu Tyr Leu Leu Tyr Asn Arg Glu Gly
                85                  90                  95

Gln Thr Leu Val Glu Arg Ser Ser Thr Trp Val Lys Lys Val Ile Trp
            100                 105                 110

Tyr Leu Ser Gly Arg Asn Gln Thr Ile Leu Gln Arg Met Pro Arg Thr
        115                 120                 125

Ala Ser Lys Pro Ser Asp Gly Asn Val Gln Ile Ser Val Glu Asp Ala
```

```
Lys Ile Phe Gly Ala His Met Val Pro Lys Gln Thr Lys Leu Leu Arg
145                 150                 155                 160

Phe Val Val Asn Asp Gly Thr Arg Tyr Gln Met Cys Val Met Lys Leu
            165                 170                 175

Glu Ser Trp Ala His Val Phe Arg Asp Tyr Ser Val Ser Phe Gln Val
        180                 185                 190

Arg Leu Thr Phe Thr Glu Ala Asn Asn Gln Thr Tyr Thr Phe Cys Thr
        195                 200                 205

His Pro Asn Leu Ile Val
    210

<210> SEQ ID NO 69
<211> LENGTH: 189
<212> TYPE: PRT
<213> ORGANISM: Artificial Sequence
<220> FEATURE:
<223> OTHER INFORMATION: mature pUL130 Y56C mutant

<400> SEQUENCE: 69

Ser Pro Trp Ser Thr Leu Thr Ala Asn Gln Asn Pro Ser Pro Pro Trp
1               5                   10                  15

Ser Lys Leu Thr Tyr Ser Lys Pro His Asp Ala Ala Thr Phe Cys Cys
            20                  25                  30

Pro Phe Leu Tyr Pro Ser Pro Arg Ser Pro Leu Gln Phe Ser Gly
        35                  40                  45

Phe Gln Arg Val Ser Thr Gly Pro Glu Cys Arg Asn Glu Thr Leu Tyr
50                  55                  60

Leu Leu Tyr Asn Arg Glu Gly Gln Thr Leu Val Glu Arg Ser Ser Thr
65                  70                  75                  80

Trp Val Lys Lys Val Ile Trp Tyr Leu Ser Gly Arg Asn Gln Thr Ile
                85                  90                  95

Leu Gln Arg Met Pro Arg Thr Ala Ser Lys Pro Ser Asp Gly Asn Val
            100                 105                 110

Gln Ile Ser Val Glu Asp Ala Lys Ile Phe Gly Ala His Met Val Pro
        115                 120                 125

Lys Gln Thr Lys Leu Leu Arg Phe Val Val Asn Asp Gly Thr Arg Tyr
130                 135                 140

Gln Met Cys Val Met Lys Leu Glu Ser Trp Ala His Val Phe Arg Asp
145                 150                 155                 160

Tyr Ser Val Ser Phe Gln Val Arg Leu Thr Phe Thr Glu Ala Asn Asn
                165                 170                 175

Gln Thr Tyr Thr Phe Cys Thr His Pro Asn Leu Ile Val
            180                 185

<210> SEQ ID NO 70
<211> LENGTH: 214
<212> TYPE: PRT
<213> ORGANISM: Artificial Sequence
<220> FEATURE:
<223> OTHER INFORMATION: pUL130 P62C mutant

<400> SEQUENCE: 70

Met Leu Arg Leu Leu Arg His His Phe His Cys Leu Leu Leu Cys
1               5                   10                  15

Ala Val Trp Ala Thr Pro Cys Leu Ala Ser Pro Trp Ser Thr Leu Thr
            20                  25                  30
```

-continued

Ala Asn Gln Asn Pro Ser Pro Pro Trp Ser Lys Leu Thr Tyr Ser Lys
           35                  40                  45

Pro His Asp Ala Ala Thr Phe Tyr Cys Pro Phe Leu Tyr Cys Ser Pro
 50                  55                  60

Pro Arg Ser Pro Leu Gln Phe Ser Gly Phe Gln Arg Val Ser Thr Gly
 65                  70                  75                  80

Pro Glu Cys Arg Asn Glu Thr Leu Tyr Leu Leu Tyr Asn Arg Glu Gly
                     85                  90                  95

Gln Thr Leu Val Glu Arg Ser Ser Thr Trp Val Lys Lys Val Ile Trp
                100                 105                 110

Tyr Leu Ser Gly Arg Asn Gln Thr Ile Leu Gln Arg Met Pro Arg Thr
            115                 120                 125

Ala Ser Lys Pro Ser Asp Gly Asn Val Gln Ile Ser Val Glu Asp Ala
130                 135                 140

Lys Ile Phe Gly Ala His Met Val Pro Lys Gln Thr Lys Leu Leu Arg
145                 150                 155                 160

Phe Val Val Asn Asp Gly Thr Arg Tyr Gln Met Cys Val Met Lys Leu
                165                 170                 175

Glu Ser Trp Ala His Val Phe Arg Asp Tyr Ser Val Ser Phe Gln Val
            180                 185                 190

Arg Leu Thr Phe Thr Glu Ala Asn Asn Gln Tyr Thr Phe Cys Thr
        195                 200                 205

His Pro Asn Leu Ile Val
        210

<210> SEQ ID NO 71
<211> LENGTH: 189
<212> TYPE: PRT
<213> ORGANISM: Artificial Sequence
<220> FEATURE:
<223> OTHER INFORMATION: mature pUL130 P62C mutant

<400> SEQUENCE: 71

Ser Pro Trp Ser Thr Leu Thr Ala Asn Gln Asn Pro Ser Pro Pro Trp
1               5                   10                  15

Ser Lys Leu Thr Tyr Ser Lys Pro His Asp Ala Ala Thr Phe Tyr Cys
            20                  25                  30

Pro Phe Leu Tyr Cys Ser Pro Pro Arg Ser Pro Leu Gln Phe Ser Gly
        35                  40                  45

Phe Gln Arg Val Ser Thr Gly Pro Glu Cys Arg Asn Glu Thr Leu Tyr
    50                  55                  60

Leu Leu Tyr Asn Arg Glu Gly Gln Thr Leu Val Glu Arg Ser Ser Thr
65                  70                  75                  80

Trp Val Lys Lys Val Ile Trp Tyr Leu Ser Gly Arg Asn Gln Thr Ile
                85                  90                  95

Leu Gln Arg Met Pro Arg Thr Ala Ser Lys Pro Ser Asp Gly Asn Val
            100                 105                 110

Gln Ile Ser Val Glu Asp Ala Lys Ile Phe Gly Ala His Met Val Pro
        115                 120                 125

Lys Gln Thr Lys Leu Leu Arg Phe Val Val Asn Asp Gly Thr Arg Tyr
130                 135                 140

Gln Met Cys Val Met Lys Leu Glu Ser Trp Ala His Val Phe Arg Asp
145                 150                 155                 160

Tyr Ser Val Ser Phe Gln Val Arg Leu Thr Phe Thr Glu Ala Asn Asn
                165                 170                 175

Gln Thr Tyr Thr Phe Cys Thr His Pro Asn Leu Ile Val
            180                 185

<210> SEQ ID NO 72
<211> LENGTH: 214
<212> TYPE: PRT
<213> ORGANISM: Artificial Sequence
<220> FEATURE:
<223> OTHER INFORMATION: pUL130 P64C mutant

<400> SEQUENCE: 72

Met Leu Arg Leu Leu Leu Arg His His Phe His Cys Leu Leu Leu Cys
1               5                   10                  15

Ala Val Trp Ala Thr Pro Cys Leu Ala Ser Pro Trp Ser Thr Leu Thr
            20                  25                  30

Ala Asn Gln Asn Pro Ser Pro Pro Trp Ser Lys Leu Thr Tyr Ser Lys
        35                  40                  45

Pro His Asp Ala Ala Thr Phe Tyr Cys Pro Phe Leu Tyr Pro Ser Cys
    50                  55                  60

Pro Arg Ser Pro Leu Gln Phe Ser Gly Phe Gln Arg Val Ser Thr Gly
65                  70                  75                  80

Pro Glu Cys Arg Asn Glu Thr Leu Tyr Leu Leu Tyr Asn Arg Glu Gly
                85                  90                  95

Gln Thr Leu Val Glu Arg Ser Ser Thr Trp Val Lys Lys Val Ile Trp
            100                 105                 110

Tyr Leu Ser Gly Arg Asn Gln Thr Ile Leu Gln Arg Met Pro Arg Thr
        115                 120                 125

Ala Ser Lys Pro Ser Asp Gly Asn Val Gln Ile Ser Val Glu Asp Ala
    130                 135                 140

Lys Ile Phe Gly Ala His Met Val Pro Lys Gln Thr Lys Leu Leu Arg
145                 150                 155                 160

Phe Val Val Asn Asp Gly Thr Arg Tyr Gln Met Cys Val Met Lys Leu
                165                 170                 175

Glu Ser Trp Ala His Val Phe Arg Asp Tyr Ser Val Ser Phe Gln Val
            180                 185                 190

Arg Leu Thr Phe Thr Glu Ala Asn Asn Gln Thr Tyr Thr Phe Cys Thr
        195                 200                 205

His Pro Asn Leu Ile Val
    210

<210> SEQ ID NO 73
<211> LENGTH: 189
<212> TYPE: PRT
<213> ORGANISM: Artificial Sequence
<220> FEATURE:
<223> OTHER INFORMATION: mature pUL130 P64C mutant

<400> SEQUENCE: 73

Ser Pro Trp Ser Thr Leu Thr Ala Asn Gln Asn Pro Ser Pro Pro Trp
1               5                   10                  15

Ser Lys Leu Thr Tyr Ser Lys Pro His Asp Ala Ala Thr Phe Tyr Cys
            20                  25                  30

Pro Phe Leu Tyr Pro Ser Cys Pro Arg Ser Pro Leu Gln Phe Ser Gly
        35                  40                  45

Phe Gln Arg Val Ser Thr Gly Pro Glu Cys Arg Asn Glu Thr Leu Tyr
    50                  55                  60

Leu Leu Tyr Asn Arg Glu Gly Gln Thr Leu Val Glu Arg Ser Ser Thr
65                  70                  75                  80

Trp Val Lys Lys Val Ile Trp Tyr Leu Ser Gly Arg Asn Gln Thr Ile
            85                  90                  95

Leu Gln Arg Met Pro Arg Thr Ala Ser Lys Pro Ser Asp Gly Asn Val
        100                 105                 110

Gln Ile Ser Val Glu Asp Ala Lys Ile Phe Gly Ala His Met Val Pro
    115                 120                 125

Lys Gln Thr Lys Leu Leu Arg Phe Val Val Asn Asp Gly Thr Arg Tyr
130                 135                 140

Gln Met Cys Val Met Lys Leu Glu Ser Trp Ala His Val Phe Arg Asp
145                 150                 155                 160

Tyr Ser Val Ser Phe Gln Val Arg Leu Thr Phe Thr Glu Ala Asn Asn
                165                 170                 175

Gln Thr Tyr Thr Phe Cys Thr His Pro Asn Leu Ile Val
            180                 185

<210> SEQ ID NO 74
<211> LENGTH: 214
<212> TYPE: PRT
<213> ORGANISM: Artificial Sequence
<220> FEATURE:
<223> OTHER INFORMATION: pUL130 E95C mutant

<400> SEQUENCE: 74

Met Leu Arg Leu Leu Arg His His Phe His Cys Leu Leu Leu Cys
1               5                   10                  15

Ala Val Trp Ala Thr Pro Cys Leu Ala Ser Pro Trp Ser Thr Leu Thr
            20                  25                  30

Ala Asn Gln Asn Pro Ser Pro Pro Trp Ser Lys Leu Thr Tyr Ser Lys
        35                  40                  45

Pro His Asp Ala Ala Thr Phe Tyr Cys Pro Phe Leu Tyr Pro Ser Pro
    50                  55                  60

Pro Arg Ser Pro Leu Gln Phe Ser Gly Phe Gln Arg Val Ser Thr Gly
65                  70                  75                  80

Pro Glu Cys Arg Asn Glu Thr Leu Tyr Leu Leu Tyr Asn Arg Cys Gly
                85                  90                  95

Gln Thr Leu Val Glu Arg Ser Ser Thr Trp Val Lys Lys Val Ile Trp
            100                 105                 110

Tyr Leu Ser Gly Arg Asn Gln Thr Ile Leu Gln Arg Met Pro Arg Thr
        115                 120                 125

Ala Ser Lys Pro Ser Asp Gly Asn Val Gln Ile Ser Val Glu Asp Ala
    130                 135                 140

Lys Ile Phe Gly Ala His Met Val Pro Lys Gln Thr Lys Leu Leu Arg
145                 150                 155                 160

Phe Val Val Asn Asp Gly Thr Arg Tyr Gln Met Cys Val Met Lys Leu
                165                 170                 175

Glu Ser Trp Ala His Val Phe Arg Asp Tyr Ser Val Ser Phe Gln Val
            180                 185                 190

Arg Leu Thr Phe Thr Glu Ala Asn Asn Gln Thr Tyr Thr Phe Cys Thr
        195                 200                 205

His Pro Asn Leu Ile Val
    210

<210> SEQ ID NO 75
<211> LENGTH: 189
<212> TYPE: PRT
<213> ORGANISM: Artificial Sequence

```
<220> FEATURE:
<223> OTHER INFORMATION: mature pUL130 E95C mutant

<400> SEQUENCE: 75

Ser Pro Trp Ser Thr Leu Thr Ala Asn Gln Asn Pro Ser Pro Pro Trp
1               5                   10                  15

Ser Lys Leu Thr Tyr Ser Lys Pro His Asp Ala Ala Thr Phe Tyr Cys
                20                  25                  30

Pro Phe Leu Tyr Pro Ser Pro Pro Arg Ser Pro Leu Gln Phe Ser Gly
            35                  40                  45

Phe Gln Arg Val Ser Thr Gly Pro Glu Cys Arg Asn Glu Thr Leu Tyr
        50                  55                  60

Leu Leu Tyr Asn Arg Cys Gly Gln Thr Leu Val Glu Arg Ser Ser Thr
65                  70                  75                  80

Trp Val Lys Lys Val Ile Trp Tyr Leu Ser Gly Arg Asn Gln Thr Ile
                85                  90                  95

Leu Gln Arg Met Pro Arg Thr Ala Ser Lys Pro Ser Asp Gly Asn Val
                100                 105                 110

Gln Ile Ser Val Glu Asp Ala Lys Ile Phe Gly Ala His Met Val Pro
            115                 120                 125

Lys Gln Thr Lys Leu Leu Arg Phe Val Val Asn Asp Gly Thr Arg Tyr
        130                 135                 140

Gln Met Cys Val Met Lys Leu Glu Ser Trp Ala His Val Phe Arg Asp
145                 150                 155                 160

Tyr Ser Val Ser Phe Gln Val Arg Leu Thr Phe Thr Glu Ala Asn Asn
                165                 170                 175

Gln Thr Tyr Thr Phe Cys Thr His Pro Asn Leu Ile Val
                180                 185

<210> SEQ ID NO 76
<211> LENGTH: 214
<212> TYPE: PRT
<213> ORGANISM: Artificial Sequence
<220> FEATURE:
<223> OTHER INFORMATION: pUL130 T167C mutant

<400> SEQUENCE: 76

Met Leu Arg Leu Leu Arg His His Phe His Cys Leu Leu Leu Cys
1               5                   10                  15

Ala Val Trp Ala Thr Pro Cys Leu Ala Ser Pro Trp Ser Thr Leu Thr
                20                  25                  30

Ala Asn Gln Asn Pro Ser Pro Pro Trp Ser Lys Leu Thr Tyr Ser Lys
            35                  40                  45

Pro His Asp Ala Ala Thr Phe Tyr Cys Pro Phe Leu Tyr Pro Ser Pro
        50                  55                  60

Pro Arg Ser Pro Leu Gln Phe Ser Gly Phe Gln Arg Val Ser Thr Gly
65                  70                  75                  80

Pro Glu Cys Arg Asn Glu Thr Leu Tyr Leu Leu Tyr Asn Arg Glu Gly
                85                  90                  95

Gln Thr Leu Val Glu Arg Ser Ser Thr Trp Val Lys Lys Val Ile Trp
                100                 105                 110

Tyr Leu Ser Gly Arg Asn Gln Thr Ile Leu Gln Arg Met Pro Arg Thr
            115                 120                 125

Ala Ser Lys Pro Ser Asp Gly Asn Val Gln Ile Ser Val Glu Asp Ala
        130                 135                 140

Lys Ile Phe Gly Ala His Met Val Pro Lys Gln Thr Lys Leu Leu Arg
```

```
145                 150                 155                 160
Phe Val Val Asn Asp Gly Cys Arg Tyr Gln Met Cys Val Met Lys Leu
                165                 170                 175

Glu Ser Trp Ala His Val Phe Arg Asp Tyr Ser Val Ser Phe Gln Val
                180                 185                 190

Arg Leu Thr Phe Thr Glu Ala Asn Asn Gln Thr Tyr Thr Phe Cys Thr
                195                 200                 205

His Pro Asn Leu Ile Val
                210

<210> SEQ ID NO 77
<211> LENGTH: 189
<212> TYPE: PRT
<213> ORGANISM: Artificial Sequence
<220> FEATURE:
<223> OTHER INFORMATION: mature pUL130 T167C mutant

<400> SEQUENCE: 77

Ser Pro Trp Ser Thr Leu Thr Ala Asn Gln Asn Pro Ser Pro Pro Trp
1               5                   10                  15

Ser Lys Leu Thr Tyr Ser Lys Pro His Asp Ala Ala Thr Phe Tyr Cys
                20                  25                  30

Pro Phe Leu Tyr Pro Ser Pro Pro Arg Ser Pro Leu Gln Phe Ser Gly
            35                  40                  45

Phe Gln Arg Val Ser Thr Gly Pro Glu Cys Arg Asn Glu Thr Leu Tyr
    50                  55                  60

Leu Leu Tyr Asn Arg Glu Gly Gln Thr Leu Val Glu Arg Ser Ser Thr
65                  70                  75                  80

Trp Val Lys Lys Val Ile Trp Tyr Leu Ser Gly Arg Asn Gln Thr Ile
                85                  90                  95

Leu Gln Arg Met Pro Arg Thr Ala Ser Lys Pro Ser Asp Gly Asn Val
                100                 105                 110

Gln Ile Ser Val Glu Asp Ala Lys Ile Phe Gly Ala His Met Val Pro
            115                 120                 125

Lys Gln Thr Lys Leu Leu Arg Phe Val Val Asn Asp Gly Cys Arg Tyr
130                 135                 140

Gln Met Cys Val Met Lys Leu Glu Ser Trp Ala His Val Phe Arg Asp
145                 150                 155                 160

Tyr Ser Val Ser Phe Gln Val Arg Leu Thr Phe Thr Glu Ala Asn Asn
                165                 170                 175

Gln Thr Tyr Thr Phe Cys Thr His Pro Asn Leu Ile Val
                180                 185

<210> SEQ ID NO 78
<211> LENGTH: 214
<212> TYPE: PRT
<213> ORGANISM: Artificial Sequence
<220> FEATURE:
<223> OTHER INFORMATION: pUL130 Y204C mutant

<400> SEQUENCE: 78

Met Leu Arg Leu Leu Arg His His Phe His Cys Leu Leu Cys
1               5                   10                  15

Ala Val Trp Ala Thr Pro Cys Leu Ala Ser Pro Trp Ser Thr Leu Thr
                20                  25                  30

Ala Asn Gln Asn Pro Ser Pro Pro Trp Ser Lys Leu Thr Tyr Ser Lys
            35                  40                  45
```

```
Pro His Asp Ala Ala Thr Phe Tyr Cys Pro Phe Leu Tyr Pro Ser Pro
    50                  55                  60

Pro Arg Ser Pro Leu Gln Phe Ser Gly Phe Gln Arg Val Ser Thr Gly
 65                  70                  75                  80

Pro Glu Cys Arg Asn Glu Thr Leu Tyr Leu Leu Tyr Asn Arg Glu Gly
                 85                  90                  95

Gln Thr Leu Val Glu Arg Ser Ser Thr Trp Val Lys Lys Val Ile Trp
            100                 105                 110

Tyr Leu Ser Gly Arg Asn Gln Thr Ile Leu Gln Arg Met Pro Arg Thr
            115                 120                 125

Ala Ser Lys Pro Ser Asp Gly Asn Val Gln Ile Ser Val Glu Asp Ala
130                 135                 140

Lys Ile Phe Gly Ala His Met Val Pro Lys Gln Thr Lys Leu Leu Arg
145                 150                 155                 160

Phe Val Val Asn Asp Gly Thr Arg Tyr Gln Met Cys Val Met Lys Leu
                165                 170                 175

Glu Ser Trp Ala His Val Phe Arg Asp Tyr Ser Val Ser Phe Gln Val
            180                 185                 190

Arg Leu Thr Phe Thr Glu Ala Asn Asn Gln Thr Cys Thr Phe Cys Thr
            195                 200                 205

His Pro Asn Leu Ile Val
210

<210> SEQ ID NO 79
<211> LENGTH: 189
<212> TYPE: PRT
<213> ORGANISM: Artificial Sequence
<220> FEATURE:
<223> OTHER INFORMATION: mature pUL130 Y204C mutant

<400> SEQUENCE: 79

Ser Pro Trp Ser Thr Leu Thr Ala Asn Gln Asn Pro Ser Pro Pro Trp
 1               5                  10                  15

Ser Lys Leu Thr Tyr Ser Lys Pro His Asp Ala Ala Thr Phe Tyr Cys
            20                  25                  30

Pro Phe Leu Tyr Pro Ser Pro Arg Ser Pro Leu Gln Phe Ser Gly
            35                  40                  45

Phe Gln Arg Val Ser Thr Gly Pro Glu Cys Arg Asn Glu Thr Leu Tyr
 50                  55                  60

Leu Leu Tyr Asn Arg Glu Gly Gln Thr Leu Val Glu Arg Ser Ser Thr
 65                  70                  75                  80

Trp Val Lys Lys Val Ile Trp Tyr Leu Ser Gly Arg Asn Gln Thr Ile
                 85                  90                  95

Leu Gln Arg Met Pro Arg Thr Ala Ser Lys Pro Ser Asp Gly Asn Val
            100                 105                 110

Gln Ile Ser Val Glu Asp Ala Lys Ile Phe Gly Ala His Met Val Pro
            115                 120                 125

Lys Gln Thr Lys Leu Leu Arg Phe Val Val Asn Asp Gly Thr Arg Tyr
            130                 135                 140

Gln Met Cys Val Met Lys Leu Glu Ser Trp Ala His Val Phe Arg Asp
145                 150                 155                 160

Tyr Ser Val Ser Phe Gln Val Arg Leu Thr Phe Thr Glu Ala Asn Asn
                165                 170                 175

Gln Thr Cys Thr Phe Cys Thr His Pro Asn Leu Ile Val
            180                 185
```

<210> SEQ ID NO 80
<211> LENGTH: 129
<212> TYPE: PRT
<213> ORGANISM: Artificial Sequence
<220> FEATURE:
<223> OTHER INFORMATION: pUL131A Y52F and A67V mutant

<400> SEQUENCE: 80

```
Met Arg Leu Cys Arg Val Trp Leu Ser Val Cys Leu Cys Ala Val Val
1               5                   10                  15

Leu Gly Gln Cys Gln Arg Glu Thr Ala Glu Lys Asn Asp Tyr Tyr Arg
            20                  25                  30

Val Pro His Tyr Trp Asp Ala Cys Ser Arg Ala Leu Pro Asp Gln Thr
        35                  40                  45

Arg Tyr Lys Phe Val Glu Gln Leu Val Asp Leu Thr Leu Asn Tyr His
    50                  55                  60

Tyr Asp Val Ser His Gly Leu Asp Asn Phe Asp Val Leu Lys Arg Ile
65                  70                  75                  80

Asn Val Thr Glu Val Ser Leu Leu Ile Ser Asp Phe Arg Gln Asn
                85                  90                  95

Arg Arg Gly Gly Thr Asn Lys Arg Thr Thr Phe Asn Ala Ala Gly Ser
            100                 105                 110

Leu Ala Pro His Ala Arg Ser Leu Glu Phe Ser Val Arg Leu Phe Ala
        115                 120                 125

Asn
```

<210> SEQ ID NO 81
<211> LENGTH: 111
<212> TYPE: PRT
<213> ORGANISM: Artificial Sequence
<220> FEATURE:
<223> OTHER INFORMATION: mature pUL131A Y52F and A67V mutant

<400> SEQUENCE: 81

```
Gln Cys Gln Arg Glu Thr Ala Glu Lys Asn Asp Tyr Tyr Arg Val Pro
1               5                   10                  15

His Tyr Trp Asp Ala Cys Ser Arg Ala Leu Pro Asp Gln Thr Arg Tyr
            20                  25                  30

Lys Phe Val Glu Gln Leu Val Asp Leu Thr Leu Asn Tyr His Tyr Asp
        35                  40                  45

Val Ser His Gly Leu Asp Asn Phe Asp Val Leu Lys Arg Ile Asn Val
    50                  55                  60

Thr Glu Val Ser Leu Leu Ile Ser Asp Phe Arg Gln Asn Arg Arg
65                  70                  75                  80

Gly Gly Thr Asn Lys Arg Thr Thr Phe Asn Ala Ala Gly Ser Leu Ala
                85                  90                  95

Pro His Ala Arg Ser Leu Glu Phe Ser Val Arg Leu Phe Ala Asn
            100                 105                 110
```

<210> SEQ ID NO 82
<211> LENGTH: 129
<212> TYPE: PRT
<213> ORGANISM: Artificial Sequence
<220> FEATURE:
<223> OTHER INFORMATION: pUL131A S86F mutant

<400> SEQUENCE: 82

```
Met Arg Leu Cys Arg Val Trp Leu Ser Val Cys Leu Cys Ala Val Val
1               5                   10                  15
```

-continued

```
Leu Gly Gln Cys Gln Arg Glu Thr Ala Glu Lys Asn Asp Tyr Tyr Arg
            20                  25                  30
Val Pro His Tyr Trp Asp Ala Cys Ser Arg Ala Leu Pro Asp Gln Thr
        35                  40                  45
Arg Tyr Lys Tyr Val Glu Gln Leu Val Asp Leu Thr Leu Asn Tyr His
     50                  55                  60
Tyr Asp Ala Ser His Gly Leu Asp Asn Phe Asp Val Leu Lys Arg Ile
 65                  70                  75                  80
Asn Val Thr Glu Val Phe Leu Leu Ile Ser Asp Phe Arg Arg Gln Asn
                85                  90                  95
Arg Arg Gly Gly Thr Asn Lys Arg Thr Thr Phe Asn Ala Ala Gly Ser
            100                 105                 110
Leu Ala Pro His Ala Arg Ser Leu Glu Phe Ser Val Arg Leu Phe Ala
        115                 120                 125
Asn

<210> SEQ ID NO 83
<211> LENGTH: 111
<212> TYPE: PRT
<213> ORGANISM: Artificial Sequence
<220> FEATURE:
<223> OTHER INFORMATION: mature pUL131A S86F mutant

<400> SEQUENCE: 83

Gln Cys Gln Arg Glu Thr Ala Glu Lys Asn Asp Tyr Tyr Arg Val Pro
  1               5                  10                  15
His Tyr Trp Asp Ala Cys Ser Arg Ala Leu Pro Asp Gln Thr Arg Tyr
            20                  25                  30
Lys Tyr Val Glu Gln Leu Val Asp Leu Thr Leu Asn Tyr His Tyr Asp
        35                  40                  45
Ala Ser His Gly Leu Asp Asn Phe Asp Val Leu Lys Arg Ile Asn Val
     50                  55                  60
Thr Glu Val Phe Leu Leu Ile Ser Asp Phe Arg Arg Gln Asn Arg Arg
 65                  70                  75                  80
Gly Gly Thr Asn Lys Arg Thr Thr Phe Asn Ala Ala Gly Ser Leu Ala
                85                  90                  95
Pro His Ala Arg Ser Leu Glu Phe Ser Val Arg Leu Phe Ala Asn
            100                 105                 110
```

MODIFIED CYTOMEGALOVIRUS PROTEINS AND STABILIZED COMPLEXES

SEQUENCE LISTING

The instant application contains an electronically submitted Sequence Listing in ASCII text file format (Name: VU66664-1_US_SeqLstg_ST25.txt; Size: 195,587 bytes; and Date of Creation: Apr. 1, 2021) which is hereby incorporated by reference in its entirety.

DISCLOSURE(S) BY AN INVENTOR OR JOINT INVENTOR

An inventor, the inventors, or another who obtained the subject matter from the inventor(s), have disclosed Chandramouli et al., 2017 Science Immunology 2(12): eaan1457, Protein Data Bank (PDB) ID 5VOB, and international patent application PCT/IB2018/000491 filed Apr. 18, 2018.

FIELD OF THE INVENTION

This invention is in the field of vaccination against human cytomegalovirus (HCMV) and in particular provides mutant gH, gL, pUL128, pUL130, and pUL131A polypeptides as well as a stabilized HCMV complex comprising two or more of gH, gL, pUL128, pUL130, and pUL131A polypeptides wherein at least one of the two polypeptides is mutant, and their use in an immunogenic composition or vaccine composition.

BACKGROUND TO THE INVENTION

Cytomegalovirus (CMV) is a genus of virus that belongs to the viral family known as Herpesviridae or herpesviruses. The species that infects humans is commonly known as HCMV or human herpesvirus-5 (HHV-5). Within Herpesviridae, HCMV belongs to the Betaherpesvirinae subfamily, which also includes cytomegaloviruses from other mammals.

Although they may be found throughout the body, HCMV infections are frequently associated with the salivary glands. HCMV infects between 50% and 80% of adults in the United States (40% worldwide), as indicated by the presence of antibodies in much of the general population. HCMV infection is typically unnoticed in healthy people, but can be life-threatening for the immunocompromised, such as HIV-infected persons, organ transplant recipients, or new born infants (Mocarski et al., Cytomegalovirus in FIELDS VIROLOGY, eds. David M Knipe and Peter M Howley, Philadelphia, Pa., USA: Lippincott Williams and Wilkins, 2006). HCMV is the virus most frequently transmitted to a developing fetus. After infection, HCMV has an ability to remain latent within the body for the lifetime of the host, with occasional reactivations from latency.

HCMV seems to have a large impact on immune parameters in later life and may contribute to increased morbidity and eventual mortality (Simanek et al., *Seropositivity to Cytomegalovirus, Inflammation, All-Cause and Cardiovascular Disease-Related Mortality in the United States*, 2011 PLoS ONE 6: e16103).

To date, the genomes of over 20 different HCMV strains have been sequenced, including those of both laboratory strains and clinical isolates. For example, the following strains of HCMV have been sequenced: Towne (NCBI GenInfo (GI) identifier 239909366), AD169 (GI: 219879600), Toledo (GI:290564358) and Merlin (GI: 155573956). HCMV strains AD169, Towne and Merlin can be obtained from the American Type Culture Collection (ATCC VR538, ATCC VR977 and ATCC VR1590, respectively).

HCMV contains an unknown number of membrane protein complexes. Of the known glycoproteins in the viral envelope, gH and gL have emerged as particularly interesting due to their presence in several different complexes: dimeric gH/gL, trimeric gH/gL/gO (also known as the gCIII complex) and the pentameric gH/gL/pUL128/pUL130/pUL131A (the latter protein is also referred to as pUL131). HCMV is thought to use the pentameric complexes to enter epithelial and endothelial cells by endocytosis and low-pH-dependent fusion but it is thought to enter fibroblasts by direct fusion at the plasma membrane in a process involving gH/gL or possibly gH/gL/gO. The gH/gL and/or gH/gL/gO complex(es) is/are sufficient for fibroblast infection, whereas the pentameric complex is required to infect endothelial and epithelial cells (Ryckman, B J, et al., *Characterization of the Human Cytomegalovirus gH/gL/UL128-131 Complex That Mediates Entry into Epithelial and Endothelial Cells*, 2008 J. Virol. 82: 60-70).

The pentameric complex is considered as a major target for CMV vaccination. Viral genes UL128, UL130 and UL131 are needed for endothelial entry (Hahn et al., *Human Cytomegalovirus UL131-128 Genes are Indispensable for Virus Growth in Endothelial Cells and Virus Transfer of Leukocytes*, 2004 Journal of Virology 78(18): 10023-10033). Fibroblast-adapted non-endothelial tropic strains contain mutations in at least one of these three genes. Towne strain, for example, contains a two base pair insertion causing a frame shift in UL130 gene, whereas AD169 contains a one base pair insertion in UL131 gene. Both Towne and AD169 could be adapted for growth in endothelial cells, and in both instances, the frame shift mutations in UL130 or UL131 genes were repaired.

Genini et al. (*Serum antibody response to the gH/gL/pUL128-131 five-protein complex of human cytomegalovirus (HCMV) in primary and reactivated HCMV infections*, 2011 J. Clin. Vir. 52: 113-118.) discloses a serum antibody response to the pentameric complex of HCMV in primary and reactivated HCMV infections. The response was determined by both indirect immunofluorescence (IFA) and ELISA, using fixed or lysed epithelial (ARPE-19) cells infected with one or more adenoviral vectors, each carrying one HCMV gene and, in parallel, with a control adenovirus vector. The specificity of results was determined by the reactivity of human neutralizing monoclonal antibodies recognizing two, three, or four proteins of the complex. In 14 cases of primary infection, an IgG antibody seroconversion to the UL128-131 gene product was consistently detected within 2-4 weeks after onset of infection, while antibodies persisted for at least 12 months. The IgG antibody response to UL128-131 gene products was generally superior to the response to gH and appeared to follow the neutralizing antibody response (as determined in epithelial cells). In reactivated infections, the antibody response showed a trend reminiscent of a booster response. IgG antibodies were detected in HCMV-seropositive healthy adult controls, but not in HCMV-seronegative individuals.

Kinzler et al. (*Expression and reconstitution of the gH/gL/gO complex of human cytomegalovirus*, 2002 J. Clin. Vir. 25(Supp.2): 87-95) co-expressed gH, gL, and gO in insect cells using a recombinant baculovirus, but were unable to produce the gH/gL/gO tripartite complex. Instead, only gH/gL heterodimers, gH/gL heteromultimers, and gO homomultimers were detected. In contrast, co-expression of gH, gL, and gO in mammalian cells produced high molecular weight complexes that closely resemble gH/gL/gO complexes formed in HCMV infected cells. Cell surface immunofluorescence showed that these complexes are expressed and displayed on the surface of transfected cells.

U.S. Pat. No. 7,704,510 discloses that pUL131A is required for epithelial cell tropism; that pUL128 and pUL130 form a complex with gH/gL, which is incorporated into virions, and that this complex is required to infect endothelial and epithelial cells but not fibroblasts. Also, anti-CD46 antibodies were found to inhibit HCMV infection of epithelial cells.

WO 2014/005959 (also published as U.S. Pre-grant Pub. No. 2016-0159864) discloses a purified HCMV pentameric complex comprising the polypeptides gH, gL, pUL128, pUL130 and pUL131A and its use in an immunogenic composition or a vaccine.

Generally, there exists an inverse relationship between the flexibility of a protein from a mesophilic organism and the thermostability of that protein as was recently shown for the Lipase A enzyme from the mesophilic organism *Bacillus subtilis* (see Rathi et al., *Structural rigidity and protein thermostability in variants of Lipase A from Bacillus subtilis*, 2015 PLOS ONE 19(7): e0130289; DOI: 10.1371/journal.pone.0130289; 24 pages). Increased stability of antigens has been previously linked with improved immunogenicity such as, for example, for the pre-fusion conformation of the respiratory syncytial virus fusion protein (McLellan et al., *Structure-Based Design of a Fusion Glycoprotein Vaccine for Respiratory Syncytial Virus*, 2013 Science 342 (6158): 592-598.) and the *Neisseria meningitidis* factor H binding protein (fHbp) (Rossi et al., *Meningococcal Factor H Binding Protein Vaccine Antigens with Increased Thermal Stability and Decreased Binding of Human Factor H*, 2016 Infect. Immun. 84(6): 1735-1742.).

It is expected that an improved thermostability of an HCMV complex such as the pentamer complex will have the following advantages: (i) facilitate its preparation and production, and (ii) have an impact on its use as an antigen, providing a better immunogenicity. Therefore, there is a need for developing an HCMV complex, specifically a pentameric complex, having an enhanced thermostability for suitable use in an immunogenic composition or a vaccine. Further, a glycan in close proximity to a neutralizing epitope on an HCMV complex is believed to limit the accessibility of the epitope. Therefore, there is a need for developing a deglycosylated HCMV complex, specifically a pentameric complex, having more accessible epitopes (optionally also having an enhanced thermostability) that is suitable for use in an immunogenic composition or vaccine.

SUMMARY OF THE INVENTION

This invention is based on the recombinant expression of a stabilized HCMV complex (e.g., a gH/gL, gH/gL/gO, or gH/gL/UL128/UL130/pUL131A complex) comprising two or more of gH, gL, pUL128, pUL130, and pUL131A polypeptides wherein at least one of the two polypeptides is mutant, and its use in an immunogenic composition or vaccine composition. Methods of making and using them are provided. The mutant polypeptides and the nucleic acid molecules encoding them, as well as antibodies, expression vectors, and host cells are also provided.

In one aspect of the invention, there is provided an HCMV gH polypeptide, or a complex-forming fragment thereof, comprising one or more stabilizing mutations. In another aspect of the invention, there is provided an HCMV gL polypeptide, or a complex-forming fragment thereof, comprising one or more stabilizing mutations. In a further aspect of the invention, there is provided an HCMV pUL128 polypeptide, or a complex-forming fragment thereof, comprising one or more stabilizing mutations. In a further aspect of the invention, there is provided an HCMV pUL130 polypeptide, or a complex-forming fragment thereof, comprising one or more stabilizing mutations. In a further aspect of the invention, there is provided an HCMV pUL131A polypeptide, or a complex-forming fragment thereof, comprising one or more stabilizing mutations.

In a further aspect of the invention, there is provided a pentameric complex of HCMV polypeptides comprising a gH polypeptide, a gL polypeptide, a pUL128 polypeptide, a pUL130 polypeptide and a pUL131A polypeptide, wherein at least one polypeptide comprises one or more amino acid stabilizing mutations. In a further aspect of the invention, that pentameric complex has an increased stability as compared to a non-mutant pentameric complex. In a further aspect of the invention, there is provided an immunogenic composition comprising that pentameric complex of HCMV polypeptides.

In a further aspect of the invention, there is provided a gH/gL complex of HCMV polypeptides comprising a gH polypeptide and a gL polypeptide wherein at least one of the polypeptides comprises one or more stabilizing mutations. In a further aspect of the invention, that gH/gL complex has an increased stability as compared to a non-mutant gH/gL complex. In a further aspect of the invention, there is provided an immunogenic composition comprising that gH/gL complex of HCMV polypeptides.

In a further aspect of the invention, there is provided a gH/gL/gO complex of HCMV polypeptides comprising a gH polypeptide, a gL polypeptide, and a gO polypeptide, wherein at least one of the gH and gL polypeptides comprise one or more amino acid stabilizing mutations. In a further aspect of the invention, that gH/gL/gO complex has an increased stability as compared to a non-mutant gH/gL/gO complex. In a further aspect of the invention, there is provided an immunogenic composition comprising that gH/gL/gO complex of HCMV polypeptides.

In a further aspect of the invention, the complexes of the invention are produced at high yields. For example, in processes involving growing host cells of the invention in growth medium, the protein complex of the invention may accumulate to a level of more than 0.4 mg per litre of growth medium (e.g. 0.45, 0.5, 0.55, 0.6, 0.65, 0.7, 0.75, 0.8, 0.85, 0.9, 0.95, 1.0, 1.2, 1.4, 1.6, 1.8, 2, 2.5, 3, 3.5, 4, 4.5 or 5 mg per litre of growth medium or more).

The present invention provides the following:

Embodiment 1. A HCMV gH polypeptide, or a complex-forming fragment thereof, comprising one or more stabilizing mutations.

Embodiment 2. The HCMV gH polypeptide, or complex-forming fragment thereof, of embodiment 1, wherein said stabilizing mutations comprise one or more cavity-filling mutations, one or more hydrophobic mutations, one or more hydrophilic mutations, one or more disulphide bridge mutations, one or more deglycosylation mutations, or a combination of one or more thereof.

Embodiment 3. The HCMV gH polypeptide, or complex-forming fragment thereof, of embodiment 1 or 2, wherein the stabilizing mutations comprise one or more cavity-filling mutations.

Embodiment 4. The HCMV gH polypeptide, or complex-forming fragment thereof, of embodiment 3, wherein one or more of the amino acid residues A102, A372, A352, and L257, relative to the sequence set forth in SEQ ID NO: 1, or at a corresponding position in other HCMV gH polypeptides, are substituted with an amino acid selected from the group consisting of tryptophan (W), phenylalanine (F), tyrosine (Y), and leucine (L).

Embodiment 5. The HCMV gH polypeptide of any of embodiments 1 to 4, wherein the stabilizing mutations comprise one or more hydrophobic mutations.

Embodiment 6. The HCMV gH polypeptide, or complex-forming fragment thereof, of embodiment 5, wherein one or more of the amino acid residues H252, K404, R255, E355, H480, 5601, and R405, relative to the sequence set forth in SEQ ID NO: 1, or at a corresponding position in other HCMV gH polypeptides, are substituted with an amino acid selected from the group consisting of tryptophan (W), phenylalanine (F), methionine (M), cysteine (C), alanine (A), leucine (L), isoleucine (I), valine (V) and proline (P).

Embodiment 7. The HCMV gH polypeptide of any of embodiments 1 to 6, or complex-forming fragment thereof, wherein the stabilizing mutations comprise one or more hydrophilic mutations.

Embodiment 8. The HCMV gH polypeptide, or complex-forming fragment thereof, of embodiment 7, wherein one or more of the amino acid residues G358 and H275 are substituted with an amino acid selected from the group consisting of serine (S), threonine (T), cysteine (C), tyrosine (Y), asparagine (N) glutamine (Q), arginine (R), glutamic acid (E), lysine (K), histidine (H), and aspartic acid (D).

Embodiment 9. The HCMV gH polypeptide, or a complex-forming fragment thereof, of any of embodiments 1 to 8, wherein the stabilizing mutations comprise one or more disulfide bridge mutations.

Embodiment 10. The HCMV gH polypeptide, or complex-forming fragment thereof, of embodiment 9, wherein amino acid residues V109 and/or L111 are substituted with a cysteine (C).

Embodiment 11. The HCMV gH polypeptide, or a complex-forming fragment thereof, of any of embodiments 1 to 10, wherein the stabilizing mutations comprise one or more deglycosylation mutations.

Embodiment 12. The HCMV gH polypeptide, or complex-forming fragment thereof, of embodiment 11, wherein one or more of the amino acid residues N55, N62, N67, N192, N641, and N700 are substituted with an amino acid selected from the group consisting of glutamine (Q), serine (S), threonine (T), alanine (A), glutamate (E), and aspartate (D).

Embodiment 13. An HCMV gH polypeptide comprising an amino acid sequence, wherein (a) the sequence is at least 90% identical to SEQ ID NO: 1, and (b) one or more of the amino acid residues A102, A372, A352, and L257 are substituted with an amino acid selected from the group consisting of tryptophan (W), phenylalanine (F), tyrosine (Y), and leucine (L).

Embodiment 14. An HCMV gH polypeptide comprising an amino acid sequence, wherein (a) the sequence is at least 90% identical to SEQ ID NO: 1, and (b) one or more of the amino acid residues H252, K404, R255, E355, H480, 5601, and R405 are substituted with an amino acid selected from the group consisting of tryptophan (W), phenylalanine (F), methionine (M), cysteine (C), alanine (A), leucine (L), isoleucine (I), valine (V) and proline (P).

Embodiment 15. An HCMV gH polypeptide comprising an amino acid sequence, wherein (a) the sequence is at least 90% identical to SEQ ID NO: 1, and (b) one or more of the amino acid residues G358 and H327 are substituted with an amino acid selected from the group consisting of serine (S), threonine (T), cysteine (C), tyrosine (Y), asparagine (N), glutamine (Q), arginine (R), glutamic acid (E), lysine (K), histidine (H), and aspartic acid (D).

Embodiment 16. An HCMV gH polypeptide comprising an amino acid sequence, wherein (a) the sequence is at least 90% identical to SEQ ID NO: 1, and (b) amino acid residues V109 and/or L11 are substituted with a cysteine (C).

Embodiment 17. An HCMV gH polypeptide comprising an amino acid sequence, wherein (a) the sequence is at least 90% identical to SEQ ID NO: 1, and (b) one or more of the amino acid residues N55, N62, N67, N192, N641, and N700 are substituted with an amino acid selected from the group consisting of glutamine (Q), serine (S), threonine (T), alanine (A), glutamate (E), and aspartate (D).

Embodiment 18. An HCMV gH polypeptide comprising the amino acid sequence SEQ ID NO: 1, or a complex-forming fragment thereof, further comprising a substitution of one or more of the amino acid residues A102, A372, A352, and L257 with an amino acid selected from the group consisting of tryptophan (W), phenylalanine (F), tyrosine (Y), and leucine (L).

Embodiment 19. An HCMV gH polypeptide comprising the amino acid sequence SEQ ID NO: 1, or a complex-forming fragment thereof, further comprising a substitution of one or more of the amino acid residues H252, K404, R255, E355, H480, 5601, and R405 with an amino acid selected from the group consisting of tryptophan (W), phenylalanine (F), methionine (M), cysteine (C), alanine (A), leucine (L), isoleucine (I), valine (V) and proline (P).

Embodiment 20. An HCMV gH polypeptide comprising the amino acid sequence SEQ ID NO: 1, or a complex-forming fragment thereof, further comprising a substitution of one or more of the amino acid residues G358 and H327 with an amino acid selected from the group consisting of serine (S), threonine (T), cysteine (C), tyrosine (Y), asparagine (N), glutamine (Q), arginine (R), glutamic acid (E), lysine (K), histidine (H), and aspartic acid (D).

Embodiment 21. An HCMV gH polypeptide comprising the amino acid sequence SEQ ID NO: 1, or a complex-forming fragment thereof, further comprising a substitution of amino acid residues V109 and/or L11 with a cysteine (C).

Embodiment 22. An HCMV gH polypeptide comprising the amino acid sequence SEQ ID NO: 1, or a complex-forming fragment thereof, further comprising a substitution of one or more of the amino acid residues N55, N62, N67, N192, N641, and N700 with an amino acid selected from the group consisting of glutamine (Q), serine (S), threonine (T), alanine (A), glutamate (E), and aspartate (D).

Embodiment 23. A nucleic acid molecule encoding the HCMV gH polypeptide, or a complex-forming fragment thereof, of any of embodiments 1-22.

Embodiment 24. An HCMV gL polypeptide, or a complex-forming fragment thereof, comprising one or more stabilizing mutations.

Embodiment 25. The HCMV gL polypeptide, or complex-forming fragment thereof, of embodiment 24, wherein said stabilizing mutations comprise one or more cavity-filling mutations, one or more hydrophobic mutations, one or more hydrophilic mutations, one or more disulphide bridge mutations, one or more deglycosylation mutations, or a combination thereof.

Embodiment 26. The HCMV gL polypeptide, or complex-forming fragment thereof, of embodiment 25, wherein the stabilizing mutations comprise one or more cavity-filling mutations.

Embodiment 27. The HCMV gL polypeptide, or complex-forming fragment thereof, of embodiment 26, wherein one or more of the amino acid residues H177, G224, G140, G145, D146, G218, L119, C233 and P272, relative to the sequence set forth in SEQ ID NO: 7, or at a corresponding position in other HCMV gL polypeptides, are substituted with an amino acid selected from the group consisting of tryptophan (W), phenylalanine (F), tyrosine (Y), and leucine (L).

Embodiment 28. The HCMV gL polypeptide of any of embodiments 24 to 27, wherein the stabilizing mutations comprise one or more hydrophobic mutations.

Embodiment 29. The HCMV gL polypeptide, or complex-forming fragment thereof, of embodiment 28, wherein one or more of the amino acid residues H267, H236, H245, G161, and C233 relative to the sequence set forth in SEQ ID NO: 7, or at a corresponding position in other HCMV gL polypeptides, are substituted with an amino acid selected from the group consisting of tryptophan (W), phenylalanine (F), methionine (M), cysteine (C), alanine (A), leucine (L), isoleucine (I), valine (V) and proline (P).

Embodiment 30. The HCMV gL polypeptide, or a complex-forming fragment thereof, of any of embodiments 24 to 29, wherein the stabilizing mutations comprise one or more disulfide bridge mutations.

Embodiment 31. The HCMV gL polypeptide, or complex-forming fragment thereof, of embodiment 30, wherein one or more of amino acid residues G161, D163, G224, G218, R166, G140, R160, and A150 are substituted with a cysteine (C).

Embodiment 32. The HCMV gL polypeptide, or a complex-forming fragment thereof, of any of embodiments 24 to 31, wherein the stabilizing mutations comprise one or more deglycosylation mutations.

Embodiment 33. The HCMV gL polypeptide, or complex-forming fragment thereof, of embodiment 32, wherein N74 is substituted with an amino acid selected from the group consisting of glutamine (Q), serine (S), threonine (T), alanine (A), glutamate (E), and aspartate (D).

Embodiment 34. An HCMV gL polypeptide comprising an amino acid sequence, wherein (a) the sequence is at least 90% identical to SEQ ID NO: 5, and (b) one or more of the amino acid residues H177, G224, G140, G145, D146, G218, L119, C233 and P272 are substituted with an amino acid selected from the group consisting of tryptophan (W), phenylalanine (F), tyrosine (Y), and leucine (L).

Embodiment 35. An HCMV gL polypeptide comprising an amino acid sequence, wherein (a) the sequence is at least 90% identical to SEQ ID NO: 7, but (b) one or more of the amino acid residues H267, H236, H245, G161, and C233 are substituted with an amino acid selected from the group consisting of tryptophan (W), phenylalanine (F), methionine (M), cysteine (C), alanine (A), leucine (L), isoleucine (I), valine (V) and proline (P).

Embodiment 36. An HCMV gL polypeptide comprising an amino acid sequence, wherein (a) the sequence is at least 90% identical to SEQ ID NO: 7, and (b) wherein one or more amino acid residues G161, D163, G224, G218, R166, G140, R160, and A150 are substituted with a cysteine (C).

Embodiment 37. An HCMV gL polypeptide comprising an amino acid sequence, wherein (a) the sequence is at least 90% identical to SEQ ID NO: 7, and (b) wherein the amino acid residue N74 is substituted with an amino acid selected from the group consisting of glutamine (Q), serine (S), threonine (T), alanine (A), glutamate (E), and aspartate (D).

Embodiment 38. An HCMV gL polypeptide comprising the amino acid sequence SEQ ID NO: 7, or a complex-forming fragment thereof, further comprising a substitution of one or more of the amino acid residues H177, G224, G140, G145, D146, G218, L119, C233 and P272 with an amino acid selected from the group consisting of tryptophan (W), phenylalanine (F), tyrosine (Y), and leucine (L).

Embodiment 39. An HCMV gL polypeptide comprising the amino acid sequence SEQ ID NO: 7, or a complex-forming fragment thereof, further comprising a substitution of one or more of the amino acid residues H267, H236, H245, G161, and C233 with an amino acid selected from the group consisting of tryptophan (W), phenylalanine (F), methionine (M), cysteine (C), alanine (A), leucine (L), isoleucine (I), valine (V) and proline (P).

Embodiment 40. An HCMV gL polypeptide comprising the amino acid sequence SEQ ID NO: 7, or a complex-forming fragment thereof, further comprising a substitution of one or more amino acid residues G161, D163, G224, G218, R166, G140, R160, and A150 with a cysteine (C).

Embodiment 41. An HCMV gL polypeptide comprising the amino acid sequence SEQ ID NO: 7, or a complex-forming fragment thereof, further comprising a substitution of residue N74 with an amino acid selected from the group consisting of glutamine (Q), serine (S), threonine (T), alanine (A), glutamate (E), and aspartate (D).

Embodiment 42. A nucleic acid molecule encoding the HCMV gL polypeptide, or a complex-forming fragment thereof, of any of embodiments 24 to 41.

Embodiment 43. An HCMV pUL128 polypeptide, or a complex-forming fragment thereof, comprising one or more stabilizing mutations.

Embodiment 44. The HCMV pUL128 polypeptide, or complex-forming fragment thereof, of embodiment 43, wherein said stabilizing mutations comprise one or more cavity-filling mutations, one or more hydrophobic mutations, one or more hydrophilic mutations, one or more disulphide bridge mutations, or a combination of one or more thereof.

Embodiment 45. The HCMV pUL128 polypeptide, or complex-forming fragment thereof, of embodiment 40, wherein said stabilizing mutations comprise one or more cavity-filling mutations.

Embodiment 46. The HCMV pUL128 polypeptide, or complex-forming fragment thereof, of embodiment 45, wherein one or more of the amino acid residues G123, V77, L103 and Q119, relative to the sequence set forth in SEQ ID NO: 13, or at a corresponding position in other HCMV pUL128 polypeptides, are substituted with an amino acid selected from the group consisting of tryptophan (W), phenylalanine (F), tyrosine (Y), and leucine (L).

Embodiment 47. The HCMV pUL128 polypeptide of any of embodiments 43 to 46, wherein the stabilizing mutations comprise one or more hydrophobic mutations.

Embodiment 48. The HCMV pUL128 polypeptide, or complex-forming fragment thereof, of embodiment 47, wherein one or more of the amino acid residues G145, H90 and G112, relative to the sequence set forth in SEQ ID NO: 13, or at a corresponding position in other HCMV pUL128 polypeptides, are substituted with an amino acid selected from the group consisting of tryptophan (W), phenylalanine (F), methionine (M), cysteine (C), alanine (A), leucine (L), isoleucine (I), valine (V) and proline (P).

Embodiment 49. The HCMV pUL128 polypeptide, or a complex-forming fragment thereof, of any of embodiments 43 to 48, wherein the stabilizing mutations comprise one or more disulfide bridge mutations.

Embodiment 50. The HCMV pUL128 polypeptide, or complex-forming fragment thereof, of embodiment 49, wherein one or more of the amino acid residues R142, N99, Y98, A124, G126, L159, D45, V88, M48, G107, R51, D106, and S83 are substituted with a cysteine (C).

Embodiment 51. An HCMV pUL128 polypeptide comprising an amino acid sequence, wherein (a) the sequence is at least 90% identical to SEQ ID NO: 13, and (b) one or more of the amino acid residues G123, V77, L103 and Q119 are substituted with an amino acid selected from the group consisting of tryptophan (W), phenylalanine (F), tyrosine (Y), and leucine (L).

Embodiment 52. An HCMV pUL128 polypeptide comprising an amino acid sequence, wherein (a) the sequence is at least 90% identical to SEQ ID NO: 13, and (b) one or more of the amino acid residues G145, H90 and G112 are substituted with an amino acid selected from the group consisting of tryptophan (W), phenylalanine (F), methionine (M), cysteine (C), alanine (A), leucine (L), isoleucine (I), valine (V) and proline (P).

Embodiment 53. An HCMV pUL128 polypeptide comprising an amino acid sequence, wherein (a) the sequence is at least 90% identical to SEQ ID NO: 13, and (b) wherein one or more of the amino acid residues R142, N99, Y98, A124, G126, L159, D45, V88, M48, G107, R51, D106, and S83 are substituted with a cysteine (C).

Embodiment 54. An HCMV pUL128 polypeptide comprising the amino acid sequence SEQ ID NO: 13, or a complex-forming fragment thereof, further comprising a substitution of one or more of the amino acid residues G123, V77, L103 and Q119 with an amino acid selected from the group consisting of tryptophan (W), phenylalanine (F), tyrosine (Y), and leucine (L).

Embodiment 55. An HCMV pUL128 polypeptide comprising the amino acid sequence SEQ ID NO: 13, or a complex-forming fragment thereof, further comprising a substitution of one or more of the amino acid residues G145, H90 and G112 with an amino acid selected from the group consisting of tryptophan (W), phenylalanine (F), methionine (M), cysteine (C), alanine (A), leucine (L), isoleucine (I), valine (V) and proline (P).

Embodiment 56. An HCMV pUL128 polypeptide comprising the amino acid sequence SEQ ID NO: 13, or a complex-forming fragment thereof, further comprising a substitution of one or more of the amino acid residues R142, N99, Y98, A124, G126, L159, D45, V88, M48, G107, R51, D106, and S83 with a cysteine (C).

Embodiment 57. A nucleic acid molecule encoding the HCMV pUL128 polypeptide, or a complex-forming fragment thereof, of any of embodiments 43 to 56.

Embodiment 58. An HCMV pUL130 polypeptide, or a complex-forming fragment thereof, comprising one or more stabilizing mutations.

Embodiment 59. The HCMV pUL130 polypeptide, or complex-forming fragment thereof, of embodiment 58, wherein said stabilizing mutations comprise one or more cavity-filling mutations, one or more hydrophobic mutations, one or more hydrophilic mutations, one or more disulphide bridge mutations, one or more deglycosylation mutations, or a combination of one or more thereof.

Embodiment 60. The HCMV pUL130 polypeptide of embodiment 59, wherein the stabilizing mutations comprise one or more cavity-filling mutations.

Embodiment 61. The HCMV pUL130 polypeptide, or complex-forming fragment thereof, of embodiment 60, wherein one or more of the amino acid residues D165 and H209, relative to the sequence set forth in SEQ ID NO: 17, or at a corresponding position in other HCMV pUL130 polypeptides, are substituted with an amino acid selected from the group consisting of tryptophan (W), phenylalanine (F), tyrosine (Y), and leucine (L).

Embodiment 62. The HCMV pUL130 polypeptide of any of embodiments 58 to 61, wherein the stabilizing mutations comprise one or more hydrophobic mutations.

Embodiment 63. The HCMV pUL130 polypeptide, or complex-forming fragment thereof, of embodiment 62, wherein one or more of the amino acid residues G116, G135, H150, and H209, relative to the sequence set forth in SEQ ID NO: 17, or at a corresponding position in other HCMV pUL130 polypeptides, are substituted with an amino acid selected from the group consisting of tryptophan (W), phenylalanine (F), methionine (M), cysteine (C), alanine (A), leucine (L), isoleucine (I), valine (V) and proline (P).

Embodiment 64. The HCMV pUL130 polypeptide of any of embodiments 54 to 63, wherein the stabilizing mutations comprise one or more disulfide bridge mutations.

Embodiment 65. The HCMV pUL130 polypeptide, or complex-forming fragment thereof, of embodiment 64, wherein one or more of the amino acid residues G116, H150, P64, S178, P62, E95, Y204, N211, I213, Y56, and T167, relative to the sequence set forth in SEQ ID NO: 17, or at a corresponding position in other HCMV pUL130 polypeptides, are substituted with a cysteine (C).

Embodiment 66. The HCMV pUL130 polypeptide of any of embodiments 54 to 65, wherein the stabilizing mutations comprise one or more deglycosylation mutations.

Embodiment 67. The HCMV pUL130 polypeptide, or complex-forming fragment thereof, of embodiment 66, wherein one or more of the amino acid residues N85, N118, and N201, relative to the sequence set forth in SEQ ID NO: 17, or at a corresponding position in other HCMV pUL130 polypeptides, are substituted with an amino acid selected from the group consisting of glutamine (Q), serine (S), threonine (T), alanine (A), glutamate (E), and aspartate (D).

Embodiment 68. An HCMV pUL130 polypeptide comprising an amino acid sequence, wherein (a) the sequence is at least 90% identical to SEQ ID NO: 17, and (b) one or more of the amino acid residues D165 and H209 are substituted with an amino acid selected from the group consisting of tryptophan (W), phenylalanine (F), tyrosine (Y), and leucine (L).

Embodiment 69. An HCMV pUL130 polypeptide comprising an amino acid sequence, wherein (a) the sequence is at least 90% identical to SEQ ID NO: 17, and (b) one or more of the amino acid residues G116, G135, H150, and H209 are substituted with an amino acid selected from the group consisting of tryptophan (W), phenylalanine (F), methionine (M), cysteine (C), alanine (A), leucine (L), isoleucine (I), valine (V), and proline (P).

Embodiment 70. An HCMV pUL130 polypeptide comprising an amino acid sequence, wherein (a) the sequence is at least 90% identical to SEQ ID NO: 17, and (b) wherein one or more of the amino acid residues G116, H150, P64, 5178, P62, E95, Y204, N211, 1213, Y56, and T167 are substituted with a cysteine (C).

Embodiment 71. An HCMV pUL130 polypeptide comprising an amino acid sequence, wherein (a) the sequence is at least 90% identical to SEQ ID NO: 17, and (b) one or more of the amino acid residues N85, N118, and N201 are substituted with an amino acid selected from the group consisting of glutamine (Q), serine (S), threonine (T), alanine (A), glutamate (E), and aspartate (D).

Embodiment 72. An HCMV pUL130 polypeptide comprising the amino acid sequence SEQ ID NO: 17, or a complex-forming fragment thereof, further comprising a substitution of one or more of the amino acid residues D165 and H209 with an amino acid selected from the group consisting of tryptophan (W), phenylalanine (F), tyrosine (Y), and leucine (L).

Embodiment 73. An HCMV pUL130 polypeptide comprising the amino acid sequence SEQ ID NO: 17, or a complex-forming fragment thereof, further comprising a substitution of one or more of the amino acid residues G116, G135, H150, and H209 with an amino acid selected from the group consisting of tryptophan (W), phenylalanine (F), methionine (M), cysteine (C), alanine (A), leucine (L), isoleucine (I), valine (V) and proline (P).

Embodiment 74. An HCMV pUL130 polypeptide comprising the amino acid sequence SEQ ID NO: 17, or a complex-forming fragment thereof, further comprising a substitution of one or more of the amino acid residues G116, H150, P64, 5178, P62, E95, Y204, N211, 1213, Y56, and T167 with a cysteine (C).

Embodiment 75. An HCMV pUL130 polypeptide comprising the amino acid sequence SEQ ID NO: 17, or a complex-forming fragment thereof, further comprising a substitution of one or more of the amino acid residues N85, N118, and N201 with an amino acid selected from the group consisting of glutamine (Q), serine (S), threonine (T), alanine (A), glutamate (E), and aspartate (D).

Embodiment 76. A nucleic acid molecule encoding the HCMV pUL130 polypeptide, or a complex-forming fragment thereof, of any of embodiments 58-75.

Embodiment 77. An HCMV pUL131A polypeptide, or a complex-forming fragment thereof, comprising one or more stabilizing mutations.

Embodiment 78. The HCMV pUL131A polypeptide, or complex-forming fragment thereof, of embodiment 77, wherein said stabilizing mutations comprise one or more cavity-filling mutations, one or more hydrophobic mutations, one or more hydrophilic mutations, one or more disulphide bridge mutations, one or more deglycosylation mutations or a combination of one or more thereof.

Embodiment 79. The HCMV pUL131A polypeptide, or a complex-forming fragment thereof, of embodiment 78, wherein the stabilizing mutations comprise one or more cavity-filling mutations.

Embodiment 80. The HCMV pUL131A polypeptide, or complex-forming fragment thereof, of embodiment 79, wherein one or more of the amino acid residues G99, S86 and S90, relative to the sequence set forth in SEQ ID NO: 21, or at a corresponding position in other HCMV pUL131A polypeptides, are substituted with an amino acid selected from the group consisting of tryptophan (W), phenylalanine (F), tyrosine (Y), and leucine (L).

Embodiment 81. The HCMV pUL131A polypeptide of any of embodiments 77 to 80, wherein the stabilizing mutations comprise one or more hydrophobic mutations.

Embodiment 82. The HCMV pUL131A polypeptide, or complex-forming fragment thereof, of embodiment 81, wherein one or more of the amino acid residues H69, H35, H64, D38, V85, Y52, and A67, relative to the sequence set forth in SEQ ID NO: 21, or at a corresponding position in other HCMV pUL131A polypeptides, are substituted with an amino acid selected from the group consisting of tryptophan (W), phenylalanine (F), methionine (M), cysteine (C), alanine (A), leucine (L), isoleucine (I), valine (V) and proline (P).

Embodiment 83. The HCMV pUL131A polypeptide of any of embodiments 77 to 82, or complex-forming fragment thereof, wherein the stabilizing mutations comprise one or more hydrophilic mutations.

Embodiment 84. The HCMV pUL131A polypeptide, or complex-forming fragment thereof, of embodiment 83, wherein the amino acid residue R118 is substituted with an amino acid selected from the group consisting of serine (S), threonine (T), cysteine (C), tyrosine (Y), asparagine (N), glutamine (Q), arginine (R), glutamic acid (E), lysine (K), histidine (H), and aspartic acid (D).

Embodiment 85. The HCMV pUL131A polypeptide, or a complex-forming fragment thereof, of any of embodiments 77 to 84, wherein the stabilizing mutations comprise one or more disulfide bridge mutations.

Embodiment 86. The HCMV pUL131A polypeptide, or complex-forming fragment thereof, of embodiment 85, wherein one or more of the amino acid residues H64 and W37, relative to the sequence set forth in SEQ ID NO: 21, or at a corresponding position in other HCMV pUL131A polypeptides, is substituted with a cysteine (C).

Embodiment 87. The HCMV pUL131A polypeptide, or a complex-forming fragment thereof, of any of embodiments 77 to 86, wherein the stabilizing mutations comprise one or more deglycosylation mutations.

Embodiment 88. The HCMV pUL131A polypeptide, or complex-forming fragment thereof, of embodiment 87, wherein the amino acid residue N81, relative to the sequence set forth in SEQ ID NO: 21, or at a corresponding position in other HCMV pUL131A polypeptides, is substituted with an amino acid selected from the group consisting of glutamine (Q), serine (S), threonine (T), alanine (A), glutamate (E), and aspartate (D).

Embodiment 89. An HCMV pUL131A polypeptide comprising an amino acid sequence, wherein (a) the sequence is at least 90% identical to SEQ ID NO: 21, and (b) one or more of the amino acid residues G99, S86 and S90 are substituted with an amino acid selected from the group consisting of tryptophan (W), phenylalanine (F), tyrosine (Y), and leucine (L).

Embodiment 90. An HCMV pUL131A polypeptide comprising an amino acid sequence, wherein (a) the sequence is at least 90% identical to SEQ ID NO: 21, and (b) one or more of the amino acid residues H69, H35, H64, D38, V85, Y52, and A67 are substituted with an amino acid selected from the group consisting of tryptophan (W), phenylalanine (F), methionine (M), cysteine (C), alanine (A), leucine (L), isoleucine (I), valine (V) and proline (P).

Embodiment 91. An HCMV pUL131A polypeptide comprising an amino acid sequence, wherein (a) the sequence is at least 90% identical to SEQ ID NO: 21, and (b) the amino acid residue R118 is substituted with an amino acid selected from the group consisting of serine (S), threonine (T), cysteine (C), tyrosine (Y), asparagine (N), glutamine (Q), arginine (R), glutamic acid (E), lysine (K), histidine (H), and aspartic acid (D).

Embodiment 92. An HCMV pUL131A polypeptide comprising an amino acid sequence, wherein (a) the sequence is at least 90% identical to SEQ ID NO: 21, and (b) one or more of the amino acid residues H64 and W37 are substituted with a cysteine (C).

Embodiment 93. An HCMV pUL131A polypeptide comprising an amino acid sequence, wherein (a) the sequence is at least 90% identical to SEQ ID NO: 21, and (b) the amino acid residue N81 is substituted with an amino acid selected from the group consisting of glutamine (Q), serine (S), threonine (T), alanine (A), glutamate (E), and aspartate (D).

Embodiment 94. An HCMV pUL131A polypeptide comprising the amino acid sequence SEQ ID NO: 21, or a complex-forming fragment thereof, further comprising a substitution of one or more of the amino acid residues G99, S86 and S90 with an amino acid selected from the group consisting of tryptophan (W), phenylalanine (F), tyrosine (Y), and leucine (L).

Embodiment 95. An HCMV pUL131A polypeptide comprising the amino acid sequence SEQ ID NO: 21, or a complex-forming fragment thereof, further comprising a substitution of one or more of the amino acid residues H69, H35, H64, D38, V85, Y52, and A67 with an amino acid selected from the group consisting of tryptophan (W), phenylalanine (F), methionine (M), cysteine (C), alanine (A), leucine (L), isoleucine (I), valine (V) and proline (P).

Embodiment 96. An HCMV pUL131A polypeptide comprising the amino acid sequence SEQ ID NO: 21, or a complex-forming fragment thereof, further comprising a substitution of the amino acid residue R118 with an amino acid selected from the group consisting of serine (S), threonine (T), cysteine (C), tyrosine (Y), asparagine (N), glutamine (Q), arginine (R), glutamic acid (E), lysine (K), histidine (H), and aspartic acid (D).

Embodiment 97. An HCMV pUL131A polypeptide comprising the amino acid sequence SEQ ID NO: 21, or a complex-forming fragment thereof, further comprising a substitution of one or more of the amino acid residues H64 and W37 with a cysteine (C).

Embodiment 98. An HCMV pUL131A polypeptide comprising the amino acid sequence SEQ ID NO: 21, or a complex-forming fragment thereof, further comprising a substitution of the amino acid residue N81 with an amino acid selected from the group consisting of glutamine (Q), serine (S), threonine (T), alanine (A), glutamate (E), and aspartate (D).

Embodiment 99. A nucleic acid molecule encoding the HCMV pUL131A polypeptide, or a complex-forming fragment thereof, of any of embodiments 77 to 98.

Embodiment 100. An isolated antibody, or antigen-binding fragment thereof, specific for the HCMV gH polypeptide of any of embodiments 1 to 22.

Embodiment 101. An isolated antibody, or antigen-binding fragment thereof, specific for the HCMV gL polypeptide of any of embodiments 24 to 41.

Embodiment 102. An isolated antibody, or antigen-binding fragment thereof, specific for the HCMV pUL128 polypeptide of any of embodiments 43 to 56.

Embodiment 103. An isolated antibody, or antigen-binding fragment thereof, specific for the HCMV pUL130 polypeptide of any of embodiments 58 to 75.

Embodiment 104. An isolated antibody, or antigen-binding fragment thereof, specific for the HCMV pUL131A polypeptide of any of embodiments 77 to 98.

Embodiment 105. A complex comprising the HCMV gH polypeptide of any of embodiments 1 to 22 and at least one of an HCMV gL polypeptide, an HCMV pUL128 polypeptide, an HCMV pUL130 polypeptide and an HCMV pUL131A polypeptide.

Embodiment 106. The complex of embodiment 105, comprising the HCMV gH polypeptide of any of embodiments 1 to 22, an HCMV gL polypeptide, an HCMV pUL128 polypeptide, an HCMV pUL130 polypeptide and an HCMV pUL131A polypeptide.

Embodiment 107. A complex comprising the HCMV gL polypeptide of any of embodiments 24 to 41 and at least one of an HCMV gH polypeptide, an HCMV pUL128 polypeptide, an HCMV pUL130 polypeptide and an HCMV pUL131A polypeptide.

Embodiment 108. The complex of embodiment 107, comprising the HCMV gL polypeptide of any of embodiments 24 to 41 and an HCMV gH polypeptide, an HCMV pUL128 polypeptide, an HCMV pUL130 polypeptide and an HCMV pUL131A polypeptide.

Embodiment 109. A complex comprising the HCMV pUL128 polypeptide of any of embodiments 43 to 56 and at least one of an HCMV gH polypeptide, an HCMV gL polypeptide, an HCMV pUL130 polypeptide and an HCMV pUL131A polypeptide.

Embodiment 110. The complex of embodiment 109, comprising the HCMV pUL128 polypeptide of any of embodiments 43 to 56 and an HCMV gH polypeptide, an HCMV gL polypeptide, an HCMV pUL130 polypeptide and an HCMV pUL131A polypeptide.

Embodiment 111. A complex comprising the HCVM pUL130 polypeptide of any of embodiments 58 to 75 and at least one of an HCMV gH polypeptide, an HCMV gL polypeptide, an HCMV pUL128 polypeptide and an HCMV pUL131A polypeptide.

Embodiment 112. The complex of embodiment 111, comprising the HCVM pUL130 polypeptide of any of embodiments 58 to 75 and an HCMV gH polypeptide, an HCMV gL polypeptide, an HCMV pUL128 polypeptide and an HCMV pUL131A polypeptide.

Embodiment 113. A complex comprising the HCMV pUL131A polypeptide of any of embodiments 77 to 98 and at least one of an HCMV gH polypeptide, an HCMV gL polypeptide, an HCMV pUL128 polypeptide and an HCMV pUL130 polypeptide.

Embodiment 114. The complex of embodiment 113, comprising the HCMV pUL131A polypeptide of any of embodiments 77 to 98 and an HCMV gH polypeptide, an HCMV gL polypeptide, an HCMV pUL128 polypeptide and an HCMV pUL130 polypeptide.

Embodiment 115. A complex comprising the HCMV gH polypeptide of any of embodiments 1 to 22, the HCMV gL polypeptide of any of embodiments 24 to 41, the HCMV pUL128 polypeptide of any of embodiments 43 to 56, the HCMV pUL130 polypeptide of any of embodiments 58 to 75, and the HCMV pUL131A polypeptide of any of embodiments 77 to 98.

Embodiment 116. The complex of any one of embodiments 105-115 that is a modified HCMV pentamer complex comprising:
((i))
(a) a pUL128 polypeptide that has cysteine (C) at residue 142, numbered with respect to SEQ ID NO: 13, and a pUL130 polypeptide that has a cysteine (C) at residue 95, numbered with respect to 17;
(b) a gL polypeptide that has glutamine (Q) at residue 74, numbered with respect to SEQ ID NO: 7;

(c) a gL polypeptide that has a phenylalanine (F) at residue 140, numbered with respect to SEQ ID NO: 7;
(d) a gL polypeptide that has a leucine (L) at residue 145, numbered with respect to SEQ ID NO: 7;
(e) a pUL131 polypeptide that has a phenylalanine (F) at residue 52 and a valine (V) at residue 67, numbered with respect to SEQ ID NO: 21;
(f) a gL polypeptide that has a valine (V) at residue 233, numbered with respect to SEQ ID NO: 7;
(g) a gH polypeptide that has an arginine (R) at residue 358, numbered with respect to SEQ ID NO: 3;
(h) a gL polypeptide that has a cysteine (C) at residue 150, numbered with respect to SEQ ID NO: 7, and a pUL130 polypeptide that has a cysteine (C) at residue 64, numbered with respect to SEQ ID NO: 17;
(i) a pUL128 polypeptide that has a cysteine (C) at residue 83, numbered with respect to SEQ ID NO: 13, and a pUL130 polypeptide that has a cysteine (C) at residue 167, numbered with respect to SEQ ID NO: 17;
(j) a gL polypeptide that has a cysteine (C) at residue 160, numbered with respect to SEQ ID NO: 7, and a pUL130 polypeptide that has a cysteine (C) at residue 56, numbered with respect to SEQ ID NO: 17;
(k) a gL polypeptide that has a cysteine (C) at residue 166, numbered with respect to SEQ ID NO: 7, and a pUL130 polypeptide that has a cysteine (C) at residue 62, numbered with respect to SEQ ID NO: 17;
(l) a pUL128 polypeptide that has a cysteine (C) at residue 98, numbered with respect to SEQ ID NO: 13, and a pUL130 polypeptide that has a cysteine (C) at residue 204, numbered with respect to SEQ ID NO: 17;
(m) a pUL131 polypeptide that has a phenylalanine (F) at residue 86, numbered with respect to SEQ ID NO: 21;
(n) a pUL128 polypeptide that has a cysteine (C) at residue 48 and a cysteine (C) at residue 107, numbered with respect to SEQ ID NO: 13;
(o) a pUL128 polypeptide that has an isoleucine (I) at residue 77, numbered with respect to SEQ ID NO: 13;
(p) a pUL128 polypeptide that has an leucine (L) at residue 145, numbered with respect to SEQ ID NO: 13; or
(q) combinations thereof.
((ii)) wherein the modified HCMV pentamer complex has an increased thermostability as compared to a control HCMV pentamer complex.

Embodiment 117. The modified HCMV pentamer complex of embodiment 116 comprising ((i))(q) and ((ii)), wherein the combination (q) comprises:
(1) (a) and one of (b), (c), (d), (f), and (g);
(2) (c) and (e); or
(3) (d) and (e).

Embodiment 118. An immunogenic composition comprising the complex of any of embodiments 105 to 117.

Embodiment 119. The immunogenic composition of embodiment 118 further comprising an HCMV gB polypeptide.

Embodiment 120. The immunogenic composition of any of embodiments 118 or 119 further comprising a non-antigen component.

Embodiment 121. The immunogenic composition of embodiment 120, wherein the non-antigen component is an immunologically effective amount of an adjuvant.

Embodiment 122. The immunogenic composition of embodiment 121, wherein the adjuvant is AS01, an oil-in-water emulsion, an aluminum salt, a TLR7 agonist (TLR7a), TLR7a conjugated to an aluminium salt (alum-TLR7a), or a combination thereof.

Embodiment 123. A composition comprising a non-antigen component and at least one of:
(i) the HCMV gH polypeptide of any of embodiments 1 to 22;
(ii) the HCMV gL polypeptide of any of embodiments 24 to 41;
(iii) the HCMV pUL128 polypeptide of any of embodiments 43 to 56;
(iv) the HCMV pUL130 polypeptide of any of embodiments 58 to 75; and
(v) the HCMV pUL131A polypeptide of any of embodiments 77 to 98.

Embodiment 124. A nucleic acid molecule comprising one or more operably linked polynucleotide sequences that together encode the complex of any of embodiments 105 to 117.

Embodiment 125. An expression vector comprising the nucleic acid molecule of embodiment 124.

Embodiment 126. An expression vector comprising the nucleic acid molecule of any of embodiments 23, 42, 57, 76, 99, and 124.

Embodiment 127. A plurality of expression vectors wherein each expression vector comprises one or more of the nucleic acid molecules of embodiments 23, 42, 57, 76, and 99 and wherein the plurality of expression vectors together encode the complex of any of embodiments 105 to 117.

Embodiment 128. The plurality of expression vectors of embodiment 127, wherein a first expression vector encodes an HCMV gH polypeptide and an HCMV gL polypeptide and wherein a second expression vector encodes an HCMV pUL128 polypeptide, an HCMV pUL130 polypeptide, and an HCMV pUL131A polypeptide.

Embodiment 129. A host cell comprising the nucleic acid molecule of any of embodiments 23, 42, 57, 76, 99, and 124.

Embodiment 130. The host cell of embodiment 129 wherein the nucleic acid molecule is incorporated into the genome of the host cell.

Embodiment 131. A host cell comprising the expression vector of embodiment 125 or 126.

Embodiment 132. A host cell comprising the plurality of expression vectors of embodiment 127.

Embodiment 133. A cell culture comprising the host cell of any of embodiments 129 to 132.

Embodiment 134. A method of making a modified HCMV polypeptide or modified HCMV complex, comprising cultivating the host cell of any of embodiments 129 to 133.

Embodiment 135. The method of embodiment 134, further comprising contacting the culture media with an antibody of any of embodiments 100 to 104.

Embodiment 136. The method of embodiment 134 or 135, further comprising isolating the modified HCMV polypeptide or modified HCMV complex away from the culture media.

Embodiment 137. The method of any of embodiments 134 to 136, wherein the HCMV complex is a modified pentameric complex.

Embodiment 138. A method of making an HCMV complex, comprising introducing the nucleic acid molecule of embodiment 124 into a host cell genome.

Embodiment 139. A modified HCMV polypeptide comprising any one or more of the mutations listed within Tables 1B, 2B, 3B, 4B, 5B, 22, or 23.

Embodiment 140. A method of inducing an immune response against cytomegalovirus (CMV), comprising administering to a subject an immunologically effective amount of the immunogenic composition of any of embodiments 118 to 122.

Embodiment 141. The method of embodiment 140, wherein the immune response comprises the production of neutralizing antibodies against CMV.

Embodiment 142. An antibody, or antigen-binding fragment thereof, produced by the method of embodiment 140 or 141 and that is:
(A) specific for the HCMV gH polypeptide of any of embodiments 1 to 22;
(B) specific for the HCMV gL polypeptide of any of embodiments 24 to 41;
(C) specific for the HCMV pUL128 polypeptide of any of embodiments 43 to 56;
(D) specific for the HCMV pUL130 polypeptide of any of embodiments 58 to 75; or
(E) specific for the HCMV pUL131A polypeptide of any of embodiments 77 to 98.

Embodiment 143. A pharmaceutical composition comprising the antibody, or antigen-binding fragment thereof, of any of embodiments 100 to 104 and 142.

Embodiment 144. The pharmaceutical composition of embodiment 143 further comprising a non-antigen component.

Embodiment 145. A method of inhibiting CMV entry into a cell, comprising contacting the cell with a complex of any of embodiments 105 to 117, an immunogenic composition of any of embodiments 118 to 122 or with an antibody, or antigen-binding fragment thereof, of any of embodiments 100 to 104 and 142.

Embodiment 146. The immunogenic composition of any of embodiments 118 to 122 for use in inducing an immune response against cytomegalovirus (CMV).

Embodiment 147. The immunogenic composition of any of embodiments 118 to 122 for use in inhibiting CMV entry into a cell.

Embodiment 147. The pharmaceutical composition of embodiment 143 or 144 for use in inhibiting CMV entry into a cell.

Embodiment 148. Use of the immunogenic composition of any one of embodiments 118 to 122 for inducing an immune response against cytomegalovirus (CMV).

Embodiment 149. Use of the immunogenic composition of any one of embodiments 118 to 122 for inhibiting CMV entry into a cell.

Embodiment 150. Use of the pharmaceutical composition of embodiment 143 or 144 for inhibiting CMV entry into a cell.

Embodiment 133. Use of the antibody, or antigen-binding fragment thereof, of any of embodiments 100 to 104 and 142 for inhibiting CMV entry into a cell.

Embodiment 151. Use of the immunogenic composition of any one of embodiments 118 to 122 for the manufacture of a medicament for inducing an immune response against cytomegalovirus (CMV).

Embodiment 152. Use of the immunogenic composition of any one of embodiments 118 to 122 for the manufacture of a medicament for inducing an immune response against cytomegalovirus (CMV), wherein the medicament is prepared to be administered.

Embodiment 153. Use of the immunogenic composition of any one of embodiments 118 to 122 for the manufacture of a medicament for inhibiting CMV entry into a cell.

Embodiment 154. Use of the antibody, or antigen-binding fragment thereof, of any of embodiments 100 to 104 and 142 for the manufacture of a medicament for inhibiting CMV entry into a cell.

Embodiment 155. Use of the pharmaceutical composition of embodiment 143 or 144 for the manufacture of a medicament for inhibiting CMV entry into a cell.

Embodiment 156. A complex comprising one or more mutant Human Cytomegalovirus (HCMV) polypeptides, wherein the one or more mutant HCMV polypeptides are:
(a) a pUL128 polypeptide, or complex-forming fragment thereof, that has cysteine (C) at residue 142, numbered with respect to SEQ ID NO: 13;
a gL polypeptide, or complex-forming fragment thereof, that has a cavity filling mutant at residue 140 and has a cysteine (C) at residue 150, numbered with respect to SEQ ID NO: 7; and
a pUL130 polypeptide, or complex-forming fragment thereof, that has a cysteine (C) at residue 64 and a cysteine (C) at residue 95, numbered with respect to SEQ ID NO: 17;
(b) a pUL128 polypeptide, or complex-forming fragment thereof, that has cysteine (C) at residue 142, numbered with respect to SEQ ID NO: 13;
a gL polypeptide, or complex-forming fragment thereof, that has a cysteine (C) at residue 150, numbered with respect to SEQ ID NO: 7; and
a pUL130 polypeptide, or complex-forming fragment thereof, that has a cysteine (C) at residue 64 and a cysteine (C) at residue 95, numbered with respect to SEQ ID NO: 17;
(c) a pUL128 polypeptide, or complex-forming fragment thereof, that has cysteine (C) at residue 142, numbered with respect to SEQ ID NO: 13;
a gL polypeptide, or complex-forming fragment thereof, that has a cavity filling mutant at residue 145 and has a cysteine (C) at residue 150, numbered with respect to SEQ ID NO: 7; and
a pUL130 polypeptide, or complex-forming fragment thereof, that has a cysteine (C) at residue 64 and a cysteine (C) at residue 95, numbered with respect to SEQ ID NO: 17;
(d) a pUL128 polypeptide, or complex-forming fragment thereof, that has cysteine (C) at residue 142, numbered with respect to SEQ ID NO: 13;
a gL polypeptide, or complex-forming fragment thereof, that has a cavity filling mutant at residue 224 and has a cysteine (C) at residue 150, numbered with respect to SEQ ID NO: 7; and
a pUL130 polypeptide, or complex-forming fragment thereof, that has a cysteine (C) at residue 64 and a cysteine (C) at residue 95, numbered with respect to SEQ ID NO: 17;
(e) a pUL128 polypeptide, or complex-forming fragment thereof, that has cysteine (C) at residue 142, numbered with respect to SEQ ID NO: 13;
a gL polypeptide, or complex-forming fragment thereof, that has a cavity filling mutant at residue 224, numbered with respect to SEQ ID NO: 7; and a pUL130 polypeptide, or complex-forming fragment thereof, that has a cysteine (C) at residue 95, numbered with respect to SEQ ID NO: 17;
(f) a pUL128 polypeptide, or complex-forming fragment thereof, that has a cavity filling mutant at residue 77 and has a cavity filling mutant at residue 103, numbered with respect to SEQ ID NO: 13; and
a gL polypeptide, or complex-forming fragment thereof, that has a cavity filling mutant at residue 140 and has a cavity filling mutant at residue 145, numbered with respect to SEQ ID NO: 7;
(g) a pUL128 polypeptide, or complex-forming fragment thereof, that has a cavity filling mutant at residue 77 and has a cavity filling mutant at residue 103, numbered with respect to SEQ ID NO: 13; and
a gL polypeptide, or complex-forming fragment thereof, that has a cavity filling mutant at residue 140, has a cavity filling mutant at residue 145, and has a cavity filling mutant at residue 224, numbered with respect to SEQ ID NO: 7;
(h) a gL polypeptide, or complex-forming fragment thereof, that has a cavity filling mutant at residue 140, numbered with respect to SEQ ID NO: 7; and
a pUL131 polypeptide, or complex-forming fragment thereof, that has a repacking hydrophobic mutant at residue 52 and has a repacking hydrophobic mutant at residue 67, numbered with respect to SEQ ID NO: 21;
(i) a pUL131 polypeptide, or complex-forming fragment thereof, that has a cavity filling mutant at residue 86, numbered with respect to SEQ ID NO: 21; or
(j) a pUL128 polypeptide, or complex-forming fragment thereof, that has a cysteine (C) at residue 83, numbered with respect to SEQ ID NO: 13; and
a pUL130 polypeptide, or complex-forming fragment thereof, that has a cysteine (C) at residue 167, numbered with respect to SEQ ID NO: 17.

Embodiment 157. The complex of embodiment 156, wherein the cavity filling mutant at residue 140, numbered with respect to SEQ ID NO: 7, is tryptophan (W), phenylalanine (F), tyrosine (Y), valine (V), isoleucine (I), or leucine (L).

Embodiment 158. The complex of embodiment 157, wherein the cavity filling mutant is phenylalanine (F).

Embodiment 159. The complex of embodiment 156, wherein the cavity filling mutant at residue 145, numbered with respect to SEQ ID NO: 7, is tryptophan (W), phenylalanine (F), tyrosine (Y), valine (V), isoleucine (I), or leucine (L).

Embodiment 160. The complex of embodiment 159, wherein residue 145, numbered with respect to SEQ ID NO: 7, is leucine (L).

Embodiment 161. The complex of embodiment 156, wherein the cavity filling mutant at residue 224, numbered with respect to SEQ ID NO: 7, is tryptophan (W), phenylalanine (F), tyrosine (Y), valine (V), isoleucine (I), or leucine (L).

Embodiment 162. The complex of embodiment 161, wherein residue 224, numbered with respect to SEQ ID NO: 7, is valine (V).

Embodiment 163. The complex of embodiment 156, wherein the cavity filling mutant at residue 77, numbered with respect to SEQ ID NO: 13, is tryptophan (W), phenylalanine (F), tyrosine (Y), valine (V), isoleucine (I), or leucine (L).

Embodiment 164. The complex of embodiment 163, wherein residue 77, numbered with respect to SEQ ID NO: 13, is isoleucine (I).

Embodiment 165. The complex of Embodiment 156, wherein the cavity filling mutant at residue 103, numbered with respect to SEQ ID NO: 13, is tryptophan (W), phenylalanine (F), tyrosine (Y), valine (V), isoleucine (I), or leucine (L).

Embodiment 166. The complex of embodiment 165, wherein residue 103, numbered with respect to SEQ ID NO: 13, is isoleucine (I).

Embodiment 167. The complex of embodiment 156, wherein the repacking hydrophobic mutant at residue 52, numbered with respect to SEQ ID NO: 21, is tryptophan (W), phenylalanine (F), methionine (M), cysteine (C), alanine (A), leucine (L), isoleucine (I), valine (V) or proline (P).

Embodiment 168. The complex of embodiment 167, wherein residue 52, numbered with respect to SEQ ID NO: 21, is phenylalanine (F).

Embodiment 169. The complex of embodiment 156, wherein the repacking hydrophobic mutant at residue 67, numbered with respect to SEQ ID NO: 21, is tryptophan (W), phenylalanine (F), methionine (M), cysteine (C), alanine (A), leucine (L), isoleucine (I), valine (V) or proline (P).

Embodiment 170. The complex of embodiment 169, wherein residue 67, numbered with respect to SEQ ID NO: 21, is valine (V).

Embodiment 171. The complex of embodiment 156, wherein the cavity filling mutant at residue 86, numbered with respect to SEQ ID NO: 21, is tryptophan (W), phenylalanine (F), tyrosine (Y), valine (V), isoleucine (I), or leucine (L).

Embodiment 172. The complex of embodiment 171, wherein residue 86, numbered with respect to SEQ ID NO: 21, is phenylalanine (F).

Embodiment 173. The complex of any of embodiments 156-172 wherein the complex has an increased thermostability as compared to a control complex in the same conditions.

Embodiment 174. The complex of any of claims 156-173, wherein the complex is an HCMV pentamer complex comprising one or more mutant HCMV polypeptides.

Embodiment 175. An immunogenic composition comprising the complex of any of claims 156-174 and, optionally, a non-antigen component.

Embodiment 176. An isolated nucleic acid molecule comprising one or more operably linked polynucleotide sequences that encode the complex of any of claims 156-174.

Embodiment 177. An expression vector comprising the isolated nucleic acid molecule of embodiment 176.

Embodiment 178. A host cell comprising the isolated nucleic acid molecule of embodiment 176 or the expression vector of embodiment 177.

Embodiment 179. A method of making a complex, comprising cultivating the host cell of embodiment 178.

Embodiment 180. A method of inducing an immune response against Human Cytomegalovirus (HCMV), comprising administering to a subject an immunologically effective amount of the immunogenic composition of embodiment 175.

Embodiment 181. A method of inhibiting Human Cytomegalovirus (HCMV) entry into a cell (e.g., an epithelial cell), comprising contacting the cell with a complex according to embodiment 174.

Embodiment 182. Use of the immunogenic composition of embodiment 175 for inducing an immune response against cytomegalovirus (CMV).

Embodiment 183. Use of the immunogenic composition of embodiment 175 for inhibiting CMV entry into a cell (e.g., an epithelial cell).

Embodiment 184. Use of the immunogenic composition of embodiment 175 for the manufacture of a medicament for inducing an immune response against cytomegalovirus (CMV).

Embodiment 185. Use of the immunogenic composition of embodiment 175 for the manufacture of a medicament for inducing an immune response against cytomegalovirus (CMV), wherein the medicament is prepared to be administered.

Embodiment 186. Use of the immunogenic composition of embodiment 175 for the manufacture of a medicament for inhibiting CMV entry into a cell (e.g., an epithelial cell).

BRIEF DESCRIPTION OF THE DRAWINGS

FIG. 1 depicts the crystal structure of the HCMV pentameric complex (Pentamer) comprising gH, gL, pUL128, pUL130, and pUL131A (the positions of each being shown by labels). In particular, FIG. 1 provides two 180°-rotated views of a cartoon representation of Pentamer. Disulfide bonds and modeled Asn-linked oligomannose are depicted as black sticks.

FIG. 2A depicts the HCMV pentameric complex comprising gH, gL, pUL128, pUL130, and pUL131A. Five interfaces are boxed and zoomed-in subpanels are provided to show the details of the interactions with key residues. Disulfides are shown as black sticks and polar contacts are shown as dashed black lines. The UL130-UL131A, UL128-UL130-UL131A, gL-UL130, gL-UL128, and gH-gL interfaces are depicted within FIG. 2A with enlarged depictions of each of those interfaces shown in FIGS. 2B-2F, respectively. FIG. 2B provides an enlarged view of the UL130-UL131A interface's subpanel from FIG. 2A. FIG. 2B shows the α2 and α3 helices of pUL130 as well as pUL130 residues L69, Y113, and N118. The placement of the pUL130 α3 helices is shown with an arrow. FIG. 2B also shows the α3 helix of pUL131A and pUL131A residues D66, H69, and L71. Disulfides are shown as black sticks and polar contacts are shown as dashed black lines. FIG. 2C provides an enlarged view of the UL128-UL130-UL131A interface's subpanel from FIG. 2A. FIG. 2C shows the α1 and α2 helices β1, β4, β5, and β6 sheets of pUL128 as well as pUL128 residues D45, K92, and L103. FIG. 2C shows the β5, β4, and β6 sheets of pUL130 (the positions of each being shown with an arrow). FIG. 2C also shows pUL130 residue H209. FIG. 2C shows the α1, α2, and α3 helices of pUL131A as well as pUL131A residue H35. The positions of the pUL131A α1 and α2 helices are shown with an arrow. Disulfides are shown as black sticks and polar contacts are shown as dashed black lines. FIG. 2D provides an enlarged view of the gL-UL130 interface's subpanel from FIG. 2A. FIG. 2D shows the 131 and β2 sheets of gL as well as gL residues L82, Y152, R160, Y162, and R166. FIG. 2D also shows the α1 helix and β3 sheet of pUL130 as well as pUL130 residues Y56, P58, F59, L60, Y61, P62, P64, P65, R66, and L99. Disulfides are shown as black sticks and polar contacts are shown as dashed black lines. FIG. 2E provides an enlarged view of the gL-UL128 interface's subpanel from FIG. 2A. FIG. 2E shows the α4, α3, and α2 helices and the β2 and β1 sheets of gL as well as gL residues L101, L106, L122, V137, and D157. FIG. 2E also shows the α3 helix of pUL128 as well as pUL128 residues R142, L146, L150, L159, V161, and C162. FIG. 2E also shows pUL130 residue Q97. Disulfides are shown as black sticks and polar contacts are shown as dashed black lines. FIG. 2F provides an enlarged view of the gH-gL interface's subpanel from FIG. 2A. FIG. 2F shows the β1, β3, β4, and β5 sheets of gH as well as the α1 helix of gH (the placement of each being shown with an arrow). FIG. 2F also shows gH residue C95. FIG. 2F shows the β5, β4, and β3 sheets of gL (the placement of each being shown with an arrow) as well as the α1 and α6 helices of gL. FIG. 2F also shows gL residues C47 and C54. Disulfides are shown as black sticks and polar contacts are shown as dashed black lines.

FIGS. 3A-3C depict the conformational flexibility of the HCMV pentamer complex (Pentamer). FIG. 3A shows side and top views of the gH-based superposition of the 4.0 Å and 3.0 Å resolution of Pentamer-8I21 Fab. FIG. 3B shows a side view of the superposition between the Pentamer-9I6 Fab and the 3.0 Å resolution Pentamer-8I21 Fab complexes. The boxed region is shown, after a rotation of 45°, in the subpanel to highlight the position of the gH helix linker that is thought to act as a hinge for the rigid arm movement of the ULs. FIG. 3C shows the pUL130/pUL131A-based superposition of the Pentamer-9I6 and the 3.0 Å resolution Pentamer-8I21 Fab complexes.

FIG. 4A depicts cavities within the pentameric complex and locations at which stabilizing mutations of the present invention may be made. Cavities are shown by irregular shapes filled in with lines and stabilizing mutation locations are shown by dots (the dots of FIG. 4A depict location only, i.e., there is not a 1:1 relationship between the number of dots in FIG. 4A and the number of stabilizing mutations of this invention). FIG. 4A also identifies the ULs Interface and gH-gL-ULs Interface with boxes. FIG. 4B provides an enlarged view of the gH-gL-ULs Interface from FIG. 4A. FIG. 4B depicts cavities within the gH-gL-ULs Interface. Cavities are shown by irregular shapes filled in with lines. FIG. 4C provides an enlarged view of the ULs Interface from FIG. 4A. FIG. 4C depicts cavities within the ULs Interface. Cavities are shown by irregular shapes filled in with lines.

FIG. 5A depicts cavity-filling within an HCMV pentamer complex due to the presence of a stabilizing mutation. Five cavity-filling mutations are shown, each within one of the pUL128, pUL130, pUL131A, gL, and gH pentamer complex subproteins. A subpanel is provided for each of the five cavity-filling mutations. Cavities are shown by irregular shapes filled in with lines. FIG. 5B provides an enlarged view of the UL128 G123W cavity-filling mutation subpanel from FIG. 5A. The location of the G123W side chain and its presence within a cavity is shown with an arrow. Cavities are shown by irregular shapes filled in with lines. FIG. 5C provides an enlarged view of the UL130 D165W cavity-filling mutation subpanel from FIG. 5A. The location of the D165W side chain and its presence within a cavity is shown with an arrow. Cavities are shown by irregular shapes filled in with lines. FIG. 5D provides an enlarged view of the UL131 G99W cavity-filling mutation subpanel from FIG. 5A. The location of the G99W side chain and its presence within a cavity is shown with an arrow. Cavities are shown by irregular shapes filled in with lines. FIG. 5E provides an enlarged view of the gL H177W cavity-filling mutation subpanel from FIG. 5A. The location of the H177W side chain and its presence within a cavity is shown with an arrow. Cavities are shown by irregular shapes filled in with lines. FIG. 5F provides an enlarged view of the gH A102W cavity-filling mutation subpanel from FIG. 5A. The location of the A102W side chain and its presence within a cavity is shown with an arrow. Cavities are shown by irregular shapes filled in with lines.

FIG. 6A depicts disulfide-bridge mutations within an HCMV pentamer complex. Sixteen disulfide-bridge mutations and the resulting eight disulfide bonds/bridges (cross-linked cysteine residues) are shown and numbered (1)-(8). Disulfide bonds are depicted by sticks. The top subpanel of FIG. 6A shows disulfide bonds (1), (2), (3), (4), (7), and (8). The bottom subpanel of FIG. 6B shows disulfide bonds (5) and (6). FIG. 6B provides an enlarged view of the top subpanel from FIG. 6A. Disulfide bonds are depicted by sticks. (1) shows the intra-disulfide bond resulting from the disulfide bridge mutations pUL130 G116C and pUL130 H150C. (2) shows the inter-disulfide bond resulting from the disulfide bridge mutations gL G161C and pUL130 P64C. (3) shows the inter-disulfide bond resulting from the disulfide bridge mutations pUL130 S178C and pUL131A H64C. (4) shows the inter-disulfide bond resulting from the disulfide bridge mutations gL D163C and pUL130 P62C. (7) shows the inter-disulfide bond resulting from the disulfide bridge mutations pUL128 R142C and pUL130 E95C. (8) shows the inter-disulfide bond resulting from the disulfide bridge mutations gL R166C and pUL130 P62C. FIG. 6C provides an enlarged view of the bottom subpanel from FIG. 6A. Disulfide bonds are depicted by sticks. (5) shows the inter-disulfide bond resulting from the disulfide bridge mutations gHV109C and gL G224C. (6) shows the inter-disulfide bond resulting from the disulfide bridge mutations gH L111C and gL G218C.

FIG. 7 further depicts the eleven glycans on the Pentamer surface. The general location of each glycan is designated with a rectangle. In particular, the face of the Pentamer molecule as shown on the left of FIG. 7 identifies ten glycans (six glycans in gH, one in gL, and four in the ULs). The other face of the Pentamer molecule, which is shown on the right of FIG. 7, identifies the one (eleventh) glycan in pUL130 which is located adjacent to site 2. The other glycans shown on the right of FIG. 7 are also shown on the left of FIG. 7. Within those rectangles are spheres denoting carbon atoms, denoting nitrogen atoms, denoting oxygen atoms, and denoting hydrogen atoms.

FIG. 8 depicts Geometric Mean Titers (GMT) of serum samples taken from mice three weeks after the second dose (3wp2) was intramuscularly administered of a composition comprising an immunogenic amount of one of the seven pentamer complexes listed along the x-axis (further described at Example 5.2 and Table 25) and $AS01_E$ adjuvant. The y-axis provides neutralizing antibody (nAb) titers (GMT, 95% Confidence Interval (CI)) on a scale of $10^1$ to $10^6$. The Lower Limit of Detection (LLOD) is shown via dashed line. Set 2_20 had the highest nAb titers, with titers higher than set 2_36, set 2_21, and control ("Penta (LSG)") (p-value<0.05 denoted by star (*)).

DETAILED DESCRIPTION

Figure 1:
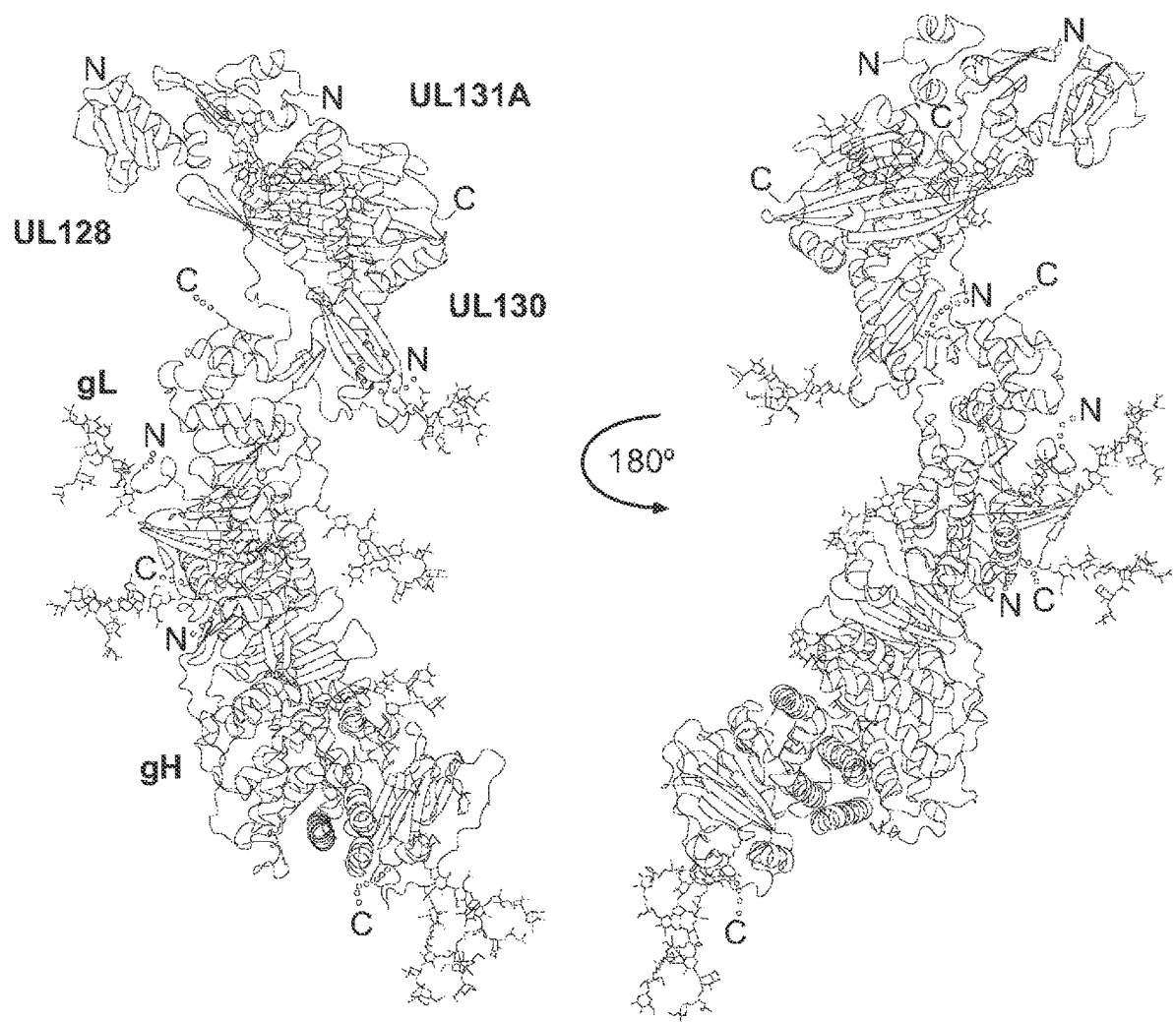
FIG. 1.
Figure 2A:
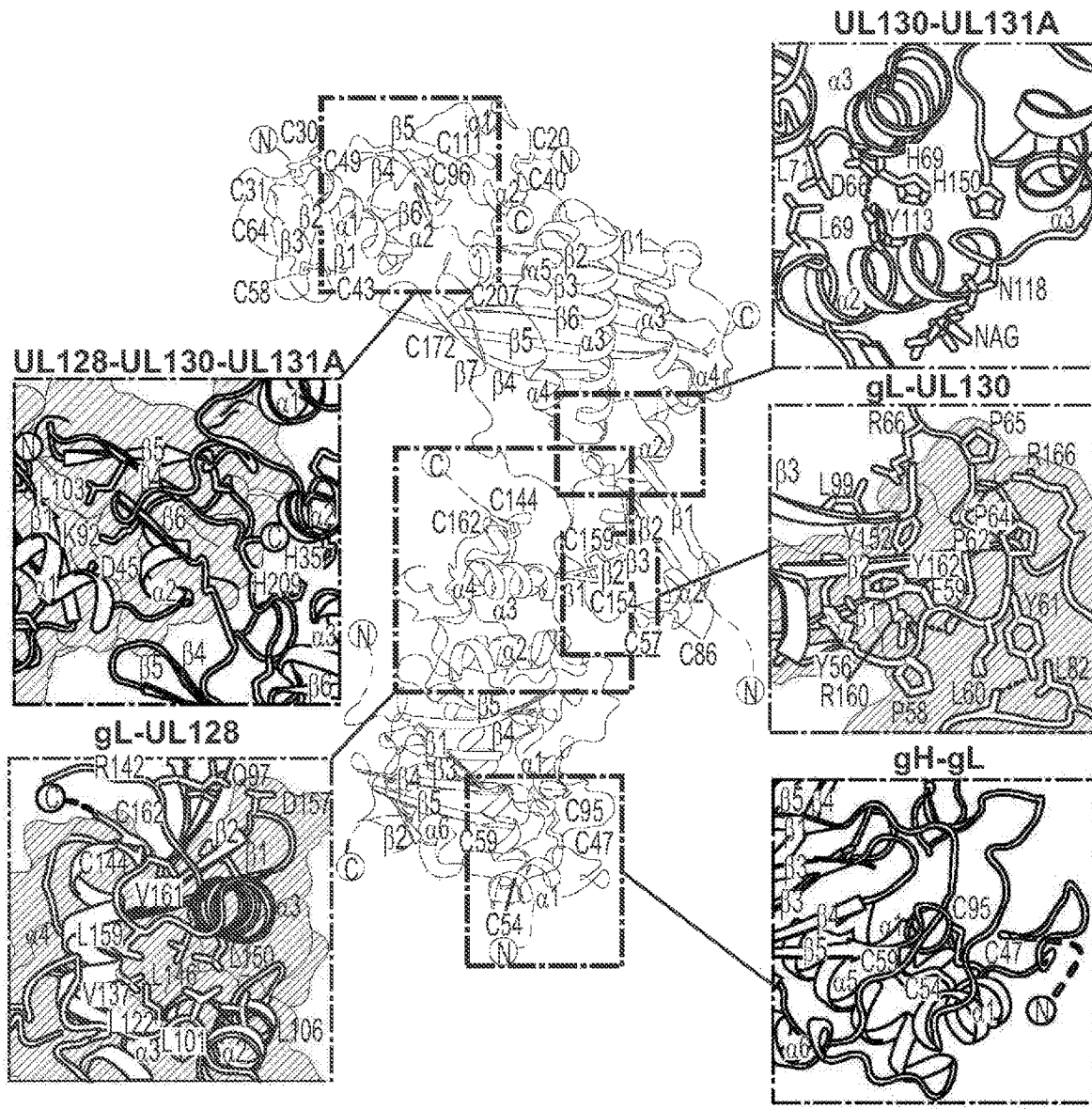
FIGS. 2A-2F.
Figure 2B:
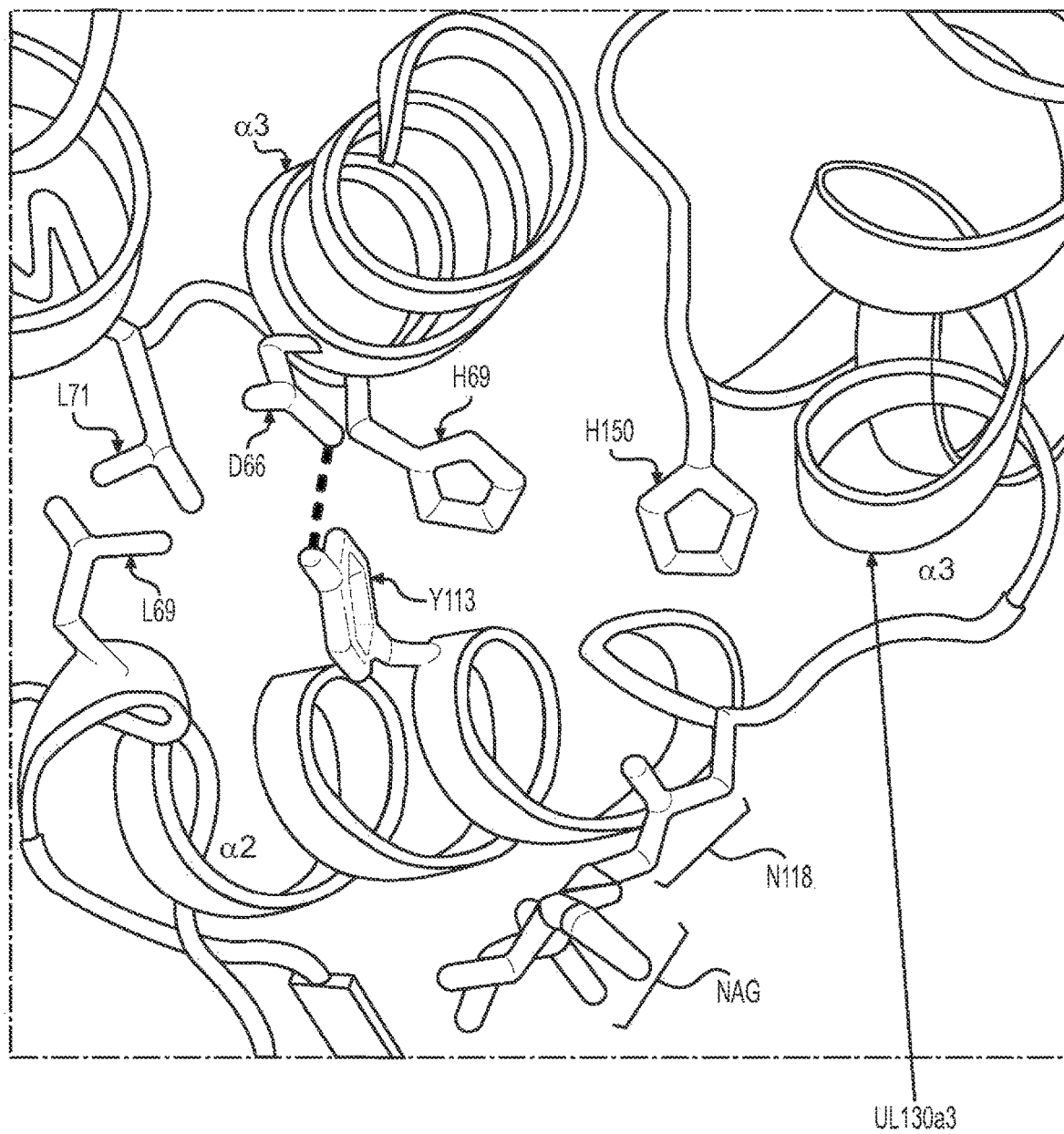
Figure 2C:
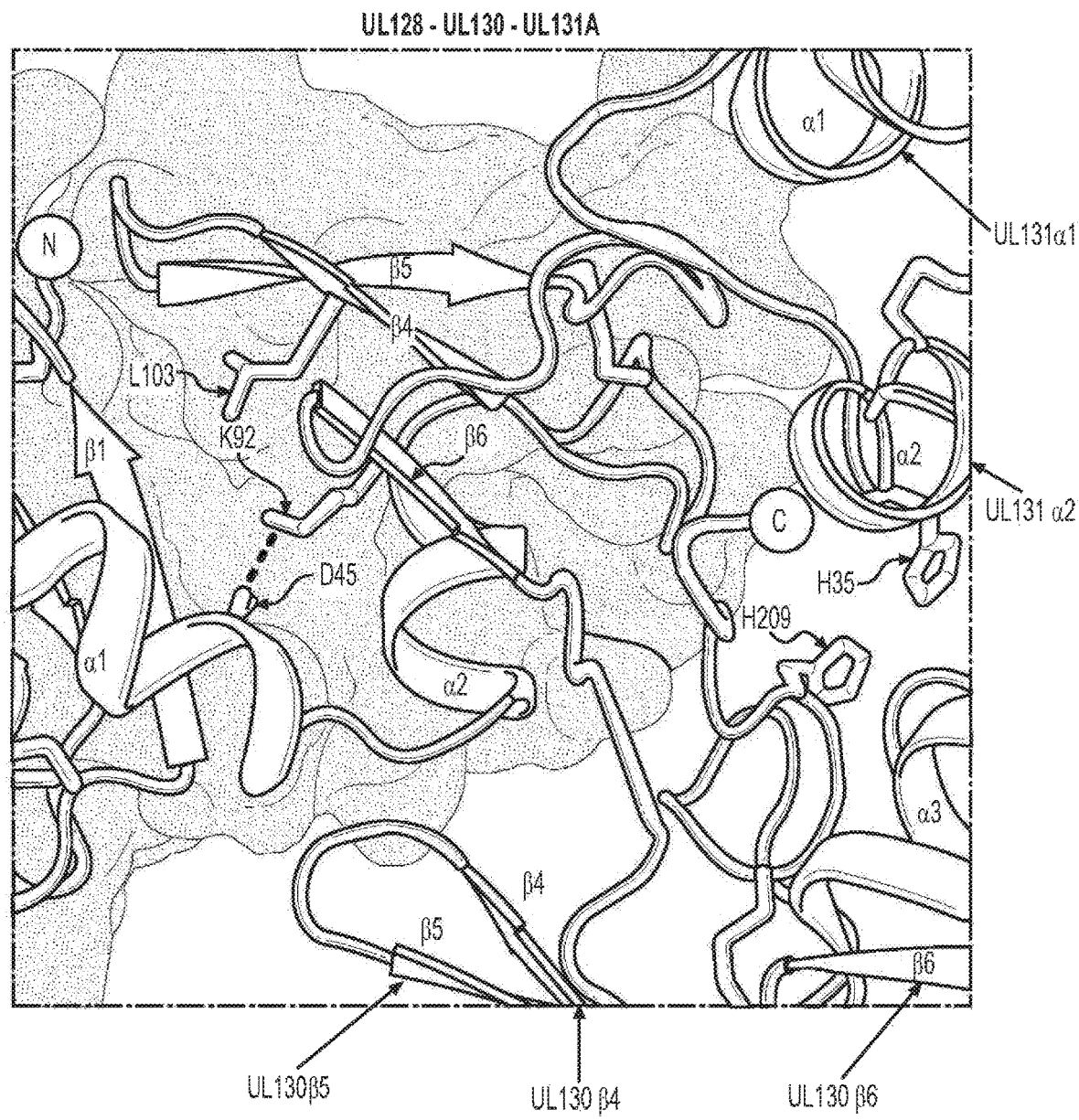
Figure 2D:
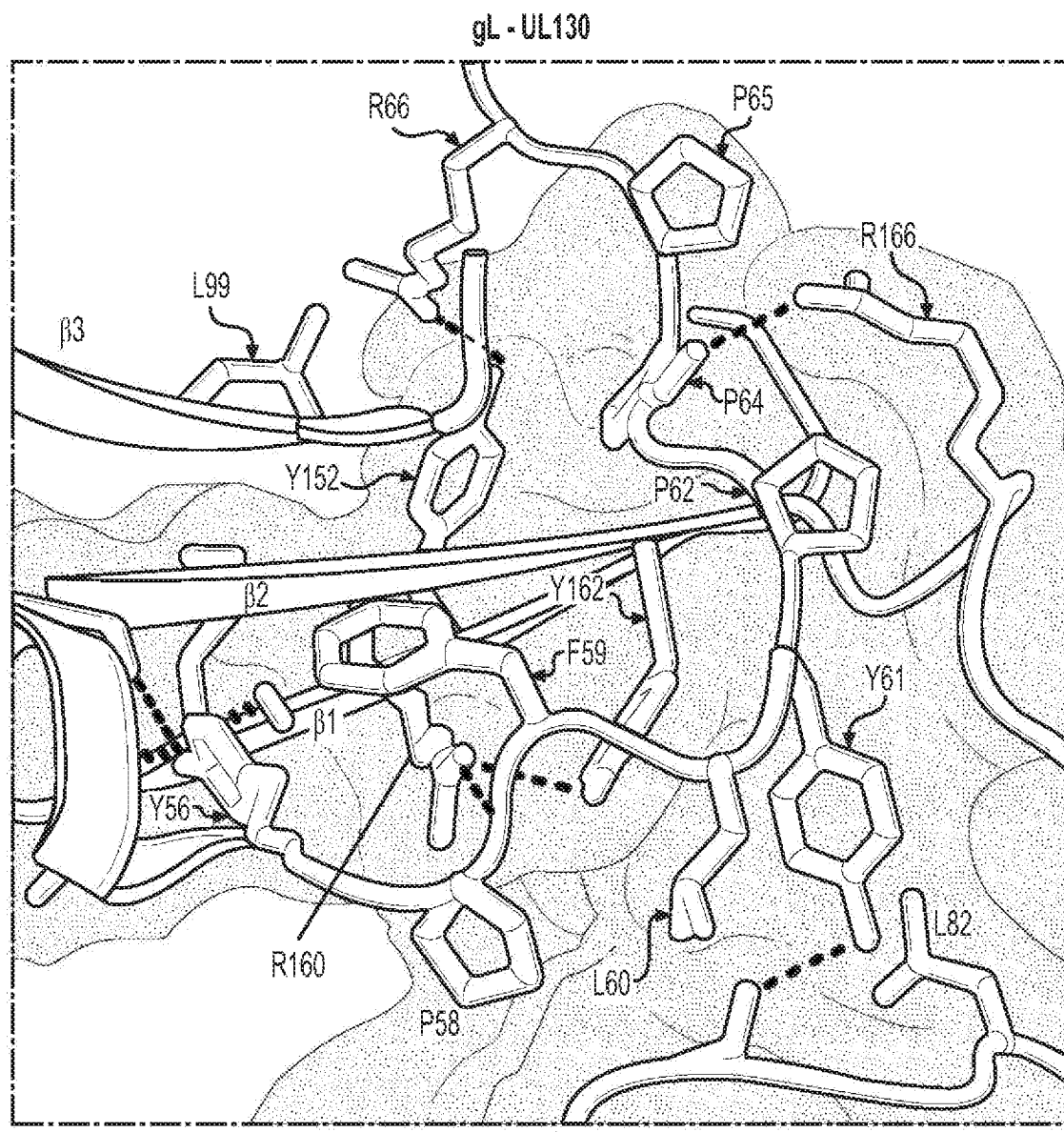
Figure 2E:
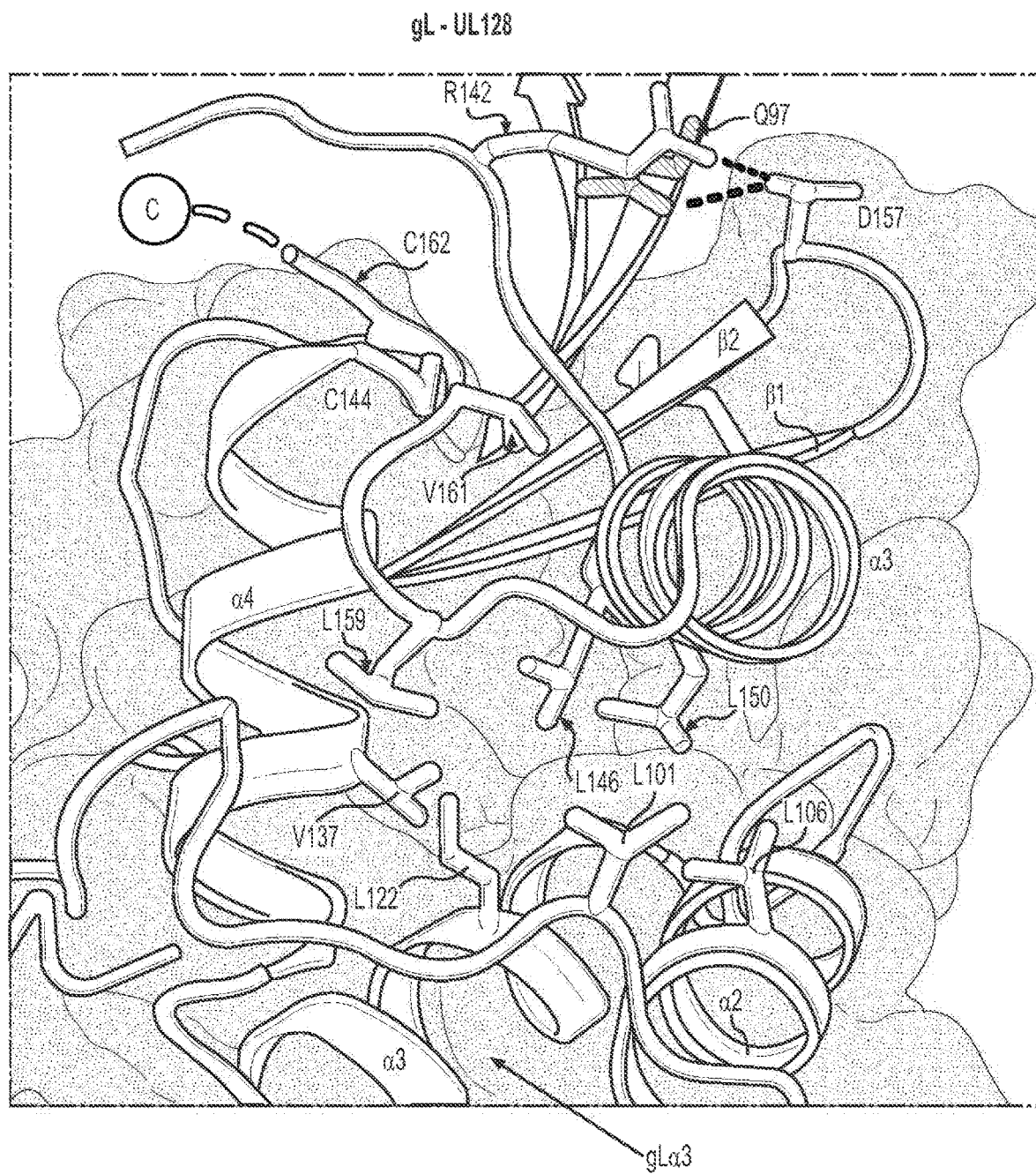
Figure 2F:
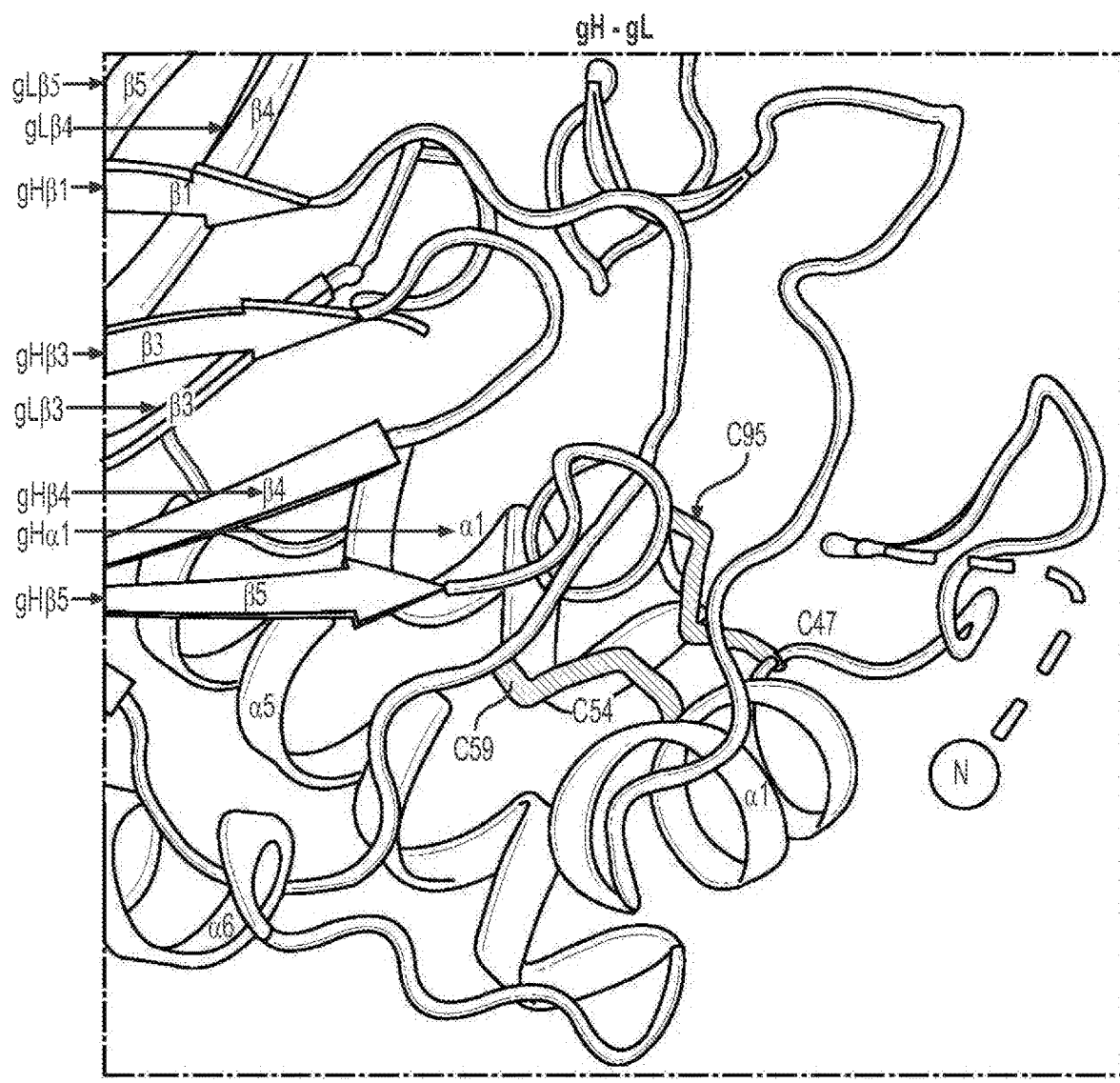

Revealed herein is the crystal structure of the HCMV pentameric complex made of the polypeptides gH, gL, pUL128, pUL130 and pUL131A in combination with fragment antigen binding (Fabs) of monoclonal antibodies (mAbs). The inventors analysed the crystal structure and characterize (i) the presence of small interfaces between some of the domains of the complex, (ii) the presence of several cavities at the domain interfaces, and (iii) an intrinsic flexibility or dynamics of the complex. The inventors also characterize and herein describe polypeptide modifications (i.e., modifications of polypeptides gH, gL, pUL128, pUL130, and/or pUL131A) that enhance the thermostability of the pentameric complex. In particular, the inventors provide specific amino acids in each of the polypeptides of the HCMV pentameric complex that, when modified as described herein, enhance the thermostability of a complex comprising them. Without wishing to be bound by theory, it is believed that an amino acid modification of this invention enhances complex thermostability by decreasing the conformational flexibility of the complex. This is believed to occur because, for example, (A) a mutant amino acid of this invention (the amino acid resulting from a presently described stabilizing mutation) has longer side-chains than the original amino acid (the amino acid which is innately present within the referenced, non-mutant protein sequence) and the atoms of the modified amino acid's side-chains fill buried cavities between domain interfaces and/or protein core cavities. In this way, the structural characteristic of a mutant amino acid having long side-chains effects the filling of buried cavities between domain interfaces and/or protein core cavities and results in enhanced complex stability. Such mutations may be referred to herein as "cavity-filling mutations" with the resulting mutant amino acid being referred to as a "cavity-filling mutant." It is further believed that the amino acid modifications of this invention enhance complex thermostability by (B) "repacking" the complex via increasing contacts of neighboring residues and/or replacing unfavorable clusters of charged residues within a protein or between proteins. Such mutations may be referred to herein as "repacking mutations", with the resulting amino acid being referred to as a "repacking mutant." Specific repacking mutations may be referred to herein as "hydrophobic mutations" or "hydrophilic mutations", with the resulting mutant amino acid being referred to as a "hydrophobic mutant" or "hydrophilic mutant," respectively. In this way, the structural characteristic of a referenced mutant amino acid being hydrophobic or hydrophilic effects an increase in contacts with its neighboring residues and/or effects the reduction of unfavorable clusters of charged residues and results in enhanced complex stability. Furthermore, it is believed that the amino acid modifications of this invention enhance complex thermostability by (C) introducing disulfide bridges throughout the complex. This is believed to occur because the newly introduced disulfide bridges lock (restrain) the polypeptides and thereby reduce their dynamics. In this way, the structural characteristic of a mutant amino acid being a cysteine or otherwise a residue structurally capable of forming disulfide bridges effects the introduction of a disulfide bridge and results in enhanced complex stability. Such mutations may be referred to herein as "disulfide bridge mutations" with the resulting amino acid being referred to as a "disulfide bridge mutation." In this way, the present invention provides modified HCMV pentameric complex proteins (gH, gL, pUL128, pUL130, and pUL131A), optionally within a HCMV complex (e.g., a pentameric, gH/gL, or gH/gL/gO complex), wherein the one or more mutant amino acid results in at least one of A-C and thereby an enhanced complex thermostability. From having analysed the HCMV pentamer complex crystal structure and its neutralizing epitopes, the inventors have selected additional glycans which are in close proximity to a neutralizing epitope and that are likewise expected to limit the accessibility of their respective HCMV pentamer epitope(s). The inventors therefore expect that by introducing one or more of the deglycosylation mutations into a HCMV complex, the corresponding epitope(s) will be more accessible as compared to those of a non-mutant. In particular, it is believed that removing one or more of the identified glycan(s) will "unmask" the corresponding epitope and increase antigenicity. The inventors specifically propose the substitution of an identified asparagine residue for any non-asparagine amino acid (e.g., glutamine) using known techniques so as to prevent N-linked glycosylation at that location and thereby unmask the corresponding epitope. In this way, the present invention provides modified HCMV pentameric complex proteins (gH, gL, pUL128, pUL130, and pUL131A), optionally within a HCMV complex (e.g., a pentameric, gH/gL, or gH/gL/gO complex), wherein the one or more mutant amino acid results in deglycosylation. Such deglycosylation may unmask an epitope, making the epitope more accessible to, for example, a neutralizing antibody or antibody fragment.

The polypeptides of the invention are mutant and therefore have a distinct structure as compared to a non-mutant (e.g., wild type or control) polypeptide. Likewise, therefore, a complex comprising a polypeptide of the invention has a distinct structure as compared to a non-mutant complex (e.g., wild type or control complex) because a complex of the invention comprises at least one mutant HCMV gH, gL, UL128, UL130, and pUL131A polypeptide. Further, the complex of the invention may have a distinct function as compared to a non-mutant (e.g., wild type or control) complex in that the complex of the invention may have an increased thermostability as compared to a non-mutant complex.

It is therefore an object of the invention to provide HCMV gH, gL, pUL128, pUL130 and pUL131A polypeptides, as defined herein, presenting the advantage of forming a complex (e.g., a pentameric, gH/gL, or gH/gL/gO complex) having an enhanced thermostability and/or more accessible epitopes. Although the present invention is applicable to polypeptides originating from any HCMV strain, in order to facilitate its understanding, when referring to amino acid positions in the present specification, the numbering is given in relation to the amino acid sequence of the polypeptides originating from the Merlin strain, unless otherwise stated. In particular, gH amino acid positions are given with respect to the Merlin gH sequence SEQ ID NO: 1; gL amino acid positions are given with respect to the Merlin gL sequence SEQ ID NO: 7; pUL128 amino acid positions are given with respect to the Merlin pUL128 sequence 13; pUL130 amino acid positions are given with respect to the Merlin pUL130 sequence SEQ ID NO: 17; pUL131A amino acid positions are given with respect to the Merlin pUL131A sequence SEQ ID NO: 21; and gO amino acid positions are given with respect to the Merlin gO sequence SEQ ID NO: 25 unless otherwise stated. The present invention is not, however, limited to the Merlin strain. Using the teachings of the invention, comparable amino acid positions in a polypeptide of any other HCMV strain can be determined easily by those of ordinary skill in the art by aligning the amino acid sequences using readily available and alignment algorithms (such as BLAST, using default settings, ClustalW2, using default settings, or algorithm disclosed by Corpet (*Multiple Sequence Alignment with Hierarchical Clustering,* 1998 Nucleic Acids Research 16(22): 10881-10890), using default parameters). Accordingly, when referring to an "HCMV polypeptide", it is to be understood as an HCMV polypeptide from any strain (in addition to Merlin strain). The actual number of the amino acid residue positions may have to be adjusted for polypeptides from other strains depending on the actual sequence alignment.

A location within a sequence, position within a sequence, residue, or amino acid "corresponding to residue ## of SEQ ID NO: ###" or "that corresponds to residue ## of SEQ ID NO: ###" or "with respect to residue ## of SEQ ID NO: ###" or "at the position corresponding to 'X' of SEQ ID NO: ###" or "at the location that corresponds to the location of residue ## of SEQ ID NO: ###" or "numbered with respect to residue ## of SEQ ID NO: ###" are exemplary phrases used in the sense of the present invention for clarity, particularly within claims, to provide a means by which a particular position within an amino acid sequence is identified. Further, these phrases are used to encompass, for example, amino acid sequences that encode a polypeptide having the same or similar function as the protein having the referenced amino acid sequence SEQ ID NO: ### but that have a disparate structure (i.e., the encompassed polypeptide has the same or similar function as the referenced protein but the encompassed polypeptide and referenced protein have different amino acid sequences). By way of example, a polypeptide comprising a mutation at "the amino acid residue corresponding to P45 of the pUL131A sequence SEQ ID NO: 21" would encompass at least a polypeptide having a mutation at P45 of the pUL131A sequence SEQ ID NO: 21 (Merlin strain), a polypeptide having a mutation at P45 of the pUL131A sequence SEQ ID NO: 23 (Towne strain), and a mutation at P49 of the pUL131A sequence SEQ ID NO: 24 (AD169 strain) (all of which are underlined in the following multiple sequence alignment of SEQ ID NOs: 21, 23, and 24; signal sequence residues are also underlined).

```
SEQIDNO21 MRLCRVWLSV CLCAVVLGQC QRETAEKNDY YRVPHYWDAC SR....ALPD
SEQIDNO23 MRLCRVWLSV CLCAVVLGQC QRETAEKNDY YRVPHYWDAC SR....ALPD
SEQIDNO24 MRLCRVWLSV CLCAVVLGQC QRETAEKKRL LPSTALLGRV LSRAARPNPL

SEQIDNO21 QTRYKYVEQL VDLTLNYHYD ASHGLDNFDV LKRINVTEVS LLISDFRRQN
SEQIDNO23 QTRYKYVEQL VDLTLNYHYD ASHGLDNFDV LKRINVTEVS LLISDFRRQN
SEQIDNO24 QVCGTARGPH VELPLR..CE P..RLGQL-- ---------- ----------

SEQIDNO21 RRGGTNKRTT FNAAGSLAPH ARSLEFSVRL FAN
SEQIDNO23 RRGGTNKRTT FNAAGSLAPH ARSLEFSVRL FAN
SEQIDNO24 ---------- ---------- ---------- ---
```

By "HCMV complex" or simply "complex", it is meant in the sense of the present invention a group of two or more associated proteins that comprises at least one of the HCMV polypeptides gH, gL, pUL128, pUL130, pUL131A, or complex-forming fragments thereof. An HCMV complex or "complex" in the sense of the present invention includes, for example, gH/UL115, gH/gL (e.g., the gH/gL heterodimer or a gH/gL dimer of heterodimers), gH/gL/gO, and pentameric complexes. A "mutant HCMV complex" or simply "mutant complex" in the sense of the present invention is a group of two or more associated proteins that comprise at least one of the HCMV polypeptides gH, gL, pUL128, pUL130, pUL131A, or complex-forming fragments thereof wherein the at least one HCMV polypeptide or complex-forming fragment thereof comprises one or more stabilizing mutant amino acid residues.

By "pentameric complex", it is meant in the sense of the present invention an HCMV complex that comprises five different HCMV polypeptides: gH, gL, pUL128, pUL130 and pUL131A. Although generally referred to as gH/gL/pUL128/pUL130/pUL131A pentamer (or pentameric complex comprising gH, gL, pUL128, pUL130 and pUL131A) in the specification, each of the 5 polypeptides does not need to be a full-length polypeptide. The term "pentameric complex" also encompasses pentamers formed by complex-forming fragments of gH, gL, pUL128, pUL130 and pUL131A polypeptides.

The term "complex subprotein" or simply "subprotein" may be used in the sense of the present invention to refer to the HCMV polypeptides that are present within the referenced HCMV complex. For example, a "subprotein" of the HCMV pentameric complex means any one of gH, gL, pUL128, pUL130, and pUL131A and in this example is a synonym for a "HCMV pentameric complex protein." In further example, a "gH/gL complex subprotein" means a gH or gL polypeptide.

By "complex-forming fragment" of an HCMV polypeptide, it is meant in the sense of the present invention any part or portion of the polypeptide that retains the ability to form a complex (e.g., the pentameric complex, gH/gL dimer, and gH/gL/gO trimer) with other HCMV polypeptides of the complex. As used herein, a "complex-forming fragment" of a mutant polypeptide comprises the one or more mutant amino acid residues (i.e., the fragment of a mutant protein comprises the mutation(s)). The ability to form a complex (e.g., a pentameric complex) of the invention can be tested by performing protein purification, and analyzing the proteins by non-reducing PAGE, Western blot and/or size exclusion chromatography. If the proteins form part of a complex, they may all be present in a single band on a native PAGE gel and/or be present in a single peak in a size exclusion chromatogram.

By "enhanced thermo-stability" or "enhanced thermostability" or "higher thermostability" or "increased thermostability" or simply "enhanced stability" or "higher stability" or "increased stability", it is meant in the sense of the present invention that the complex (e.g., the pentameric complex) has at least a lower rate of unfolding, under the same conditions, than the same complex which does not comprise any stabilizing mutation (said another way, the complex unfolds slower than a non-mutant complex under the same conditions). "Conditions" as used herein includes, for example, experimental and physiological conditions. It may be specified that a composition comprising a stabilized complex of the present invention has an increased shelf life as compared to a composition comprising a non-mutant complex. See, e.g., U.S. Pub. No. 2011/0229507 A1, hereby incorporated by reference in its entirety; Clapp et al., *Vaccines with Aluminum-Containing Adjuvants: Optimizing Vaccine Efficacy and Thermal Stability*, 2011 J. Pharm. Sci. 100(2): 388-401, discussing increased stability via adjuvants and assessing antigen stability in altered pH, hydration, and temperature conditions; and Rossi et al., 2016 Infect. Immun. 84(6): 1735-1742. Stability herein may be provided by the delta stability (dStability or dS) scoring method, which is the computationally-determined difference between the relative thermostability of an in-silico mutant protein and that of the corresponding wild type or non-mutant protein. Methods of determining dStability are provided at Example 3 and include, for example, known tools such as Molecular Operating Environment (MOE) software (REF: Molecular Operating Environment (MOE) software; Chemical Computing Group Inc., available at WorldWideWeb(www).chemcomp.com). dS is measured by kcal/mol. Lower dS values indicate higher protein stability, inversely higher dS values indicate lower protein stability. It may be specified that the mutant polypeptides of the present invention have a higher relative thermostability (in kcal/mol) as compared to a non-mutant polypeptide under the same experimental conditions. It may be further specified that the mutant polypeptides of the present invention have a lower dS value than a non-mutant polypeptide under the same experimental conditions. It will be understood from the present invention that a mutant polypeptide having a lower dS value as compared to a non-mutant polypeptide under the same experimental conditions is more stable than the non-mutant polypeptide. The stability enhancement can be assessed using differential scanning calorimetry (DSC), for example as discussed in Bruylants et al. (*Differential Scanning calorimetry in Life Sciences: Thermodynamics, Stability, Molecular Recognition and Application in Drug Design*, 2005 Curr. Med. Chem. 12: 2011-2020) and calorimetry Sciences Corporation's "Characterizing Protein stability by DSC" (Life Sciences Application Note, Doc. No. 2021102136 February 2006) or by differential scanning fluorimetry (DSF). An increase in stability may be characterized as an at least about 2° C. increase in thermal transition midpoint ($T_m$), as assessed by DSC or DSF. See, for example, Thomas et al., *Effect of single-point mutations on the stability and immunogenicity of a recombinant ricin A chain subunit vaccine antigen*, 2013 Hum. Vaccin. Immunother. 9(4): 744-752. A "significant" increase in, or enhancement of, thermostability is defined as an increase of at least about 5° C. in the calculated Tm of a complex (calculated by, for example, the protocol provided at Example 4.7).

By "mutation", it is meant in the sense of the present invention a substitution of an amino acid residue with another amino acid residue. With respect to the nucleic acid sequence, this substitution is effected via a missense mutation within the corresponding codon of the coding region (the mutant polypeptide encoded by one such mutant nucleic acid sequence may be referred to as a "mutein"). The term "mutation" as used herein also includes modifications that introduce a non-naturally occurring amino acid or an amino acid analog into a polypeptide. A "mutation" as used herein does not include an "identical mutation," which is the substitution of an amino acid residue with a natural or synthetically produced amino acid having the same chemical structure. By way of example, the substitution of alanine at position 102 of the sequence SEQ ID NO: 1 with an alanine (A102A) is an "identical mutation" as used herein and is not within the meaning of "mutation" in the sense of the present invention. Therefore, the mutations of the present invention may be clarified with the proviso that an identical mutation is excluded.

By "stabilizing mutations" or "stabilizing mutant", it is meant in the sense of the present invention any mutation in the HCMV polypeptides resulting, upon formation of the pentameric complex, into a complex having an enhanced thermo-stability, as compared with a pentameric complex formed with the HCMV polypeptides containing no such mutation. Stabilizing mutations in the sense of the present invention encompass, in particular, cavity-filling mutations, repacking mutations (which includes hydrophobic mutations and hydrophilic mutations), and disulfide bridge mutations.

A stabilizing mutation of the present invention is not detrimental to the use of the mutated protein as an antigen. In particular, the stabilizing mutation does not prohibit all epitopes that can elicit the production of antibodies that can bind to at least a HCMV complex as described herein and/or antibodies that can neutralize the biological effects of said HCMV complex. In addition, a stabilizing mutation of the present invention does not prevent the mutant polypeptides to form a complex. By "stabilized complex", it is meant in the sense of the present invention a complex (e.g., a pentameric complex) comprising at least one polypeptide that comprises at least one stabilizing mutation.

The terms "amino acid", "residue", and "amino acid residue" as used herein all refer to an organic chemical compound that contains at least one amino group (—NH$_2$) and one carboxyl group (—COOH). For clarity, however, and particularly within the claims, the amino acid present at a particular position within a wild type or non-mutant sequence (e.g., the wild type amino acid) may be referred to as an "amino acid" whereas the compound present at that corresponding position within the mutant sequence (the mutant amino acid) may be referred to as a "residue" (i.e., the amino acid resulting from a missense mutation may be referred to as a "residue").

By "non-mutant", it is meant in the sense of the present invention that the referenced molecule (e.g., the sequence, polypeptide, or complex) does not comprise a stabilizing mutation or deglycosylation mutation of the present invention. In this way, the term "non-mutant" encompasses "wild type" structure but it also encompasses, for example, a truncated wild type polypeptide. For example, an HCMV gH polypeptide having the amino acid sequence of SEQ ID NO: 3 is a "non-mutant" polypeptide at least because it is truncated and therefore does not have "wild type" HCMV gH structure. Further by example, an HCMV gL polypeptide having the amino acid sequence of SEQ ID NO: 9 or SEQ ID NO: 29 is a "non-mutant" polypeptide in the sense of the present invention. To be clear, "non-mutant" is used herein as a reference to structure and not as a reference to function. A non-mutant polypeptide, for example, may be described as having wild type function (such as the HCMV gH polypeptide comprising SEQ ID NO: 3).

By "cavity-filling mutation", it is meant in the sense of the present invention the substitution of a first amino acid (e.g., a wild type amino acid) with a second amino acid wherein the second amino acid has a longer side chain than the first amino acid. Such second amino acid may be referred to as a "cavity filling mutant." Said another way, a cavity-filling mutation herein is the substitution of an amino acid with a residue wherein the residue has a longer side chain than the amino acid. Such amino acid residues having a long side chain include: tryptophan (W), phenylalanine (F), tyrosine (Y), valine (V), isoleucine (I), and leucine (L).

By "repacking mutations", it is meant in the sense of the present invention the substitution of a first amino acid residue (e.g., a wild type amino acid) with a second amino acid residue which increases the interaction of neighboring residues in a polypeptide. Such second amino acid may be referred to as a "repacking mutant." Repacking mutations include amino acid substitutions that, for example, (1) enhance hydrophobic interactions (e.g., through hydrophobic amino acids) or hydrogen-bond formation (e.g., through polar or charged (i.e., hydrophilic) amino acids), or (2) reduce unfavourable or repulsive interactions of neighboring residues (e.g., by eliminating clusters of similarly charged residues). A repacking mutation in the sense of the present invention encompasses, in particular, hydrophobic mutations and hydrophilic mutations".

By "hydrophobic mutation", it is meant in the sense of the present invention the substitution of a first amino acid residue (e.g., a wild type amino acid) with a second amino acid residue wherein the second amino acid has a hydrophobic side chain. Such second amino acid may be referred to as a "hydrophobic mutant" or "hydrophobic repacking mutant." Such amino acid residues having a hydrophobic side chain include: tryptophan (W), phenylalanine (F), methionine (M), cysteine (C), alanine (A), leucine (L), isoleucine (I), valine (V) and proline (P). Tyrosine (Y) may also be classified as hydrophobic.

By "hydrophilic mutation", it is meant in the sense of the present invention the substitution of a first residue (e.g., a wild type amino acid residue) with a second amino acid wherein the second amino acid has a hydrophilic side chain. Such second amino acid may be referred to as a "hydrophilic mutant" or "hydrophilic repacking mutant." "Hydrophilic side chain" encompasses both a substitution to an amino acid having a polar side chain and a substitution to an amino acid having a charged side chain. It is generally understood in the art that polar amino acid side chains are hydrophilic but are not charged and charged amino acid side chains are hydrophilic and are charged. By "polar mutation", it is meant in the sense of the present invention the substitution of a first amino acid residue (e.g., a wild type amino acid) with a second amino acid residue wherein the second amino acid has a polar side chain Amino acid residues having a polar side chain include: serine (S), threonine (T), cysteine (C), tyrosine (Y), asparagine (N) and glutamine (Q). By "charged mutation", it is meant in the sense of the present invention the substitution of a first amino acid residue (e.g., a wild type amino acid) with a second amino acid residue wherein the second amino acid has a charged side chain Amino acid residues having a charged side chain include: arginine (R), glutamic acid (E), lysine (K), histidine (H), and aspartic acid (D).

By "disulfide bridge mutations", it is meant in the sense of the present invention the substitution of an amino acid residue with a cysteine (C) residue, so as to form disulfide bridges within a polypeptide or between polypeptides. The present invention includes individual proteins (e.g., gH, gL, pUL128, pUL130, and pUL131A) consisting of one disulfide bridge mutation (i.e., the substitution of one amino acid with cysteine). Disulfide bridges are formed between two residues and are either an "intra-disulfide bridge" (formed between two residues within the same polypeptide) or an "inter-disulfide bridge" (formed between two residues, the first residue being within a first polypeptide and the second residue being within a second polypeptide). Therefore, to increase the stability of a complex of proteins using only disulfide bridge mutations, the disulfide bridge mutations must be introduced into the complex in pairs (multiples of 2) wherein each of the at least one pair of disulfide bridge mutations is within one or more of the complex subproteins. It may be specified that the complex comprises 2n disulfide bridge mutations wherein "n" is any positive integer including zero. It may be further specified that the complex comprises two, four, six, eight, ten, twelve, fourteen, sixteen, eighteen, twenty, twenty-two, twenty-four, twenty-six, twenty-eight, thirty, thirty-two, thirty-four, thirty-six, thirty-eight, forty, forty-two, forty-four, forty-six, or a higher multiple of 2, disulfide bridge mutations. For example, the present invention encompasses a stabilized pentameric complex consisting of one pair of disulfide bridge mutations wherein the first disulfide bridge mutation is at the residue corresponding to G116C of pUL130 having the sequence SEQ ID NO: 17 and the second disulfide bridge mutation is at the residue corresponding to H150C of pUL130 having the sequence SEQ ID NO: 17 (see Table 21 below). Further for example, the present invention encompasses a stabilized pentameric complex consisting of one pair of disulfide bridge mutations wherein the first disulfide bridge mutation is at the residue corresponding to D163C of gL having the sequence SEQ ID NO: 7 and the second disulfide bridge mutation is at the residue corresponding to P62C of pUL130 having the sequence SEQ ID NO: 17 (see Table 21 below). Further for example, the present invention includes a stabilized pentameric complex consisting of two pairs of disulfide bridge mutations wherein the first pair of disulfide bridge mutations consists of a first disulfide bridge mutation at the residue corresponding to D163C of gL having the sequence SEQ ID NO: 7 and a second disulfide bridge mutation at the residue corresponding to P62C of pUL130 having the sequence SEQ ID NO: 17 and wherein the second pair of disulfide bridge mutations consists of a third disulfide bridge mutation at the residue corresponding to V109C of gH having the sequence SEQ ID NO: 1 and a fourth disulfide bridge mutation at the residue corresponding to G224C of gL having the sequence SEQ ID NO: 7 (see Table 21 below). For a stabilized complex of the present invention comprising, for example, one repacking mutation and one disulfide bridge mutation, a person with ordinary skill in the art will recognize that it is not necessary to specify a pair of disulfide bridge mutations because the one repacking mutation alone may be sufficient to effect increased stability.

By "deglycosylation mutation(s)", it is meant in the sense of the present invention the substitution of an asparagine amino acid (e.g., a wild type asparagine amino acid) with a second amino acid which thereby prevents the addition of a glycan to an asparagine nitrogen atom at that residue location (i.e., prevents N-linked glycosylation at that location). Such second amino acid may be referred to as a "deglycosylation mutant." The second amino acid may be any non-asparagine residue. It may therefore be specified that a polypeptide or complex comprising a deglycosylation mutation comprises a glutamine (Q), serine (S), threonine (T), alanine (A), glutamate (E), or aspartate (D) residue where a non-mutant (e.g., wild type or control) polypeptide or complex, respectively, comprises an asparagine (N) residue. An HCMV polypeptide, or complex-forming fragment thereof, or an HCMV complex of the present invention may comprise one or more deglycosylation mutations or may comprise a combination of one or more stabilizing mutations (i.e., a cavity-filling, repacking, and/or disulfide bridge mutation) and one or more deglycosylation mutations.

"Antigenicity" is used herein to refer to an antigen's ability to combine with an antibody, for example, to bind to a neutralizing antibody. An "increased antigenicity" or "enhanced antigenicity" therefore encompasses, for example, an increased binding affinity of a neutralizing antibody for the mutant antigen as compared to its binding affinity for a non-mutant antigen. An increased binding affinity may be provided as a decreased dissociation constant ($K_d$) value (in nM). See generally, e.g., Ma et al. *Envelope Deglycosylation Enhances Antigenicity of HIV-1 gp41 Epitopes for Both Broad Neutralizing Antibodies and Their Unmutated Ancestor Antibodies*, 2011 PLoS Path. 7(9), e1002200.

"Immunogenicity" is used herein to refer to an antigen's ability to induce an immune response. See generally, e.g., Ma et al., 2011 PLoS Path. 7(9), e1002200.

As used in the present disclosure and claims, the singular forms "a," "an," and "the" include plural forms unless the context clearly dictates otherwise; i.e., "a" means "one or more" unless indicated otherwise.

The terms "about" or "approximately" mean roughly, around, or in the regions of. The terms "about" or "approximately" further mean within an acceptable contextual error range for the particular value as determined by one of ordinary skill in the art, which will depend in part on how the value is measured or determined, i.e. the limitations of the measurement system or the degree of precision required for a particular purpose, e.g. the amount of a complex within media. When the terms "about" or "approximately" are used in conjunction with a numerical range, it modifies that range by extending the boundaries above and below the numerical values set forth. For example, "between about 5.5 to 6.5 mg/ml" means the boundaries of the numerical range extend below 5.5 and above 6.5 so that the particular value in question achieves the same functional result as within the range. For example, "about" and "approximately" can mean within 1 or more than 1 standard deviation as per the practice in the art. Alternatively, "about" and "approximately" can mean a range of up to 20%, preferably up to 10%, more preferably up to 5%, and more preferably up to 1% of a given value.

The term "and/or" as used in a phrase such as "A and/or B" is intended to include "A and B," "A or B," "A," and "B." Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

Unless specified otherwise, all of the designations "A %-B %," "A-B %," "A % to B %," "A to B %," "A %-B," "A % to B" are given their ordinary and customary meaning. In some embodiments, these designations are synonyms.

The term "comprising" encompasses "including" as well as "consisting" e.g. a composition "comprising" X may consist exclusively of X or may include something additional e.g. X+Y. The terms "comprising" and "having" when used as a transition phrase herein are open-ended whereas the term "consisting of" when used as a transition phrase herein is closed (i.e., limited to that which is listed and nothing more).

The word "substantially" does not exclude "completely" e.g. a composition which is "substantially free" from Y may be completely free from Y. Where necessary, the word "substantially" may be omitted from the definition of the invention.

An "effective amount", such as in "a therapeutically effective amount of an antigen and/or adjuvant", means an amount sufficient to cause the referenced effect or outcome. An "effective amount" can be determined empirically and in a routine manner using known techniques in relation to the stated purpose.

Unless specifically stated, a process comprising a step of mixing two or more components does not require any specific order of mixing. Thus components can be mixed in any order. Where there are three components then two components can be combined with each other, and then the combination may be combined with the third component, etc. Similarly, while steps of a method may be numbered (such as (1), (2), (3), etc. or (i), (ii), (iii)), the numbering of the steps does not mean that the steps must be performed in that order (i.e., step 1 then step 2 then step 3, etc.). The word "then" may be used to specify the order of a method's steps.

"Recombinant" as used herein to describe a polynucleotide means a polynucleotide of genomic, cDNA, RNA (including mRNA) semisynthetic, or synthetic origin which, by virtue of its origin or manipulation: (1) is not associated with all or a portion of the polynucleotide with which it is associated in nature; and/or (2) is linked to a polynucleotide other than that to which it is linked in nature. The term "recombinant" as used with respect to a protein or polypeptide means a polypeptide produced by expression of a recombinant polynucleotide. When a nucleic acid molecule is operably linked to another polynucleotide that it is not associated with in nature, the nucleic acid molecule may be referred to as "heterologous" (i.e., the nucleic acid molecule is heterologous to at least the polynucleotide). Similarly, when a polypeptide is in contact with or in a complex with another protein that it is not associated with in nature, the polypeptide may be referred to as "heterologous" (i.e., the polypeptide is heterologous to the protein). Further, when a host cell comprises a nucleic acid molecule or polypeptide that it does not naturally comprise, the nucleic acid molecule and polypeptide may be referred to as "heterologous" (i.e., the nucleic acid molecule is heterologous to the host cell and the polypeptide is heterologous to the host cell).

Sequence identity between polypeptide sequences is preferably determined by pairwise alignment algorithm using the Needleman-Wunsch global alignment algorithm (Needleman and Wunsch, A *General Method Applicable to the Search for Similarities in the Amino Acid Sequence of Two Proteins,* 1970 J. Mol. Biol. 48(3): 443-453), using default parameters (e.g. with Gap opening penalty=10.0, and with Gap extension penalty=0.5, using the EBLOSUM62 scoring matrix). This algorithm is conveniently implemented in the needle tool in the EMBOSS package (Rice et al., *EMBOSS: The European Molecular Biology Open Software Suite,* 2000 Trends Genetics 16: 276-277). Sequence identity should be calculated over the entire length of the polypeptide sequence of the invention.

gH Polypeptide

HCMV glycoprotein H (gH), which is encoded by the UL75 gene, is a virion glycoprotein that is essential for infectivity and which is conserved among members of the alpha-, beta- and gamma-herpesviruses.

The gH from HCMV strain Merlin has been reported (NCBI GI:52139248 (which is also NCBI GenBank Accession No. YP_081523.1), SEQ ID NO: 1) to consist of 742 amino acids. The gH from HCMV strain Towne (NCBI GI:138314 which is also NCBI UniProtKB Accession No. P17176.1; SEQ ID NO: 5) also consists of 742 amino acids (SEQ ID NO: 5). The gH from HCMV strain AD169 is published as NCBI UniProtKB Accession No. P12824.1 (herein SEQ ID NO: 6). HCMV gH has been reported to have six N-glycosylation sites (at residues 55, 62, 67, 192, 641 and 700), and consists of a hydrophobic signal sequence at its N-terminus (amino acid residues 1-23 of SEQ ID NO: 1), an ectodomain (residues 24-717 of SEQ ID NO: 1) that projects out of the cell into the extracellular space, a hydrophobic TM domain (residues 718-736 of SEQ ID NO: 1) and a C-terminal cytoplasmic domain (residues 737-742 of SEQ ID NO: 1).

The ectodomain of gH corresponds to the portion of gH which lacks the hydrophobic TM. The location and length of the ectodomain can be predicted based on pairwise alignment of a given sequence to SEQ ID NO: 1, for example by aligning the amino acid sequence of a gH polypeptide of interest to SEQ ID NO: 1 and identifying the sequence that aligns to residues 24-717 of SEQ ID NO: 1. Similarly, the locations of the TM and C-terminal domains can be predicted by aligning the amino acid sequence of a gH polypeptide of interest to SEQ ID NO: 1 and identifying the sequences that align to residues 718-736 and 737-742 of SEQ ID NO: 1, respectively. Alternatively, the location and length of the ectodomain, the signal sequence and the TM domain can be predicted based on computational analysis of the hydrophobicity along the length of a given gH protein sequence. The signal sequence and the TM domain have the highest levels of hydrophobicity and these two regions flank the ectodomain, which is less hydrophobic. The absence of a TM domain means that the modified polypeptide cannot reside within a lipid bilayer. In some embodiments, the gH polypeptide lacks the full-length natural TM domain; in other embodiments, it can retain a portion of the natural TM domain, but not enough to let the protein reside in a lipid bilayer. Thus, the polypeptide can contain up to 10 amino acids (e.g. 1, 2, 3, 4, 5, 6, 7, 8, 9 or 10 amino acids) of the natural gH TM domain.

Typically, the N-terminal signal sequence of gH polypeptides is cleaved by a host cell signal peptidase to produce mature gH proteins. In a preferred embodiment, the HCMV gH polypeptide mutated in accordance with the present invention lack an N-terminal signal sequence. An example of HCMV gH polypeptide lacking the N-terminal sequence is SEQ ID NO: 2. In a further preferred embodiment, the HCMV gH polypeptide mutated in accordance with the present invention lacks an N-terminal signal sequence, the transmembrane (TM) domain, and the C-terminal domain. Expression of the full-length UL75 gene sequence hinders purification of soluble complexes comprising gH. Rather, complexes comprising gH can be purified at high yield and purity by omitting at least a portion of the TM domain of gH. For example, constructs encoding just the N-terminal signal sequence and the ectodomain of gH (or a majority of the gH ectodomain), but not the TM domain can be used to express a form of gH which is easily purified (see, e.g., WO 2014/005959, also published as U.S. Pre-grant Pub. No. 2016-0159864). Said constructs may encode the majority (e.g. 70%, 80%, 85%, 90%, 95%, 96%, 97%, 98%, 99%, 99.5% or more) of the ectodomain of gH, but none or only a small portion of the TM domain. gH polypeptides of the invention may include the whole of the gH ectodomain or a truncated form of the gH ectodomain (such as the gH polypeptide consisting of SEQ ID NOs: 3 or 4 which do not comprise residues 716 or 717 of the ectodomain of SEQ ID NO: 1 and also do not comprise either the TM or C-terminal domains). Said truncated forms of the ectodomain may lack between 1 and 20 amino acids (e.g. 1, 2, 3, 4, 5, 6, 7, 8, 9, 10, 11, 12, 13, 14, 15, 16, 17, 18, 19 or 20 amino acid residues) at their N-termini and/or C-termini relative to a full-length HCMV gH protein. In alternative embodiments, the HCMV gH polypeptides mutated in accordance with the present invention lack the N-terminal signal sequence, the TM domain and the C-terminal domain. An example of a preferred HCMV gH polypeptide for use in the invention is SEQ ID NO: 3, which has a truncated ectodomain, lacks the transmembrane (TM) domain, and lacks the C-terminal cytoplasmic domain of gH sequence SEQ ID NO: 1. SEQ ID NO: 3 consists of amino acid residues 1-715 of SEQ ID NO: 1. An example of a preferred gH protein of the invention is SEQ ID NO: 4, which lacks the N-terminal signal sequence, has a truncated ectodomain, lacks the TM domain, and lacks the C-terminal domain of gH sequence SEQ ID NO: 1. SEQ ID NO: 4 consists of amino acid residues 24-715 of SEQ ID NO: 1.

As shown within the Examples, gH polypeptides are glycosylated (comprise glycans via N-linked glycosylation) at six asparagine residues: N55, N62, N67, N192, N641, and N700 numbered with respect to gH amino acid sequence SEQ ID NO: 1. An HCMV gH polypeptide, or complex-forming fragment thereof, for use in the invention may comprise a deglycosylation mutation at one or more of the asparagines located at residues 55, 62, 67, 192, 641, and 700 numbered with respect to gH sequence SEQ ID NO: 1. The deglycosylation mutation may be glutamine (Q), serine (S), threonine (T), alanine (A), glutamate (E), or aspartate (D). In particular, the deglycosylation mutation may be glutamine (Q), serine (S), threonine (T), or alanine (A). Further in particular, the deglycosylation mutation may be glutamine (Q).

gH proteins of the invention may contain additional amino acid residues, such as N-terminal or C-terminal extensions. Such extensions may include one or more tags, which can facilitate detection (e.g. an epitope tag for detection by monoclonal antibodies) and/or purification (e.g. a polyhistidine-tag to allow purification on a nickel-chelating resin) of the gH protein. For example, gH proteins of the invention may comprise a truncated gH ectodomain fused to a C-terminal extension (see, e.g., WO 2014/005959, also published as U.S. Pre-grant Pub. No. 2016-0159864).

gH proteins of the invention can have various degrees of identity to SEQ ID NO: 1, such as an at least 60%, 70%, 80%, 81%, 82%, 83%, 84%, 85%, 86%, 87%, 88%, 89%, 90%, 91%, 92%, 93%, 94%, 95%, 96%, 97%, 98% or 99% identity to the sequence recited in SEQ ID NO: 1. gH proteins of the invention can have various degrees of identity to SEQ ID NO: 2, such as an at least 60%, 70%, 80%, 81%, 82%, 83%, 84%, 85%, 86%, 87%, 88%, 89%, 90%, 91%, 92%, 93%, 94%, 95%, 96%, 97%, 98% or 99% identity to the sequence recited in SEQ ID NO: 2. gH proteins of the invention can have various degrees of identity to SEQ ID NO: 3, such as an at least 60%, 70%, 80%, 81%, 82%, 83%, 84%, 85%, 86%, 87%, 88%, 89%, 90%, 91%, 92%, 93%, 94%, 95%, 96%, 97%, 98% or 99% identity to the sequence recited in SEQ ID NO: 3. gH proteins of the invention can have various degrees of identity to SEQ ID NO: 4, such as an at least 60%, 70%, 80%, 81%, 82%, 83%, 84%, 85%, 86%, 87%, 88%, 89%, 90%, 91%, 92%, 93%, 94%, 95%, 96%, 97%, 98% or 99% identity to the sequence recited in SEQ ID NO: 4. gH proteins of the invention can have various degrees of identity to SEQ ID NO: 5, such as an at least 60%, 70%, 80%, 81%, 82%, 83%, 84%, 85%, 86%, 87%, 88%, 89%, 90%, 91%, 92%, 93%, 94%, 95%, 96%, 97%, 98% or 99% identity to the sequence recited in SEQ ID NO: 5. gH proteins of the invention can have various degrees of identity to SEQ ID NO: 6, such as an at least 60%, 70%, 80%, 81%, 82%, 83%, 84%, 85%, 86%, 87%, 88%, 89%, 90%, 91%, 92%, 93%, 94%, 95%, 96%, 97%, 98% or 99% identity to the sequence recited in SEQ ID NO: 6. Preferred gH proteins or fragments thereof: (i) can dimerize with HCMV gL; (ii) form part of the trimeric gH/gL/gO complex; (iii) form part of the pentameric gH/gL/pUL128/pUL130/pUL131A complex; (iv) comprise at least one epitope from SEQ ID NO: 1, 2, 3, 4, 5, or 6 and/or (v) can elicit antibodies in vivo which immunologically cross-react with an HCMV virion. An exemplary complex-forming fragment of gH comprises residues Arg1 through Leu125 of SEQ ID NO: 2 which, when in complex with full length gL (perhaps using the flexible C-terminus of gL as a linker), full length pUL128, full length pUL130, and full length pUL131A; may form a truncated HCMV pentamer complex that nonetheless maintains the five conformational epitope sites described in FIG. 7.

The HCMV gH polypeptides, or complex-forming fragments thereof, of the invention comprise one or more stabilizing mutations, suitably, one or more cavity-filling mutations, one or more hydrophobic mutations, one or more hydrophilic mutations, one or more disulfide bridge mutations, or any combination of one or more thereof. Any of the gH polypeptides having the sequence as set forth in SEQ ID NO: 1, SEQ ID NO: 2, SEQ ID NO: 3 or SEQ ID NO: 4, or any gH polypeptide having a sequence at least 90% identical to SEQ ID NO: 1, SEQ ID NO: 2, SEQ ID NO: 3 or SEQ ID NO: 4 may suitably comprise any one or more stabilizing mutations as identified and defined herein. Accordingly, in some embodiments, the HCMV gH polypeptide having the sequence set forth in SEQ ID NO: 1, or complex-forming fragments thereof, comprises one or more cavity-filling mutations, one or more hydrophobic mutations, one or more hydrophilic mutations, one or more disulfide bridge mutations, or any combination of one or more thereof. In alternative embodiments, the HCMV gH polypeptide having the sequence set forth in SEQ ID NO: 2, or complex-forming fragments thereof, comprises one or more cavity-filling mutations, one or more hydrophobic mutations, one or more hydrophilic mutations, one or more disulfide bridge mutations, or any combination of one or more thereof. In further alternative embodiments, the HCMV gH polypeptide having the sequence set forth in SEQ ID NO: 3, or complex-forming fragments thereof, comprises one or more cavity-filling mutations, one or more hydrophobic mutations, one or more hydrophilic mutations, one or more disulphide bridge mutations, or any combination of one or more thereof. In further alternative embodiments, the HCMV gH polypeptide having the sequence set forth in SEQ ID NO: 4, or complex-forming fragments thereof, comprises one or more cavity-filling mutations, one or more hydrophobic mutations, one or more hydrophilic mutations, one or more disulfide bridge mutations, or any combination of one or more thereof.

As further detailed in Example 3 and illustrated in FIGS. 2A-2F, the present inventors identified, in the crystal structure of the pentameric complex, some cavities at the gH/gL/ULs interface. Therefore, any cavity-filling mutation, the purpose of which being to fill the cavities observed at such interface in the HCMV gH polypeptide, is expected to advantageously contribute to the stability of a complex (e.g., a pentameric, gH/gL, or gH/gL/gO complex), when associated with the other components of said complex. Similarly, any repacking mutation, such as any hydrophobic mutation, or any hydrophilic mutation, the purpose of which being to increase the contact of the neighboring residues in the HCMV gH polypeptide, is expected to advantageously contribute to the stability of a complex (e.g., a pentameric, gH/gL, or gH/gL/gO complex), when associated with the other components of said complex. Similarly, any disulfide bridge mutation, the purpose of which being to introduce intra-disulfide bridges into the HCMV gH polypeptide and/or inter-disulfide bridges between the HCMV gH polypeptide and any of the other components of a complex (e.g., HCMV gL, HCMV pUL128, HCMV pUL130 or HCMV pUL131A polypeptide of the HCMV pentameric complex), is expected to advantageously contribute to the complex having an enhanced thermo-stability.

The identification of relevant amino acid residues, in the HCMV gH polypeptide, to mutate for cavity-filling and/or repacking and/or disulfide bridges may be performed, for example, by both visual inspection of the three-dimensional structure with the aid of molecular graphics softwares, or by using any appropriate in-silico mutagenesis method. For example, softwares, such as Molecular Operating Environment (MOE) (edited by Chemical Computing Group Inc.) allows for a systematic analysis of amino acid sequences to identify specific regions in the polypeptide or specific amino acids, the mutation of which is predicted to enhance thermostability.

Suitable non-limiting exemplary amino acid residues to mutate in HCMV gH polypeptides are provided in Table 1, using the sequence set forth as SEQ ID NO: 1 as a reference only. Mutations at similar positions in other HCMV gH polypeptides, such as for example, polypeptides having the sequence as set forth in SEQ ID NO: 2, SEQ ID NO: 3 or SEQ ID NO: 4, or gH polypeptides originating from HCMV strains different from the Merlin strain, are also contemplated in the present invention. It is within the skilled person's abilities to determine such similar positions in other HCMV gH polypeptides. Comparable amino acid positions in a given HCMV polypeptide can be determined by aligning the amino acid sequences using readily available and well-known alignment and algorithms (such as BLAST or ClustalW2). The actual number of the amino acid position may have to be adjusted for other HCMV gH polypeptides depending on the actual sequence alignment.

TABLE 1A

Mutant HCMV gH polypeptides
(positions provided with respect to SEQ ID NO: 1)

| Cavity-filling mutations | Hydrophobic mutations | Hydrophilic mutations | Disulfide mutations | Deglycosylation mutations |
|---|---|---|---|---|
| A102 | H252 | G358 | V109 | N55 |
| A372 | K404 | H275 | L111 | N62 |
| A352 | R255 |  |  | N67 |
| L257 | E355 |  |  | N192 |
|  | H480 |  |  | N641 |
|  | S601 |  |  | N700 |
|  | R405 |  |  |  |

Accordingly, in some embodiments, amino acids to mutate in HCMV gH polypeptide for cavity filling are A102, A372, A352, or L257 of the sequence set forth in SEQ ID NO: 1, or at a corresponding position in HCMV gH polypeptides originating from different HCMV strains. Suitably, the mutation of these amino acid residues may consist of substituting any of them and/or more than one of them, possibly all of them, with amino acid residues, selected from the group consisting of tryptophan (W), phenylalanine (F), tyrosine (Y), valine (V), isoleucine (I), and leucine (L). Accordingly, in some embodiments, the HCMV gH polypeptides of the invention comprise at least an amino acid substitution at positions corresponding to 102, 372, 352, and 257 of SEQ ID NO: 1 with amino acids selected from the group consisting of tryptophan (W), phenylalanine (F), tyrosine (Y), valine (V), isoleucine (I), and leucine (L).

Suitable non-limiting exemplary amino acids to mutate in HCMV gH polypeptides for hydrophobic mutations are H252, K404, R255, E355, H480, 5601, or R405, of the sequence set forth in SEQ ID NO: 1, or at a corresponding position in HCMV gH polypeptides originating from different HCMV strains. Suitably, the mutation of these amino acid residues may consist of substituting any of them and/or more than one of them, possibly all of them, with amino acid residues, selected from the group consisting of tryptophan (W), phenylalanine (F), methionine (M), cysteine (C), alanine (A), leucine (L), isoleucine (I), valine (V) and proline (P). Accordingly, in some embodiments, the HCMV gH polypeptides of the invention comprise at least an amino acid substitution at positions 252, 404, 255, 355, 480, 601, and 405 with amino acids selected from the group consisting of tryptophan (W), phenylalanine (F), methionine (M), cysteine (C), alanine (A), leucine (L), isoleucine (I), valine (V) and proline (P).

Suitable non-limiting exemplary amino acids to mutate in HCMV gH polypeptides for hydrophilic mutations are G358 or H275 of the sequence set forth in SEQ ID NO: 1, or at a corresponding position in HCMV gH polypeptides originating from different HCMV strains. Suitably, the mutation of these amino acid residues may consist of substituting any of them and/or more than one of them, possibly all of them, with amino acid residues, selected from the group consisting of serine (S), threonine (T), cysteine (C), tyrosine (Y), asparagine (N), glutamine (Q), arginine (R), and glutamic acid (E). Accordingly, in some embodiments, the HCMV gH polypeptides of the invention comprise at least an amino acid substitution at positions corresponding to G358 and H275 of SEQ ID NO: 1 with amino acids selected from the group consisting of serine (S), threonine (T), cysteine (C), tyrosine (Y), asparagine (N), glutamine (Q), arginine (R), and glutamic acid (E). Suitable non-limiting exemplary amino acids to mutate in HCMV gH polypeptides for polar mutations are G358 or H275 of the sequence set forth in SEQ ID NO: 1, or at a corresponding position in HCMV gH polypeptides originating from different HCMV strains. Suitably, the mutation of these amino acid residues may consist of substituting any of them and/or more than one of them, possibly all of them, with amino acid residues, selected from the group consisting of serine (S), threonine (T), cysteine (C), tyrosine (Y), asparagine (N), and glutamine (Q). Accordingly, in some embodiments, the HCMV gH polypeptides of the invention comprise at least an amino acid substitution at positions corresponding to G358 and H275 of SEQ ID NO: 1 with amino acids selected from the group consisting of serine (S), threonine (T), cysteine (C), tyrosine (Y), asparagine (N), and glutamine (Q). Suitable non-limiting exemplary amino acids to mutate in HCMV gH polypeptides for charged mutations are G358 or H275 of the sequence set forth in SEQ ID NO: 1, or at a corresponding position in HCMV gH polypeptides originating from different HCMV strains. Suitably, the mutation of these amino acid residues may consist of substituting any of them and/or more than one of them, possibly all of them, with the amino acid residue arginine (R) or glutamic acid (E). Accordingly, in some embodiments, the HCMV gH polypeptides of the invention comprise at least an amino acid substitution at positions corresponding to G358 and H275 of SEQ ID NO: 1 with the amino acid arginine (R) or glutamic acid (E).

Suitable non-limiting exemplary amino acids to mutate in HCMV gH polypeptides for disulphide bridge mutations are V109 or L111 of the sequence set forth in SEQ ID NO: 1, or at a corresponding position in HCMV gH polypeptides originating from different HCMV strains. Accordingly, in some embodiments, the HCMV polypeptides of the invention comprise at least a substitution of the residue corresponding to V109 of SEQ ID NO: 1 with a cysteine (C) or of the residue corresponding to L111 of SEQ ID NO: 1 with a cysteine (C), suitably, both.

Accordingly, in some embodiments, amino acids to mutate in HCMV gH polypeptides for deglycosylation are N55, N62, N67, N192, N641, and N700 of the sequence set forth in SEQ ID NO: 1, or at a corresponding position in HCMV gH polypeptides originating from different HCMV strains. Suitably, the mutation of these amino acid residues may consist of substituting any of them and/or more than one of them, possibly all of them, with amino acid residues selected from the group consisting of glutamine (Q), serine (S), threonine (T), alanine (A), glutamate (E), and aspartate (D). Accordingly, in some embodiments, the HCMV gH polypeptides of the invention comprise at least an amino acid substitution at positions corresponding to 55, 62, 67, 192, 641, and 700 of SEQ ID NO: 1 with amino acids selected from the group consisting of glutamine (Q), serine (S), threonine (T), alanine (A), glutamate (E), and aspartate (D).

TABLE 1B

Modified HCMV gH polypeptides of the present invention comprise, with respect to the sequence SEQ ID NO: 1, one or more of:

A102W, A102F, A102Y, A102V, A102I, A102L, A372W, A372F, A372Y, A372V, A372I, A372L, A352W, A352F, A352Y, A352V, A352I, A352L, L257W, L257F, L257Y, L257V, L257I, L257L,
H252W, H252F, H252M, H252C, H252A, H252L, H252I, H252V, H252P, H252Y, K404W, K404F, K404M, K404C, K404A, K404L, K404I, K404V, K404P, K404Y, R255W, R255F, R255M, R255C, R255A, R255L, R255I, R255V, R255P, R255Y, E355W, E355F, E355M, E355C, E355A, E355L, E355I, E355V, E355P, E355Y, H480W, H480F, H480M, H480C, H480A, H480L, H480I, H480V, H480P, H480Y, S601W, S601F, S601M, S601C, S601A, S601L, S601I, S601V, S601P, S601Y, R405W, R405F, R405M, R405C, R405A, R405L, R405I, R405V, R405P, R405Y,
G358S, G358T, G358C, G358Y, G358N, G358Q, G358R, G358E, G358K, G358H, G358D, H275S, H275T, H275C, H275Y, H275N, H275Q, H275R, H275E, H275K, H275H, H275D,
V109C, L111C,
N55Q, N55S, N55T, N55A, N55E, N55D, N62Q, N62S, N62T, N62A, N62E, N62D, N67Q, N67S, N67T, N67A, N67E, N67D, N192Q, N192S, N192T, N192A, N192E, N192D, N641Q, N641S, N641T, N641A, N641E, N641D, N700Q, N700S, N700T, N700A, N700E, and N700D.

gL Polypeptide

HCMV glycoprotein L (gL), which is encoded by the UL115 gene is thought to be essential for viral replication. All known functional properties of gL are directly associated with its dimerization with gH. The gL/gH complex is required for the fusion of viral and plasma membranes leading to virus entry into the host cell. gL from HCMV strain Merlin (NCBI GI:39842115 (which is also NCBI GenBank Accession No. AAR31659.1), SEQ ID NO: 7) and HCMV strain Towne (NCBI GI:239909463 which is also NCBI GenBank Accession No. ACS32410.1; SEQ ID NO: 11 herein) have been reported to be 278 amino acids in length. gL from HCMV strain AD169 (NCBI GI:2506510 which is also NCBI UniProtKB Accession No. P16832.2; SEQ ID NO: 12 herein) has been reported to be 278 amino acids in length, include a signal sequence at its N-terminus (amino acid residues 1-35), have two N-glycosylation sites (at residues 74 and 114) and lack a TM domain (Rigoutsos et al., *In silico pattern-based analysis of the human cytomegalovirus genome*, 2003 J. of Virology 77: 4326-44). Sequencing of the full-length gL gene from 22 to 39 clinical isolates, as well as laboratory strains AD169, Towne and Toledo revealed less than 2% variation in the amino acid sequences among the isolates (Rasmussen et al., *The Genes Encoding the gCIII Complex of Human Cytomegalovirus Exist in Highly Diverse Combinations in Clinical Isolates*, 2002 J. of Virology 76: 10841-10888). Typically, the N-terminal signal sequence of gL proteins is cleaved by a host cell signal peptidase to produce mature gL polypeptides. The gL polypeptides for use in the invention may lack an N-terminal signal sequence. An example of HCMV gL polypeptide lacking the N-terminal sequence is SEQ ID NO: 8, which consists of amino acid residues 31-278 of SEQ ID NO: 7. An example of a preferred gL polypeptide for use in the invention is SEQ ID NO: 9 or 10, which comprise an LSG mutation at what is believed to be a protease recognition site, wherein said mutation reduces protease cleavage. An example of a preferred gL polypeptide for use in the invention is SEQ ID NO: 29 or 30, which comprise an IDG mutation at what is believed to be a protease recognition site, wherein said mutation reduces protease cleavage.

As shown within the Examples, gL polypeptides are glycosylated (comprise glycans via N-linked glycosylation) at one asparagine residue, N74 numbered with respect to gL amino acid sequence SEQ ID NO: 7. An HCMV gL polypeptide, or complex-forming fragment thereof, for use in the invention may comprise a deglycosylation mutation at residue 74 numbered with respect to gL sequence SEQ ID NO: 7. The deglycosylation mutation may be glutamine (Q), serine (S), threonine (T), alanine (A), glutamate (E), or aspartate (D). In particular, the deglycosylation mutation may be glutamine (Q), serine (S), threonine (T), or alanine (A). Further in particular, the deglycosylation mutation may be glutamine (Q).

gL proteins of the invention can have various degrees of identity to SEQ ID NO: 7, such as an at least 60%, 70%, 80%, 81%, 82%, 83%, 84%, 85%, 86%, 87%, 88%, 89%, 90%, 91%, 92%, 93%, 94%, 95%, 96%, 97%, 98% or 99% identity to the sequence recited in SEQ ID NO: 7. gL proteins of the invention can have various degrees of identity to SEQ ID NO: 8, such as an at least 60%, 70%, 80%, 81%, 82%, 83%, 84%, 85%, 86%, 87%, 88%, 89%, 90%, 91%, 92%, 93%, 94%, 95%, 96%, 97%, 98% or 99% identity to the sequence recited in SEQ ID NO: 8. gL proteins of the invention can have various degrees of identity to SEQ ID NO: 9, such as an at least 60%, 70%, 80%, 81%, 82%, 83%, 84%, 85%, 86%, 87%, 88%, 89%, 90%, 91%, 92%, 93%, 94%, 95%, 96%, 97%, 98% or 99% identity to the sequence recited in SEQ ID NO: 9. gL proteins of the invention can have various degrees of identity to SEQ ID NO: 10, such as an at least 60%, 70%, 80%, 81%, 82%, 83%, 84%, 85%, 86%, 87%, 88%, 89%, 90%, 91%, 92%, 93%, 94%, 95%, 96%, 97%, 98% or 99% identity to the sequence recited in SEQ ID NO: 10. gL proteins of the invention can have various degrees of identity to SEQ ID NO: 11, such as an at least 60%, 70%, 80%, 81%, 82%, 83%, 84%, 85%, 86%, 87%, 88%, 89%, 90%, 91%, 92%, 93%, 94%, 95%, 96%, 97%, 98% or 99% identity to the sequence recited in SEQ ID NO: 11. gL proteins of the invention can have various degrees of identity to SEQ ID NO: 12, such as an at least 60%, 70%, 80%, 81%, 82%, 83%, 84%, 85%, 86%, 87%, 88%, 89%, 90%, 91%, 92%, 93%, 94%, 95%, 96%, 97%, 98% or 99% identity to the sequence recited in SEQ ID NO: 12. gL proteins of the invention can have various degrees of identity to SEQ ID NO: 29, such as an at least 60%, 70%, 80%, 81%, 82%, 83%, 84%, 85%, 86%, 87%, 88%, 89%, 90%, 91%, 92%, 93%, 94%, 95%, 96%, 97%, 98% or 99% identity to the sequence recited in SEQ ID NO: 29. gL proteins of the invention can have various degrees of identity to SEQ ID NO: 30, such as an at least 60%, 70%, 80%, 81%, 82%, 83%, 84%, 85%, 86%, 87%, 88%, 89%, 90%, 91%, 92%, 93%, 94%, 95%, 96%, 97%, 98% or 99% identity to the sequence recited in SEQ ID NO: 30. Preferred gL proteins or fragments thereof: (i) can dimerize with HCMV gH; (ii) form part of the trimeric gH/gL/gO complex; (iii) form part of the pentameric gH/gL/pUL128/pUL130/pUL131A complex; (iv) comprise at least one epitope from SEQ ID NOs: 7, 8, 9, 10, 11, 12, 29, or 30; and/or (v) can elicit antibodies in vivo which immunologically cross-react with an HCMV virion. An exemplary complex-forming fragment of gL comprises residues Thr76 through Tyr169 of SEQ ID NO: 7 which, when in complex with full length pUL128, full length pUL130, and full length pUL131A (i.e., gH is not present); may form a truncated HCMV pentamer complex that nonetheless maintains the five conformational epitope sites described in FIG. 7.

The HCMV gL polypeptides, or complex-forming fragments thereof, of the invention comprise one or more stabilizing mutations, suitably, one or more cavity-filling mutations, one or more hydrophobic mutations, one or more hydrophilic mutations, one or more disulfide bridge mutations, or any combination of one or more thereof. Any of the gL polypeptides having the sequence as set forth in SEQ ID NO: 7, SEQ ID NO: 8, SEQ ID NO: 9, SEQ ID NO: 10, SEQ ID NO: 11, SEQ ID NO: 12, SEQ ID NO: 29, or SEQ ID NO: 30 or any gL polypeptide having a sequence at least 90% identical to SEQ ID NO: 7, SEQ ID NO: 8, SEQ ID NO: 9, SEQ ID NO: 10, SEQ ID NO: 11, SEQ ID NO: 12, SEQ ID NO: 29, or SEQ ID NO: 30, or complex-forming fragments thereof, may suitably comprise any one or more stabilizing mutations as identified and defined herein. Accordingly, in some embodiments, the HCMV gL polypeptide having the sequence set forth in SEQ ID NO: 7, or complex-forming fragments thereof, comprises one or more cavity-filling mutations, one or more hydrophobic mutations, one or more hydrophilic mutations, one or more disulfide bridge mutations, or any combination of one or more thereof. In alternative embodiments, the HCMV gL polypeptide having the sequence set forth in SEQ ID NO: 8, or complex-forming fragments thereof, comprises one or more cavity-filling mutations, one or more hydrophobic mutations, one or more hydrophilic mutations, one or more disulfide bridge mutations, or any combination of one or more thereof. In further alternative embodiments, the HCMV gL polypeptide having the sequence set forth in SEQ ID NO: 9, or complex-forming fragments thereof, comprises one or more cavity-filling mutations, one or more hydrophobic mutations, one or more hydrophilic mutations, one or more disulphide bridge mutations, or any combination of one or more thereof. In further alternative embodiments, the HCMV gL polypeptide having the sequence set forth in SEQ ID NO: 10, or complex-forming fragments thereof, comprises one or more cavity-filling mutations, one or more hydrophobic mutations, one or more hydrophilic mutations, one or more disulphide bridge mutations, or any combination of one or more thereof. In further alternative embodiments, the HCMV gL polypeptide having the sequence set forth in SEQ ID NO: 29, or complex-forming fragments thereof, comprises one or more cavity-filling mutations, one or more hydrophobic mutations, one or more hydrophilic mutations, one or more disulphide bridge mutations, or any combination of one or more thereof. In further alternative embodiments, the HCMV gL polypeptide having the sequence set forth in SEQ ID NO: 30, or complex-forming fragments thereof, comprises one or more cavity-filling mutations, one or more hydrophobic mutations, one or more hydrophilic mutations, one or more disulphide bridge mutations, or any combination of one or more thereof.

As further detailed in Example 3 and illustrated in FIGS. 2A-2F, the present inventors identified, in the crystal structure of the pentameric complex, some cavities at the gH/gL/ULs interface. Therefore, any cavity-filling mutation, the purpose of which being to fill the cavities observed at such interface in the HCMV gL polypeptide, is expected to advantageously contribute to the stability of a complex (e.g., a pentameric, gH/gL, or gH/gL/gO complex), when associated with the other components of said complex. Similarly, any repacking mutation, such as any hydrophobic mutation, or any hydrophilic mutation, the purpose of which being to increase the contact of the neighboring residues in the HCMV gL polypeptide, is expected to advantageously contribute to the stability of a complex (e.g., a pentameric, gH/gL, or gH/gL/gO complex), when associated with the other components of said complex. Similarly, any disulfide bridge mutation, the purpose of which being to introduce intra-disulfide bridges into the HCMV gL polypeptide and/or inter-disulfide bridges between the HCMV gL polypeptide and any other components of a complex (e.g., HCMV gH, HCMV pUL128, HCMV pUL130 or HCMV pUL131A polypeptide of the HCMV pentameric complex), is expected to advantageously contribute to the complex having an enhanced thermo-stability.

The identification of relevant amino acid residues, in the HCMV gL polypeptide, to mutate for cavity-filling and/or repacking and/or disulfide bridges may be performed, for example, by both visual inspection of the three-dimensional structure with the aid of molecular graphics softwares, or by using any appropriate in-silico mutagenesis method. For example, softwares, such as Molecular Operating Environment (MOE) (edited by Chemical Computing Group Inc.) allows for a systematic analysis of amino acid sequences to identify specific regions in the polypeptide or specific amino acids, the mutation of which is predicted to enhance thermo-stability.

Suitable non-limiting exemplary amino acid residues to mutate in HCMV gL polypeptides are provided in Table 2, using the sequence set forth as SEQ ID NO: 7 as a reference only. Mutations at similar positions in other HCMV gL polypeptides, such as for example, polypeptides having the sequence as set forth in SEQ ID NO: 8, SEQ ID NO: 9, SEQ ID NO: 10, SEQ ID NO: 29, or SEQ ID NO: 30, or gL polypeptides originating from HCMV strains different from the Merlin strain, are also contemplated in the present invention. It is within the skilled person's abilities to determine such similar positions in other HCMV gL polypeptides. Comparable amino acid positions in a given HCMV gL polypeptide can be determined by aligning the amino acid sequences using readily available and well-known alignment and algorithms (such as BLAST or ClustalW2). The actual number of the amino acid position may have to be adjusted for other HCMV gL polypeptides depending on the actual sequence alignment.

Accordingly, in some embodiments, an amino acid to mutate in HCMV gL polypeptides for deglycosylation is N74 of the sequence set forth in SEQ ID NO: 7, or at a corresponding position in HCMV gL polypeptides originating from different HCMV strains. Suitably, the mutation of this amino acid residue may consist of substituting it with an amino acid residue selected from the group consisting of glutamine (Q), serine (S), threonine (T), alanine (A), glutamate (E), and aspartate (D). Accordingly, in some embodiments, the HCMV gL polypeptides of the invention comprise at least an amino acid substitution at the position corresponding to 74 of SEQ ID NO: 7 with an amino acid selected from the group consisting of glutamine (Q), serine (S), threonine (T), alanine (A), glutamate (E), and aspartate (D).

TABLE 2A

Mutant HCMV gL polypeptides
(positions provided with respect to SEQ ID NO: 7)

| Cavity-filling mutations | Hydrophobic mutations | Hydrophilic mutations | Disulfide mutations | Deglycosylation mutation |
|---|---|---|---|---|
| H177 | H267 | | G161 | N74 |
| G224 | H236 | | D163 | |

TABLE 2A-continued

Mutant HCMV gL polypeptides
(positions provided with respect to SEQ ID NO: 7)

| Cavity-filling mutations | Hydrophobic mutations | Hydrophilic mutations | Disulfide mutations | Deglycosylation mutation |
|---|---|---|---|---|
| G140 | H245 | | G224 | |
| G145 | G161 | | G218 | |
| D146 | C233 | | R166 | |
| G218 | | | G140 | |
| L119 | | | R160 | |
| P272 | | | A150 | |
| C233 | | | | |

Accordingly, in some embodiments, amino acids to mutate in HCMV gL polypeptides for cavity filling are H177, G224, G140, G145, D146, G218, L119, C233 or P272 of the sequence set forth in SEQ ID NO: 7, or at a corresponding position in HCMV gL polypeptides originating from different HCMV strains. Suitably, the mutation of these amino acid residues may consist of substituting any of them and/or more than one of them, possibly all of them, with amino acid residues, selected from the group consisting of tryptophan (W), phenylalanine (F), tyrosine (Y), valine (V), isoleucine (I), and leucine (L). Accordingly, in some embodiments, the HCMV gL polypeptides of the invention comprise at least an amino acid substitution at positions corresponding to 177, 224, 140, 145, 146, 218, 119, 233 and 272 of SEQ ID NO: 7 with amino acids selected from the group consisting of tryptophan (W), phenylalanine (F), tyrosine (Y), valine (V), isoleucine (I), and leucine (L).

Suitable non-limiting exemplary amino acids to mutate in HCMV gL polypeptides for hydrophobic mutations are H267, H236, H245, G161, or C233 of the sequence set forth in SEQ ID NO: 7, or at a corresponding position in HCMV gL polypeptides originating from different HCMV strains. Suitably, the mutation of these amino acid residues may consist of substituting any of them and/or more than one of them, possibly all of them, with amino acid residues, selected from the group consisting of tryptophan (W), phenylalanine (F), methionine (M), cysteine (C), alanine (A), leucine (L), isoleucine (I), valine (V), proline (P), and tyrosine (Y). Accordingly, in some embodiments, the HCMV gL polypeptides of the invention comprise at least an amino acid substitution at positions corresponding to 267, 236, 245, 161, and 233 of SEQ ID NO: 7 with amino acids selected from the group consisting of tryptophan (W), phenylalanine (F), methionine (M), cysteine (C), alanine (A), leucine (L), isoleucine (I), valine (V) and proline (P).

Suitable non-limiting exemplary amino acids to mutate in HCMV gL polypeptides for disulphide bridge mutations are G161, D163, G224, G218, R166, G140, R160, or A150 of the sequence set forth in SEQ ID NO: 7, or at a corresponding position in HCMV gL polypeptides originating from different HCMV strains. Accordingly, in some embodiments, the HCMV gL polypeptides of the invention comprise at least a substitution selected from the group consisting of: G161C, D163C, G224C, G218C, R166C, G140C, R160C, A150C, and combinations thereof.

TABLE 2B

Modified HCMV gL polypeptides of the present invention comprise, with respect to the sequence SEQ ID NO: 7, one or more of:

H177W, H177F, H177Y, H177V, H177I, H177L, G224W, G224F, G224Y, G224V, G224I, G224L, G140W, G140F, G140Y, G140V,

TABLE 2B-continued

Modified HCMV gL polypeptides of the present invention comprise, with respect to the sequence SEQ ID NO: 7, one or more of:

G140I, G140L, G145W, G145F, G145Y, G145V, G145I, G145L, D146W, D146F, D146Y, D146V, D146I, D146L, G218W, G218F, G218Y, G218V, G218I, G218L, L119W, L119F, L119Y, L119V, L119I, L119L, C233W, C233F, C233Y, C233L, P272W, P272F, P272Y, P272V, P272I, P272L,
H267W, H267F, H267M, H267C, H267A, H267L, H267I, H267V, H267P, H267Y, H236W, H236F, H236M, H236C, H236A, H236L, H236I, H236V, H236P, H236Y, H245W, H245F, H245M, H245C, H245A, H245L, H245I, H245V, H245P, H245Y, G161W, G161F, G161M, G161C, G161A, G161L, G161I, G161V, G161P, G161Y, C233W, C233F, C233M, C233C, C233A, C233L, C233I, C233V, C233P, C233Y,
G161C, D163C, G224C, G218C, R166C, G140C, R160C, A150C, N74Q, N74S, N74T, N74A, N74E, and N74D.

pUL128 Polypeptide

The pUL128 (or simply "UL128") from HCMV strain Merlin has been reported (NCBI GI:39842124 (which is also NCBI GenBank Accession No. AAR31668.1), SEQ ID NO: 13) to consist of 130 amino acids and to contain a one (1) nucleotide substitution causing premature termination. The pUL128 from HCMV strains Towne (NCBI GI:39841882 (which is also NCBI GenBank Accession No. AAR31451.1), SEQ ID NO: 15) and AD169 (NCBI GI:59803078 (which is also NCBI UniProtKB Accession No. P16837.2), SEQ ID NO: 16) have been reported to consist of 171 amino acids. Due to the premature termination of SEQ ID NOs: 13, 15 and 17 only share 75% identity over the full-length of SEQ ID NO: 13. pUL128 is predicted to have an N-terminal signal sequence, which is located at residues 1-27 of SEQ ID NO: 13, but it is predicted to lack a TM domain. Typically, the N-terminal signal sequence of pUL128 polypeptides is cleaved by a host cell signal peptidase to produce mature pUL128 polypeptides. The pUL128 polypeptides for use in the invention may lack an N-terminal signal sequence. An example of HCMV pUL128 polypeptide lacking the N-terminal sequence is SEQ ID NO: 14, which consists of amino acid residues 28-130 of SEQ ID NO: 13.

pUL128 proteins of the invention can have various degrees of identity to SEQ ID NO: 13, such as an at least 60%, 70%, 80%, 81%, 82%, 83%, 84%, 85%, 86%, 87%, 88%, 89%, 90%, 91%, 92%, 93%, 94%, 95%, 96%, 97%, 98% or 99% identity to the sequence recited in SEQ ID NO: 13. pUL128 proteins of the invention can have various degrees of identity to SEQ ID NO: 14, such as an at least 60%, 70%, 80%, 81%, 82%, 83%, 84%, 85%, 86%, 87%, 88%, 89%, 90%, 91%, 92%, 93%, 94%, 95%, 96%, 97%, 98% or 99% identity to the sequence recited in SEQ ID NO: 14. pUL128 proteins of the invention can have various degrees of identity to SEQ ID NO: 15, such as an at least 60%, 70%, 80%, 81%, 82%, 83%, 84%, 85%, 86%, 87%, 88%, 89%, 90%, 91%, 92%, 93%, 94%, 95%, 96%, 97%, 98% or 99% identity to the sequence recited in SEQ ID NO: 15. pUL128 proteins of the invention can have various degrees of identity to SEQ ID NO: 16, such as an at least 60%, 70%, 80%, 81%, 82%, 83%, 84%, 85%, 86%, 87%, 88%, 89%, 90%, 91%, 92%, 93%, 94%, 95%, 96%, 97%, 98% or 99% identity to the sequence recited in SEQ ID NO: 16. Preferred pUL128 proteins or fragments thereof: (i) can form part of the pentameric gH/gL/pUL128/pUL130/pUL131A complex, (ii) comprise at least one epitope of SEQ ID NOs: 13, 14, 15, or 16, and/or (iii) can elicit antibodies in vivo which immunologically cross-react with an HCMV virion.

The HCMV pUL128 polypeptides, or complex-forming fragments thereof, of the invention comprise one or more stabilizing mutations, suitably, one or more cavity-filling mutations, one or more hydrophobic mutations, one or more hydrophilic mutations, one or more disulfide bridge mutations, or any combination of one or more thereof. Any of the pUL128 polypeptides having the sequence as set forth in SEQ ID NO: 13, SEQ ID NO: 14, SEQ ID NO: 15, or SEQ ID NO: 16, or any pUL128 polypeptide having a sequence at least 90% identical to SEQ ID NO: 13, SEQ ID NO: 14, SEQ ID NO: 15, or SEQ ID NO: 16, or complex-forming fragments thereof, may suitably comprise any one or more stabilizing mutations as identified and defined herein. Accordingly, in some embodiments, the HCMV pUL128 polypeptide having the sequence set forth in SEQ ID NO: 13, or complex-forming fragments thereof, comprises one or more cavity-filling mutations, one or more hydrophobic mutations, one or more hydrophilic mutations, one or more disulfide bridge mutations, or any combination of one or more thereof. In alternative embodiments, the HCMV pUL128 polypeptide having the sequence set forth in SEQ ID NO: 14, or complex-forming fragments thereof, comprises one or more cavity-filling mutations, one or more hydrophobic mutations, one or more hydrophilic mutations, one or more disulfide bridge mutations, or any combination of one or more thereof. In further alternative embodiments, the HCMV pUL128 polypeptide having the sequence set forth in SEQ ID NO: 15, or complex-forming fragments thereof, comprises one or more cavity-filling mutations, one or more hydrophobic mutations, one or more hydrophilic mutations, one or more disulphide bridge mutations, or any combination of one or more thereof. In further alternative embodiments, the HCMV pUL128 polypeptide having the sequence set forth in SEQ ID NO: 16, or complex-forming fragments thereof, comprises one or more cavity-filling mutations, one or more hydrophobic mutations, one or more hydrophilic mutations, one or more disulphide bridge mutations, or any combination of one or more thereof.

As further detailed in Example 3 and illustrated in FIGS. 2A-2F, the present inventors identified, in the crystal structure of the pentameric complex, some cavities at the gH/gL/ULs interface. Therefore, any cavity-filling mutation, the purpose of which being to fill the cavities observed at such interface in the HCMV pUL128 polypeptide, is expected to advantageously contribute to the stability of a complex (e.g., a pentameric complex), when associated with the other components of said complex. Similarly, any repacking mutation, such as any hydrophobic mutation, or any hydrophilic mutation, the purpose of which being to increase the contact of the neighboring residues in the HCMV pUL128 polypeptide, is expected to advantageously contribute to the stability of a complex (e.g., a pentameric complex), when associated with the other components of said complex, having an enhanced thermo-stability. Similarly, any disulfide bridge mutation, the purpose of which being to introduce intra-disulfide bridges into the HCMV pUL128 polypeptide and/or inter-disulfide bridges between the HCMV pUL128 polypeptide and any of the other components of a complex (e.g., HCMV gH, HCMV gL, HCMV pUL130 or HCMV pUL131A polypeptide of the HCMV pentameric complex), is expected to advantageously contribute to the complex having an enhanced thermo-stability.

The identification of relevant amino acid residues, in the HCMV pUL128 polypeptide, to mutate for cavity-filling and/or repacking and/or disulfide bridges may be performed, for example, by both visual inspection of the three-dimensional structure with the aid of molecular graphics softwares, or by using any appropriate in-silico mutagenesis method. Such methods are known to the skilled person. For example, softwares, such as Molecular Operating Environment (MOE) (edited by Chemical Computing Group Inc.) allows for a systematic analysis of amino acid sequences to identify specific regions in the polypeptide or specific amino acids, the mutation of which is predicted to enhance thermo-stability.

Suitable non-limiting exemplary amino acid residues to mutate in HCMV pUL128 polypeptides are provided in Table 3, using the sequence set forth as SEQ ID NO: 13 as a reference only. Mutations at similar positions in other HCMV pUL128 polypeptides, such as for example, polypeptides having the sequence as set forth in SEQ ID NO: 14, or gL polypeptides originating from HCMV strains different from the Merlin strain, such as SEQ ID NO: 15 or SEQ ID NO: 16, are also contemplated in the present invention. It is within the skilled person's abilities to determine such similar positions in other HCMV pUL128 polypeptides. Comparable amino acid positions in a given HCMV pUL128 polypeptide can be determined by aligning the amino acid sequences using readily available and well-known alignment and algorithms (such as BLAST or ClustalW2). The actual number of the amino acid position may have to be adjusted for other HCMV pUL128 polypeptides depending on the actual sequence alignment.

TABLE 3A

Mutant HCMV pUL128 polypeptides
(positions provided with respect to SEQ ID NO: 13)

| Cavity-filling mutations | Hydrophobic mutations | Hydrophilic mutations | Disulfide mutations |
| --- | --- | --- | --- |
| G123 | G145 | | R142 |
| V77 | H90 | | N99 |
| L103 | G112 | | Y98 |
| Q119 | | | A124 |
| | | | G126 |
| | | | L159 |
| | | | D45 |
| | | | V88 |
| | | | M48 |
| | | | G107 |
| | | | R51 |
| | | | D106 |
| | | | S83 |

Accordingly, in some embodiments, amino acids to mutate in HCMV pUL128 polypeptides for cavity filling are G123, V77, L103 or Q119 of the sequence set forth in SEQ ID NO: 13, or at a corresponding position in HCMV pUL128 polypeptides originating from different HCMV strains. Suitably, the mutation of these amino acid residues may consist of substituting any of them and/or more than one of them, possibly all of them, with amino acid residues, selected from the group consisting of tryptophan (W), phenylalanine (F), tyrosine (Y), valine (V), isoleucine (I), and leucine (L). Accordingly, in some embodiments, the HCMV pUL128 polypeptides of the invention comprise at least an amino acid substitution at positions corresponding to 123, 77, 103, and 119 of SEQ ID NO: 13 with amino acids selected from the group consisting of tryptophan (W), phenylalanine (F), tyrosine (Y), valine (V), isoleucine (I), and leucine (L).

Suitable non-limiting exemplary amino acids to mutate in HCMV pUL128 polypeptides for hydrophobic mutations are G145, H90, or G112 of the sequence set forth in SEQ ID NO: 13, or at a corresponding position in HCMV pUL128 polypeptides originating from different HCMV strains. Suitably, the mutation of these amino acid residues may consist of substituting any of them and/or more than one of them, possibly all of them, with amino acid residues, selected from the group consisting of tryptophan (W), phenylalanine (F), methionine (M), cysteine (C), alanine (A), leucine (L), isoleucine (I), valine (V) and proline (P). Accordingly, in some embodiments, the HCMV pUL128 polypeptides of the invention comprise at least an amino acid substitution at positions corresponding to 145, 90, and 112 of SEQ ID NO: 13 with amino acids selected from the group consisting of tryptophan (W), phenylalanine (F), methionine (M), cysteine (C), alanine (A), leucine (L), isoleucine (I), valine (V) and proline (P).

Suitable non-limiting exemplary amino acids to mutate in HCMV pUL128 polypeptides for disulphide bridge mutations are R142, N99, Y98, A124, G126, L159, D45, V88, M48, G107, R51, D106, or S83 of the sequence set forth in SEQ ID NO: 13, or at a corresponding position in HCMV pUL128 polypeptides originating from different HCMV strains. Accordingly, in some embodiments, the HCMV pUL128 polypeptides of the invention comprise at least a substitution selected from the group consisting of: R142C, N99C, Y98C, A124C, G126C, L159C, D45C, V88C, M48C, G107C, R51C, D106C, S83C, and combinations thereof.

TABLE 3B

Modified HCMV pUL128 polypeptides of the present invention comprise, with respect to the sequence SEQ ID NO: 13, one or more of:

G123W, G123F, G123Y, G123V, G123I, G123L, V77W, V77F, V77Y, V77I, V77L, L103W, L103F, L103Y, L103V, L103I, L103L, Q119W, Q119F, Q119Y, Q119V, Q119I, Q119L,
G145W, G145F, G145M, G145C, G145A, G145L, G145I, G145V, G145P, G145Y, H90W, H90F, H90M, H90C, H90A, H90L, H90I, H90V, H90P, H90Y, G112W, G112F, G112M, G112C, G112A, G112L, G112I, G112V, G112P, G112Y,
R142C, N99C, Y98C, A124C, G126C, L159C, D45C, V88C, M48C, G107C, R51C, D106C, and S83C.

pUL130 Polypeptide pUL130 (or simply "UL130") is the central and the largest (214 codons) gene of the HCMV UL131A-128 locus. The sequence of pUL130 from HCMV strain Merlin is publicly available (NCBI GI: 39842125 (which is also NCBI GenBank Accession No. AAR31669.1) and SEQ ID NO: 17 herein. The sequence of pUL130 from HCMV strain Towne is publicly available (NCBI GI:239909473 (which is also NCBI ACS32420.1) and SEQ ID NO: 19 herein). Likewise, the sequence of pUL130 from HCMV strain AD169 is publicly available (NCBI UniprotKB Accession No. P16772 and SEQ ID NIO: 20 herein). The Merlin and Towne pUL130 sequences consist of 214 and 229 amino acids, respectively. Merlin pUL130 sequence SEQ ID NO: 17 comprises a 25 amino acid long N-terminal signal sequence at residues 1-25 that precedes a hydrophilic protein containing two potential N-linked glycosylation sites (Asn85 and Asn118) within a putative chemokine domain (amino acids 46 to 120) and an additional N-glycosylation site (Asn201) close to the end of a unique C-terminal region. pUL130 is predicted to lack a TM domain.

Typically, the N-terminal signal sequence of pUL130 polypeptides is cleaved by a host cell signal peptidase to produce mature pUL130 proteins. The pUL130 polypeptides for use in the invention may lack an N-terminal signal sequence. An example of HCMV pUL130 polypeptide lacking the N-terminal sequence is SEQ ID NO: 18, which consists of amino acid residues 26-214 of SEQ ID NO: 17.

As shown within the Examples, pUL30 polypeptides are glycosylated (comprise glycans via N-linked glycosylation) at three asparagine residues: N85, N118, and N201 numbered with respect to pUL130 amino acid sequence SEQ ID NO: 17. An HCMV pUL130 polypeptide, or complex-forming fragment thereof, for use in the invention may comprise a deglycosylation mutation at one or more of the asparagines located at residues 85, 118, and 201 numbered with respect to pUL130 sequence SEQ ID NO: 17. The deglycosylation mutation may be glutamine (Q), serine (S), threonine (T), alanine (A), glutamate (E), or aspartate (D). In particular, the deglycosylation mutation may be glutamine (Q), serine (S), threonine (T), or alanine (A). Further in particular, the deglycosylation mutation may be glutamine (Q).

pUL130 proteins of the invention can have various degrees of identity to SEQ ID NO: 17, such as an at least 60%, 70%, 80%, 81%, 82%, 83%, 84%, 85%, 86%, 87%, 88%, 89%, 90%, 91%, 92%, 93%, 94%, 95%, 96%, 97%, 98% or 99% identity to the sequence recited in SEQ ID NO: 17. pUL130 proteins of the invention can have various degrees of identity to SEQ ID NO: 18, such as an at least 60%, 70%, 80%, 81%, 82%, 83%, 84%, 85%, 86%, 87%, 88%, 89%, 90%, 91%, 92%, 93%, 94%, 95%, 96%, 97%, 98% or 99% identity to the sequence recited in SEQ ID NO: 18. pUL130 proteins of the invention can have various degrees of identity to SEQ ID NO: 19, such as an at least 60%, 70%, 80%, 81%, 82%, 83%, 84%, 85%, 86%, 87%, 88%, 89%, 90%, 91%, 92%, 93%, 94%, 95%, 96%, 97%, 98% or 99% identity to the sequence recited in SEQ ID NO: 19. pUL130 proteins of the invention can have various degrees of identity to SEQ ID NO: 20, such as an at least 60%, 70%, 80%, 81%, 82%, 83%, 84%, 85%, 86%, 87%, 88%, 89%, 90%, 91%, 92%, 93%, 94%, 95%, 96%, 97%, 98% or 99% identity to the sequence recited in SEQ ID NO: 20. Preferred pUL130 proteins or fragments thereof: (i) can form a pentameric gH/gL/pUL128/pUL130/pUL131A complex; (ii) comprise at least one epitope of SEQ ID NO: 17, 18, 19, or 20; and/or (iii) can elicit antibodies in vivo which immunologically cross-react with an HCMV virion. An exemplary complex-forming fragment of pUL130 comprises residues Thr45 through Val214 of SEQ ID NO: 17 which, when in complex with full length full length pUL131A (i.e., none of gH, gL, or pUL128 are present); may form a truncated HCMV pentamer complex that nonetheless maintains the five conformational epitope sites described in FIG. 7. Alternatively, a complex-forming fragment of pUL130 comprises residues Thr45 through Val214 of SEQ ID NO: 17 which, when in complex with a complex-forming fragment of pUL131A comprising residues Gln19 through Asn129 of SEQ ID NO: 21 (i.e., none of gH, gL, or pUL128 are present); may form a truncated HCMV pentamer complex that nonetheless maintains the five conformational epitope sites described in FIG. 7.

The HCMV pUL130 polypeptides, or complex-forming fragments thereof, of the invention comprise one or more stabilizing mutations, suitably, one or more cavity-filling mutations, one or more hydrophobic mutations, one or more hydrophilic mutations, one or more disulfide bridge mutations, or any combination of one or more thereof. Any of the pUL130 polypeptides having the sequence as set forth in SEQ ID NO: 17, SEQ ID NO: 18, SEQ ID NO: 19, or SEQ ID NO: 20, or any pUL130 polypeptide having a sequence at least 90% identical to SEQ ID NO: 17, SEQ ID NO: 18, SEQ ID NO: 19, or SEQ ID NO: 20, or complex-forming fragments thereof, may suitably comprise any one or more stabilizing mutations as identified and defined herein. Accordingly, in some embodiments, the HCMV pUL130 polypeptide having the sequence set forth in SEQ ID NO: 17, or complex-forming fragments thereof, comprises one or more cavity-filling mutations, one or more hydrophobic mutations, one or more hydrophilic mutations, one or more disulfide bridge mutations, or any combination of one or more thereof. In alternative embodiments, the HCMV pUL130 polypeptide having the sequence set forth in SEQ ID NO: 18, or complex-forming fragments thereof, comprises one or more cavity-filling mutations, one or more hydrophobic mutations, one or more hydrophilic mutations, one or more disulfide bridge mutations, or any combination of one or more thereof. In alternative embodiments, the HCMV pUL130 polypeptide having the sequence set forth in SEQ ID NO: 19, or complex-forming fragments thereof, comprises one or more cavity-filling mutations, one or more hydrophobic mutations, one or more hydrophilic mutations, one or more disulfide bridge mutations, or any combination of one or more thereof. In alternative embodiments, the HCMV pUL130 polypeptide having the sequence set forth in SEQ ID NO: 20, or complex-forming fragments thereof, comprises one or more cavity-filling mutations, one or more hydrophobic mutations, one or more hydrophilic mutations, one or more disulfide bridge mutations, or any combination of one or more thereof.

As further detailed in Example 3 and illustrated in FIGS. 2A-2F, the present inventors identified, in the crystal structure of the pentameric complex, some cavities at the gH/gL/ULs interface. Therefore, any cavity-filling mutation, the purpose of which being to fill the cavities observed at such interface in the HCMV pUL130 polypeptide, is expected to advantageously contribute to the stability of a complex (e.g., a pentameric complex), when associated with the other components of said complex. Similarly, any repacking mutation, such as any hydrophobic mutation, or any hydrophilic mutation, the purpose of which being to increase the contact of the neighboring residues in the HCMV pUL130 polypeptide, is expected to advantageously contribute to the stability of a complex (e.g., a pentameric, complex), when associated with the other components of said complex. Similarly, any disulfide bridge mutation, the purpose of which being to introduce intra-disulfide bridges into the HCMV pUL130 polypeptide and/or inter-disulfide bridges between the HCMV gH polypeptide and any of the other components of a complex (e.g., HCMV gH, HCMV gL, HCMV pUL128, or HCMV pUL131A polypeptide of the HCMV pentameric complex), is expected to advantageously contribute to the complex having an enhanced thermo-stability.

The identification of relevant amino acid residues, in the HCMV pUL130 polypeptide, to mutate for cavity-filling and/or repacking and/or disulfide bridges may be performed, for example, by both visual inspection of the three-dimensional structure with the aid of molecular graphics softwares, or by using any appropriate in-silico mutagenesis method. Such methods are known to the skilled person. For example, softwares, such as Molecular Operating Environment (MOE) (edited by Chemical Computing Group Inc.) allows for a systematic analysis of amino acid sequences to identify specific regions in the polypeptide or specific amino acids, the mutation of which is predicted to enhance thermo-stability.

Suitable non-limiting exemplary amino acid residues to mutate in HCMV pUL130 polypeptides are provided in Table 4, using the sequence set forth as SEQ ID NO: 17 as a reference only. Mutations at similar positions in other HCMV pUL130 polypeptides, such as for example, polypeptides having the sequence as set forth in SEQ ID NO: 18, SEQ ID NO: 19, SEQ ID NO: 20, or pUL130 polypeptides originating from HCMV strains different from the Merlin strain, are also contemplated in the present invention. It is within the skilled person's abilities to determine such similar positions in other HCMV pUL130 polypeptides. Comparable amino acid positions in a given HCMV pUL130 polypeptide can be determined by aligning the amino acid sequences using readily available and well-known alignment and algorithms (such as BLAST or ClustalW2). The actual number of the amino acid position may have to be adjusted for other HCMV pUL130 polypeptides depending on the actual sequence alignment.

TABLE 4A

| Mutant HCMV pUL130 polypeptides (positions provided with respect to SEQ ID NO: 17) | | | | |
|---|---|---|---|---|
| Cavity-filling mutations | Hydrophobic mutations | Hydrophilic mutations | Disulfide mutations | Deglycosylation mutations |
| D165 | G116 | | G116 | N85 |
| H209 | G135 | | H150 | N118 |
| | H150 | | P64 | N201 |
| | H209 | | S178 | |
| | | | P62 | |
| | | | E95 | |
| | | | Y204 | |
| | | | N211 | |
| | | | I213 | |
| | | | Y56 | |
| | | | T167 | |

Accordingly, in some embodiments, amino acids to mutate in HCMV pUL130 polypeptides for cavity filling are D165 or H209 of the sequence set forth in SEQ ID NO: 17, or at a corresponding position in HCMV pUL130 polypeptides originating from different HCMV strains. Suitably, the mutation of these amino acid residues may consist of substituting any of them and/or more than of them, possibly all of them, with amino acid residues, selected from the group consisting of tryptophan (W), phenylalanine (F), tyrosine (Y), valine (V), isoleucine (I), and leucine (L). Accordingly, in some embodiments, the HCMV pUL130 polypeptides of the invention comprise at least an amino acid substitution at positions corresponding to 165 and 209 of SEQ ID NO: 17 with amino acids selected from the group consisting of tryptophan (W), phenylalanine (F), tyrosine (Y), valine (V), isoleucine (I), and leucine (L).

Suitable non-limiting exemplary amino acids to mutate in HCMV pUL130 polypeptides for hydrophobic mutations are G116, G135, H150, or H209 of the sequence set forth in SEQ ID NO: 17, or at a corresponding position in HCMV pUL130 polypeptides originating from different HCMV strains. Suitably, the mutation of these amino acid residues may consist of substituting any of them and/or more than one of them, possibly all of them, with amino acid residues, selected from the group consisting of tryptophan (W), phenylalanine (F), methionine (M), cysteine (C), alanine (A), leucine (L), isoleucine (I), valine (V) and proline (P). Accordingly, in some embodiments, the HCMV pUL130 polypeptides of the invention comprise at least an amino acid substitution at positions corresponding to G116, G135, H150, and H209 of SEQ ID NO: 17 with amino acids selected from the group consisting of tryptophan (W), phenylalanine (F), methionine (M), cysteine (C), alanine (A), leucine (L), isoleucine (I), valine (V) and proline (P).

Suitable non-limiting exemplary amino acids to mutate in HCMV pUL130 polypeptides for disulphide bridge mutations are G116, H150, P64, 5178, P62, E95, Y204, N211, 1213, Y56, or T167 of the sequence set forth in SEQ ID NO: 17, or at a corresponding position in HCMV pUL130 polypeptides originating from different HCMV strains. Accordingly, in some embodiments, the HCMV pUL130 polypeptides of the invention comprise at least a substitution selected from the group consisting of: G116C, H150C, P64C, S178C, P62C, E95C, Y204C, N211C, I213C, Y56C, T167C, and combinations thereof.

Accordingly, in some embodiments, amino acids to mutate in HCMV pUL130 polypeptides for deglycosylation are N85, N118, and N201 of the sequence set forth in SEQ ID NO: 17, or at a corresponding position in HCMV pUL130 polypeptides originating from different HCMV strains. Suitably, the mutation of these amino acid residues may consist of substituting any of them and/or more than one of them, possibly all of them, with amino acid residues selected from the group consisting of glutamine (Q), serine (S), threonine (T), alanine (A), glutamate (E), and aspartate (D). Accordingly, in some embodiments, the HCMV pUL130 polypeptides of the invention comprise at least an amino acid substitution at positions corresponding to 85, 118, and 201 of SEQ ID NO: 17 with amino acids selected from the group consisting of glutamine (Q), serine (S), threonine (T), alanine (A), glutamate (E), and aspartate (D).

TABLE 4B

| Modified HCMV pUL130 polypeptides of the present invention comprise, with respect to the sequence SEQ ID NO: 17, one or more of: |
|---|
| D165W, D165F, D165Y, D165L, H209W, H209F, H209Y, H209L, G116W, G116F, G116M, G116C, G116A, G116L, G116I, G116V, G116P, G116Y, G135W, G135F, G135M, G135C, G135A, G135L, G135I, G135V, G135P, G135Y, H150W, H150F, H150M, H150C, H150A, H150L, H150I, H150V, H150P, H150Y, H209W, H209F, H209M, H209C, H209A, H209L, H209I, H209V, H209P, H209Y, G116C, H150C, P64C, S178C, P62C, E95C, Y204C, N211C, I213C, Y56C, T167C, N85Q, N85S, N85T, N85A, N85E, N85D, N118Q, N118S, N118T, N118A, N118E, N118D, N201Q, N201S, N201T, N201A, N201E, and N201D. | pUL131A Polypeptide pUL131A function is required for HCMV replication not only in endothelial cells but also in epithelial cells. The pUL131A from HCMV strains Merlin (NCBI GI:39842126 (which is also NCBI GenBank Accession No. AAR31670.1), SEQ ID NO: 21) and Towne (NCBI GI:239909474 (which is also NCBI GenBank Accession No. ACS32421.1), SEQ ID NO: 23) and AD169 (NCBI GI:219879712 (which is also NCBI GenBank Accession No. DAA06452.1), SEQ ID NO: 24) have been reported to consist of 129, 129 and 76 amino acids, respectively. pUL131A contains an N-terminal signal sequence, which is located at residues 1-18 of SEQ ID NO: 21, and lacks a TM domain. The UL131A from strain AD169 has been reported to contain a one (1) base-pair insertion, which causes a frame-shift (Wang and Shenk, *Human Cytomegalovirus UL131 Open Reading Frame Is Required for Epithelial Cell Tropism,* 2005 J. Virol. 79: 10330-10338). SEQ ID NO: 21 is 96% identical to SEQ ID NO: 24 over the N-terminal 28 amino acids, but it is only 36% identical to SEQ ID NO: 24 over the full-length of SEQ ID NO: 21 due to the frame-shift in the AD169 UL131A gene.

Typically, the N-terminal signal sequence of pUL131A polypeptides is cleaved by a host cell signal peptidase to produce mature pUL131A proteins. The pUL131A polypeptides for use in the invention may lack an N-terminal signal sequence. An example of HCMV pUL131A polypeptide lacking the N-terminal sequence is SEQ ID NO: 22, which consists of amino acid residues 19-129 of SEQ ID NO: 21.

As shown within the Examples, pUL131A polypeptides are glycosylated (comprise glycans via N-linked glycosylation) at asparagine residue N81 numbered with respect to gH amino acid sequence SEQ ID NO: 21. An HCMV pUL131A polypeptide, or complex-forming fragment thereof, for use in the invention may comprise a deglycosylation mutation at the asparagine located at residue 81 numbered with respect to pUL131A sequence SEQ ID NO: 21. The deglycosylation mutation may be glutamine (Q), serine (S), threonine (T), alanine (A), glutamate (E), or aspartate (D). In particular, the deglycosylation mutation may be glutamine (Q), serine (S), threonine (T), or alanine (A). Further in particular, the deglycosylation mutation may be glutamine (Q).

pUL131A proteins of the invention can have various degrees of identity to SEQ ID NO: 21, such as an at least 60%, 70%, 80%, 81%, 82%, 83%, 84%, 85%, 86%, 87%, 88%, 89%, 90%, 91%, 92%, 93%, 94%, 95%, 96%, 97%, 98% or 99% identity to the sequence recited in SEQ ID NO: 21. pUL131A proteins of the invention can have various degrees of identity to SEQ ID NO: 22, such as an at least 60%, 70%, 80%, 81%, 82%, 83%, 84%, 85%, 86%, 87%, 88%, 89%, 90%, 91%, 92%, 93%, 94%, 95%, 96%, 97%, 98% or 99% identity to the sequence recited in SEQ ID NO: 22. pUL131A proteins of the invention can have various degrees of identity to SEQ ID NO: 23, such as an at least 60%, 70%, 80%, 81%, 82%, 83%, 84%, 85%, 86%, 87%, 88%, 89%, 90%, 91%, 92%, 93%, 94%, 95%, 96%, 97%, 98% or 99% identity to the sequence recited in SEQ ID NO: 23. pUL131A proteins of the invention can have various degrees of identity to SEQ ID NO: 24, such as an at least 60%, 70%, 80%, 81%, 82%, 83%, 84%, 85%, 86%, 87%, 88%, 89%, 90%, 91%, 92%, 93%, 94%, 95%, 96%, 97%, 98% or 99% identity to the sequence recited in SEQ ID NO: 24. Preferred pUL131A proteins: (i) can form pentameric gH/gL/pUL128/pUL130/pUL131A complexes, (ii) comprise at least one epitope of SEQ ID NO: 21, 22, 23, or 24; and/or (iii) can elicit antibodies in vivo which immunologically cross-react with an HCMV virion. An exemplary complex-forming fragment of pUL131A comprises residues Gln19 through Asn129 of SEQ ID NO: 21 which, when in complex with full length pUL130 (i.e., none of gH, gL, or pUL128 are present); may form a truncated HCMV pentamer complex that nonetheless maintains the five conformational epitope sites described in FIG. 7. Alternatively, a complex-forming fragment of pUL131A comprises residues Gln19 through Asn129 of SEQ ID NO: 21 which, when in complex with a complex-forming fragment of pUL130 comprising residues Thr45 through Va1214 of SEQ ID NO: 17 (i.e., none of gH, gL, or pUL128 are present); may form a truncated HCMV pentamer complex that nonetheless maintains the five conformational epitope sites described in FIG. 7.

The HCMV pUL131A polypeptides, or complex-forming fragments thereof, of the invention comprise one or more stabilizing mutations, suitably, one or more cavity-filling mutations, one or more hydrophobic mutations, one or more hydrophilic mutations, one or more disulfide bridge mutations, or any combination of one or more thereof. Any of the pUL131A polypeptides having the sequence as set forth in SEQ ID NO: 21, SEQ ID NO: 22, SEQ ID NO: 23, or SEQ ID NO: 24, or any pUL131A polypeptide having a sequence at least 90% identical to SEQ ID NO: 21, SEQ ID NO: 22, SEQ ID NO: 23, or SEQ ID NO: 24, or complex-forming fragments thereof, may suitably comprise any one or more stabilizing mutations as identified and defined herein. Accordingly, in some embodiments, the HCMV pUL131A polypeptide having the sequence set forth in SEQ ID NO: 21, or complex-forming fragments thereof, comprises one or more cavity-filling mutations, one or more hydrophobic mutations, one or more hydrophilic mutations, one or more disulfide bridge mutations, or any combination of one or more thereof. In alternative embodiments, the HCMV pUL131A polypeptide having the sequence set forth in SEQ ID NO: 22, or complex-forming fragments thereof, comprises one or more cavity-filling mutations, one or more hydrophobic mutations, one or more hydrophilic mutations, one or more disulfide bridge mutations, or any combination of one or more thereof. In alternative embodiments, the HCMV pUL131A polypeptide having the sequence set forth in SEQ ID NO: 23, or complex-forming fragments thereof, comprises one or more cavity-filling mutations, one or more hydrophobic mutations, one or more hydrophilic mutations, one or more disulfide bridge mutations, or any combination of one or more thereof. In alternative embodiments, the HCMV pUL131A polypeptide having the sequence set forth in SEQ ID NO: 24, or complex-forming fragments thereof, comprises one or more cavity-filling mutations, one or more hydrophobic mutations, one or more hydrophilic mutations, one or more disulfide bridge mutations, or any combination of one or more thereof.

As further detailed in Example 3 and illustrated in FIGS. 2A-2F, the present inventors identified, in the crystal structure of the pentameric complex, some cavities at the gH/gL/ULs interface. Therefore, any cavity-filling mutation, the purpose of which being to fill the cavities observed at such interface in the HCMV pUL131A polypeptide, is expected to advantageously contribute to the stability of a complex (e.g., a pentameric complex), when associated with the other components of said complex. Similarly, any repacking mutation, such as any hydrophobic mutation, or any hydrophilic mutation, the purpose of which being to increase the contact of the neighboring residues in the HCMV pUL131A polypeptide, is expected to advantageously contribute to the stability of a complex (e.g., a pentameric, complex), when associated with the other components of said complex. Similarly, any disulfide bridge mutation, the purpose of which being to introduce intra-disulfide bridges into the HCMV pUL131A polypeptide and/or inter-disulfide bridges between the HCMV gH polypeptide and any of the other components of a complex (e.g., HCMV gH, HCMV gL, HCMV pUL128, or HCMV pUL130 polypeptide of the HCMV pentameric complex), is expected to advantageously contribute to the complex having an enhanced thermostability.

The identification of relevant amino acid residues, in the HCMV pUL131A polypeptide, to mutate for cavity-filling and/or repacking and/or disulfide bridges may be performed, for example, by both visual inspection of the three-dimensional structure with the aid of molecular graphics softwares, or by using any appropriate in-silico mutagenesis method. Such methods are known to the skilled person. For example, softwares, such as Molecular Operating Environment (MOE) (edited by Chemical Computing Group Inc.) allows for a systematic analysis of amino acid sequences to identify specific regions in the polypeptide or specific amino acids, the mutation of which is predicted to enhance thermostability.

Suitable non-limiting exemplary amino acid residues to mutate in HCMV pUL131A polypeptides are provided in Table 5, using the sequence set forth as SEQ ID NO: 21 as a reference only. Mutations at similar positions in other HCMV pUL131A polypeptides, such as for example, polypeptides having the sequence as set forth in SEQ ID NO: 22, SEQ ID NO: 23, SEQ ID NIO: 24, or pUL131A polypeptides originating from HCMV strains different from the Merlin strain, are also contemplated in the present invention. It is within the skilled person's abilities to determine such similar positions in other HCMV pUL131A polypeptides. Comparable amino acid positions in a given HCMV pUL131A polypeptide can be determined by aligning the amino acid sequences using readily available and well-known alignment and algorithms (such as BLAST or ClustalW2). The actual number of the amino acid position may have to be adjusted for other HCMV pUL130 polypeptides depending on the actual sequence alignment.

TABLE 5A

Mutant HCMV pUL131A polypeptides
(positions provided with respect to SEQ ID NO: 21)

| Cavity-filling mutations | Hydrophobic mutations | Hydrophilic mutations | Disulfide mutations | Deglycosylation mutation |
|---|---|---|---|---|
| G99 | H69 | R118 | H64 | N81 |
| S86 | H35 | | W37 | |
| S90 | H64 | | | |
| | D38 | | | |
| | V85 | | | |
| | Y52 | | | |
| | A67 | | | |

Accordingly, in some embodiments, amino acids to mutate in HCMV pUL131A polypeptides for cavity filling are G99, S86 or S90 of the sequence set forth in SEQ ID NO: 21, or at a corresponding position in HCMV pUL131A polypeptides originating from different HCMV strains. Suitably, the mutation of these amino acid residues may consist of substituting any of them and/or more than of them, possibly all of them, with amino acid residues, selected from the group consisting of tryptophan (W), phenylalanine (F), tyrosine (Y), valine (V), isoleucine (I), and leucine (L). Accordingly, in some embodiments, the HCMV pUL131A polypeptides of the invention comprise at least an amino acid substitution at positions corresponding to 99, 86 or 90 of SEQ ID NO: 21 with amino acids selected from the group consisting of tryptophan (W), phenylalanine (F), tyrosine (Y), valine (V), isoleucine (I), and leucine (L).

Suitable non-limiting exemplary amino acids to mutate in HCMV pUL131A polypeptides for hydrophobic mutations are H69, H35, H64, D38, V85, Y52, or A67 of the sequence set forth in SEQ ID NO: 21, or at a corresponding position in HCMV pUL131A polypeptides originating from different HCMV strains. Suitably, the mutation of these amino acid residues may consist of substituting any of them and/or more than one of them, possibly all of them, with amino acid residues, selected from the group consisting of tryptophan (W), phenylalanine (F), methionine (M), cysteine (C), alanine (A), leucine (L), isoleucine (I), valine (V) and proline (P). Accordingly, in some embodiments, the HCMV pUL131A polypeptides of the invention comprise at least an amino acid substitution at positions corresponding to 69, 35, 64, 38, 85, 52, and 67 of SEQ ID NO: 21 with amino acids selected from the group consisting of tryptophan (W), phenylalanine (F), methionine (M), cysteine (C), alanine (A), leucine (L), isoleucine (I), valine (V) and proline (P).

Suitable non-limiting exemplary amino acids to mutate in HCMV pUL131A polypeptides for hydrophilic mutations is R118 of the sequence set forth in SEQ ID NO: 21, or at a corresponding position in HCMV gH polypeptides originating from different HCMV strains. Suitably, the mutation of this amino acid residue may consist of substituting it for an amino acid selected from the group consisting of serine (S), threonine (T), cysteine (C), tyrosine (Y), asparagine (N), glutamine (Q), arginine (R), and glutamic acid (E). Accordingly, in some embodiments, the HCMV pUL131A polypeptides of the invention comprise at least an amino acid substitution at the position corresponding to R118 of SEQ ID NO: 21 with an amino acid selected from the group consisting of serine (S), threonine (T), cysteine (C), tyrosine (Y), asparagine (N) glutamine (Q), arginine (R), and glutamic acid (E). Suitable non-limiting exemplary amino acids to mutate in HCMV pUL131A polypeptides for polar mutations is R118 of the sequence set forth in SEQ ID NO: 21, or at a corresponding position in HCMV gH polypeptides originating from different HCMV strains. Suitably, the mutation of this amino acid residue may consist of substituting it for an amino acid selected from the group consisting of serine (S), threonine (T), cysteine (C), tyrosine (Y), asparagine (N), and glutamine (Q). Accordingly, in some embodiments, the HCMV pUL131A polypeptides of the invention comprise at least an amino acid substitution at position R118 with an amino acid selected from the group consisting of serine (S), threonine (T), cysteine (C), tyrosine (Y), asparagine (N), and glutamine (Q). Suitable non-limiting exemplary amino acids to mutate in HCMV pUL131A polypeptides for charged mutations is R118 of the sequence set forth in SEQ ID NO: 21, or at a corresponding position in HCMV gH polypeptides originating from different HCMV strains. Suitably, the mutation of this amino acid residue may consist of substituting it for arginine (R) or glutamic acid (E). Accordingly, in some embodiments, the HCMV gH polypeptides of the invention comprise at least an amino acid substitution at the position corresponding to R118 of SEQ ID NO: 21 with the amino acid arginine (R) or glutamic acid (E).

Suitable non-limiting exemplary amino acids to mutate in HCMV pUL131A polypeptides for disulphide bridge mutations are H64 or W37 of the sequence set forth in SEQ ID NO: 21, or at a corresponding position in HCMV gH polypeptides originating from different HCMV strains.

Accordingly, in some embodiments, the HCMV polypeptides of the invention comprise at least a substitution of the residue corresponding to H64 of SEQ ID NO: 21 with a cysteine (C) or of the residue corresponding to W37 of SEQ ID NO: 21 with a cysteine (C), suitably, both.

Accordingly, in some embodiments, an amino acid to mutate in HCMV pUL131A polypeptides for deglycosylation is N81 of the sequence set forth in SEQ ID NO: 21, or at a corresponding position in HCMV gH polypeptides originating from different HCMV strains. Suitably, the mutation of this amino acid residue may consist of substituting it with an amino acid residue selected from the group consisting of glutamine (Q), serine (S), threonine (T), alanine (A), glutamate (E), and aspartate (D). Accordingly, in some embodiments, the HCMV pUL131A polypeptides of the invention comprise at least an amino acid substitution at position 81 of SEQ ID NO: 21 with an amino acid selected from the group consisting of glutamine (Q), serine (S), threonine (T), alanine (A), glutamate (E), and aspartate (D).

TABLE 5B

Modified HCMV pUL131A polypeptides of the present invention comprise, with respect to the sequence SEQ ID NO: 21, one or more of:

G99W, G99F, G99Y, G99V, G99I, G99L, S86W, S86F, S86Y, S86V, S86I, S86L, S90W, S90F, S90Y, S90V, S90I, S90L,
H69W, H69F, H69M, H69C, H69A, H69L, H69I, H69V, H69P, H69Y, H35W, H35F, H35M, H35C, H35A, H35L, H35I, H35V, H35P, H35Y, H64W, H64F, H64M, H64C, H64A, H64L, H64I, H64V, H64P, H64Y, D38W, D38F, D38M, D38C, D38A, D38L, D38I, D38V, D38P, D38Y, V85W, V85F, V85M, V85C, V85A, V85L, V85I, V85Y, V85P, V85Y, Y52W, Y52F, Y52M, Y52C, Y52A, Y52L, Y52I, Y52V, Y52P, Y52Y, A67W, A67F, A67M, A67C, A67A, A67L, A67I, A67V, A67P, A67Y,
R118S, R118T, R118C, R118Y, R118N, R118Q, R118R, R118E, R118K, R118H, R118D,
H64C, W37C,
N81Q, N81A, N81T, N81A, N81E, and N81D.

gO Polypeptide

HCMV glycoprotein 0 (gO), which is encoded by the UL74 gene, has been reported to act as a molecular chaperone, increasing gH/gL ER export and incorporation into virions. It has been proposed that gO competes with pUL128-131A for binding onto gH/gL but is released from gH/gL, so that gH/gL (lacking pUL128-131A) is incorporated into virions (Ryckman et al., *Human Cytomegalovirus TR Strain Glycoprotein O Acts as a Chaperone Promoting gH/gL Incorporation into Virions but Is Not Present in Virions*, 2010 Journal of Virology 84: 2597-2609). Compared with other viral genes, HCMV gO is unusually variable among different HCMV strains: the variability of the gO amino acid sequence among 22 to 39 clinical isolates, as well as laboratory strains AD169, Towne and Toledo approached 45% (i.e. there was only 55% identity between the gO amino acid sequences between different isolates) (Rasmussen, et al., *The Genes Encoding the gCIII Complex of Human Cytomegalovirus Exist in Highly Diverse Combinations in Clinical Isolates*, 2002 J. Virol. 76: 10841-10888). The gO from HCMV strains Merlin (NCBI GI:39842082 (which is also NCBI GenBank Accession No. AAR31626.1), SEQ ID NO: 25 herein), AD169 (NCBI GI:136968 (which is also NCBI UniProtKB Accession No. P16750.1), SEQ ID NO: 28 herein) and Towne (NCBI GI:239909431 (which is also NCBI GenBank Accession No. ACS32378.1), SEQ ID NO: 27 herein) have been reported to consist of 472, 466 and 457 amino acids, respectively. The gO of HCMV strain AD169, which shares a 73% amino acid similarity to SEQ ID NO: 25, has 18 N-glycosylation sites (at residues 75, 83, 87, 103, 130, 157, 162, 171, 219, 242, 288, 292, 350, 385, 392, 399, 433 and 454), and may include a cleavable signal sequence at its N-terminus (predicted to consist of amino acid residues 1-30), which is absent from the mature polypeptide. Rigoutsos et al. (*In silico pattern-based analysis of the human cytomegalovirus genome*, 2003 J. Virol. 77: 4326-4344) predicted the presence of TM domains (in regions 10-28 and 190-212) and a coiled coil region (residues 240-272).

Typically, the N-terminal signal sequence of gO proteins is cleaved by a host cell signal peptidase to produce mature gO proteins. The gO proteins in HCMV membrane complexes of the invention may lack an N-terminal signal sequences. An example of a preferred gO protein of the invention is SEQ ID NO: 26, which lacks an N-terminal signal sequence and consists of amino acid residues 31-472 of SEQ ID NO: 25.

gO proteins of the invention can have various degrees of identity to SEQ ID NO: 25, such as an at least 60%, 70%, 80%, 81%, 82%, 83%, 84%, 85%, 86%, 87%, 88%, 89%, 90%, 91%, 92%, 93%, 94%, 95%, 96%, 97%, 98% or 99% identity to the sequence recited in SEQ ID NO: 25. gO proteins of the invention can have various degrees of identity to SEQ ID NO: 26, such as an at least 60%, 70%, 80%, 81%, 82%, 83%, 84%, 85%, 86%, 87%, 88%, 89%, 90%, 91%, 92%, 93%, 94%, 95%, 96%, 97%, 98% or 99% identity to the sequence recited in SEQ ID NO: 26. gO proteins of the invention can have various degrees of identity to SEQ ID NO: 27, such as an at least 60%, 70%, 80%, 81%, 82%, 83%, 84%, 85%, 86%, 87%, 88%, 89%, 90%, 91%, 92%, 93%, 94%, 95%, 96%, 97%, 98% or 99% identity to the sequence recited in SEQ ID NO: 27. gO proteins of the invention can have various degrees of identity to SEQ ID NO: 28, such as an at least 60%, 70%, 80%, 81%, 82%, 83%, 84%, 85%, 86%, 87%, 88%, 89%, 90%, 91%, 92%, 93%, 94%, 95%, 96%, 97%, 98% or 99% identity to the sequence recited in SEQ ID NO: 28. gO nucleotide sequences of the invention can have various degrees of identity to SEQ ID NO: 39, such as an at least 60%, 70%, 80%, 81%, 82%, 83%, 84%, 85%, 86%, 87%, 88%, 89%, 90%, 91%, 92%, 93%, 94%, 95%, 96%, 97%, 98% or 99% identity to the sequence recited in SEQ ID NO: 39. Preferred gO proteins or fragments thereof: (i) can form part of the trimeric gH/gL/gO complex; (ii) cannot form part of the pentameric gH/gL/pUL128/pUL130/pUL131A complex, (iii) comprise at least one epitope of SEQ ID NO: 25, 26, 27, or 28; and/or (iv) can elicit antibodies in vivo which immunologically cross-react with an HCMV virion.

Complexes

In another aspect, the invention provides a pentameric complex comprising the mutated HCMV polypeptides, or complex-forming fragments thereof, described herein. Such complexes include, e.g. (i) any of the above HCMV gH polypeptide comprising one or more stabilizing mutations, (ii) any of the above HCMV gL polypeptide comprising one or more stabilizing mutations, (iii) any of the above HCMV pUL128 polypeptide comprising one or more stabilizing mutations, (iv) any of the above HCMV pUL130 polypeptide comprising one or more stabilizing mutations, and (v) any of the above HCMV pUL131A polypeptide comprising one or more stabilizing mutations. Such complexes may further include, e.g., (vi) any of the above HCMV gH, gL, pUL130, and pUL131A deglycosylation mutations.

In another aspect, the invention provides a gH/gL complex comprising the mutated HCMV polypeptides, or complex-forming fragments thereof, described herein. Such complexes include, e.g. (i) any of the above HCMV gH polypeptide comprising one or more stabilizing mutations, and/or (ii) any of the above HCMV gL polypeptide comprising one or more stabilizing mutations. Such complexes may further include, e.g., (iii) any of the above HCMV gH and gL deglycosylation mutations.

In another aspect, the invention provides a gH/gL/gO complex comprising the mutated HCMV polypeptides, or complex-forming fragments thereof, described herein. Such complexes include, e.g. (i) any of the above HCMV gH polypeptide comprising one or more stabilizing mutations and/or (ii) any of the above HCMV gL polypeptide comprising one or more stabilizing mutations. Such complexes may further include, e.g., (iii) any of the above HCMV gH and gL deglycosylation mutations.

In another aspect, the invention provides a pentameric complex comprising the mutated HCMV polypeptides, or complex-forming fragments thereof, described herein. Such complexes include, e.g. (i) any of the above HCMV gH polypeptide comprising one or more deglycosylation mutations, (ii) any of the above HCMV gL polypeptide compris- ing a deglycosylation mutation, (iii) any of the above HCMV pUL130 polypeptide comprising one or more deglycosylation mutations, and (iv) any of the above HCMV pUL131A polypeptide comprising a deglycosylation mutation. Such complexes may further include, e.g., (vi) any of the above HCMV gH, gL, pUL130, and pUL131A stabilization mutations.

In another aspect, the invention provides a gH/gL complex comprising the mutated HCMV polypeptides, or complex-forming fragments thereof, described herein. Such complexes include, e.g. (i) any of the above HCMV gH polypeptide comprising one or more deglycosylation mutations, and/or (ii) any of the above HCMV gL polypeptide comprising a deglycosylation mutation. Such complexes may further include, e.g., (iii) any of the above HCMV gH and gL stabilization mutations.

In another aspect, the invention provides a gH/gL/gO complex comprising the mutated HCMV polypeptides, or complex-forming fragments thereof, described herein. Such complexes include, e.g. (i) any of the above HCMV gH polypeptide comprising one or more deglycosylation mutations, and/or (ii) any of the above HCMV gL polypeptide comprising a deglycosylation mutation. Such complexes may further include, e.g., (iii) any of the above HCMV gH and gL stabilization mutations.

Compositions

In another aspect, the invention provides a composition comprising a mutant polypeptide, or a mutant complex-forming fragment thereof, wherein the mutant polypeptide or mutant fragment is at least one of HCMV gH, gL, pUL128, pUL130, and pUL131A and wherein the mutant polypeptide or mutant fragment comprises at least one stabilizing mutation. In another aspect, the invention provides a composition comprising a mutant polypeptide, or a mutant complex-forming fragment thereof, wherein the mutant polypeptide or mutant fragment is at least one of HCMV gH, gL, pUL130, and pUL131A and wherein the mutant polypeptide or mutant fragment comprises at least one deglycosylation mutation. In another aspect, the invention provides a composition comprising a complex having at least one mutant polypeptide, or a mutant complex-forming fragment thereof, wherein the mutant polypeptide or mutant fragment is at least one of HCMV gH, gL, pUL128, pUL130, and pUL131A and wherein the mutant polypeptide or mutant fragment comprises at least one stabilizing mutation. In another aspect, the invention provides a composition comprising a complex having at least one mutant polypeptide, or a mutant complex-forming fragment thereof, wherein the mutant polypeptide or mutant fragment is at least one of HCMV gH, gL, pUL130, and pUL131A and wherein the mutant polypeptide or mutant fragment comprises at least one deglycosylation mutation. The complexes of the present invention include gH/gL, gH/gL/gO, and pentameric complexes. The composition of the present invention may be an immunogenic composition. The composition of the present invention may be a vaccine composition. Such compositions can be used to raise antibodies in a mammal (e.g. a human, murine, guinea pig, or macaque).

The invention provides pharmaceutical compositions comprising a stabilized HCMV complex (e.g., pentamer complex) as described herein. Similarly, the invention provides processes for making a pharmaceutical composition involving combining a stabilized HCMV complex (e.g., pentamer complex) of the invention with a pharmaceutically acceptable carrier.

In addition to their antigens, immunogenic and pharmaceutical compositions of the invention typically include a "non-antigen component" which as used with respect to the present invention may be an adjuvant or a pharmaceutically acceptable carrier. A thorough discussion of such carriers is available in Remington: The Science and Practice of Pharmacy. Pharmaceutically acceptable carriers include any carrier that does not itself induce the production of neutralizing antibodies. Suitable carriers are typically large, slowly metabolised macromolecules such as proteins, polysaccharides, polylactic acids, polyglycolic acids, polymeric amino acids, amino acid copolymers, sucrose, trehalose, lactose, and lipid aggregates (such as oil droplets or liposomes). Sterile pyrogen-free, phosphate-buffered physiologic saline is a typical carrier. Such carriers are well known to those of ordinary skill in the art. The non-antigen component may be a diluent, such as water, saline, glycerol, etc. Additionally, a non-antigen component may be auxiliary substances, such as wetting or emulsifying agents, pH buffering substances, and the like. Non-antigen components of the invention include an antimicrobial, particularly when packaged in multiple dose format. Non-antigen components of the invention include detergents, e.g., a TWEEN™ (polysorbate), such as TWEEN80™. Detergents are generally present at low levels e.g. <0.01%. Non-antigen components of the invention include sodium salts (e.g., sodium chloride) to give tonicity. A concentration of 1.0±2 mg/ml NaCl is typical. Non-antigen components of the invention include a buffer, such as a phosphate buffer. Non-antigen components of the invention include a sugar alcohol (e.g. mannitol) or a disaccharide (e.g., sucrose or trehalose), e.g., at around 15-30 mg/ml (e.g. 25 mg/ml).

The pH of the composition is usually between 6 and 8, and more preferably between 6.5 and 7.5 (e.g. about 7). Stable pH may be maintained by the use of a buffer e.g. a Tris buffer, a citrate buffer, phosphate buffer, or a histidine buffer. Thus, a composition will generally include a buffer. A composition may be sterile and/or pyrogen-free. Compositions may be isotonic with respect to humans. A composition comprises an immunologically effective amount of the referenced antigen(s). An 'immunologically effective amount' is an amount which, when administered to a subject, is effective for eliciting an antibody response against the antigen. This amount can vary depending upon the health and physical condition of the individual to be treated, their age, the capacity of the individual's immune system to synthesize antibodies, the degree of protection desired, the formulation of the vaccine, the treating doctor's assessment of the medical situation, and other relevant factors. It is expected that the amount will fall in a relatively broad range that can be determined through routine trials. The antigen content of compositions of the invention will generally be expressed in terms of the mass of protein per dose. A dose of 10-500 µg (e.g. 50 µg) per antigen can be useful. Immunogenic compositions may include an immunological adjuvant.

Compositions may include an antimicrobial, particularly when packaged in multiple dose format. Antimicrobials such as thiomersal and 2-phenoxyethanol are commonly found in vaccines, but it is preferred to use either a mercury-free preservative or no preservative at all. Compositions may comprise detergent e.g. a polysorbate, such as polysorbate 80. Detergents are generally present at low levels e.g. <0.01%. Compositions may include sodium salts (e.g. sodium chloride) to give tonicity. A concentration of 10+2 mg/ml NaCl is typical e.g. about 9 mg/ml.

Compositions of the invention will generally be administered directly to a subject. Direct delivery may be accomplished by parenteral injection (e.g. subcutaneously, intraperitoneally, intravenously, intramuscularly, or to the interstitial space of a tissue), or by any other suitable route. Intramuscular administration is preferred e.g. to the thigh or the upper arm. Injection may be via a needle (e.g. a hypodermic needle), but needle-free injection may alternatively be used.

Vaccines of the invention may be prophylactic (i.e. to prevent disease) or therapeutic (i.e. to reduce or eliminate the symptoms of a disease).

Expression Systems

In one aspect, the invention provides a process for expressing the mutant HCMV polypeptide(s) of the invention. Suitable expression systems for use in the present invention are described in detail in, for example, Doyle (*High Throughput Protein Expression and Purification: Methods and Protocols* in METHODS IN MOLECULAR BIOLOGY, Humana Press, Doyle ed., 2008). A system or vector that is suitable to maintain, propagate and express nucleic acid molecules to produce a polypeptide in the required host may be used. The appropriate nucleotide sequence may be inserted into an expression system by, for example, the techniques described in Sambrook (J. Molecular Cloning: A Laboratory Manual. 3rd. Cold Spring Harbor Laboratory Press, 2000). Generally, the encoding gene can be placed under the control of a control element such as a promoter, and, optionally, an operator, so that the DNA sequence encoding the desired peptide is transcribed into RNA in the transformed host cell.

Examples of suitable expression systems include, for example, chromosomal, episomal and virus-derived systems, including, for example, vectors derived from: bacterial plasmids, bacteriophage, transposons, yeast episomes, insertion elements, yeast chromosomal elements, viruses such as baculoviruses, papovaviruses such as SV40, vaccinia viruses, adenoviruses, fowl poxviruses, pseudorabies viruses and retroviruses, or combinations thereof, such as those derived from plasmid and bacteriophage genetic elements, including cosmids and phagemids. Human artificial chromosomes (HACs) may also be employed to deliver larger fragments of DNA than can be contained and expressed in a plasmid. Suitable expression systems include microorganisms such as bacteria transformed with recombinant bacteriophage, plasmid or cosmid DNA expression vectors; yeast transformed with yeast expression vectors; insect cell systems infected or transfected with virus expression vectors (for example, baculovirus); plant cell systems transformed with virus expression vectors (for example, cauliflower mosaic virus, CaMV; tobacco mosaic virus, TMV) or with bacterial expression vectors (for example, Ti or pBR322 plasmids); or animal cell systems. Cell-free translation systems can also be employed to produce the proteins of the invention. Preferably, the proteins of the invention are produced in eukaryotic cells, such as mammalian cells.

Recombinant polypeptides may be expressed transiently or stably. Preferably, the recombinant proteins are expressed stably. For example, cell lines that stably express the peptide of interest may be transfected using expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells that successfully express the introduced sequences. Resistant clones of stably transformed cells may be proliferated using tissue culture techniques appropriate to the cell type.

Mammalian cell lines available as hosts (or host cells) for expression are known in the art and include many immortalised cell lines available from the American Type Culture Collection (ATCC) including, but not limited to, Chinese hamster ovary (CHO), HeLa, baby hamster kidney (BHK), monkey kidney (COS), C127, 3T3, BHK, human embryonic kidney (HEK) 293, Bowes melanoma and human hepatocellular carcinoma (for example Hep G2) cells and a number of other cell lines. Expression in mammalian cells is preferable because the proteins that are produced will have authentic mammalian glycosylation patterns, and thus possess epitopes that are present on infectious HCMV particles. Accordingly, production of membrane protein complexes of the invention in mammalian cells will lead to the production of antibodies that are able to bind to naturally occurring HCMV particles during infection.

In the baculovirus system, the materials for baculovirus/insect cell expression systems are commercially available in kit form from, inter alia, Invitrogen, San Diego Calif. (the "MaxBac" kit). These techniques are described fully in Summers et al. (Summers and Smith, *A manual of methods for baculovirus vectors and insect cell culture procedures*, Texas Agricultural Experiment Station Bulletin No. 1555, 1987). Particularly suitable host cells for use in this system include insect cells such as *Drosophila* S2 (i.e. by recombinant baculovirus infection of stably transfected *Drosophila* S2 cells) and *Spodoptera* Sf9 cells. In some embodiments, the proteins of the invention are not produced in insect cells. There are many plant cell culture and whole plant genetic expression systems known in the art. Examples of suitable plant cellular genetic expression systems include those described in U.S. Pat. Nos. 5,693,506; 5,659,122; 5,608,143. In particular, all plants from which protoplasts can be isolated and cultured to give whole regenerated plants can be utilised, so that whole plants are recovered which contain the transferred gene. Practically all plants can be regenerated from cultured cells or tissues, including but not limited to all major species of sugar cane, sugar beet, cotton, fruit and other trees, legumes and vegetables.

Examples of prokaryotic expression systems include those that use streptococci, staphylococci, *E. coli, Streptomyces* and *Bacillus subtilis* as host cells.

Examples of fungal expression systems include those that use yeast (for example, *S. cerevisiae*) and *Aspergillus* as host cells.

HEK293 cells are suitable for transient expression of the HCMV proteins of the invention due to their high transfectability by various techniques, including the calcium phosphate and polyethylenimine (PEI) methods. A useful cell line of HEK293 is one that expresses the EBNA1 protein of EBV, such as 293-6E (Loignon et al., *Stable high volumetric production of glycosylated human recombinant IFNalpha2b in HEK293 cells*, 2008 BMC Biotechnology 8:65). Transformed HEK293 cells have been shown to secrete high levels of the protein complexes of the invention into the growth medium, thus allowing the purification of such protein complexes directly from the growth medium.

CHO cells are particularly suitable mammalian hosts for industrial production of the HCMV proteins of the invention for use as immunogens or antigens because they allow long-term, stable gene expression and high yields of proteins.

In some embodiments, the mutant HCMV polypeptide(s) or mutant complex of the invention is secreted from the cells in which they are expressed. In other embodiments of the invention, the mutant polypeptide or mutant complex of the invention is not secreted. In *E. coli*, for example, non-secreted proteins may accumulate in inclusion bodies. Methods for purifying recombinant proteins from inclusion bodies are well known in the art.

Transfection can be carried out by a range of methods including using calcium phosphate, electroporation, or by mixing a cationic lipid with the material to produce liposomes which fuse with the cell membrane and deposit their cargo inside.

Nucleic Acid Molecules

The invention provides recombinant nucleic acid molecules having a nucleotide sequence which encode the mutated HCMV gH polypeptides, the mutated HCMV gL polypeptides, the mutated HCMV pUL128 polypeptides, the mutated HCMV pUL130 polypeptides and/or the mutated HCMV pUL131A polypeptides described herein. The recombinant nucleic acid molecules of the present invention may be within a vector (an expression vector, for example) and may be operably linked to one or more control element (a promoter and/or an enhancer, for example). An example of said recombinant nucleic acid may be a single molecule which encodes a gL polypeptide of the invention, a gH polypeptide of the invention, a pUL128 polypeptide of the invention, a pUL130 polypeptide of the invention and a pUL131A polypeptide of the invention. A further example of said recombinant nucleic acid may be a single molecule which encodes a gL polypeptide of the invention and a gH polypeptide of the invention, optionally further encoding a gO polypeptide of the invention. The invention also provides a plurality of recombinant nucleic acid molecules which encode one or more mutated polypeptides of the invention. For example, in one embodiment the invention provides two nucleic acid molecules: the first molecule encoding a gH polypeptide of the invention and a gL polypeptide of the invention, and the second molecule encoding a pUL128 protein of the invention, a pUL130 protein of the invention and a pUL131A polypeptide of the invention. For example, in one embodiment the invention provides three nucleic acid molecules: a first recombinant nucleic acid molecule which encodes a gL protein of the invention; a second recombinant nucleic acid molecule which encodes a gH protein of the invention; and a third recombinant nucleic acid molecule which encodes one or more additional HCMV proteins such as gO, pUL128, pUL130, or pUL131A. For example, in one embodiment the invention provides five nucleic acid molecules: a first recombinant nucleic acid molecule which encodes a gL protein of the invention; a second recombinant nucleic acid molecule which encodes a gH protein of the invention; a third recombinant nucleic acid molecule which encodes a pUL128 protein of the invention; a fourth recombinant nucleic acid molecule which encodes a pUL130 protein of the invention; and a fifth recombinant nucleic acid molecule which encodes a pUL131A protein of the invention. Preferably, the recombinant nucleic acid molecules of the present invention (a) is/are not a self-replicating RNA molecule; (b) is/are not (an) alphavirus replicon(s); (c) do(es) not encode any alphavirus nonstructural proteins, such as NSP1, NSP2, NSP3 and NSP4; (d) do(es) not contain an Internal Ribosomal Entry Site (IRES), such as EMCV or EV71; and/or (e) do(es) not contain a viral 2A site, such as FMDV. Thus, the sequences encoding each individual polypeptide in a complex can be present in a single nucleic acid molecule, or distributed among two or more nucleic acid molecules.

In one embodiment, the invention provides a plurality of recombinant nucleic acids comprising: (i) a first recombinant nucleic acid molecule which encodes a gL protein of the invention, (ii) a second recombinant nucleic acid molecule which encodes a gH protein of the invention, (iii) a third recombinant nucleic acid molecule which encodes a pUL128 protein of the invention, (iv) a fourth recombinant nucleic acid molecule which encodes a pUL130 protein of the invention, and (v) a fifth recombinant nucleic acid molecule which encodes a pUL131A protein of the invention. See, e.g., WO 2014/005959 (also published as U.S. Pre-grant Pub. No. 2016-0159864. Preferably, said first, second, third, fourth and/or fifth recombinant nucleic acid molecule(s): (a) is/are not a self-replicating RNA molecule; (b) is/are not (an) alphavirus replicon(s); (b) do(es) not encode any alphavirus nonstructural proteins, such as NSP1, NSP2, NSP3 and NSP4; (c) do(es) not contain an Internal Ribosomal Entry Site (IRES), such as EMCV or EV71; and/or (d) do(es) not contain a viral 2A site, such as FMDV.

Nucleic acid molecules which encode a gH protein of the invention can have various degrees of identity to SEQ ID NO: 1 such as at least 89% 90%, 91%, 92%, 93%, 94%, 95%, 96%, 97%, 98% or 99% identity to the sequence of SEQ ID NO: 1. Nucleic acid molecules which encode a gH protein of the invention can have various degrees of identity to SEQ ID NO: 3 such as at least 89% 90%, 91%, 92%, 93%, 94%, 95%, 96%, 97%, 98% or 99% identity to the sequence of SEQ ID NO: 3. Nucleic acid molecules which encode a gL protein of the invention can have various degrees of identity to SEQ ID NO: 7 such as at least 89% 90%, 91%, 92%, 93%, 94%, 95%, 96%, 97%, 98% or 99% identity to the sequence of SEQ ID NO: 7. Nucleic acid molecules which encode a gL protein of the invention can have various degrees of identity to SEQ ID NO: 9 such as at least 89% 90%, 91%, 92%, 93%, 94%, 95%, 96%, 97%, 98% or 99% identity to the sequence of SEQ ID NO: 9. Nucleic acid molecules which encode a gL protein of the invention can have various degrees of identity to SEQ ID NO: 29 such as at least 89% 90%, 91%, 92%, 93%, 94%, 95%, 96%, 97%, 98% or 99% identity to the sequence of SEQ ID NO: 29. Nucleic acid molecules which encode a pUL128 protein of the invention can have various degrees of identity to SEQ ID NO: 13 such as at least 89% 90%, 91%, 92%, 93%, 94%, 95%, 96%, 97%, 98% or 99% identity to the sequence of SEQ ID NO: 13. Nucleic acid molecules which encode a pUL130 protein of the invention can have various degrees of identity to SEQ ID NO: 17 such as at least 89% 90%, 91%, 92%, 93%, 94%, 95%, 96%, 97%, 98% or 99% identity to the sequence of SEQ ID NO: 17. Nucleic acid molecules which encode a pUL131A protein of the invention can have various degrees of identity to SEQ ID NO: 21 such as at least 89% 90%, 91%, 92%, 93%, 94%, 95%, 96%, 97%, 98% or 99% identity to the sequence of SEQ ID NO: 21.

The recombinant nucleic acid molecules of the invention may comprise DNA, optionally including introns, and/or cDNA. Some genes are expressed more efficiently when introns are present. Genomic UL128 and UL131A genes each consist of two exons, whereas UL130 does not contain any introns. The recombinant nucleic acid molecule of the invention may comprise ribonucleic acid (RNA), including mRNA, with the proviso that the RNA molecule of the present invention (a) is/are not a self-replicating RNA molecule; (b) is/are not (an) alphavirus replicon(s); (c) do(es) not encode any alphavirus nonstructural proteins, such as NSP1, NSP2, NSP3 and NSP4; (d) do(es) not contain an Internal Ribosomal Entry Site (IRES), such as EMCV or EV71; and/or (e) do(es) not contain a viral 2A site, such as FMDV. The nucleic acid molecules of the invention may comprise polynucleotide sequences (DNA or RNA) that have been codon optimized for expression within a host cell, for example, codon optimized for expression within a bacterial or mammalian host cell.

The invention provides vectors that comprise the nucleic acid molecules of this invention. A vector of this invention may be an expression vector comprising promoters and terminators suitable for expression within a host cell. Such promoters and terminators have been described by, for example, U.S. Pre-grant Pub. Nos. 2015/0322115 and 2015/0359879. Said recombinant nucleic acid molecules may be plasmids, or may be incorporated into the genome of a cell. The promoters in these vectors can be HCMV promoters or non-HCMV promoters (see, e.g., U.S. Pre-grant Pub. Nos. 2015/0322115 and 2015/0359879).

Exemplary procedures sufficient to guide one of ordinary skill in the art through the production of recombinant HCMV nucleic acids of the invention can be found in Sambrook et al., *Molecular Cloning: A Laboratory Manual*, 2d ed., Cold Spring Harbor Laboratory Press, 1989; Sambrook et al., *Molecular Cloning: A Laboratory Manual*, 3d ed., Cold Spring Harbor Press, 2001; Ausubel et al., *Current Protocols in Molecular Biology*, Greene Publishing Associates, 1992 (and Supplements to 2003); and Ausubel et al., *Short Protocols in Molecular Biology: A Compendium of Methods from Current Protocols in Molecular Biology*, 4th ed., Wiley & Sons, 1999.

The invention also provides a process for expressing a HCMV complex (e.g., a HCMV pentameric complex) comprising one or more mutated HCMV gH, gL, pUL128, pUL13 and/or pUL131A polypeptides of the invention by introducing one or more recombinant nucleic acid molecules which encode said one or more mutated polypeptides into an expression system; expressing said one or more nucleic acid molecules in said expression system; and purifying said HCMV complex. In some embodiments, this process comprises transfecting cells with a first nucleic acid construct which encodes: mutated HCMV gH, gL, pUL128, pUL130 and pUL131A polypeptides of the invention. In some embodiments, this process may comprise transfecting cells with a first nucleic acid construct which encodes a HCMV gH polypeptide of the invention, a second nucleic acid construct which encodes a HCMV gL polypeptides of the invention; and one or more third nucleic acid construct(s) which encode(s) one or more additional HCMV glycoprotein(s) of the invention. In some embodiments, this process may comprise transfecting cells with a first nucleic acid construct which encodes a gH polypeptide of the invention and a gL polypeptide of the invention; and a second nucleic acid construct which encodes a HCMV pUL128, a HCMV pUL130 and a HCMV pUL131A polypeptide of the invention. Said HCMV complex may be expressed in a mammalian cell. Said isolated HCMV membrane protein complex may optionally be purified.

Cells

The invention also provides a cell that expresses a nucleic acid molecule or plurality of nucleic acid molecules of the invention, wherein said cell does not comprise the full HCMV genome. Said cell may be stably transformed with said nucleic acid molecule or plurality of nucleic acid molecules of the invention. Preferably, said cell is a mammalian cell, for example a 293-6E cell (see WO 2014/005959, also published as U.S. Pre-grant Pub. No. 2016/0159864) or a CHO cell (see WO 2016/116904).

The invention also provides a cell that produces a complex of the present invention, wherein the cell does not (i)

contain an HCMV genome, and/or (ii) produce HCMV virions, and/or (iii) express any non-envelope HCMV proteins. Ideally the cell lacks one of (i), (ii) or (iii); preferably, it lacks two; more preferably, it lacks all three of (i), (ii) and (iii). It may therefore be specified that a cell of the present invention does not contain the HCMV genome and/or does not produce HCMV virions and/or does not express any non-envelope HCMV proteins.

Antibodies

While their structure is distinct from non-mutant polypeptides, the modified polypeptides of the present invention (and mutant, construct-forming fragments thereof) maintain immunogenic properties or epitope(s), so it is a further object of the present invention to utilize the mutant polypeptides and mutant fragments thereof in polypeptide/antibody interactions. Polypeptide/antibody interactions of non-mutant polypeptides have been described by, for example, WO 2014/005959 (also published as U.S. Pre-grant Pub. No. 2016/0159864); Macagno et al., *Isolation of Human Monoclonal Antibodies that Potently Neutralize Human Cytomegalovirus Infection by Targeting Different Epitopes on the gH/gL/UL128-131A complex,* 2010 J. Virol. 84(2): 1005-1013; and Gerna et al., *Monoclonal antibodies to different components of the human cytomegalovirus (HCMV) pentamer gH/gL/pUL128L and Trimer gH/gL/gO as well as antibodies elicited during primary HCMV infection prevent epithelial cell syncytium formation,* 2016 J. Virol. 90(14): 6216-6223. See also U.S. Pat. No. 9,527,902. Prior to the present invention, a range of conformational epitopes for the pentameric complex were known. For example, Macagno et al. (2010 J. Virol. 84: 1005-1013) isolated a panel of human monoclonal antibodies that neutralized HCMV infection of endothelial, epithelial, and myeloid cells. With the single exception of an antibody that bound to a conserved epitope in the UL128 gene product, all other antibodies bound to conformational epitopes that required expression of two or more proteins of the gH/gL/UL128-131A complex. Preferably, the pentameric complexes of the invention possess one or more of the conformational epitopes identified by Macagno et al. (2010 J. Virol. 84: 1005-1013) and/or further described by the Examples herein.

The invention provides antibodies which recognise a modified HCMV gH, gL, pUL128, pUL130, or pUL131A polypeptide; or complex of the present invention. The antibodies of the invention may have been raised using an isolated polypeptide, or isolated complex comprising it, of the invention as an antigen. Preferably, the antibodies of the invention are neutralizing antibodies. The antibodies of the present invention may be a monoclonal antibody, polyclonal antibody, multispecific antibody (e.g., bispecific antibodies), labelled antibody, or antibody fragment so long as they exhibit the desired antigen-binding activity. An "antibody fragment" or "antigen-binding fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments. Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

Alternatively, an HCMV polypeptide or HCMV complex of the invention may be used to identify antibodies using in vitro selection methods, such as phage display using diverse antibody libraries. The invention also provides a method for raising antibodies using an isolated HCMV polypeptide or HCMV complex of the invention. Antibodies of the invention may be human or humanised antibodies. The antibodies of the invention may be used in a diagnostic assay and may be labelled directly or indirectly. In some embodiments, the antibodies of the invention may be used in therapy, for example in the treatment of HCMV infection and may be in the form of neutralizing antibodies, which can inhibit or neutralize the antigen's biological activity.

Isolation and Purification of Complexes

Complexes of the invention are preferably prepared and used in isolated form. The term "isolated" as used herein means removed from its natural environment. Hence, an "isolated HCMV membrane protein complex" does not encompass the HCMV membrane protein complex on the surface of HCMV infected cells or within an infectious HCMV virion or bound to an antibody (or antibody fragment). Using the expression methods described in the examples and, for example, WO 2014/005959 (also published as U.S. Pre-grant Pub. No. 2016/0159864, and WO 2016/116904), the complexes of the invention can be produced at high yields. For example, in processes involving growing cells of the invention in growth medium, the protein complex of the invention may accumulate to a level of more than 0.4 mg per litre of growth medium (e.g. 0.45, 0.5, 0.55, 0.6, 0.65, 0.7, 0.75, 0.8, 0.85, 0.9, 0.95, 1.0, 1.2, 1.4, 1.6, 1.8, 2, 2.5, 3, 3.5, 4, 4.5 or 5 mg per litre of growth medium or more).

The invention provides processes for purifying HCMV membrane complexes of the invention. Such processes of the invention allow for production of the HCMV membrane protein complex at a purity of >85%, >86%, >87%, >88%, >89%, >90%, >91%, >92%, >93%, >94% or >95% of total protein by mass, as determined by gel electrophoresis. These high levels of purity make the complexes suitable for use as an immunogen in diagnostic applications or as an antigen in vaccine formulations. The HCMV membrane protein complex of the invention can be prepared at various levels of purity e.g. at least 80%, 85%, 90%, 95%, or 99% of total protein by mass, i.e. the complex makes up at least 80% of the total proteinaceous mass in a composition. The composition may be free from polyacrylamide.

The invention provides a process for purifying an HCMV complex (e.g., an HCMV pentamer complex) of the invention. In an embodiment of the invention, said purification comprises one or more chromatographic steps. Said one or more chromatographic steps comprises affinity chromatography, such as Ni2+ affinity chromatography and/or size exclusion chromatography. In an embodiment of the invention, said one or more chromatographic steps comprises ion exchange chromatography. See, e.g., WO 2014/005959 (also published as U.S. Pre-grant Pub. No. 2016/0159864); WO 2016/116904; and WO2015/181142. A polypeptide of the present invention may therefore comprise a tag (e.g., an affinity tag such as a strep tag, myc tag, polyhistidine tag, or combinations thereof) for, for example, isolation of the polypeptide (see Kimple et al., *Overview of Affinity Tags for Protein Purification,* 2015 Curr. Protoc. Protein. Sci. 73: Unit-9.9. doi:10.1002/0471140864.ps0909s73, summarizing known tags and their use for biotechnology applications).

Adjuvants

Vaccine and immunogenic compositions of the invention may comprise an adjuvant in addition to the antigen. Adjuvants are "non-antigen components" used in vaccines in order to enhance and modulate the immune response to the antigen. However, adjuvants can result in increased reactogenicity. adjuvants include (but are not limited to) ASO1, oil-in-water emulsions (for example MF59, and AS03), liposomes, saponins, TLR2 agonists, TLR3 agonists, TLR4 agonists, TLR5 agonists, TLR6 agonists, TLR7 agonists, TLR8 agonists, TLR9 agonists, aluminium salts, nanoparticles, microparticles, ISCOMS, calcium fluoride and organic compound composites or combinations thereof. See, e.g., U.S. Pre-grant Pub. No. 2015/0093431 and WO2011/027222 (also published as U.S. Pre-grant Pub. No. 2012/0237546). In a particular embodiment, the vaccine or immunogenic composition of the invention comprises an antigen and an adjuvant wherein the adjuvant is ASO1, an oil-in-water emulsion (e.g., MF59, and AS03 and their respective subtypes including subtypes B and E), an aluminum salt (e.g., aluminum phosphate and aluminum hydroxide), a saponin (e.g. QS21), an agonist of Toll-like receptors (TLRa) (e.g., TLR4a and TLR7a), or a combination thereof (e.g., Alum-TLR7a (Buonsanti et al., *Novel adjuvant Alum-Tlr7a significantly potentiates immune response to glycoconjugate vaccines*, 2016 Sci. Rep. 6:29063 (DOI: 10.1038/srep29063)). By "TLR agonist" it is meant a component which is capable of causing a signaling response through a TLR signaling pathway, either as a direct ligand or indirectly through generation of endogenous or exogenous ligand (Sabroe et al, *Toll-like Receptors in Health and Disease: Complex Questions Remain*, 2003 J. Immunol. 171(4): 1630-1635). A TLR4 agonist, for example, is capable of causing a signalling response through a TLR-4 signalling pathway. A suitable example of a TLR-4 agonist is a lipopolysaccharide, suitably a non-toxic derivative of lipid A, particularly monophosphoryl lipid A or more particularly 3-Deacylated monophoshoryl lipid A (3D—MPL). The adjuvants described herein may be combined with any of the antigen(s) herein described.

The following embodiments are contemplated in the present invention:

An HCMV gH polypeptide, or complex-forming fragment thereof, comprising a mutation at a location determined with respect to the sequence SEQ ID NO: 1 and that is:

A102W, A102F, A102Y, A102V, A102I, A102L, A372W, A372F, A372Y, A372V, A372I, A372L, A352W, A352F, A352Y, A352V, A352I, A352L, L257W, L257F, L257Y, L257V, L257I, L257L, H252W, H252F, H252M, H252C, H252A, H252L, H252I, H252V, H252P, H252Y, K404W, K404F, K404M, K404C, K404A, K404L, K404I, K404V, K404P, K404Y, R255W, R255F, R255M, R255C, R255A, R255L, R255I, R255V, R255P, R255Y, E355W, E355F, E355M, E355C, E355A, E355L, E355I, E355V, E355P, E355Y, H480W, H480F, H480M, H480C, H480A, H480L, H480I, H480V, H480P, H480Y, S601W, S601F, S601M, S601C, S601A, S601L, S601I, S601V, S601P, S601Y, R405W, R405F, R405M, R405C, R405A, R405L, R405I, R405V, R405P, R405Y, G358S, G358T, G358C, G358Y, G358N, G358Q, G358R, G358E, G358K, G358H, G358D, H275S, H275T, H275C, H275Y, H275N, H275Q, H275R, H275E, H275K, H275H, H275D,

V109C, L111C,

N55Q, N55S, N55T, N55A, N55E, N55D, N62Q, N62S, N62T, N62A, N62E, N62D, N67Q, N67S, N67T, N67A, N67E, N67D, N192Q, N192S, N192T, N192A, N192E, N192D, N641Q, N641S, N641T, N641A, N641E, N641D, N700Q, N700S, N700T, N700A, N700E, N700D or a combination thereof.

An HCMV gL polypeptide, or complex-forming fragment thereof, comprising a mutation at a location determined with respect to the sequence SEQ ID NO: 7 and that is:

H177W, H177F, H177Y, H177V, H177I, H177L, G224W, G224F, G224Y, G224V, G224I, G224L, G140W, G140F, G140Y, G140V, G140I, G140L, G145W, G145F, G145Y, G145V, G145I, G145L, D146W, D146F, D146Y, D146V, D146I, D146L, G218W, G218F, G218Y, G218V, G218I, G218L, L119W, L119F, L119Y, L119V, L119I, L119L, C233W, C233F, C233Y, C233L, P272W, P272F, P272Y, P272V, P272I, P272L, H267W, H267F, H267M, H267C, H267A, H267L, H267I, H267V, H267P, H267Y, H236W, H236F, H236M, H236C, H236A, H236L, H236I, H236V, H236P, H236Y, H245W, H245F, H245M, H245C, H245A, H245L, H245I, H245V, H245P, H245Y, G161W, G161F, G161M, G161C, G161A, G161L, G161I, G161V, G161P, G161Y, C233W, C233F, C233M, C233C, C233A, C233L, C233I, C233V, C233P, C233Y,

G161C, D163C, G224C, G218C, R166C, G140C, R160C, A150C,

N74Q, N74S, N74T, N74A, N74E, and N74D or a combination thereof.

A HCMV pUL128 polypeptide, or complex-forming fragment thereof, comprising a mutation at a location determined with respect to the sequence SEQ ID NO: 13 and that is:

G123W, G123F, G123Y, G123V, G123I, G123L, V77W, V77F, V77Y, V77V, V77L, L103W, L103F, L103Y, L103V, L103I, L103L, Q119W, Q119F, Q119Y, Q119V, Q119I, Q119L, G145W, G145F, G145M, G145C, G145A, G145L, G145I, G145V, G145P, G145Y, H90W, H90F, H90M, H90C, H90A, H90L, H90I, H90V, H90P, H90Y, G112W, G112F, G112M, G112C, G112A, G112L, G112I, G112V, G112P, G112Y,

R142C, N99C, Y98C, A124C, G126C, L159C, D45C, V88C, M48C, G107C, R51C, D106C, S83C, or a combination thereof.

A HCMV pUL130 polypeptide, or complex-forming fragment thereof, comprising a mutation at a location determined with respect to the sequence SEQ ID NO: 17 and that is:

D165W, D165F, D165Y, D165L, H209W, H209F, H209Y, H209L,

G116W, G116F, G116M, G116C, G116A, G116L, G116I, G116V, G116P, G116Y, G135W, G135F, G135M, G135C, G135A, G135L, G135I, G135V, G135P, G135Y, H150W, H150F, H150M, H150C, H150A, H150L, H150I, H150V, H150P, H150Y, H209W, H209F, H209M, H209C, H209A, H209L, H209I, H209V, H209P, H209Y,

G116C, H150C, P64C, S178C, P62C, E95C, Y204C, N211C, I213C, Y56C, T167C,

N85Q, N85S, N85T, N85A, N85E, N85D, N118Q, N118S, N118T, N118A, N118E, N118D, N201Q, N201S, N201T, N201A, N201E, and N201D or a combination thereof.

A HCMV pUL131A polypeptide, or complex-forming fragment thereof, comprising a mutation at a location determined with respect to the sequence SEQ ID NO: 21 and that is:

G99W, G99F, G99Y, G99V, G99I, G99L, S86W, S86F, S86Y, S86V, S86I, S86L, S90W, S90F, S90Y, S90V, S90I, S90L, H69W, H69F, H69M, H69C, H69A, H69L, H69I, H69V, H69P, H69Y, H35W, H35F, H35M, H35C, H35A, H35L, H35I, H35V, H35P, H35Y, H64W, H64F, H64M, H64C, H64A, H64L, H64I, H64V, H64P, H64Y, D38W, D38F, D38M, D38C, D38A, D38L, D38I, D38V, D38P, D38Y, V85W, V85F, V85M, V85C, V85A, V85L, V85I, V85V, V85P, V85Y, Y52W, Y52F, Y52M, Y52C, Y52A, Y52L, Y52I, Y52V, Y52P, Y52Y, A67W, A67F, A67M, A67C, A67A, A67L, A67I, A67V, A67P, A67Y, R118S, R118T, R118C, R118Y, R118N, R118Q, R118R, R118E, R118K, R118H, R118D,

H64C, W37C,

N81Q, N81A, N81T, N81A, N81E, and N81D or a combination thereof.

EXAMPLES

Many modifications and variations of the present invention are possible in light of the above teachings. It is therefore to be understood that, within the scope of the appended claims, a person with skill in the art would recognize that the invention may be practiced otherwise than as specifically described. The illustrative embodiments and examples should not be construed as limiting the invention.

Example 1—Expression of the Pentameric Complex in Mammalian Cells

Expression of wild type or selenomethionine-labelled (SeMet)-Pentamer was carried out in 293GnTi-cells through transient or stable transfection of two vectors, with one vector encoding gH and gL (having the sequences SEQ ID NOs: 3 and 7, respectively), and the other encoding pUL128, pUL130 and pUL131A (having the sequences SEQ ID NOs: 13, 17, and 21, respectively) two-vector strategy as outlined in Hofmann et al. (*Expression of the Human Cytomegalovirus Pentamer Complex for Vaccine use in a CHO System*, 2015 Biotech. & Bioeng. 112(12): 2505-2515).

For anti-Pentamer Fab expression, the heavy chain Fab fragment and the full length light chain were each cloned into the mammalian pRS5a expression vector (Novartis AG). A cleavable double Strep-tag was present on the C-terminus of the heavy chain Fab. Anti-Pentamer Fab was expressed transiently in 293Expi cells (Invitrogen Inc.) using Expifectamine 293 transfection kit (ThermoFisher) according to manufacturer's recommendations by transfecting the two vectors encoding the Fab fragment of the heavy chain and the full length light chain of the antibody in a 1:1 ratio.

Example 2—Purification of the Pentameric Complex

For Pentamer purification, expression medium was loaded directly onto a StrepTrap HP column (GE Lifesciences) and the protein was eluted according to manufacturer's recommendations using 0.1M Tris pH 8.0, 150 mM NaCl and 2.5 mM desthiobiotin in the elution buffer (IBA Lifesciences). The eluate was incubated with TEV protease (ThermoFisher) overnight at 4 C. The sample was diluted 3-fold with 20 mM Hepes pH 7 to lower total salt concentration to 50 mM prior to loading onto MonoS10/30 column (GE Lifesciences) for ion exchange chromatography. The protein was eluted off the column with a linear gradient of 0 to 1 M NaCl over 10 column volumes. The protein was concentrated and loaded onto a Superose 6 10/300 column and the eluted peak was concentrated to greater than 1 mg/mL.

For Fab purification, expression medium was concentrated 10-fold and buffer exchanged into 25 mM Tris pH 8.0, 150 mM NaCl and 1 mM EDTA using a tangential flow filtration system (Millipore) with a 10 kDa cutoff. The sample was subsequently loaded onto a StrepTrap HP column and eluted similar to the Pentamer purification described above. The Strep tag was cleaved off using PreScission protease (GE Lifesciences) according to manufacturer's recommendations. The cleaved Fab was then purified by size exclusion chromatography over an 5200 column (GE Lifesciences) equilibrated with buffer containing 25 mM Tris pH 8.0 and 150 mM NaCl.

For Pentamer-Fab complex purification for crystallization, the Pentamer eluted from the MonoS column was incubated with a 2-fold molar excess of purified Fab and incubated for at least 15 minutes at room temperature. The sample was subsequently loaded over a Superose 6 10/300 column to separate the Pentamer-Fab complex from excess Fab. Peak fractions were pooled and concentrated to >5 mg/mL.

Example 3—Crystallization of the Pentameric Complex

For crystallization experiments purified wild type or selenomethione-labelled (SeMet)-Pentamer was deglycosylated using Endo Hf (New England Biolabs), according to the manufacturer's guidelines, prior to complex formation with Fabs. Initial crystal hits were obtained for a complex between Pentamer and the fragment antigen binding (Fab) of monoclonal antibody (mAb) 8I21 and 9I6 (Macagno et al. (2010 J. Virol. 84:1005-1013), and these appeared as small microcrystals in a drop containing 0.1 µl protein and 0.1 µl of 20% ethanol, 0.1 M Tris pH 8.5 at 20° C. Ethanol was replaced with the less volatile isopropanol in subsequent experiments, and benzamidine was used as additive (from the Hampton Research additive screening) in order to optimize this crystallization condition. The best crystals for WT or SeMet-Pentamer-8I21 Fab crystals were obtained using a reservoir containing 10% (wt/vol) PEG400, 10% isopropanol, 2% (wt/vol) benzamidine and 0.1 M Tris pH 8.2. Crystal hits for Pentamer in complex with the 9I6 Fab were initially obtained in 0.1 M MES pH 6.5 and 15% (wt/vol) PEG methylether 500. These crystals were optimized for growth with various additives. The best diffracting crystal was obtained using a reservoir containing 10% (wt/vol) PEG methyl ether 500, 0.1 M MES pH 6.2 and 10 µM phenol.

3.1 Results—Crystal Structure

The Pentamer structure adopts a helicoid-shape 180 Å in length and 30-80 Å in cross-over (FIG. 1). The gH/gL part of the complex has a similar domain organization and structure as other herpesvirus gH/gLs, with four gH domains (D-I to D-IV) stacking on top of each other and the most N-terminal one (D-I) co-folding with gL. The polypeptide chains of the ULs are highly interconnected and form a gently curved sub-complex that binds to an extension at the N-terminus gL. Analysis of the Pentamer surface reveals 11 N-linked glycosylation sites: 6 in gH, 1 in gL and the remaining 4 on the ULs.

Although structural comparisons reveal a close similarity of HCMV gH with gH of the γ-herpesvirus Epstein Barr Virus (EBV), the HCMV gH adopts a boot shape, reminiscent of the α-herpesviruses Varicella Zoster Virus (VZV) and Herpes Simplex Virus-2 (HSV-2) gH/gL, rather than the rod-like conformation of EBV gH/gL. A significant difference between EBV and HCMV gH is the presence in the latter of three additional N-terminal β-strands that interact with residues from gH.

The ULs form a central core domain flanked at opposite ends by two small globular domains (FIGS. 1 and 2A-2F). The core domain is formed by the pUL130 C-terminal end and pUL131A, both composed of N-terminal α-helices followed by 3 β-strands of similar length (FIGS. 2A-2F). The strands assemble in a large and rather flat anti-parallel β-sheet covered on one face by helices. The N-terminal of UL128 form a globular domain located at the tip of the Pentamer, with the first 80 residues adopting a CC-type chemokine fold, while the C-terminal UL128 is anchored to gH/gL by a 50 Å long linker, and a terminal helix docking on a hydrophobic groove formed by 3 α-helices and 2 β-strands of gL.

10P3 (site 4) and 15D8 (site 1) bind into the concave surface of the ULs, and 10F7 (site 2) binds on the other face of the Pentamer along the UL130/UL131A β sheet.

9I6 CDRs contact both UL128 (residues 47-52 on the chemokine domain and residues 92-93 and 106-109 on α2β4β5β6) and UL131A (residues 23-24 and 27-31). The epitope is consistent with published NS-EM data and mapping studies suggesting that site 5 antibodies require all three ULs for binding, likely due to the co-folding of UL130 and UL131A.

The main feature of the Pentamer-8I21 Fab complex is the interaction between the long HCDR3 of the Fab and the UL130 chemokine domain. Arg104 and Trp105, at the tip of HCDR3, protrude into a crevice composed of hydrophobic and polar residues from the N-terminal UL130-α1 helix and UL130/gL β-sheet establishing H-bonds with UL130 Ser47 and gL Asp156, respectively. Mutation of HCDR3 Trp105 to alanine resulted in an over 150-fold decrease in binding affinity consistent with its prominent role in the interaction. Several other interactions stabilize the complex including hydrogen bonds between the guanidinium group of HCDR3 Arg107 and the hydroxyl group of UL130 Tyr46, and H-bonds between main chain carbonyl oxygens of HCDR3 and the side chains of LCDR3 Trp94 and Trp97.

Figure 3A:
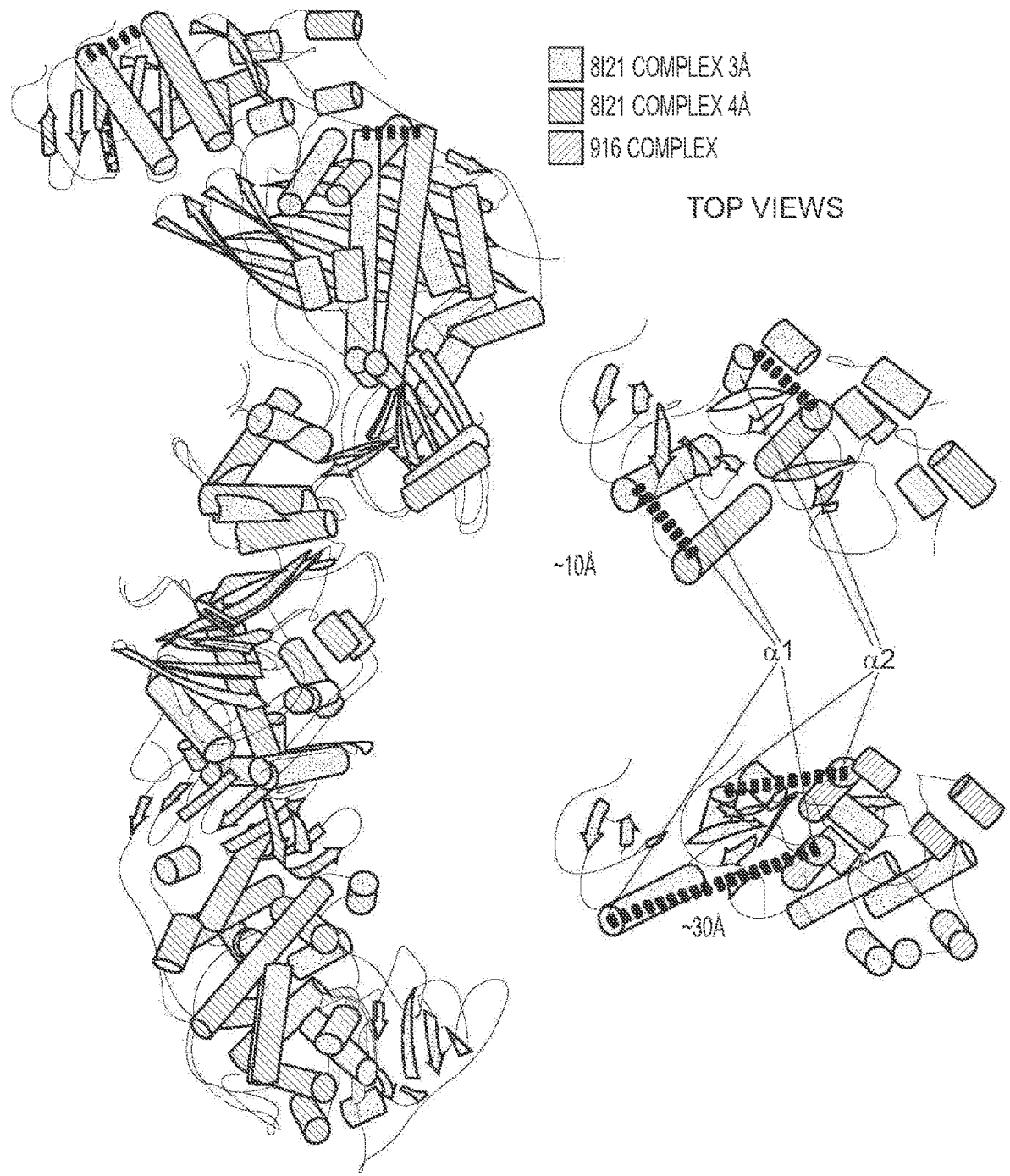
FIGS. 3A-3C.
Figure 3B:
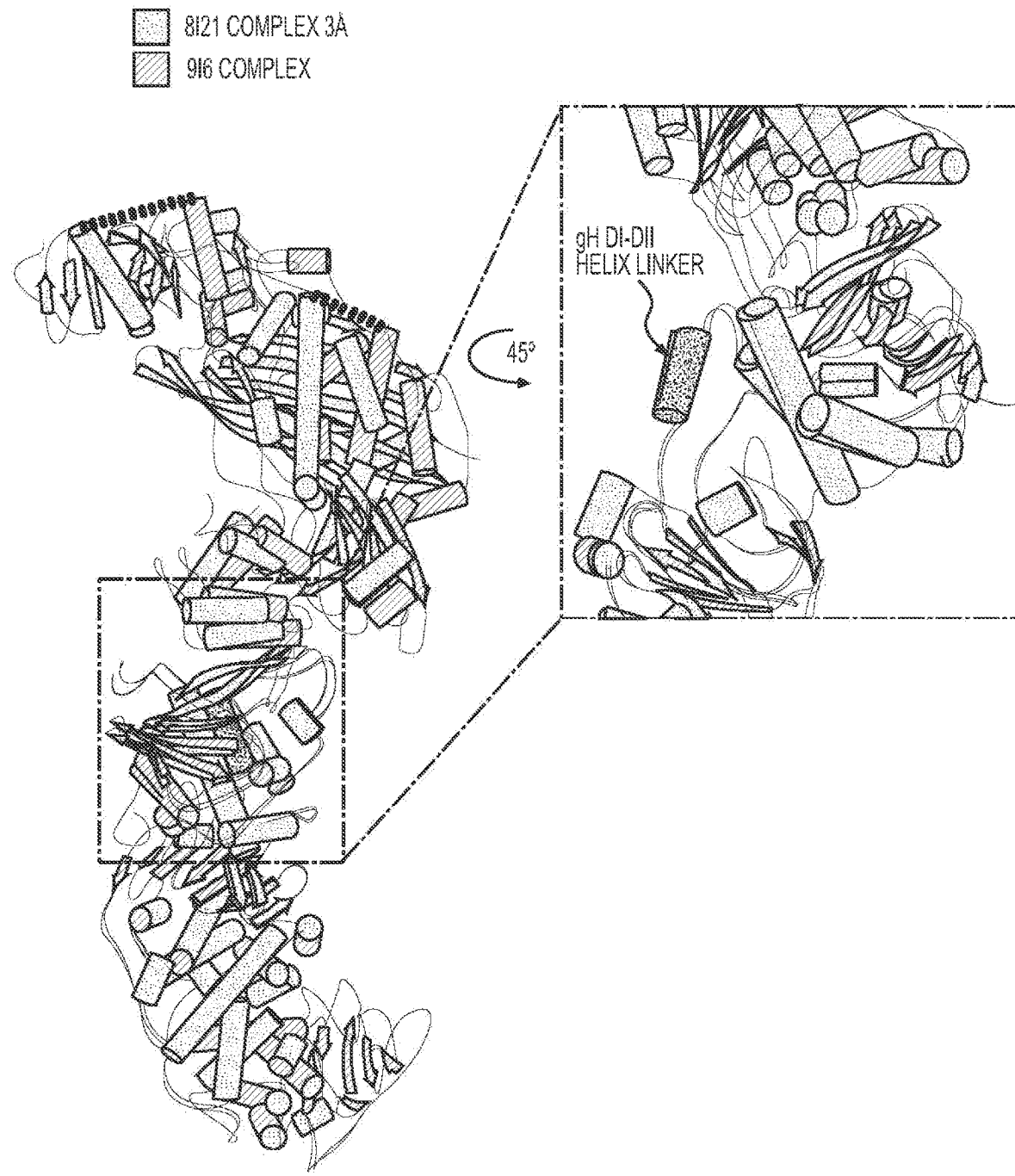
Figure 3C:
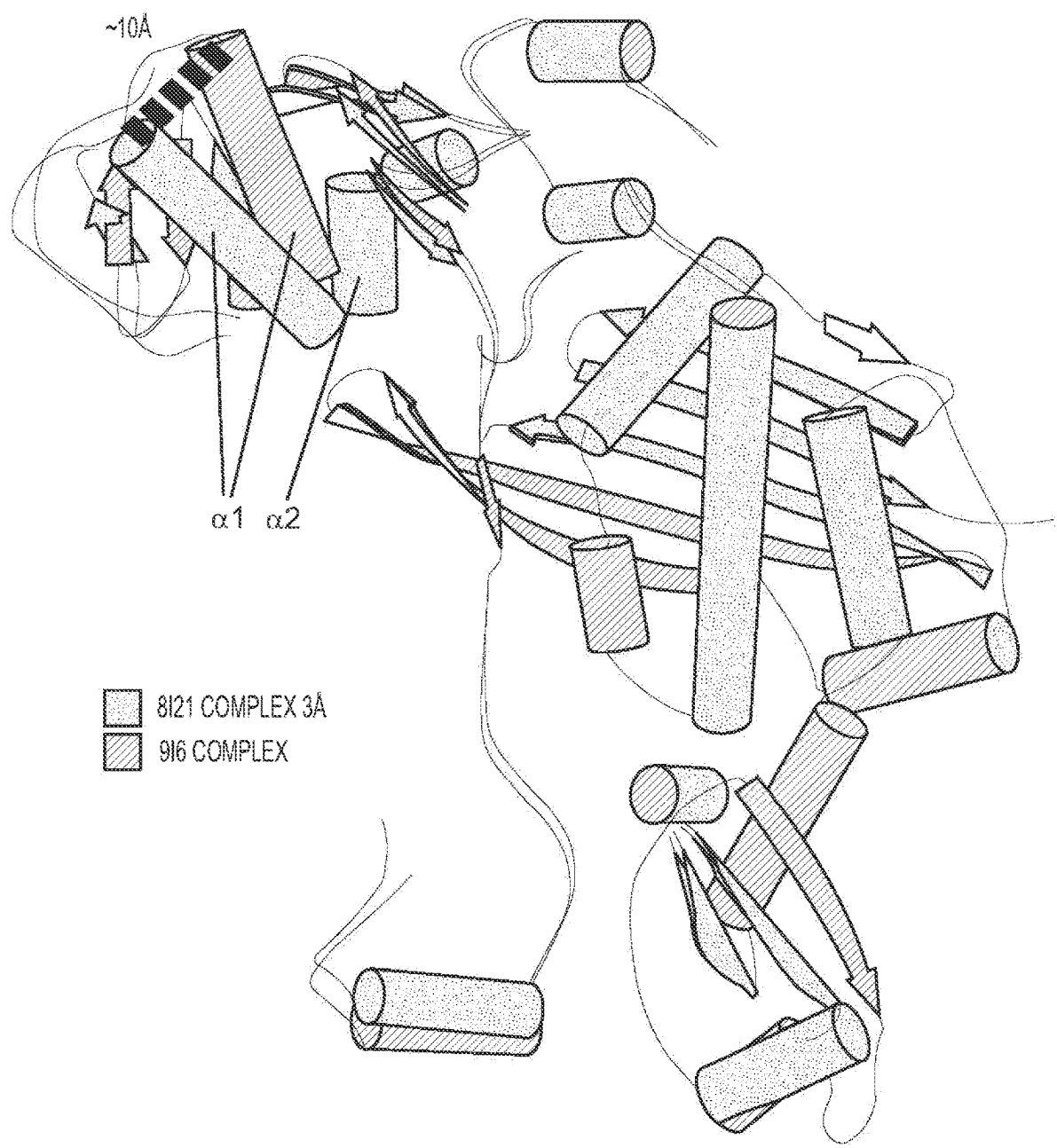
Figure 4A:
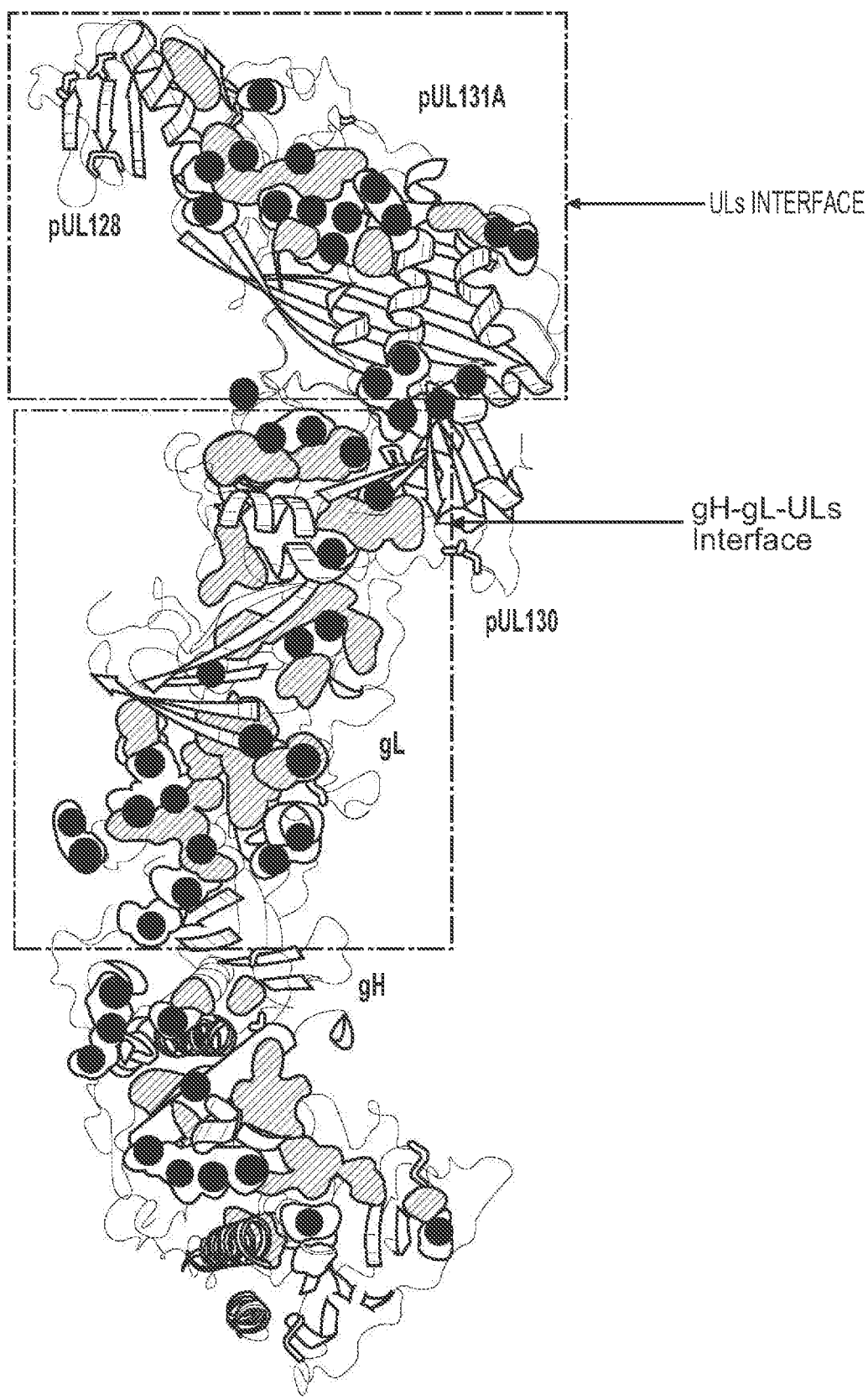
FIGS. 4A-4C.
Figure 4B:
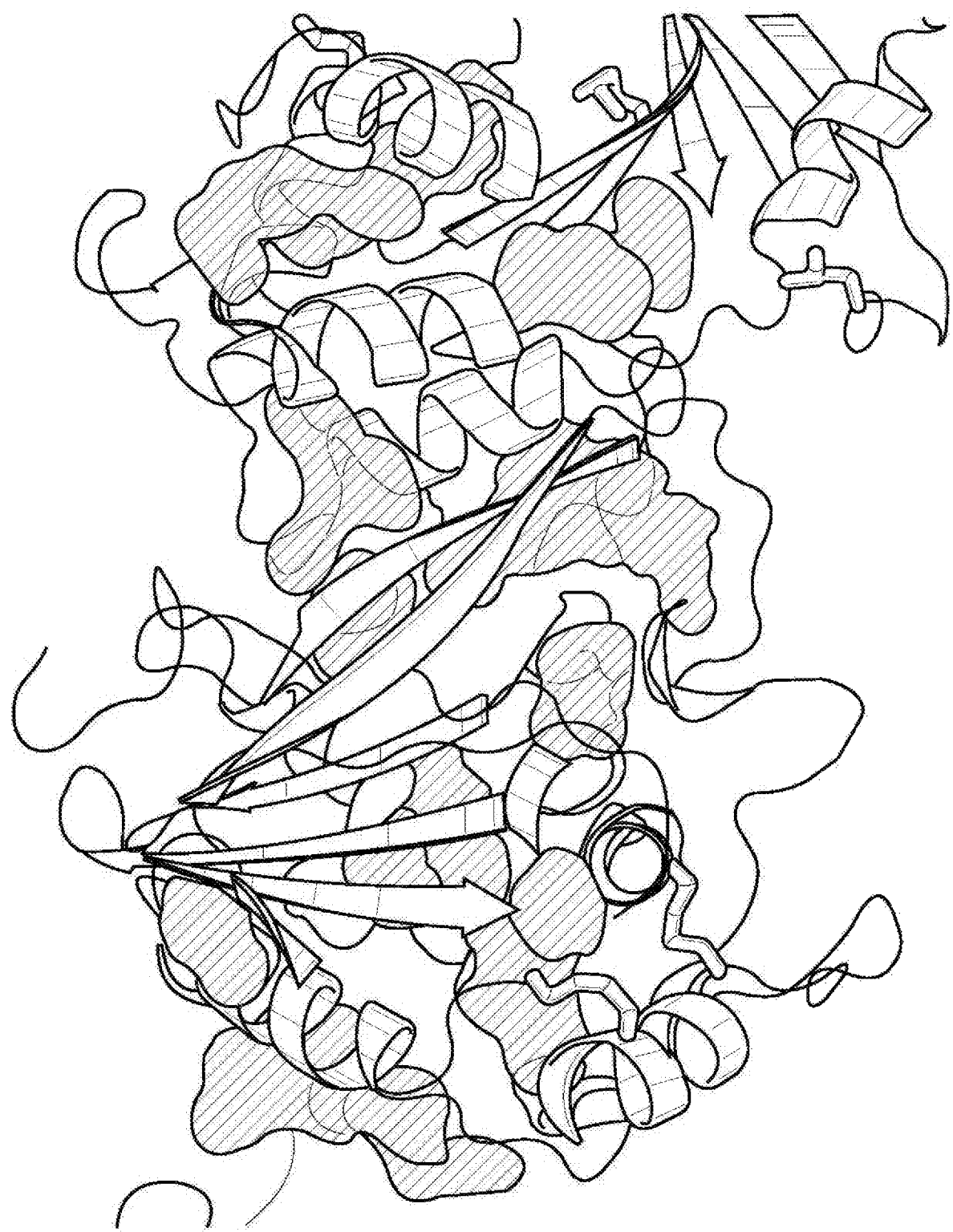
Figure 4C:
Figure 5A:
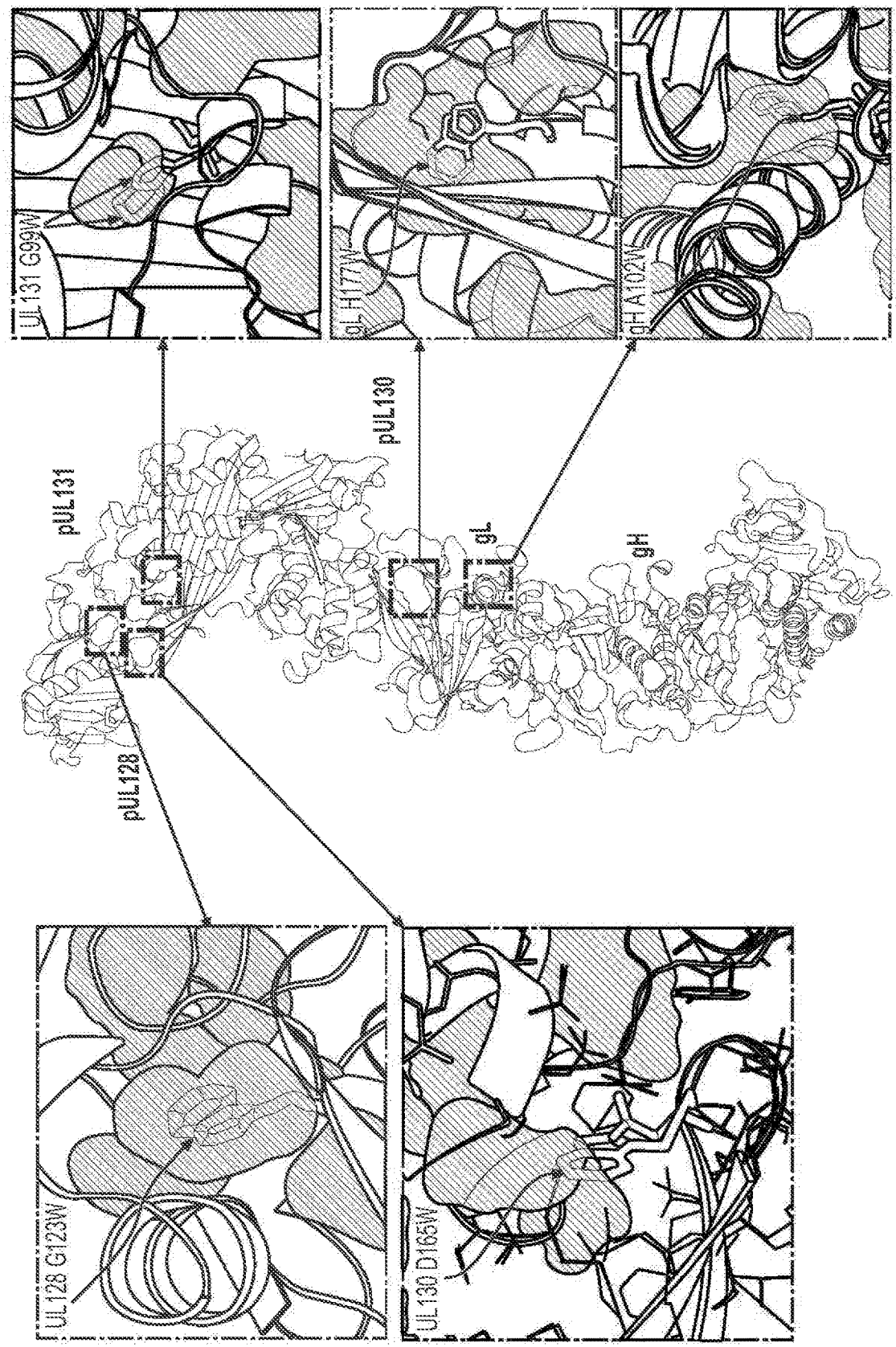
FIGS. 5A-5F.
Figure 5B:
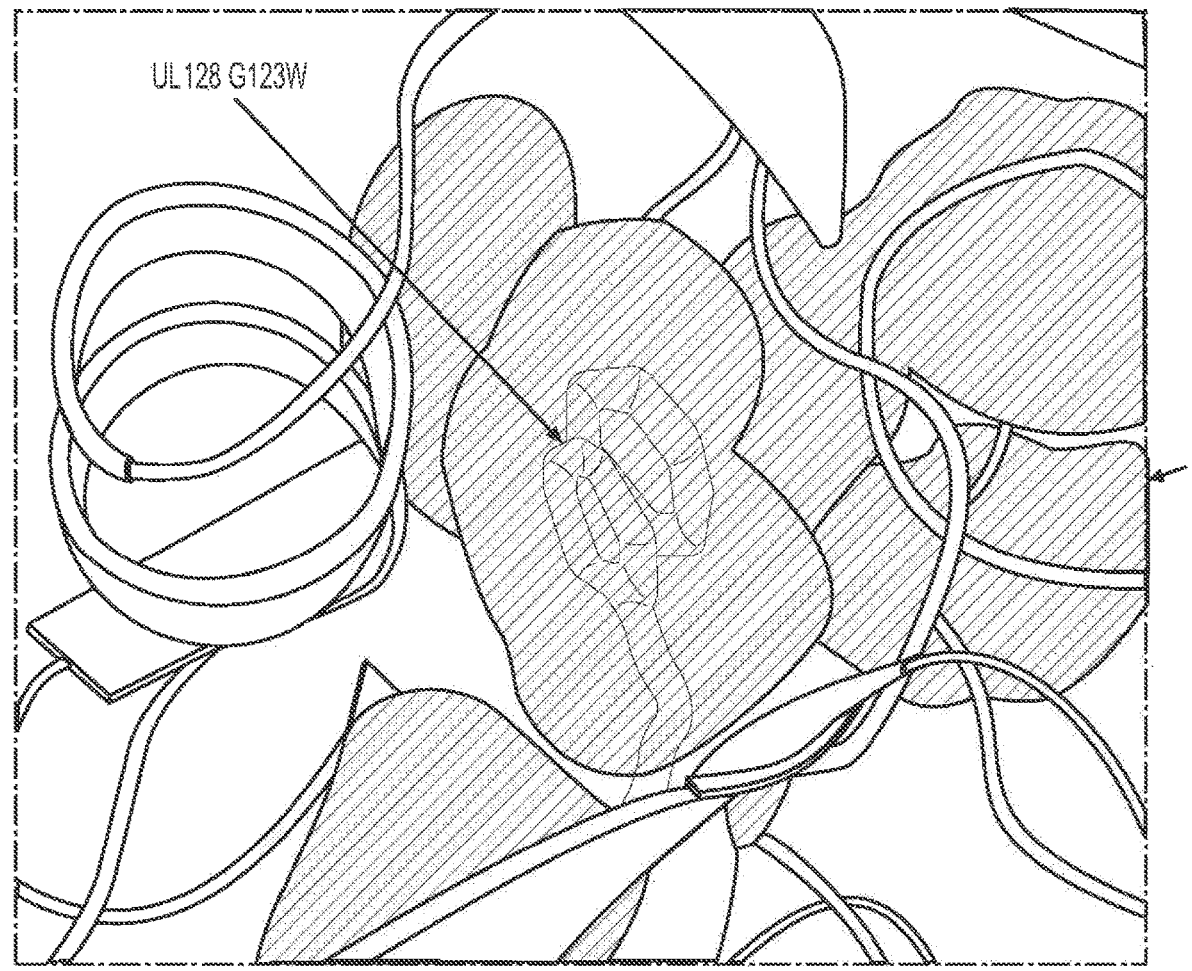
Figure 5C:
Figure 5D:
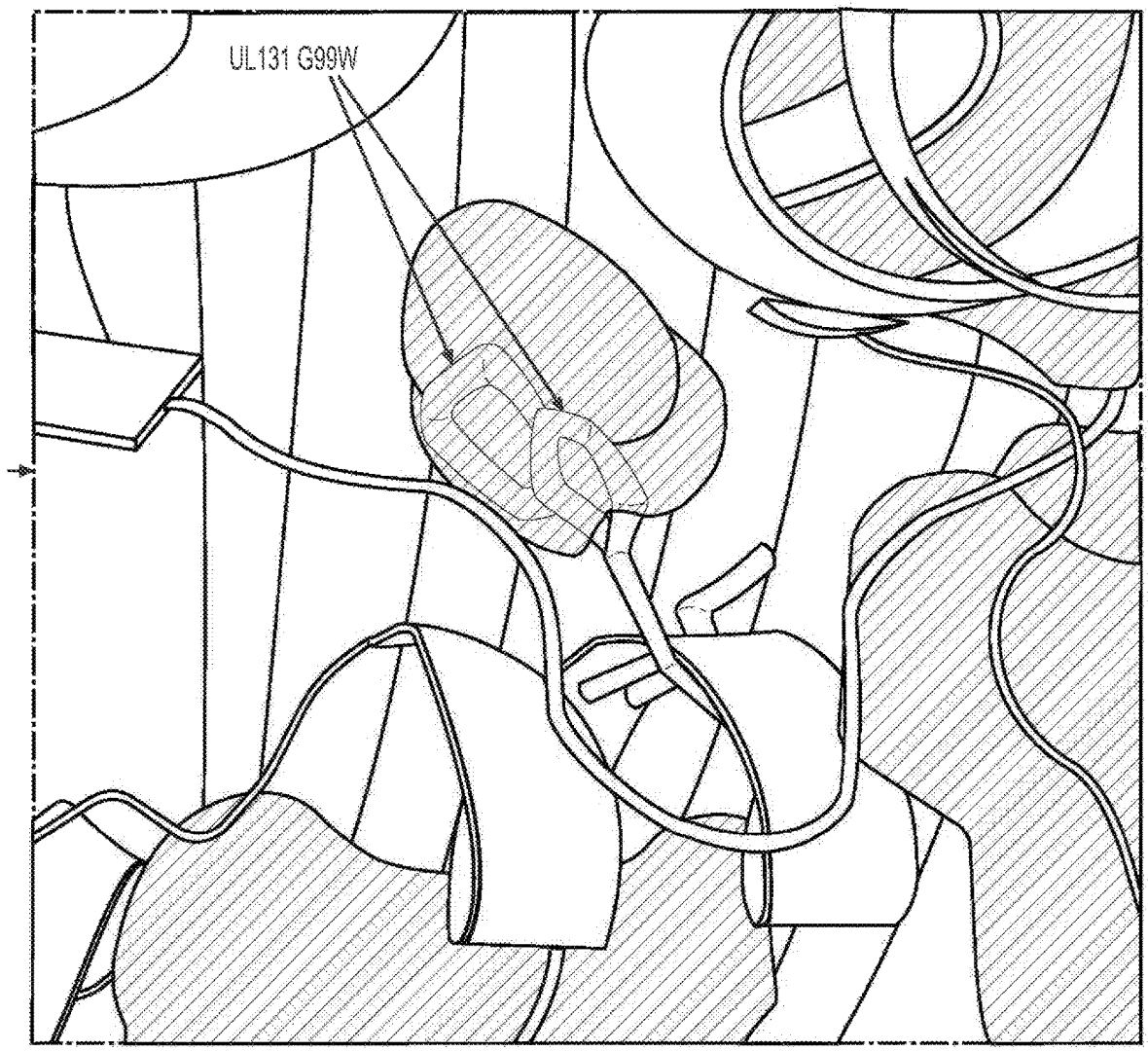
Figure 5E:
Figure 5F:
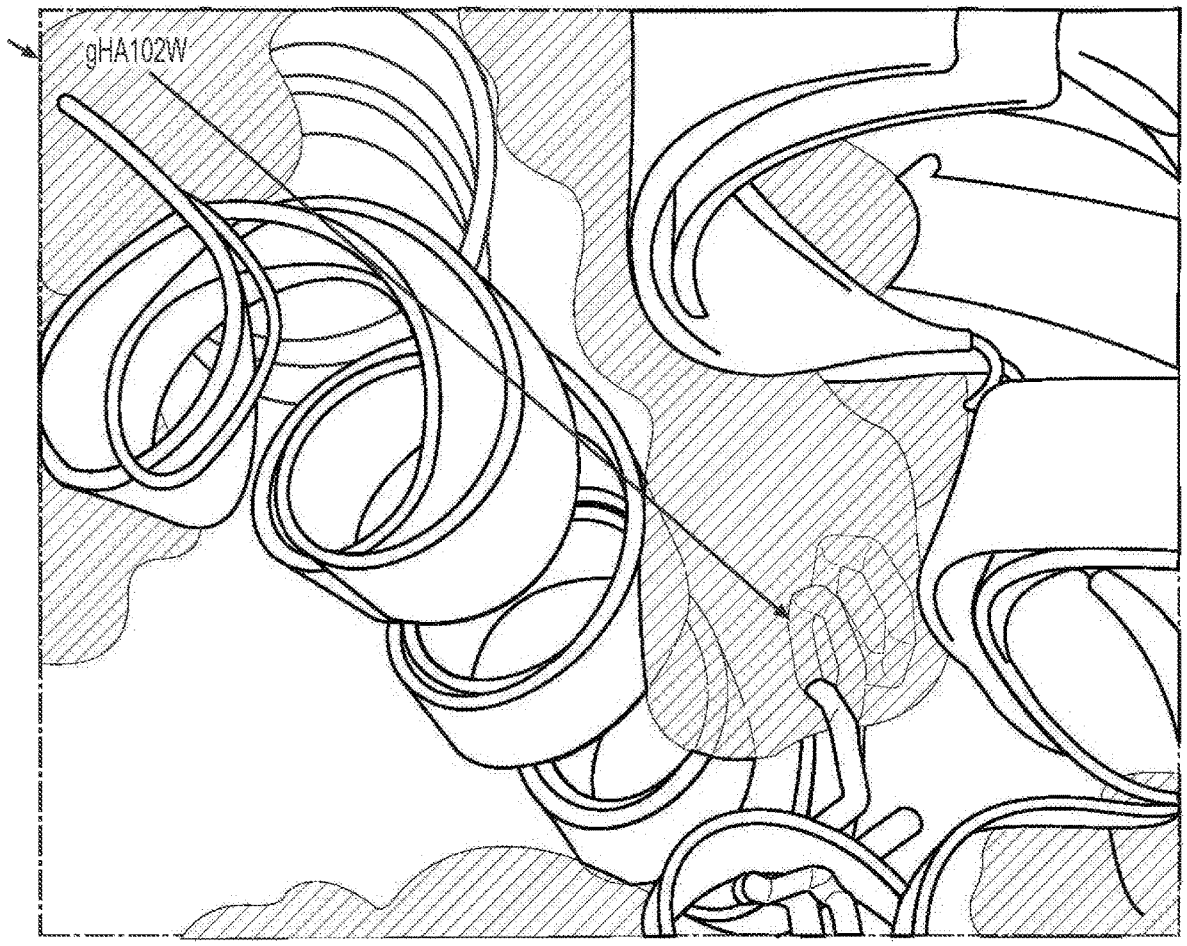

In Summary:

The Pentamer structure reveals the presence of small interfaces between some of the domains, as well as the presence of several cavities at the domain interfaces (FIG. 2). Analysis was conducted of data from negative-stain electron microscopy (NS-EM) of Pentamer-nAbs complexes (previously published, see Ciferri et al., *Antigenic Characterization of the HCMV gH/gL/gO and Pentamer Cell Entry Complexes Reveals Binding Sites for Potently Neutralizing Human Antibodies*, 2015 PLOS Path DOI:10.1371/journal.ppat.1005230), data from hydrogen-deuterium exchange coupled to mass-spectrometry (HDX-MS) and the superposition of Pentamer crystal structures solved in complex with two different neutralizing antibodies. Together, this information revealed the presence of intrinsic flexibility of the Pentamer protein complex. Specifically, the ULs undergo a rigid body rotation around the gH D-I/D-II linker-helix, which acts as a hinge or "shoulder". As a result, the ULs can move as a rigid arm, with displacement of up to 30 Å (FIG. 3). The HDX-MS data also showed how the binding of antibodies to Pentamer can affect peptides located far away from the epitopes (or the regions directly involved in binding of the antibodies), suggesting that upon binding by the antibodies, the Pentamer complex can be stabilized.

The Pentamer structure revealed herein shows that the gH and gL components of the complex have a close structural similarity with EBV gH/gL while the ULs are characterized by an α/β core domain flanked at opposite ends by UL128 and UL130 chemokine domains. Notably, HCMV gL has a unique N-terminal extension, missing in EBV and HSV gLs, which forms a docking site for the UL128 C-terminal α3 helix and the UL130 chemokine domain.

Characteristic features of the Pentamer structure include relatively small interfaces and cavities between some domains, suggesting intrinsic flexibility of the complex. Structure comparisons revealed large rigid body rotations of the gH/gL D-I domain and ULs arm around the gH D-I/D-II linker-helix resulting in a large displacement of the ULs. Though the 8I21 epitope remains the same in the Pentamer-9I6 Fab complex, it is believed that antibody binding stabilizes Pentamer in discrete, yet different, conformational states. Indeed, single particle reconstructions reveal a large rigid body rotation of the ULs in Pentamer bound to 10F7 Fab compared to the 8I21 and 9I6 Fab complexes. Consistent with this belief, HDX-MS analysis of Pentamer-Fab complexes shows that antibodies stabilize regions of Pentamer distant from their corresponding epitopes. Therefore, the combination of HDX-MS and crystallographic data reveal areas of Pentamer where mutations may be introduced to generate a more stable complex (see, e.g., McLellan et al., 2013 Science 342: 592-598, showing greater stability of a pre-fusion conformation of the respiratory syncytial virus fusion protein was linked with improved immunogenicity).

This structural analysis of the Pentamer-Fab complexes together with cell binding analysis provides new insights into the mechanism of antibody-mediated HCMV neutralization. We show that Pentamer binds to adult retinal pigment epithelial cells (ARPE-19) and human umbilical vein endothelial cells (HUVEC) cells but not MRC-5 cells.

Figure 6A:
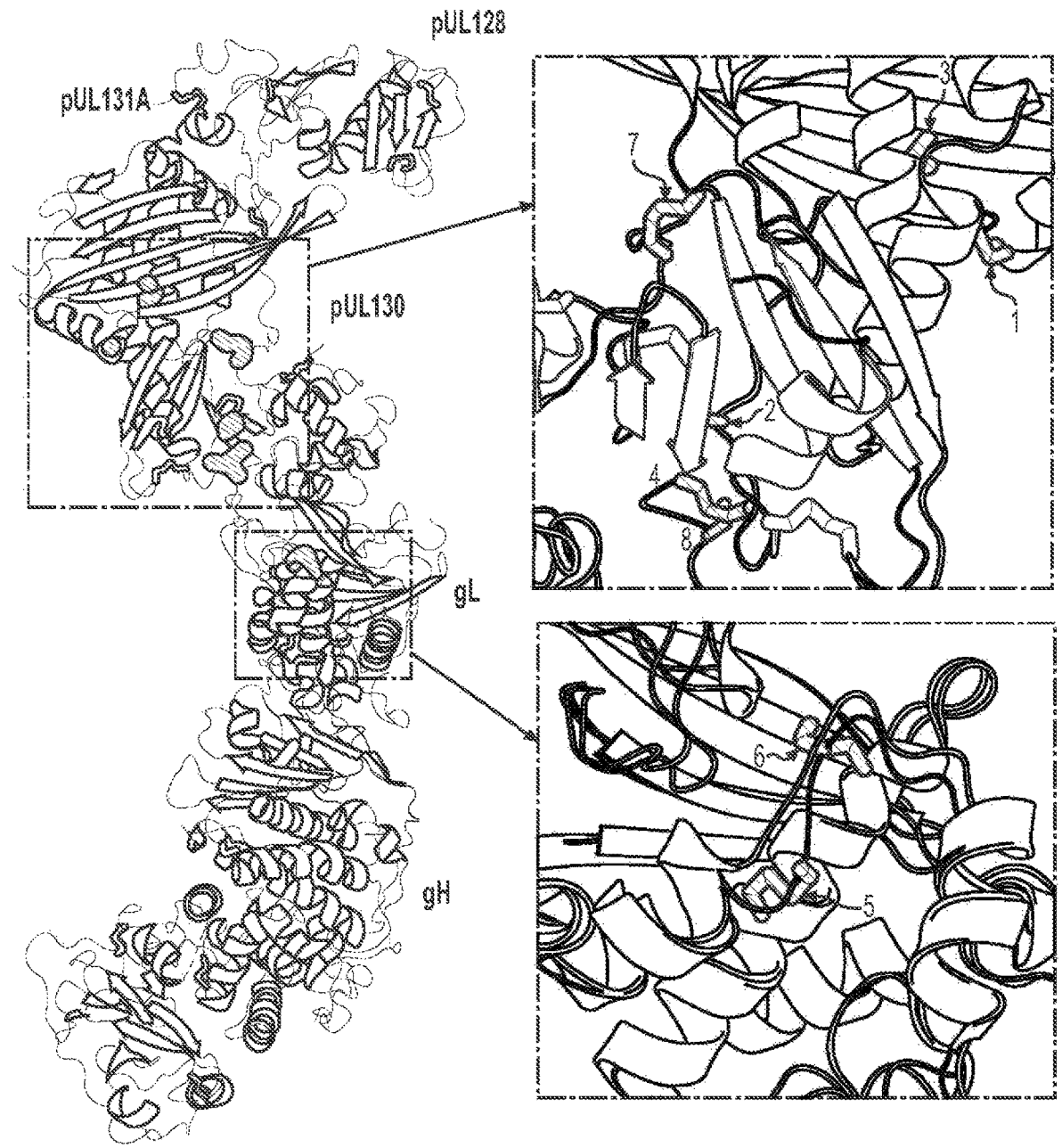
FIGS. 6A-6C.
Figure 6B:
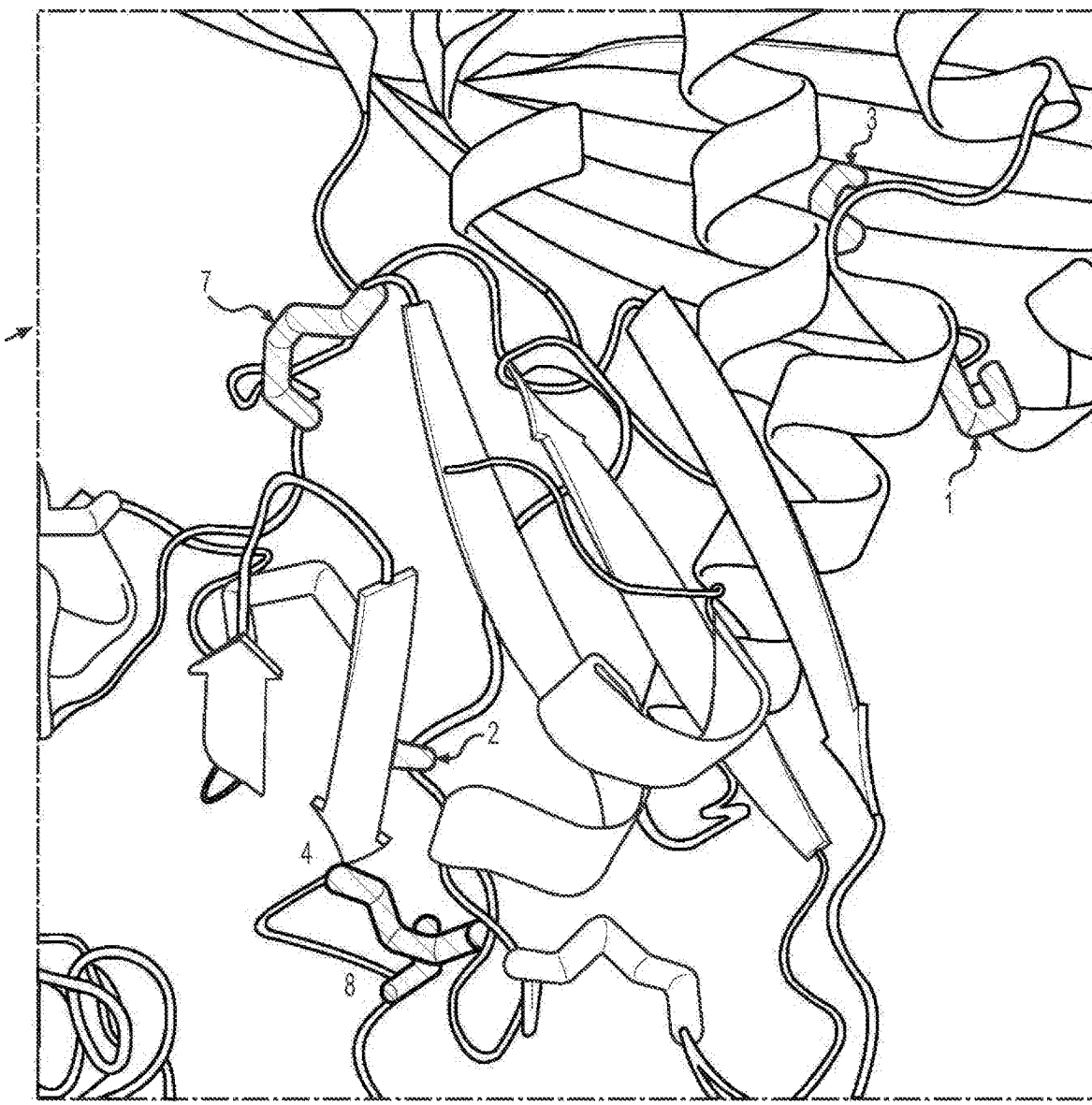
Figure 6C:
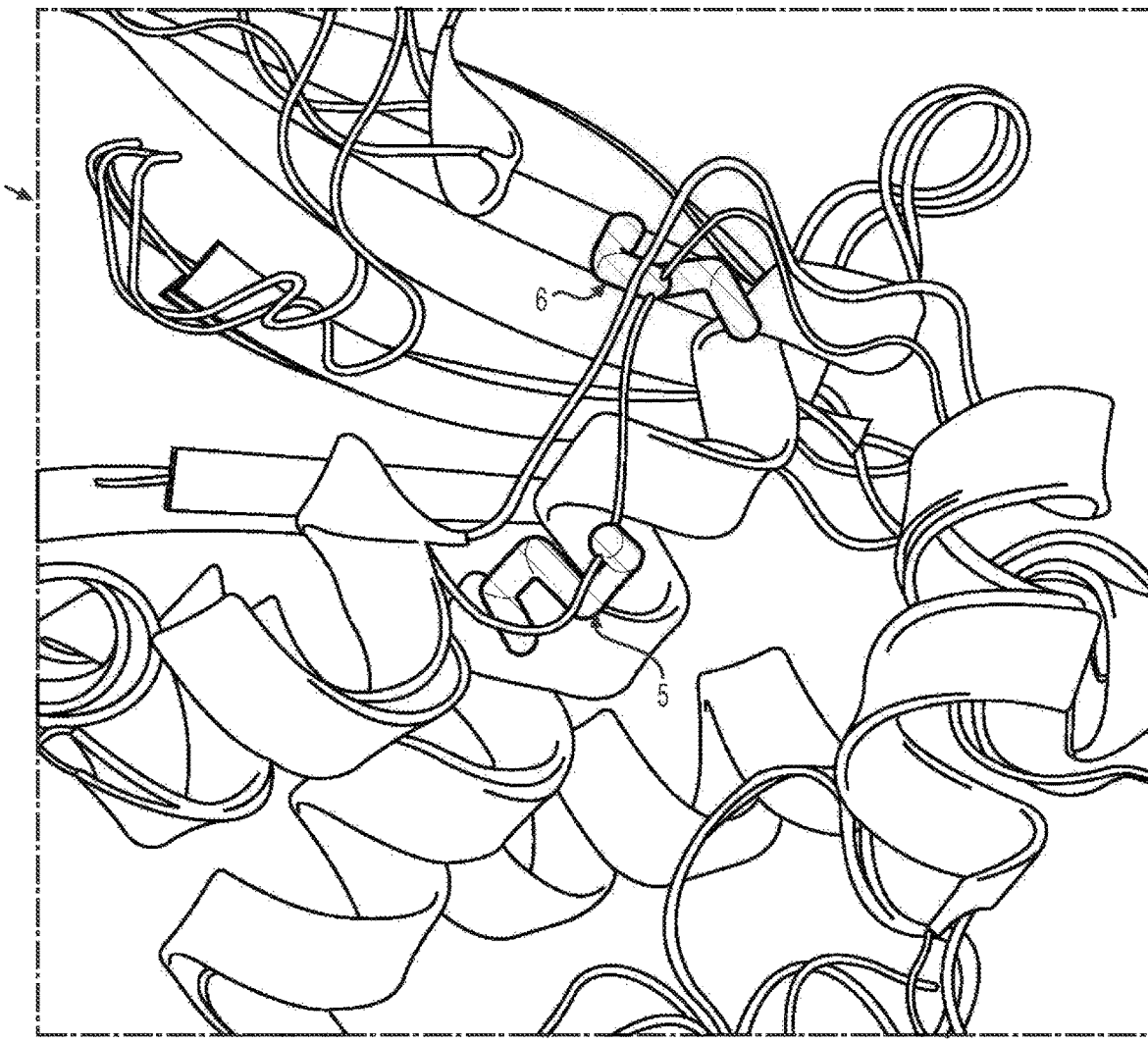

Pre-incubating Pentamer with mAbs 15D8 (site 1), 10P3 (site 4), 2C12 and 9I6 (site 5) or 7113 (site 6), inhibited Pentamer binding to endothelial cells (FIG. 6A-6C). In contrast, mAbs 4N10 and 8I21 (sites 3 and 7, respectively) and 10F7 (site 2), did not affect Pentamer binding to cells. Thus, our data suggest that Pentamer-specific antibodies likely neutralize HCMV through interference of multiple Pentamer functions during viral infection. The inventors show that antibodies binding to UL128 and UL131A residues located at the tip of the Pentamer (9I6, site 5), UL128-α3 helix (15D8, site 1) and close to the linker connecting UL128-α2β4β5β6 to UL128-α3 (10P3, sites 4 and 6) prevent Pentamer binding to cells. Therefore, these antibodies may inhibit the interaction of Pentamer with a cell surface receptor, either by direct competition or steric hindrance, and the antibody binding sites are believed to correspond to the site on the surface of the Pentamer for cell surface receptor binding.

In contrast, antibody binding to the elbow of the ULs arm (4N10 and 8I21, sites 3 and 7 respectively) and the solvent exposed side of the UL130/UL131A β-sheet (10F7, site 2) did not affect Pentamer binding to cells, suggesting a different mechanism of neutralization. 8I21 binds to a positively charged surface on UL130 with a long heavy chain CDR3 (HCDR3) simultaneously protruding into a groove in the UL130 chemokine domain and contacting UL130 N-terminal residues, both of which are implicated in receptor binding in chemokines. It is believed that this site in UL130 binds to a co-receptor at the cell surface or in a post-entry step. Therefore, site 2 and site 3/7 antibodies may interfere with these interactions and processes without affecting Pentamer binding to cells.

Without wishing to be bound by theory and based on the structural and functional characterizations of neutralizing mAbs, the inventors propose a potential mechanism for Pentamer-mediated activation of HCMV entry. The inventors suggest that a cell receptor would bind to a surface in proximity of UL128 and the epitopes for site 1 and 4/6 neutralizing antibodies. Receptor binding may in turn result in a rotation of gH/gL D-I mediated by the UL128 linker and UL128-α3 interaction with the gL 3-helix bundle. Repositioning of D-I may affect the width of the D-I/D-II groove, implicated in gB binding in EBV gH/gL, ultimately triggering membrane fusion.

In conclusion, the herein described structure of Pentamer reveals binding sites for potent and broadly neutralizing mAbs suggesting the location of important functional sites and targets for antibody therapeutics. The structures also reveal a dynamic repositioning of the ULs upon antibody binding suggesting a mechanism of ligand-induced conformational change during cell entry. Finally, the structural, biochemical and cell-based functional analyses of HCMV Pentamer reported here provide an atomic-level framework for at least the mechanism of Pentamer activity and for antigen design.

3.2 Analysis of the Glycans that Mask Pentamer Epitopes and Deglycosylation Mutations Seven neutralizing epitopes (sites 1 to 7) on Pentamer have previously been identified and broadly mapped (See, e.g., Macagno et al., 2010 J. Virol. 84: 1005-1013 and U.S. Pat. No. 9,527,902). Five of the sites are non-overlapping (sites 1, 2, 3, 4, and 5) but site 3 overlaps site 7 and site 4 overlaps site 6. Antibodies that bind those seven sites are also known and include, for example, the 15D8 antibody known to bind site 1, the 10F7 antibody known to bind site 2, the 4N10 antibody known to bind site 3, the 10P3 antibody known to bind site 4, the 9I6 and 2C12 antibodies known to bind site 5, the 7I13 antibody known to bind site 6, and the 8I21 antibody known to bind site 7 (See, e.g., Macagno et al., 2010 J. Virol. 84: 1005-1013 and U.S. Pat. No. 9,527,902). Using the Pentamer structure obtained as described above, the present inventors characterized site 1, 4, 5, and 2 epitopes with greater specificity by first mapping Pentamer epitope sequences (the amino acid residues of neutralizing epitopes on the Pentamer) with differential HDX incorporation upon Fab binding (15D8, 10P3, 2C12, and 10F7 Fabs were used as representative neutralizing antibodies that bind to sites 1, 4, 5, and 2, respectively). Second, the inventors manually inspected and analyzed X-ray structures, HDX-MS data, and EM fitting results to propose that the site 1 epitope sequence corresponds to pUL128 residues 149-171 numbered with respect to the sequence SEQ ID NO: 13; the site 4 epitope sequence corresponds to pUL128 residues 56-72 and 131-148 numbered with respect to the sequence SEQ ID NO: 13; the site 5 epitope sequence corresponds to pUL131A residues 31-40 and 42-56 numbered with respect to the sequence SEQ ID NO: 21; and that the site 2 epitope sequence corresponds to pUL131A residues 92-122 numbered with respect to the sequence SEQ ID NO: 21. The locations of each of these epitope sequences on the surface of the Pentamer structure are shown in FIG. 7 (general locations designated with ovals).

Figure 7:
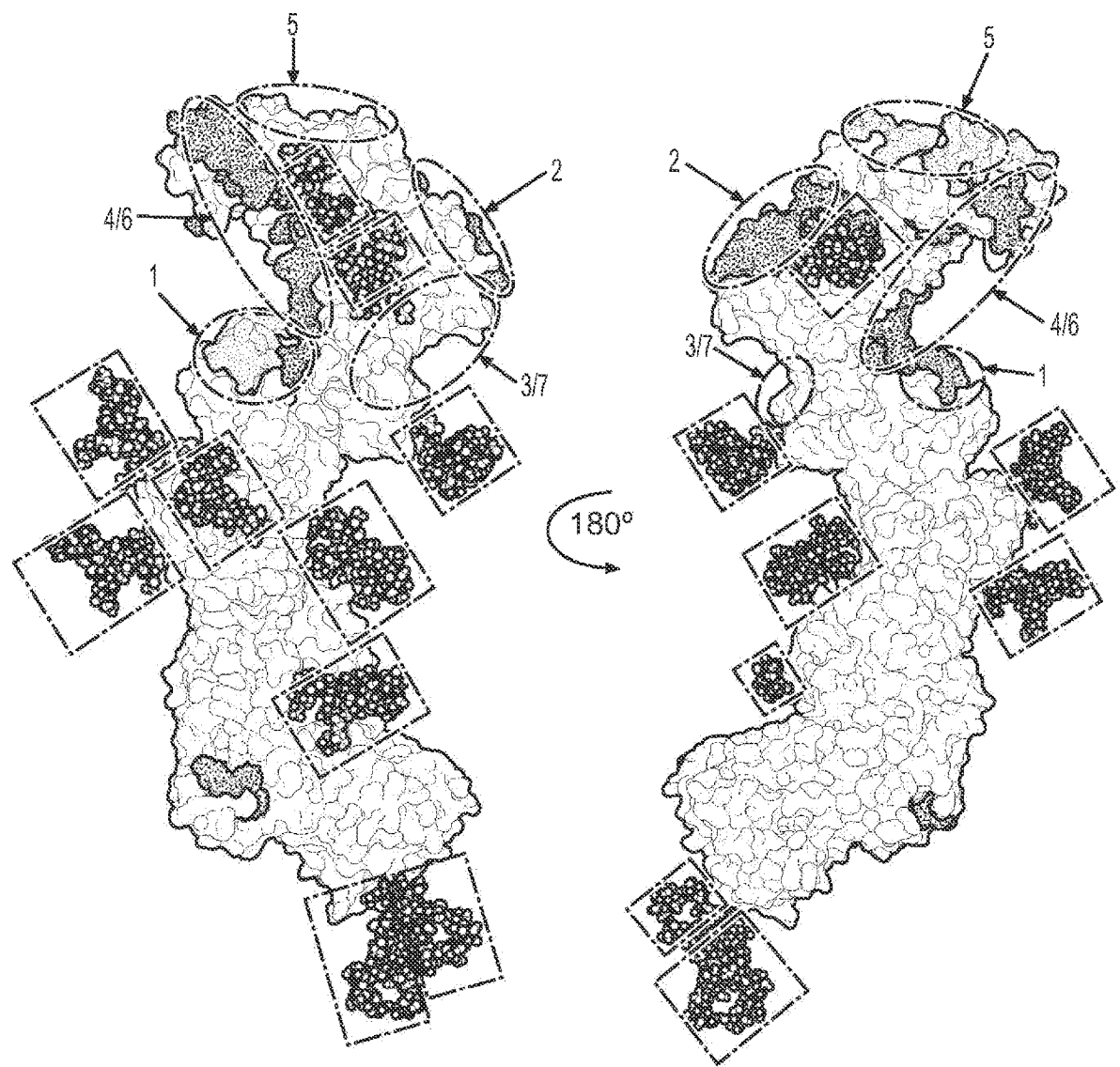
FIG. 7 depicts the locations of the five non-overlapping neutralizing epitopes on Pentamer (sites 1, 2, 3, 4, and 5) with ovals. The label at site 4 is shown as "4/6" to denote the overlapping of site 4 atop site 6 and the label at site 3 is shown as "3/7" to denote the overlapping of site 3 atop site 7.

The general locations of eleven glycans on the surface of Pentamer are also shown in FIG. 7 (locations designated with rectangles, within those rectangles are spheres denoting carbon atoms, denoting nitrogen atoms, denoting oxygen atoms, and denoting hydrogen atoms). There are ten on one face of the Pentamer with six glycans in gH, one in gL, and four in the ULs (see the Pentamer face shown on the left side of FIG. 7). The other face of the Pentamer features one glycan in UL130 (shown on the right side of FIG. 7, adjacent to site 2) and positively-charged areas with clusters of exposed arginine and lysine residues. The Pentamer-8I21 Fab structure reveals that two glycans (those attached to pUL130-Asn85 and pUL130-Asn118 with respect to sequence SEQ ID NO: 17) flank the 8I21 epitope. Based on the structural information obtained and the inventors' analysis thereof, the inventors believe that the UL130-Asn85 and pUL130-Asn118 glycans limit the accessibility of the epitope (i.e., that the glycans "mask" or "shield" the epitope). The inventors therefore expect that removing one or both of these glycans will make the epitope more accessible. In particular, that removing a glycan will "unmask" the epitope.

The inventors have selected additional glycans which are in close proximity to a neutralizing epitope and that are likewise expected to limit the accessibility of their respective epitope(s): glycans at gH-Asn55, gH-Asn62, gH-Asn67, gH-Asn192, gH-Asn641, and gH-Asn700 numbered with respect to SEQ ID NO: 1; at gL-Asn74 numbered with respect to SEQ ID NO: 7; pUL130-Asn201 (which are in addition to pUL130-Asn85 and pUL130-118) numbered with respect to SEQ ID NO: 17; and pUL131A-Asn81 numbered with respect to SEQ ID NO: 21. The inventors therefore expect that by removing one or more of the above-listed glycans, the corresponding epitope(s) will be more accessible. In particular, that removing the glycan will "unmask" the epitope. The inventors specifically propose the substitution of an above-listed asparagine residue for any non-asparagine amino acid (e.g., glutamine) using known techniques so as to prevent N-linked glycosylation at that location and thereby unmask an epitope of Pentamer. Whether or not a deglycosylation mutation unmasks an epitope and/or renders the epitope more accessible may be assayed by comparing the mutant polypeptide's or mutant complex's antigenicity to that of a non-mutant polypeptide or complex using known techniques (see, e.g., Zhou et al., *Quantification of the Impact of the HIV-1-Glycan Shield on Antibody Elicitation,* 2017 Cell Reports 19:719-732; and Ma et al. *Envelope Deglycosylation Enhances Antigenicity of HIV-1 gp41 Epitopes for Both Broad Neutralizing Antibodies and Their Unmutated Ancestor Antibodies,* 2011 PLoS Path. 7(9), e1002200). Enhanced binding of a neutralizing antibody to the epitope (i.e., increased antigenicity) indicates that the deglycosylation mutation has the effect of unmasking the epitope and/or making the epitope more accessible (Id.).

Based on the known positive affect deglycosylation and the resulting unmasking of epitopes has had on the immunogenicity of various antigens, but not wishing to be bound by theory, it is believed that by unmasking an HCMV Pentamer epitope via the deglycosylation mutations described herein, the mutant HCMV polypeptide (or fragment thereof) or mutant HCMV complex will have an increased immunogenicity as compared to a non-mutant (e.g., wild type) polypeptide or complex, respectively (see Liu et al., *Unmasking Stem-Specific Neutralizing Epitopes by Abolishing N-Linked Glycosylation Sites of Influenza Virus Hemagglutinin Proteins for Vaccine Design,* 2016 J. of Virol. 90(19): 8496-8508; Zhou et al., 2017 Cell Reports 19:719-732; and Ma et al., 2011 PLoS Path. 7(9), e1002200). An increase in antigenicity following deglycosylation has been an acceptable proof-of-concept for increasing immunogenicity via deglycosylation (See, e.g., Ma et al., 2011 PLoS Path. 7(9), e1002200).

3.3 Computational Analysis of the Amino Acids Involved in Pentameric Complex Stability In addition to manual inspection, analyses of the structures from section 3.1 above was performed using the molecular graphics programs Pymol (The PyMOL Molecular Graphics System, Version 1.8 Schrödinger, LLC, available at WorldWideWeb(www).pymol.org) and the Crystallographic Object-Oriented Toolkit ("Coot") (Emsley et al., 2010, available at WorldWideWeb(www)2.mrc-lmb.cam.ac.uk/Personal/pemsley/coot/). Thereafter, the Molecular Operating Environment (MOE) software (REF: Molecular Operating Environment (MOE) software; Chemical Computing Group Inc., available at WorldWideWeb(www).chemcomp.com) was used. In particular, the "Residue Scanning" and "Sample Sequence" variants of the "Protein design" module within MOE were applied to the pentameric complex crystal structure obtained as described in the sections above. "Residue Scanning" simulation sequentially mutates all or a subset of residues of the input protein. "Sample Sequence" mutates, in a random fashion, all of the specified residues. Both single and multiple point mutations were generated using MOE.

In addition, the in silico "Disulfide Scan" variant of the Protein Design module within MOE was applied to the crystal structure of the pentameric complex obtained as described in the sections above. With this tool, the surrounding environment of a residue was analyzed to evaluate the presence of other residue(s) close enough to form a disulfide bond. In general terms, two residues were characterized as close enough to form a disulfide bond if the β carbons of the two amino acids are within 5 Å of each other.

Once pairs of such residues were selected, MOE was utilized to mutate both residues to Cysteine and to characterize the resulting impact on the stability of the protein complex.

The results from each MOE protocol were compiled and manually inspected. For all MOE protocols above, the impact of each proposed mutation was scored for stability using the delta stability scoring method (indicated as dS, and measured as kcal/mol). The dS is defined in MOE as the relative thermo-stability of a certain mutation with respect to the wild type or non-mutant protein, and more negative values of dS indicate more stable mutations. This scoring method takes into account both the conformational change upon mutation and the change with respect to the wild type or non-mutant. Further, dS is predicted from the difference in stability between a mutant protein and its wild type (or non-mutant) both in the folded and unfolded states.

TABLE 6

MOE dStability data of a pentameric complex comprising stabilizing mutations within gH - all mutants have a negative dStability value and, therefore, indicate an enhanced stability compared to a non-mutant complex (sorted from lowest dStability value to highest).

| HCMV Polypeptide | Mutation(s) | dStability (kcal/mol) |
|---|---|---|
| gH (residue numbers correspond to those of the sequence SEQ ID NO: 3) | A372W | −4.782173997 |
| | A102W | −4.425084332 |
| | H252A | −4.199853332 |
| | H480A | −3.248787991 |
| | K404Y | −3.110607369 |
| | R255W | −3.032284905 |
| | A352Y | −2.866359913 |

TABLE 6-continued

MOE dStability data of a pentameric complex comprising stabilizing mutations within gH - all mutants have a negative dStability value and, therefore, indicate an enhanced stability compared to a non-mutant complex (sorted from lowest dStability value to highest).

| HCMV Polypeptide | Mutation(s) | dStability (kcal/mol) |
|---|---|---|
| | R405W | −2.62994826 |
| | E355F | −2.620476918 |
| | G358R | −2.615057138 |
| | L257W | −2.469949916 |
| | S601F | −2.218661931 |
| | H275E | −2.131270358 |

TABLE 7

MOE dStability data of a pentameric complex comprising stabilizing mutations within gL - all mutants have a negative dStability value and, therefore, indicate an enhanced stability compared to a non-mutant complex (sorted from lowest dStability value to highest).

| HCMV Polypeptide | Mutation(s) | dStability (kcal/mol) |
|---|---|---|
| gL (residue numbers correspond to those of the sequence SEQ ID NO: 7) | H177W | −8.081763114 |
| | H267W | −7.862691061 |
| | G224W | −7.51272317 |
| | G140W | −7.443449994 |
| | G145W | −6.917331182 |
| | H236Y | −6.513895235 |
| | D146W | −6.497084677 |
| | H245F | −6.25805229 |
| | P272W | −6.119082054 |
| | G161F | −5.437107008 |
| | G218L | −3.95449847 |
| | L119W | −3.44970218 |

TABLE 8

MOE dStability data of a pentameric complex comprising stabilizing mutations within UL128 - all mutants have a negative dStability value and, therefore, indicate an enhanced stability compared to a non-mutant complex (sorted from lowest dStability value to highest).

| HCMV Polypeptide | Mutation(s) | dStability (kcal/mol) |
|---|---|---|
| UL128 (residue numbers correspond to those of the sequence SEQ ID NO: 13) | H90W | −7.802532718 |
| | G123W | −7.379533122 |
| | G112W | −5.824979606 |
| | G145Y | −4.511071754 |

TABLE 9

MOE dStability data of a pentameric complex comprising stabilizing mutations within UL130 - all mutants have a negative dStability value and, therefore, indicate an enhanced stability compared to a non-mutant complex (sorted from lowest dStability value to highest).

| HCMV Polypeptide | Mutation(s) | dStability (kcal/mol) |
|---|---|---|
| UL130 (residue numbers correspond to those of the sequence SEQ ID NO: 17) | G116C and H150C | −9.40803663 |
| | G116W | −6.623393049 |
| | D165W | −5.978228876 |
| | H150Y | −5.94497919 |
| | H209Y | −5.828196726 |
| | G135V | −3.474547248 |

TABLE 10

MOE dStability data of a pentameric complex comprising stabilizing mutations within pUL131A - all mutants have a negative dStability value and, therefore, indicate an enhanced stability compared to a non-mutant complex (sorted from lowest dStability value to highest).

| HCMV Polypeptide | Mutation(s) | dStability (kcal/mol) |
|---|---|---|
| PUL131A | H69W | −8.151149662 |
| (residue numbers correspond | G99W | −7.129219316 |
| to those of the sequence | H64W | −7.055214485 |
| SEQ ID NO: 21) | H69W and R118N | −5.774199469 |
|  | S86W | −5.560842288 |
|  | H35I | −4.84219667 |
|  | D38V and E84C | −3.543297022 |
|  | V85W and A110A | −3.316524209 |
|  | S90F | −3.279504851 |
|  | Y52F and A67V | −1.525594485 |

TABLE 11

MOE dStability data of a pentameric complex comprising stabilizing mutations within both gH and gL - all mutants have a negative dStability value and, therefore, indicate an enhanced stability compared to a non-mutant complex (sorted from lowest dStability value to highest).

| HCMV Polypeptide(s) | Mutation(s) | dStability (kcal/mol) |
|---|---|---|
| gH and gL | gH: V109C | −4.678721492 |
| (residue numbers correspond | gL: G224C |  |
| to those of the gH sequence | gH: L111C | −4.32060893 |
| SEQ ID NO: 3 & the gL | gL: G218C |  |
| sequence SEQ ID NO: 7) |  |  |

TABLE 12

MOE dStability data of a pentameric complex comprising stabilizing mutations within both pUL128 and pUL130 - all mutants have a negative dStability value and, therefore, indicate an enhanced stability compared to a non-mutant complex (sorted from lowest dStability value to highest).

| HCMV Polypeptide(s) | Mutation(s) | dStability (kcal/mol) |
|---|---|---|
| pUL128 and pUL130 | UL128: R142C | −4.242791808 |
| (residue numbers correspond | UL130: E95C |  |
| to those of the UL128 sequence |  |  |
| SEQ ID NO: 13 & the UL130 |  |  |
| sequence SEQ ID NO: 17) |  |  |

TABLE 13

MOE dStability data of a pentameric complex comprising stabilizing mutations within both gL and pUL130 - all mutants have a negative dStability value and, therefore, indicate an enhanced stability compared to a non-mutant complex (sorted from lowest dStability value to highest).

| HCMV Polypeptide(s) | Mutation(s) | dStability (kcal/mol) |
|---|---|---|
| gL and pUL130 | gL: G161C | −6.787844932 |
| (residue numbers correspond | UL130: P64C |  |
| to those of the gL sequence | gL: D163C | −5.031859049 |
| SEQ ID NO: 7 & the UL130 | UL130: P62C |  |
| sequence SEQ ID NO: 17) | gL: R166C | −4.054395863 |
|  | UL130: P62C |  |

TABLE 14

MOE dStability data of a pentameric complex comprising stabilizing mutations within both pUL130 and pUL131A - all mutants have a negative dStability value and, therefore, indicate an enhanced stability compared to a non-mutant complex (sorted from lowest dStability value to highest).

| HCMV Polypeptide(s) | Mutation(s) | dStability (kcal/mol) |
|---|---|---|
| pUL130 and pUL131A | UL130: S178C | −6.461428098 |
| (residue numbers correspond | UL131: H64C |  |
| to those of the pUL130 sequence |  |  |
| SEQ ID NO: 17 & the pUL131A |  |  |
| sequence SEQ ID NO: 21) |  |  |

Example 4—Stabilization Assays of Mutant Pentameric Complex 4.1 Characterization of Complex Stability with Respect to at Least gH Structural analyses of gH revealed the presence of several buried cavities mainly localized in the gH N-terminal region (near the interface with gL) and in the C-terminus of the gH ectodomain. With respect to the gH sequence SEQ ID NO: 3, residue A102 of wild type (WT) gH is located on a short α-helix (made of gH residues 100-108) that runs parallel to a gL α-helix (made of gL residues 216-234, with respect to gL sequence SEQ ID NO: 7). The methyl (CH3) side-chain group of gH A102 points towards the interface with the gL α-helix, where an apparent cavity is present. The inventors therefore suggest that a cavity filling mutation of gH A102 might contribute to better packing within this buried interface environment. In addition, gH residue H480 is observed to be partially exposed on the surface and is thus identified by the inventors as a target site for a repacking mutation to introduce more favourable packing with the residue's surrounding environment. Also, in view of the introduction of two additional disulphide bridges at the gH-gL interface (see mutations V109C(gH)-G224C(gL) and L111C(gH)-G218C (gL) at Table 11), the inventors suggest that this region be stabilized by introducing a disulfide bridge mutation and thereby locking together in a more rigid fashion gH to the gL α-helix at gL residues 216-234.

4.2 Characterization of Complex Stability with Respect to at Least gL

The localization of buried cavities within gL spans the entire N- to C-terminus buried regions. Notably, gL residue H177 (numbered with respect to gL sequence SEQ ID NO: 7) is located centrally within gL, sandwiched between three structures: one loop on its side, one loop on its bottom, and an α-helix on top. The sidechain of gL H177 points towards a cavity that covers most of the region within these two loops. Therefore, the inventors propose a mutation of H177 into a hydrophobic, cavity filling residue to stabilize this region (i.e., introducing a cavity filling mutation at gL H177). Likewise, because at gL residue G224 and its surrounding environment, a large cavity can be observed buried between a gH helix-loop-helix motif (gH residues corresponding to 108-122 of SEQ ID NO: 3) and the gL α-helix (gL residues corresponding to 216-234 of SEQ ID NO: 7), the inventors propose introducing a cavity filling mutation there (gL residue G224) to stabilize the region. Also, at the interface between the gH helix-loop-helix region at gH residues 92-101 (numbered with respect to SEQ ID NO: 3) and the gL helix-loop-helix region at about gL residues 228-242 (numbered with respect to SEQ ID NO: 7), there is a cavity anterior to the sidechain of gL C233. The inventors therefore propose introducing a cavity filling mutation or a hydrophobic mutation at gL residue C233. Finally, the gL-UL130 interface is made of main- and side-chain hydrogen bonds and hydrophobic contacts of large side chains. Based in part on structure analyses of this region, the inventors suggest the insertion of a disulphide bond into the gL-UL130 interface via a disulfide bridge mutation to lock together these two subunits (by, for example, a G161C mutation at the gL residue corresponding to G161 of SEQ ID NO: 7 with a P64C mutation at the UL130 residue corresponding to P64 of SEQ ID NO: 17).

4.3 Characterization of Complex Stability with Respect to at Least UL128

The UL128 residue corresponding to G123 of SEQ ID NO: 13 is located below a significant buried cavity and is buried in a small domain of 30-residues at the interface between pUL128 and pUL130 and pUL131A. At least because residue G123 is located below a significant buried cavity, the inventors propose making cavity filling mutations at UL128 G123 to increase complex stability. In addition, the small UL128 G145 residue (numbered with respect to SEQ ID NO: 13) is located in the final UL128 C-terminal α-helix that docks onto the gL 3-helix bundle, and is therefore an inventor-identified target for introducing a repacking mutation to increase interactions at the gL-UL128 interface and, thereby, increase complex stability. Finally, due to the environment and three-dimensional arrangement of residues UL128 R142 and UL130 E95 (numbered with respect to UL128 sequence SEQ ID NO: 13 and UL130 sequence SEQ ID NO: 17, respectively) along the 50A-long linker that connects the N-terminal domain of UL128 to gL, the inventors propose introducing a UL128 R142C and a UL130 E95C disulfide bridge mutation into the complex to lock UL128 to UL130 and to thus contribute to increased stability of the ULs region and increased stability of the complex generally.

4.4 Characterization of Complex Stability with Respect to at Least UL130

In the pUL130-pUL131A interface, pUL130 residue H209 (numbered with respect to pUL130 sequence SEQ ID NO: 17) points towards pUL131A H35 (numbered with respect to pUL131A sequence SEQ ID NO: 21), based on which the inventors suggest that if protonated, these histidines would repel each other causing conformational changes or conferring flexibility to this region. Therefore, the inventors propose introducing a repacking mutation into the residue corresponding to UL130 H209 to decrease flexibility of this region of the ULs and increase complex stability. Moreover, a significant buried cavity is detected near pUL130 H209 into which the inventors propose introducing either or both of a cavity-filling and repacking mutation for increased complex stability. Also in the pUL130-pUL131A interface, the pUL130 residue corresponding to H150 of the sequence SEQ ID NO: 17 points towards pUL131A H69 (numbered with respect to SEQ ID NO: 21), so the inventors likewise propose introducing a repacking mutation into pUL130 H150 to decrease flexibility of this UL region and increase complex stability.

4.5 Characterization of Complex Stability with Respect to at Least pUL131A

In the pUL130-pUL131A interface (αβ-core), pUL131A G99 (numbered with respect to pUL131A sequence SEQ ID NO: 21) lies on a peripheral strand of the flat 130-131-mixed large I3-sheet, and its C-b backbone atom (i.e., the first carbon atom of the G99 side chain) points towards the buried region where pUL130 and pUL131A helices as well as a large buried cavity are located. The inventors target pUL131A G99 for the introduction of a cavity-filling mutation to enhance complex stability. Similarly, pUL131A residue S86 (numbered with respect to pUL131A sequence SEQ ID NO: 21) is located on a pUL131A helix and points towards the flat large pUL130-pUL131A mixed β-sheet. Therefore, the inventors propose introducing a cavity-filling mutation at pUL131A S86 for increased complex stability. Likewise, pUL131A residue H64 (numbered with respect to pUL131A sequence SEQ ID NO: 21) points towards the buried environment between the pUL130-pUL131A mixed αβ-core, so the inventors propose introducing a repacking mutation (specifically, a hydrophobic mutation) of pUL131A H64 to, for example, a bulky more hydrophobic residue (such as tryptophan (W)) to introduce interactions that increase thermal stability of the complex.

4.6 Designed Stabilizing Mutants

As indicated in the sections above, the inventors conducted computational analysis (summarized above at Example 3.3), processed that data by manual inspection and manipulation (summarized above at Examples 4.1-4.5), and have thereby designed mutations within gH, gL, pUL128, pUL130, and pUL131A to, when alone or combined, improve the stability of a complex comprising them. While not wishing to be bound by theory, it is believed that conformational flexibility is decreased and the over-all thermostability of a complex is increased by (A) filling buried cavities between domain interfaces with atoms from amino acids made of longer side-chains than the one found in the wild type protein, by (B) increasing contacts of neighboring residues or replacing unfavorable clusters of charged residues, and/or by (C) introducing intra- or inter-disulfide bridges throughout the structure. Exemplary inventor-designed mutants to effect one or more of A-C are listed in Tables 15-21 below.

While the below tables are organized so as to exemplify specific mutations within a particular pentamer complex subunit, the designed mutants include combinations of these mutations ("stacked mutations", i.e., combinations of mutations within one polypeptide (e.g., several mutations within gH) as well as combinations of mutations within different polypeptides (e.g., mutant gH and mutant gL, both of which may comprise more than one mutation). By way of example, an inventor-designed mutant HCMV pentamer complex comprises any one or more mutations listed within Tables 20 and 21 below.

TABLE 15

Stabilizing Mutations of gH
(residues numbered with respect to gH sequence SEQ ID NO: 3)

| | Repacking Mutations | | |
|---|---|---|---|
| Cavity-filling mutations | Hydrophobic mutations | Hydrophilic mutations | Disulfide mutations |
| A102W | H252A | G358R | V109C |
| A372F | K404A | H275E | L111C |
| A352F | R255A | | |
| L257W | E355V | | |
| | H480V | | |
| | S601V | | |
| | R405A | | |

TABLE 16

Stabilizing Mutations of gL
(residues numbered with respect to gL sequence SEQ ID NO: 7)

| Cavity-filling mutations | Repacking Mutations | | |
|---|---|---|---|
| | Hydrophobic mutations | Hydrophilic mutations | Disulfide mutations |
| H177W | H267F | | G161C |
| G224F | H236I | | D163C |
| G140W | H245F | | G224C |
| G145W | G161V | | G218C |
| D146W | C233I | | R166C |
| G218L | C233V | | G140C |
| L119W | | | R160C |
| P272F | | | A150C |
| C233F | | | |
| C233W | | | |
| C233L | | | |

TABLE 17

Stabilizing Mutations of pUL128
(residues numbered with respect to pUL128 sequence SEQ ID NO: 13)

| Cavity-filling mutations | Repacking Mutations | | |
|---|---|---|---|
| | Hydrophobic mutations | Hydrophilic mutations | Disulfide mutations |
| G123W | G145V | | R142C |
| V77F | H90A | | N99C |
| L103F | G112V | | Y98C |
| Q119F | | | A124C |
| | | | G126C |
| | | | L159C |
| | | | D45C and V88C |
| | | | D45C |
| | | | V88C |
| | | | M48C and G107C |
| | | | M48C |
| | | | G107C |
| | | | R51C and D106C |
| | | | R51C |
| | | | D106C |
| | | | S83C |

TABLE 18

Stabilizing Mutations of pUL130
(residues numbered with respect to pUL130 sequence SEQ ID NO: 17)

| Cavity-filling mutations | Repacking Mutations | | |
|---|---|---|---|
| | Hydrophobic mutations | Hydrophilic mutations | Disulfide mutations |
| D165W | G116V | | G116C and H150C |
| H209Y | G135V | | G116C |
| | H150F | | H150C |
| | H209F | | P64C |
| | | | S178C |
| | | | P62C |
| | | | E95C |
| | | | Y204C |
| | | | N211C |
| | | | I213C |
| | | | Y56C |
| | | | T167C |

TABLE 19

Stabilizing Mutations of pUL131A
(residues numbered with respect to pUL131A sequence SEQ ID NO: 21)

| Cavity-filling mutations | Repacking Mutations | | |
|---|---|---|---|
| | Hydrophobic mutations | Hydrophilic mutations | Disulfide mutations |
| G99W | H69V | R118N | H64C |
| S86W | H35I | | W37C |
| S90F | H64V | | |
| | H69F (hydrophobic) and R118N (hydrophilic) | | |
| | H69F | | |
| | D38V | | |
| | V85F | | |
| | Y52F and A67V | | |
| | Y52F | | |
| | A67V | | |

TABLE 20

Summary of Cavity Filling and Repacking Stabilizing Mutations
(residues numbered with respect to gH sequence SEQ ID NO: 3; gL sequence SEQ ID NO: 7; pUL128 sequence SEQ ID NO: 13; pUL130 sequence SEQ ID NO: 17; and pUL131A sequence SEQ ID NO: 21)

| gH | gL | PUL128 | PUL130 | PUL131A |
|---|---|---|---|---|
| *A102W* | *H177W* | *G123W* | *G116V* | *H69V* |
| *A372F* | H267F | G145V | *D165W* | *G99W* |
| H252A | *G224F* | H90A | *H209Y* | S86W |
| K404A | *G140W* | G112V | H209F | H35I |
| R255A | *G145W* | *V77F* | G135V | *S90F* |
| A352F | H236I | *L103F* | H150F | H64V |
| R405A | H245F | *Q119F* | H209F | H69F and R118N |
| E355V | *D146W* | | | H69F |
| G358R | *G218L* | | | R118N |
| L257W | L119W | | | D38V |
| H480V | G161V | | | V85F |
| S601V | *P272F* | | | Y52F and A67V |
| H275E | C233F | | | Y52F |
| | C233W | | | A67V |
| | C233L | | | |
| | C233I | | | |
| | C233V | | | |

Cavity filling mutations in *italics*, Repacking mutations are underlined

While the above tables 15-20 exemplify disulfide bridge mutations for introduction into a complex subunit (e.g., into one of the pentamer complex subunit proteins gH, gL, pUL128, pUL130, and pUL131A), because disulfide bridges are formed between two residues (two cysteine residues within the same polypeptide (intra disulfide bridge) or between two cysteine residues, one cysteine in each of a first polypeptide and a second polypeptide (inter disulfide bridge)), the inventors provide at Table 21 below a summary of combined designed disulfide bridge mutations (numbered in the left-most column as groups of disulfide bridge mutations) to increase the stability of a complex comprising them. The combinations of disulfide bridge mutations provided in Table 21 may be stacked (for example, the mutations listed in Group No. 1 may be combined with the mutations listed in Group No. 2) or combined with at least one cavity-filling mutation and/or repacking mutation listed in Tables 15-20 above.

TABLE 21

Combinations of Disulfide Bridge Mutations
(each row representing a separate combination)

| Group No. | gH (SEQ ID NO: 3) | gL (SEQ ID NO: 7) | pUL128 (SEQ ID NO: 13) | pUL130 (SEQ ID NO: 17) | pUL131A (SEQ ID NO: 21) |
|---|---|---|---|---|---|
| 1 | | | | G116C and H150C | |
| 2 | | G161C | | P64C | |
| 3 | | | | S178C | H64C |
| 4 | | D163C | | P62C | |
| 5 | V109C | G224C | | | |
| 6 | L111C | G218C | | | |
| 7 | | | R142C | E95C | |
| 8 | | R166C | | P62C | |
| 9 | | | N99C | | W37C |
| 10 | | | Y98C | Y204C | |
| 11 | | | A124C | N211C | |
| 12 | | | G126C | I213C | |
| 13 | | G140C | L159C | | |
| 14 | | R160C | | Y56C | |
| 15 | | D163C | | P64C | |
| 16 | | A150C | | P64C | |
| 17 | | | D45C and V88C | | |
| 18 | | | M48C and G107C | | |
| 19 | | | R51C and D106C | | |
| 20 | | | S83C | T167C | |

4.7 Express and Purify a Complex Comprising at Least One Designed Mutant

A HCMV pentameric complex shows bimodal unfolding, which is reflected by it having two thermal transition midpoint (Tm) values (two peaks) in a differential scanning fluorimetry (DSF) assay (the first, lower temperature value being referred to as "Tm1" and the second, higher temperature value being referred to as "Tm2"). A cavity-filling, repacking, disulfide bridging, or deglycosylation mutation of the present invention may shift (i.e., increase or decrease) one or several Tm peaks of a complex. Increasing a Tm value (i.e. shifting a Tm peak toward the right in the resulting sigmoidal graph of a DSF assay) is denoted with a temperature change greater than zero (a positive Tm shift). Decreasing a Tm value (i.e., shifting a Tm peak toward the left) is denoted with a temperature change less than zero (a negative Tm shift). For an HCMV pentamer complex, a mutation of the present invention may shift just one, or both, of Tm1 and Tm2. For these experiments, whether or not a mutation, or combination of mutations, is Stabilizing, Neutral, or Destabilizing depends on the size of the Tm1 shift, Tm2 shift, or both. Increasing at least one of Tm1 and Tm2 by at least 2° C. as compared to control is considered an increase in the thermostability of the HCMV complex (i.e., the mutation or combination of mutations are said to be "Stabilizing" if they result in a Tm1 shift or Tm2 shift of at least 2° C. as compared to control). Increasing at least one of Tm1 and Tm2 by at least 5° C. as compared to control is considered a significant increase in the thermostability of the complex (i.e., the mutation or combination of mutations are said to be "Significantly Stabilizing" if they result in a Tm1 shift or Tm2 shift of at least 5° C. as compared to control). When both of the Tm1 shift and Tm2 shift values are between 2° C. and −2° C. (exclusive of endpoints) as compared to control, the mutation or combination of mutations are said to be "Neutral." When at least one of the Tm1 shift and Tm2 shift values is −2° C. or less as compared to control, the mutation or combination of mutations are said to be "Destabilizing" Here, if the Tm1 shift, Tm2 shift, or both and/or any effect on stability could not be evaluated due to, for example, insufficient expression or amount of protein in the assay, the mutant or combination of mutants are labelled "Inconclusive."

Modified HCMV pentameric complexes were expressed and purified as described in Example 1 and 2 above. The HCMV pentameric complexes each comprised at least one modified subunit polypeptide gH, gL, UL128, UL130, and pUL131A, wherein the modified subunit polypeptide comprised the mutations as listed in Tables 22-23. Purified, mutant HCMV pentamer complex was assessed in a differential scanning fluorimetry (DSF) assay, using a Nanotemper Prometheus NT.48 instrument. The intrinsic fluorescence of aromatic residues, such as Tyr and Trp, was obtained by exciting at 280 nm wavelength and measuring emission spectra at 330 nm (representing the folded state) and 350 nm (representing the unfolded state) over a temperature ramp (25-85° C.). The instrument software was used to plot the differential of the fluorescence ratio (350 nm/330 nm), and the temperature corresponding to the inflection point of the curve was taken as the melting temperature of the mutant HCMV pentamer complex (the Tm). The Tm1 and Tm2 of each mutant HCMV pentamer complex was compared to the corresponding Tm1 or Tm2 of a control (non-mutant) HCMV pentamer complex. The control complex utilized was a HCMV pentamer complex comprising a gH complex-forming fragment and a gL polypeptide having mutations within a protease recognition site (specifically, the gH polypeptide comprised the sequence SEQ ID NO: 4; the gL polypeptide comprised the sequence SEQ ID NO: 10; the pUL128 polypeptide comprised the sequence SEQ ID NO: 14; the pUL130 polypeptide comprised the sequence SEQ ID NO: 18; and the pUL131A polypeptide comprised the sequence SEQ ID NO: 22). Any change (shift) in Tm1 and/or Tm2 as compared to control was calculated, if possible, and is summarized in Tables 22 and 23. The residue numbers in Tables 22 and 23 are with respect to gH sequence SEQ ID NO: 3, gL sequence SEQ ID NO: 7, pUL128 sequence SEQ ID NO: 13, pUL130 sequence SEQ ID NO: 17, and pUL131A sequence SEQ ID NO: 21, respectively. An increase of at least 5° C. in the calculated Tm is considered a significant increase in the thermostability of the complex. The stabilizing mutant HCMV pentamer complexes described in Tables 22 and 23 were assayed for the presence of wild type conformational epitopes using Bio-layer Interferometry (BLI) technology and the 10P3 antibody. All complexes listed in Table 22 and 23 maintain the wild type HCMV pentamer complex conformational epitope recognized by the 10P3 antibody.

4.8 Effect of Designed Mutations on Stability of the Pentameric Complex

While some of the mutant HCMV pentamer complexes produced by these methods were more thermostable than the control, others were neutral in effect or destabilizing Mutant HCMV pentamer complexes comprising disulfide mutations within gL and pUL130 polypeptides; pUL128 and pUL130 polypeptides; or within just the pUL128 polypeptide had an increased thermostability as compared to control (Table 22). Likewise, mutant HCMV pentamer complexes comprising a cavity filling mutation in the gL polypeptide; pUL128 polypeptide; or pUL131 polypeptide had an increased thermostability as compared to control (Table 22).

Stacking (combining) one type of mutation (see column A of Table 23) with a second type of mutation (see column B of Table 23) was also stabilizing (Table 23). In particular, combining a cavity filling mutation within gL with disulfide bridge mutations within pUL128 and pUL130; combining disulfide bridge mutations within pUL128 and pUL130 with a deglycosylation mutation within gL; combining a repacking (hydrophilic) mutation within gH with disulfide bridge mutations within pUL128 and pUL130; combining a repacking (hydrophobic) mutation within gL with disulfide bridge mutations within pUL128 and pUL130; and combining two repacking (hydrophobic) mutations within pUL131 with a cavity filling mutation within gL were all stabilizing (Table 23).

Without wishing to be bound by theory, it is believed that these cavity filling, repacking, and disulfide bridge mutations enhance the thermostability of the HCMV pentameric complex by optimizing local interactions or decreasing conformational flexibility. It is likewise believed that these deglycosylation mutations make the HCMV pentamer complex epitopes more accessible.

TABLE 22

| Identification No. | Type of Mutation(s) | HCMV pentamer polypeptide mutation(s) (polypeptide_mutation) | Tm1 shift (° C.) of mutant HCMV pentamer complex as compared to control [St. Dev. Of +/- 0.3° C.] | Tm2 shift (° C.) of mutant HCMV pentamer complex as compared to control [St. Dev. Of +/- 0.3° C.) | Sum of Tm1 & Tm2 shifts (° C.) | Results** |
|---|---|---|---|---|---|---|
| 67 | Disulfide | gL_A150C_UL130_P64C | 4.30 | 5.85 | 10.15 | Significantly Stabilizing |
| 72 | Disulfide | UL128_S83C_UL130_T167C | 9.05 | -0.8 | 8.25 | Significantly Stabilizing |
| 56 | Disulfide | UL128_R142C_UL130_E95C | 1.45 | 6.05 | 7.50 | Significantly Stabilizing |
| 65 | Disulfide | gL_R160C_UL130_Y56C | 3.70 | 3.15 | 6.85 | Stabilizing |
| 57 | Disulfide | gL_R166C_UL130_P62C | 3.60 | 1.9 | 5.50 | Stabilizing |
| 59 | Disulfide | UL128_Y98C_UL130_Y204C | 4.15 | -1.05 | 3.10 | Stabilizing |
| 154 | Cavity Filling | UL131_S86F | 2.40 | -0.1 | 2.30 | Stabilizing |
| 104 | Cavity Filling | gL_G140F | 0.25 | 1.95 | 2.20 | Stabilizing |
| 70 | Disulfide | UL128_M48C_G107C | 2.55 | -0.5 | 2.05 | Stabilizing |
| 129 | Cavity Filling | UL128_V77I | 2.00 | -0.25 | 1.75 | Stabilizing |
| 132 | Cavity Filling | UL128_L103I | 1.90 | -0.2 | 1.70 | Stabilizing |
| 106 | Cavity Filling | gL_G145L | -0.65 | 1.95 | 1.30 | Stabilizing |
| 131 | Cavity Filling | UL128_L103V | 1.25 | 0.16 | 1.41 | Neutral |
| 105 | Cavity Filling | gL_G145V | -0.15 | 1.4 | 1.25 | Neutral |
| 47 | Repacking, Hydrophobic and Repacking, Hydrophobic | UL131_Y52F_A67V | 1.00 | 0.15 | 1.15 | Neutral |
| 95 | Cavity Filling | gL_H177I | -0.25 | 1.4 | 1.15 | Neutral |
| 128 | Cavity Filling | UL128_V77L | 1.20 | -0.1 | 1.10 | Neutral |
| 107 | Cavity Filling | gL_G145I | -0.55 | 1.6 | 1.05 | Neutral |
| 39 | Cavity Filling | UL131_G99W | 0.75 | 0 | 0.75 | Neutral |
| 16 | Cavity Filling | gL_G224F | -0.15 | 0.85 | 0.70 | Neutral |
| 82 | Cavity Filling | gH_A352L | 0.65 | -0.1 | 0.55 | Neutral |
| 81 | Cavity Filling | gH_A352V | 0.65 | -0.15 | 0.50 | Neutral |
| 160 | Repacking, Hydrophobic | gL_C233F | -0.20 | 0.7 | 0.50 | Neutral |
| 161 | Repacking, Hydrophobic | gL_C233L | -0.25 | 0.7 | 0.45 | Neutral |
| 83 | Cavity Filling | gH_A352I | 0.55 | -0.15 | 0.40 | Neutral |
| 149 | Cavity Filling | UL131_G99I | 0.60 | -0.25 | 0.35 | Neutral |
| 147 | Cavity Filling | UL131_G99V | 0.45 | -0.1 | 0.35 | Neutral |
| 18 | Cavity Filling | gL_G145W | 0.10 | 0.2 | 0.30 | Neutral |
| 79 | Cavity Filling | gH_A372I | 0.30 | 0 | 0.30 | Neutral |
| 96 | Cavity Filling | gL_H177F | -1.05 | 1.35 | 0.30 | Neutral |
| 150 | Cavity Filling | UL131_G99F | 0.60 | -0.3 | 0.30 | Neutral |
| 168 | Deglycosylation | gH_N192Q | 0.35 | -0.1 | 0.25 | Neutral |
| 102 | Cavity Filling | gL_G140L | -0.35 | 0.6 | 0.25 | Neutral |
| 171 | Deglycosylation | gL_N74Q | 0.05 | 0.15 | 0.20 | Neutral |
| 78 | Cavity Filling | gH_A372L | 0.10 | 0.05 | 0.15 | Neutral |
| 84 | Cavity Filling | gH_A352W | 0.35 | -0.25 | 0.10 | Neutral |
| 36 | Repacking, Hydrophobic | UL130_G135V | -0.15 | 0.25 | 0.10 | Neutral |
| 148 | Cavity Filling | UL131_G99L | 0.45 | -0.35 | 0.10 | Neutral |
| 108 | Cavity Filling | gL_G145F | 0.50 | -0.65 | -0.15 | Neutral |
| 6 | Cavity Filling | gH_A352F | -0.50 | 0.15 | -0.35 | Neutral |
| 120 | Cavity Filling | gL_P272V | -0.05 | -0.3 | -0.35 | Neutral |
| 89 | Repacking, Hydrophobic | gH_R405W | -0.50 | 0.1 | -0.40 | Neutral |
| 166 | Deglycosylation | gH_N62Q | 0.15 | -0.6 | -0.45 | Neutral |
| 5 | Repacking, Hydrophobic | gH_R255A | -0.15 | -0.3 | -0.45 | Neutral |
| 90 | Cavity Filling | gH_L257V | 0.00 | -0.6 | -0.60 | Neutral |
| 24 | Repacking, Hydrophobic | gL_G161V | 0.15 | -0.85 | -0.70 | Neutral |
| 4 | Repacking, Hydrophobic | gH_K404A | -0.65 | -0.05 | -0.70 | Neutral |
| 77 | Cavity Filling | gH_A372V | -0.60 | -0.15 | -0.75 | Neutral |
| 92 | Cavity Filling | gH_L257F | -0.45 | -0.45 | -0.90 | Neutral |
| 169 | Deglycosylation | gH_N641Q | -0.60 | -0.3 | -0.90 | Neutral |
| 11 | Repacking, Hydrophobic | gH_H480V | -1.15 | 0.25 | -0.90 | Neutral |
| 91 | Cavity Filling | gH_L257I | -0.15 | -0.8 | -0.95 | Neutral |
| 121 | Cavity Filling | gL_P272L | -0.50 | -0.5 | -1.00 | Neutral |

TABLE 22-continued

| Identification No. | Type of Mutation(s) | HCMV pentamer polypeptide mutation(s) (polypeptide_mutation) | Tm1 shift (° C.) of mutant HCMV pentamer complex as compared to control [St. Dev. Of +/- 0.3° C.] | Tm2 shift (° C.) of mutant HCMV pentamer complex as compared to control [St. Dev. Of +/- 0.3° C.] | Sum of Tm1 & Tm2 shifts (° C.) | Results** |
|---|---|---|---|---|---|---|
| 134 | Cavity Filling | UL128_Q119V | −0.45 | −0.55 | −1.00 | Neutral |
| 135 | Cavity Filling | UL128_Q119L | −0.40 | −0.65 | −1.05 | Neutral |
| 167 | Deglycosylation | gH_N67Q | −0.05 | −1 | −1.05 | Neutral |
| 73 | Cavity Filling | gH_A102V | −0.15 | −0.95 | −1.10 | Neutral |
| 12 | Repacking, Hydrophobic | gH_S601V | −1.15 | 0.05 | −1.10 | Neutral |
| 122 | Cavity Filling | gL_P272I | −0.95 | −0.25 | −1.20 | Neutral |
| 136 | Cavity Filling | UL128_Q119I | −0.65 | −0.6 | −1.25 | Neutral |
| 3 | Repacking, Hydrophobic | gH_H252A | −0.60 | −0.65 | −1.25 | Neutral |
| 14 | Cavity Filling | gL_H177W | −1.30 | 0 | −1.30 | Neutral |
| 8 | Repacking, Hydrophobic | gH_E355V | −1.40 | 0.1 | −1.30 | Neutral |
| 123 | Cavity Filling | gL_P272W | −0.40 | −1.05 | −1.45 | Neutral |
| 162 | Repacking, Hydrophobic | gL_C233I | 0.00 | −1.45 | −1.45 | Neutral |
| 151 | Cavity Filling | UL131_S86V | −1.65 | 0.15 | −1.50 | Neutral |
| 117 | Cavity Filling | gL_L119V | −0.65 | −0.9 | −1.55 | Neutral |
| 173 | Deglycosylation | UL130_N118Q | −1.25 | −0.3 | −1.55 | Neutral |
| 69 | Disulfide | UL128_D45C_V88C | −1.10 | −0.55 | −1.65 | Neutral |
| 9 | Repacking, Hydrophilic | gH_G358R | −1.40 | −0.25 | −1.65 | Neutral |
| 163 | Repacking, Hydrophobic | gL_C233V | −0.20 | −1.5 | −1.70 | Neutral |
| 164 | Repacking, Hydrophobic | gL_C233Y | −0.85 | −1.1 | −1.95 | Neutral |
| 133 | Cavity Filling | UL128_L103W | −1.80 | −0.25 | −2.05 | Neutral |
| 28 | Repacking, Hydrophobic | UL128_H90A | −1.95 | −0.25 | −2.20 | Neutral |
| 153 | Cavity Filling | UL131_S86I | −2.00 | −0.25 | −2.25 | Neutral |
| 174 | Deglycosylation | UL130_N201Q | −2.00 | −0.6 | −2.60 | Neutral |
| 32 | Cavity Filling | UL128_Q119F | −2.15 | −0.65 | −2.80 | Neutral |
| 172 | Deglycosylation | UL130_N85Q | −2.60 | −0.2 | −2.80 | Neutral |
| 155 | Cavity Filling | UL131_S90V | −2.20 | −0.75 | −2.95 | Neutral |
| 152 | Cavity Filling | UL131_S86L | −2.65 | −0.45 | −3.10 | Neutral |
| 130 | Cavity Filling | UL128_V77W | −2.55 | −0.6 | −3.15 | Neutral |
| 27 | Repacking, Hydrophobic | UL128_G145V | −4.85 | 1.2 | −3.65 | Neutral |
| 71 | Disulfide | UL128_R51C_D106C | −3.75 | −0.9 | −4.65 | Neutral |
| 30 | Cavity Filling | UL128_V77F | −3.90 | −0.85 | −4.75 | Neutral |
| 33 | Repacking, Hydrophobic | UL130_G116V | −4.80 | −0.75 | −5.55 | Neutral |
| 111 | Cavity Filling | gL_D146I | 1.45 | −2 | −0.55 | Destabilizing |
| 17 | Cavity Filling | gL_G140W | 0.50 | −1.9 | −1.40 | Destabilizing |
| 159 | Repacking, Hydrophobic | gL_C233W | 0.35 | −2 | −1.65 | Destabilizing |
| 110 | Cavity Filling | gL_D146L | 0.45 | −2.4 | −1.95 | Destabilizing |
| 63 | Disulfide | gL_G140C_UL128_L159C | 0.15 | −2.2 | −2.05 | Destabilizing |
| 75 | Cavity Filling | gH_A102I | −0.10 | −2.05 | −2.15 | Destabilizing |
| 165 | Deglycosylation | gH_N55Q | −0.20 | −2.5 | −2.70 | Destabilizing |
| 137 | Cavity Filling | UL128_Q119W | −0.75 | −1.95 | −2.70 | Destabilizing |
| 101 | Cavity Filling | gL_G140V | −0.80 | −2.05 | −2.85 | Destabilizing |
| 103 | Cavity Filling | gL_G140I | −0.45 | −2.45 | −2.90 | Destabilizing |
| 112 | Cavity Filling | gL_D146F | −1.20 | −1.9 | −3.10 | Destabilizing |
| 76 | Cavity Filling | gH_A102F | 0.05 | −3.6 | −3.55 | Destabilizing |
| 109 | Cavity Filling | gL_D146V | −1.30 | −3.05 | −4.35 | Destabilizing |
| 97 | Cavity Filling | gL_G224V | −0.15 | −4.2 | −4.35 | Destabilizing |
| 74 | Cavity Filling | gH_A102L | 0.45 | −4.95 | −4.50 | Destabilizing |
| 94 | Cavity Filling | gL_H177L | −0.75 | −4 | −4.75 | Destabilizing |
| 20 | Repacking, Hydrophobic | gL_H245F | −2.25 | −2.8 | −5.05 | Destabilizing |
| 119 | Cavity Filling | gL_L119F | −1.25 | −3.9 | −5.15 | Destabilizing |
| 93 | Cavity Filling | gL_H177V | −0.50 | −5 | −5.50 | Destabilizing |
| 15 | Repacking, Hydrophobic | gL_H267F | 0.75 | −6.65 | −5.90 | Destabilizing |
| 100 | Cavity Filling | gL_G224W | −0.25 | −5.7 | −5.95 | Destabilizing |
| 54 | Disulfide | gH_V109C_gL_G224C | −0.05 | −6.05 | −6.10 | Destabilizing |
| 115 | Cavity Filling | gL_G218F | 0.85 | −7.45 | −6.60 | Destabilizing |
| 21 | Cavity Filling | gL_D146W | 0.75 | −7.4 | −6.65 | Destabilizing |
| 99 | Cavity Filling | gL_G224I | 0.00 | −6.8 | −6.80 | Destabilizing |
| 98 | Cavity Filling | gL_G224L | 0.10 | −6.95 | −6.85 | Destabilizing |
| 1 | Cavity Filling | gH_A102W | 0.00 | −7.1 | −7.10 | Destabilizing |
| 113 | Cavity Filling | gL_G218V | 0.35 | −8.75 | −8.40 | Destabilizing |
| 22 | Cavity Filling | gL_G218L | −1.40 | −8.65 | −10.05 | Destabilizing |
| 23 | Cavity Filling | gL_L119W | −1.65 | −8.75 | −10.40 | Destabilizing |
| 13 | Repacking, Hydrophilic | gH_H275E | | | | Inconclusive |
| 51 | Disulfide | UL130_S178C_UL131_H64C | | | | Inconclusive |
| 52 | Disulfide | gL_D163C_UL130_P62C | | | | Inconclusive |
| 175 | Deglycosylation | UL131_N81Q | | | | Inconclusive |
| 139 | Cavity Filling | UL130_D165L | | | | Inconclusive |
| 141 | Cavity Filling | UL130_D165F | | | | Inconclusive |
| 143 | Cavity Filling | UL130_H209L | | | | Inconclusive |
| 145 | Cavity Filling | UL130_H209F | | | | Inconclusive |
| 146 | Cavity Filling | UL130_H209W | | | | Inconclusive |

TABLE 22-continued

| Identification No. | Type of Mutation(s) | HCMV pentamer polypeptide mutation(s) (polypeptide_mutation) | Tm1 shift (° C.) of mutant HCMV pentamer complex as compared to control [St. Dev. Of +/− 0.3° C.] | Tm2 shift (° C.) of mutant HCMV pentamer complex as compared to control [St. Dev. Of +/− 0.3° C.] | Sum of Tm1 & Tm2 shifts (° C.) | Results** |
|---|---|---|---|---|---|---|
| 114 | Cavity Filling | gL_G218I | | | | Inconclusive |
| 31 | Cavity Filling | UL128_L103F | | | | Inconclusive |
| 37 | Repacking, Hydrophobic | UL130_H150F | | | | Inconclusive |
| 40 | Cavity Filling | UL131_S86W | | | | Inconclusive |
| 43 | Repacking, Hydrophobic | UL131_H64V | | | | Inconclusive |
| 45 | Repacking, Hydrophobic | UL131_D38V | | | | Inconclusive |
| 46 | Repacking, Hydrophobic | UL131_V85F | | | | Inconclusive |
| 48 | Disulfide | UL130_G116C_H150C | | | | Inconclusive |
| 49 | Disulfide | gL_G161C_UL130_P64C | | | | Inconclusive |
| 50 | Disulfide | gL_D163C_UL130_P64C | | | | Inconclusive |
| 38 | Repacking, Hydrophobic | UL131_H69V | | | | Inconclusive |
| 44 | Repacking, Hydrophobic and Repacking, Hydrophilic | UL131_H69F_R118N | | | | Inconclusive |
| 170 | Deglycosylation | gH_N700Q | | | | Inconclusive |
| 25 | Cavity Filling | gL_P272F | | | | Inconclusive |
| 118 | Cavity Filling | gL_L119I | | | | Inconclusive |
| 61 | Disulfide | UL128_G126C_UL130_I213C | | | | Inconclusive |
| 42 | Cavity Filling | UL131_S90F | | | | Inconclusive |
| 158 | Cavity Filling | UL131_S90W | | | | Inconclusive |
| 60 | Disulfide | UL128_A124C_UL130_N211C | | | | Inconclusive |
| 156 | Cavity Filling | UL131_S90L | | | | Inconclusive |
| 157 | Cavity Filling | UL131_S90I | | | | Inconclusive |
| 124 | Cavity Filling | UL128_G123V | | | | Inconclusive |
| 127 | Cavity Filling | UL128_G123F | | | | Inconclusive |
| 126 | Cavity Filling | UL128_G123I | | | | Inconclusive |
| 35 | Cavity Filling | UL130_H209Y | | | | Inconclusive |
| 29 | Repacking, Hydrophobic | UL128_G112V | | | | Inconclusive |
| 125 | Cavity Filling | UL128_G123L | | | | Inconclusive |
| 41 | Repacking, Hydrophobic | UL131_H35I | | | | Inconclusive |
| 26 | Cavity Filling | UL128_G123W | | | | Inconclusive |
| 34 | Cavity Filling | UL130_D165W | | | | Inconclusive |
| 116 | Cavity Filling | gL_G218W | | | | Inconclusive |
| 80 | Cavity Filling | gH_A372W | | | | Inconclusive |

**Stabilizing: At least one Tm shift is 2° C. or greater
Neutral: Both Tm shifts are between 2° C. & −2° C. (exclusive of endpoints)
Destabilizing: At least one Tm shift is −2° C. or lower
Inconclusive: Tm shift(s) and/or effect on thermostability could not be determined

TABLE 23

| ID No. | Type of Mutation(s) | HCMV pentamer polypeptide mutations(s) (polypeptide_mutation) A | Type of Mutation(s) | HCMV pentamer polypeptide mutations(s) (polypeptide_mutation) B |
|---|---|---|---|---|
| 19 | Cavity Filling | gL_G140F | Disulfide | UL128_R142C_UL130_E95C |
| 20 | Cavity Filling | gL_G145L | Disulfide | UL128_R142C_UL130_E95C |
| 30 | Disulfide | UL128_R142C_UL130_E95C | Deglycosylation | gL_N74Q |
| 13 | Repacking, Hydrophilic | gH_G358R | Disulfide | UL128_R142C_UL130_E95C |
| 14 | Repacking, Hydrophobic | gL_C233V | Disulfide | UL128_R142C_UL130_E95C |
| 3 | Repacking, Hydrophobic and Repacking, Hydrophobic | UL131_Y52F_A67V | Cavity Filling | gL_G140F |
| 7 | Repacking, Hydrophobic and Repacking, Hydrophobic | UL131_Y52F_A67V | Cavity Filling | gL_G140F |

TABLE 23-continued

| ID | | | | |
|---|---|---|---|---|
| 4 | Repacking, Hydrophobic and Repacking, Hydrophobic | UL131_Y52F_A67V | Cavity Filling | gL_G145L |
| 8 | Repacking, Hydrophobic and Repacking, Hydrophobic | UL131_Y52F_A67V | Cavity Filling | gL_G145L |
| 22 | Repacking, Hydrophobic and Repacking, Hydrophobic | UL131_Y52F_A67V | Deglycosylation | gL_N74Q |
| 25 | Cavity Filling | UL128_L103I | Deglycosylation | gL_N74Q |
| 26 | Cavity Filling | gL_G140F | Deglycosylation | UL130_N118Q |
| 27 | Cavity Filling | gL_G145L | Deglycosylation | UL130_N118Q |
| 21 | Repacking, Hydrophilic | gH_G358R | Deglycosylation | UL130_N118Q |
| 23 | Repacking, Hydrophobic | gL_C233V | Deglycosylation | UL130_N118Q |
| 5 | Repacking, Hydrophobic | gL_C233V | Cavity Filling | UL128_G123V |
| 6 | Repacking, Hydrophobic | gL_C233V | Cavity Filling | UL128_L103I |
| 9 | Repacking, Hydrophilic | gH_G358R | Disulfide | UL128_G126C UL130_I213C |
| 10 | Repacking, Hydrophobic | gL_C233V | Disulfide | UL128_G126C_UL130_I213C |
| 11 | Repacking, Hydrophilic | gH_G358R | Disulfide | UL128_A124C_UL130_N211C |
| 12 | Repacking, Hydrophobic | gL_C233V | Disulfide | UL128_A124C_UL130_N211C |
| 15 | Cavity Filling | gL_G140F | Disulfide | UL128_G126C UL130_I213C |
| 16 | Cavity Filling | gL_G145L | Disulfide | UL128_G126C_UL130_I213C |
| 17 | Cavity Filling | gL_G140F | Disulfide | UL128_A124C_UL130_N211C |
| 18 | Cavity Filling | gL_G145L | Disulfide | UL128_A124C_UL130_N211C |
| 24 | Cavity Filling | UL128_G123V | Deglycosylation | gL_N74Q |
| 28 | Disulfide | UL128_G126C_UL130_I213C | Deglycosylation | gL_N74Q |
| 29 | Disulfide | UL128_A124C_UL130_N211C | Deglycosylation | gL_N74Q |
| 1 | Repacking, Hydrophilic | gH_G358R | Cavity Filling | UL128_G123V |
| 2 | Repacking, Hydrophilic | gH_G358R | Cavity Filling | UL128_L103I |

| ID No. | Tm1 shift (° C.) of mutant HCMV pentamer complex as compared to control [St. Dev. Of +/− 0.3° C.] | Tm2 shift (° C.) of mutant HCMV pentamer complex as compared to control [St. Dev. Of +/− 0.3° C.) | Sum of Tm1 & Tm2 shifts (° C.) | Results** |
|---|---|---|---|---|
| 19 | 0.95 | 7.65 | 8.6 | Significantly Stabilizing |
| 20 | 0.3 | 7.6 | 7.9 | Significantly Stabilizing |
| 30 | 0.4 | 7.35 | 7.75 | Significantly Stabilizing |
| 13 | 0.25 | 7.1 | 7.35 | Significantly Stabilizing |
| 14 | 0.1 | 7.15 | 7.25 | Significantly Stabilizing |
| 3 | 0.7 | 2 | 2.7 | Stabilizing |
| 7 | 0.7 | 1.95 | 2.65 | Stabilizing |
| 4 | 0.5 | 1.8 | 2.3 | Stabilizing |
| 8 | 0.35 | 1.85 | 2.2 | Stabilizing |
| 22 | 0.5 | 0.15 | 0.65 | Neutral |
| 25 | 1.5 | −0.9 | 0.6 | Neutral |
| 26 | −1.8 | 2.2 | 0.4 | Destabilizing |
| 27 | −2.65 | 1.9 | −0.75 | Destabilizing |
| 21 | −2.1 | −0.2 | −2.3 | Destabilizing |
| 23 | −1.75 | −1.2 | −2.95 | Destabilizing |
| 5 | | | | Inconclusive |
| 6 | | | | Inconclusive |
| 9 | | | | Inconclusive |
| 10 | | | | Inconclusive |
| 11 | | | | Inconclusive |

TABLE 23-continued

| | |
|---|---|
| 12 | Inconclusive |
| 15 | Inconclusive |
| 16 | Inconclusive |
| 17 | Inconclusive |
| 18 | Inconclusive |
| 24 | Inconclusive |
| 28 | Inconclusive |
| 29 | Inconclusive |
| 1 | Inconclusive |
| 2 | Inconclusive |

**Stabilizing: At least one Tm shift is 2° C. or greater
Neutral: Both Tm shifts are between 2° C. & −2° C. (exclusive of endpoints)
Destabilizing: At least one Tm shift is −2° C. or lower
Inconclusive: Tm shift(s) and/or effect on thermostability could not be determined Example 5—Further Stabilization Assays of Mutant Pentameric Complex 5.1 Express and Purify a Complex Comprising at Least One Designed Mutant Modified HCMV pentameric complexes were expressed and purified as described in the Examples above. The HCMV pentameric complexes each comprised at least one modified subunit polypeptide gH, gL, UL128, UL130, and pUL131A, wherein the modified subunit polypeptide comprised the mutations as listed in Table 24. Purified, mutant HCMV pentamer complex was assessed in a differential scanning fluorimetry (DSF) assay, using a Nanotemper Prometheus NT.48 instrument. The intrinsic fluorescence of aromatic residues, such as Tyr and Trp, was obtained by exciting at 280 nm wavelength and measuring emission spectra at 330 nm (representing the folded state) and 350 nm (representing the unfolded state) over a temperature ramp (25-85° C.). The instrument software was used to plot the differential of the fluorescence ratio (350 nm/330 nm), and the temperature corresponding to the inflection point of the curve was taken as the melting temperature of the mutant HCMV pentamer complex (the Tm). The Tm1 and Tm2 of each mutant HCMV pentamer complex was compared to the corresponding Tm1 or Tm2 of a control (non-mutant) HCMV pentamer complex under the same experimental conditions. The control complex utilized was a HCMV pentamer complex comprising a gH complex-forming fragment and a gL polypeptide having mutations within a protease recognition site (specifically, the gH polypeptide comprised the sequence SEQ ID NO: 4; the gL polypeptide comprised the sequence SEQ ID NO: 10; the pUL128 polypeptide comprised the sequence SEQ ID NO: 14; the pUL130 polypeptide comprised the sequence SEQ ID NO: 18; and the pUL131A polypeptide comprised the sequence SEQ ID NO: 22).

Any change (shift) in Tm1 and/or Tm2 as compared to control was calculated and is summarized in Table 24. The residue numbers in Tables 24 are with respect to gH sequence SEQ ID NO: 3, gL sequence SEQ ID NO: 7, pUL128 sequence SEQ ID NO: 13, pUL130 sequence SEQ ID NO: 17, and pUL131A sequence SEQ ID NO: 21, respectively. As in Example 4 and taking into consideration a standard deviation of +/−0.3° C., a "stabilizing" result is when Tm1, Tm2, or both shift at least 2° C.; an increase of at least 5° C. in either Tm1 or Tm2 is considered a significantly stabilizing increase in the thermostability of the complex; a "neutral" result is when both Tm1 and Tm2 shifts are between −2° C. and 2° C.; a "destabilizing" result is when either the Tm1 or Tm2 shift is −2° C. or lower. The stabilizing mutant HCMV pentamer complexes described in Tables 24 were assayed for the presence of wild type conformational epitopes using Bio-layer Interferometry (BLI) technology and the 10P3, 8I21, 9I6, 10F7, 13H11 or MSL-109, and 15D8 antibodies. All complexes listed in Table 24 maintain the wild type HCMV pentamer complex conformational epitopes recognized by the 10P3, 8I21, 9I6, 10F7, 13H11 or MSL-109, and 15D8 antibodies.

For ID No. 176, stacking the disulphide mutations in column C to the previously-assessed mutations in columns A and B is significantly stabilizing; For ID No. 177, stacking the previously-assessed disulphide mutations in column B to the previously-assessed disulphide mutations in column A is significantly stabilizing; For ID No. 178, stacking the disulphide mutations in column C to the previously-stacked and assessed mutations in columns A (cavity filling) and B (disulphide) is significantly stabilizing; For ID Nos. 179 and 180, cavity filling mutation gL_G22V was not previously stacked with another mutation and assessed for effect on thermostability. Stacking the cavity filling mutation gL_G22V with the previously-assessed disulphide mutations in columns B and C (of ID No. 179) or column B (of ID No. 180) is significantly stabilizing Regarding ID Nos. 181 and 182, the cavity filling mutant UL128_V77I was not previously stacked with another mutation and assessed for effect on thermostability. Likewise regarding ID Nos. 181, 182, and 184, the cavity filling mutations gL_G140F and gL_G145L were not previously combined and assessed for effect on thermostability. For ID No. 181, stacking the cavity filling mutations of column A with the cavity filling mutations of column B is stabilizing. For ID No. 182, stacking the three cavity filling mutations of column A with the cavity filling mutations of column B is stabilizing. For ID No. 183, stacking the previously-assessed repacking hydrophobic mutations in column A to the previously-assessed cavity filling mutation in column B is stabilizing; For ID No. 184, stacking the three cavity filling mutations in column A is destabilizing. It was surprising to find that while stacking the three cavity filling mutations of ID No. 184 is destabilizing, combining the mutants of ID No. 184 with the cavity filling mutations at column B of ID No. 182 is stabilizing. All but one of the mutant HCMV pentamer complexes in Table 24 are more thermostable than the control, with some being significantly stabilizing

TABLE 24

| ID No. | Type of Mutation A | (polypeptide_mutation) A | Type of Mutation B | (polypeptide_mutation) B | Type of Mutation C | (polypeptide_mutation) C |
|---|---|---|---|---|---|---|
| 176 | Cavity Filling | gL_G140F | Disulfide | UL128_R142C_UL130_E95C | Disulfide | gL_A150C_UL130_P64C |
| 177 | Disulfide | UL128_R142C_UL130_E95C | Disulfide | gL_A150C_UL130_P64C | | |
| 178 | Cavity Filling | gL_G145L | Disulfide | UL128_R142C_UL130_E95C | Disulfide | gL_A150C_UL130_P64C |
| 179 | Cavity Filling | gL_G224V | Disulfide | UL128_R142C_UL130_E95C | Disulfide | gL_A150C_UL130_P64C |
| 180 | Cavity Filling | gL_G224V | Disulfide | UL128_R142C_UL130_E95C | | |
| 181 | Cavity Filling and Cavity Filling | gL_G140F_G145L | Cavity Filling and Cavity Filling | UL128_V77I_L103I | | |
| 182 | Cavity Filling and Cavity Filling And Cavity Filling | gL_G140F_G145L_G224V | Cavity Filling and Cavity Filling | UL128_V77I_L103I | | |
| 183 | Repacking, Hydrophobic and Repacking, Hydrophobic | UL131_Y52F_A67V | Cavity Filling | gL_G140F | | |
| 184 | Cavity Filling and Cavity Filling And Cavity Filling | gL_G140F_G145L_G224V | | | | |

| ID No. | Tm1 shift (° C.) [St. Dev. Of +/− 0.3° C.] | Tm2 shift (° C.) [St. Dev. Of +/− 0.3° C.] | Sum of Tm1 & Tm2 shifts (° C.) | Results** |
|---|---|---|---|---|
| 176 | 2.8 | 6.4 | 9.2 | Significantly Stabilizing |
| 177 | 2.1 | 6.55 | 8.65 | Significantly Stabilizing |
| 178 | 2.65 | 5.9 | 8.55 | Significantly Stabilizing |
| 179 | 2.85 | 4.8 | 7.65 | Significantly Stabilizing |
| 180 | 1.5 | 5.35 | 6.85 | Significantly Stabilizing |
| 181 | 2.3 | 3.25 | 5.55 | Stabilizing |
| 182 | 3.8 | −1.05 | 2.75 | Stabilizing |
| 183 | 0.7 | 2.0 | 2.7 | Stabilizing |
| 184 | −1.35 | −1.05 | −2.4 | Destabilizing |

**Stabilizing: At least one Tm shift is 2° C. or greater; Destabilizing: At least one Tm shift is −2° C. or lower; Neutral: Both Tm shifts are between 2° C. & −2° C. (exclusive of endpoints); Inconclusive: Tm shift(s) and/or effect on thermostability could not be determined 5.2 Express and Purify Additional Complexes Comprising at Least One Designed Mutant, Confirm Antigenicity and Immunogenicity Modified HCMV pentameric complexes were expressed and purified as described in the Examples above. The HCMV pentameric complexes each comprised at least one modified subunit polypeptide (gH, gL, UL128, UL130, and/or pUL131A), wherein the modified subunit polypeptide comprised the mutations as listed in Table 25. Purified, mutant HCMV pentamer complex was assessed for thermostability in a differential scanning fluorimetry (DSF) assay, using a Nanotemper Prometheus NT.48 instrument (NanoDSF). The intrinsic fluorescence of aromatic residues, such as Tyr and Trp, was obtained by exciting at 280 nm wavelength and measuring emission spectra at 330 nm (representing the folded state) and 350 nm (representing the unfolded state) over a temperature ramp (25-85° C.). The instrument software was used to plot the differential of the fluorescence ratio (350 nm/330 nm), and the temperature corresponding to the inflection point of the curve was taken as the melting temperature of the mutant HCMV pentamer complex (the Tm). The Tm1 and Tm2 of each mutant HCMV pentamer complex was compared to the corresponding Tm1 or Tm2 of a control (non-mutant) HCMV pentamer complex under the same experimental conditions. The control complex utilized was a known HCMV pentamer complex (the "LSG mutant penta" of WO 2016/116904) comprising a gH complex-forming fragment and a gL polypeptide having mutations within a protease recognition site (specifically, the gH polypeptide comprised the sequence SEQ ID NO: 4; the gL polypeptide comprised the sequence SEQ ID NO: 10; the pUL128 polypeptide comprised the sequence SEQ ID NO: 14; the pUL130 polypeptide comprised the sequence SEQ ID NO: 18; and the pUL131A polypeptide comprised the sequence SEQ ID NO: 22).

Any change (shift) in Tm1 and/or Tm2 as compared to control was calculated and is summarized in Table 25. The residue numbers in Tables 25 are with respect to gH sequence SEQ ID NO: 3, gL sequence SEQ ID NO: 7, pUL128 sequence SEQ ID NO: 13, pUL130 sequence SEQ ID NO: 17, and pUL131A sequence SEQ ID NO: 21, respectively. As in Example 4 and taking into consideration a standard deviation of +/−0.3° C., a "stabilizing" result is when Tm1, Tm2, or both shift at least 2° C.; an increase of at least 5° C. in either Tm1 or Tm2 is considered a significantly stabilizing increase in the thermostability of the complex; a "neutral" result is when both Tm1 and Tm2 shifts are between −2° C. and 2° C.; a "destabilizing" result is when either the Tm1 or Tm2 shift is −2° C. or lower. The results are that all mutants have an increase in melting temperature (Tm) with the disulphide bond mutations having a higher impact on thermostability than the cavity filling mutations. In particular:

While the mutant HCMV pentamer complex comprising a pUL131 polypeptide having a S86F mutation, numbered according to SEQ ID NO: 21, (set 1_154) has an increased thermostability as compared to control, it was only a neutral total Tm shift.

The mutant HCMV pentamer complex comprising a gL polypeptide having G140F and G145L mutations, numbered according to SEQ ID NO: 7, and comprising a pUL128 polypeptide having V77I and L103I mutations, numbered according to SEQ ID NO: 13, (Set 2_36) has an increased thermostability as compared to control in an amount that is significantly stabilizing.

The mutant HCMV pentamer complex comprising a gL polypeptide having an A150C mutation, numbered according to SEQ ID NO: 7; a pUL128 polypeptide having an R142C mutation, numbered according to SEQ ID NO: 13; and a pUL130 polypeptide having P64C and E95C mutations, numbered according to SEQ ID NO: 17, (Set 2_20) has an increased thermostability as compared to control in an amount that is significantly stabilizing The mutant HCMV pentamer complex comprising a gL polypeptide having A150C and G140F mutations, numbered according to SEQ ID NO: 7; a pUL128 polypeptide having an R142C mutation, numbered according to SEQ ID NO: 13; and a pUL130 polypeptide having P64C and E95C mutations, numbered according to SEQ ID NO: 17, (Set 2_21) has an increased thermostability as compared to control in an amount that is significantly stabilizing The mutant HCMV pentamer complex comprising a gL polypeptide having A150C and G145L mutations, numbered according to SEQ ID NO: 7; a pUL128 polypeptide having an R142C mutation, numbered according to SEQ ID NO: 13; and a pUL130 polypeptide having P64C and E95C mutations, numbered according to SEQ ID NO: 17, (Set 2_22) has an increased thermostability as compared to control in an amount that is significantly stabilizing The mutant HCMV pentamer complex comprising a pUL128 polypeptide having an S83C mutation, numbered according to SEQ ID NO: 13; and a pUL130 polypeptide having a T167C mutation, numbered according to SEQ ID NO: 17, (Set 1_72) has an increased thermostability as compared to control in an amount that is significantly stabilizing

TABLE 25

| Penta Set | Type of Mutation A | (polypeptide_mutation) A | Type of Mutation B | (polypeptide_mutation) B | Type of Mutation C | (polypeptide_mutation) C |
|---|---|---|---|---|---|---|
| 1_154 | Cavity Filling | UL131_S86F | | | | |
| 2_36 | Cavity Filling and Cavity Filling | gL_G140F_G145L | Cavity Filling and Cavity Filling | UL128_V77I_L103I | | |
| 2_20 | Disulfide | gL_A150C_UL130_P64C | Disulfide | UL128_R142C_UL130_E95C | | |
| 2_21 | Disulfide | gL_A150C_UL130_P64C | Disulfide | UL128_R142C_UL130_E95C | Cavity Filling | gL_G140F |
| 2_22 | Disulfide | gL_A150C_UL130_P64C | Disulfide | UL128_R142C_UL130_E95C | Cavity Filling | gL_G145L |
| 1_72 | Disulfide | UL128_S83C_UL130_T167C | | | | |

| Penta Set | Tm1 shift (° C.) [St. Dev. Of +/− 0.3° C.] | Tm2 shift (° C.) [St. Dev. Of +/− 0.3° C.] | Sum of Tm1 & Tm2 shifts (° C.) | Results** |
|---|---|---|---|---|
| 1_154 | 1.4 | 0 | 1.4 | Neutral |
| 2_36 | 1.9 | 2.7 | 4.6 | Significantly Stabilizing |
| 2_20 | 1.5 | 7.9 | 9.4 | Significantly Stabilizing |
| 2_21 | 0.6 | 5.9 | 6.5 | Significantly Stabilizing |
| 2_22 | 1.3 | 7.0 | 8.3 | Significantly Stabilizing |
| 1_72 | 0.9 | 7.8 | 8.7 | Significantly |

**Stabilizing: At least one Tm shift is 2° C. or greater; Destabilizing: At least one Tm shift is −2° C. or lower; Neutral: Both Tm shifts are between 2° C. & −2° C. (exclusive of endpoints); Inconclusive: Tm shift(s) and/or effect on thermostability could not be determined The antigenicity of the stabilizing mutant HCMV pentamer complexes in Tables 25 was confirmed by Octet-Biolayer Interferometry (Octet-BLI) utilizing known, site-specific monoclonal antibodies (MAbs) 15D8 (site 1), 2F4 (site 2), 8I21 (sites 3&7), 10P3 (sites 4&6), 9I6 (site 5), and 3G16 (specific to gH). All MAbs bound to each mutant HCMV pentamer complex of Table 25, thereby confirming conformational epitope integrity and antigenicity of the mutant complexes.

0.03 μg of each of the mutant HCMV pentamer complexes of Table 25 and the control HCMV pentamer complex (7 total groups) were formulated with AS01$_E$ adjuvant (a liposome-based adjuvant containing 2.5 μg each of monophosphoryl lipid A (MPL) and QS21). Three separate doses of 50 of composition was administered intramuscularly to the hind leg of C57BL/6 mice (12 mice per group) on days 1, 22, and 43 with non-terminal bleeds on days 21 and 42 for all mice; exsanguination and terminal bleed on day 64 for all mice. See regimen in the table below.

| Group | Number of mice | CMV Pentamer | Adjuvant | Pentamer Dose (µg) | Vaccine Regimen (Days) | Bleed (Days) |
|---|---|---|---|---|---|---|
| 1 | 12 | Control (LSG Penta) | AS01$_E$ | 0.03 | 1, 22, 43 | 21, 42, 64 |
| 2 | 12 | Penta Set 1-154 | | | | |
| 3 | 12 | Penta Set 2-36 | | | | |
| 4 | 12 | Penta Set 2-20 | | | | |
| 5 | 12 | Penta Set 2-21 | | | | |
| 6 | 12 | Penta Set 2-22 | | | | |
| 7 | 12 | Penta Set 1-72 | | | | |

Figure 8:
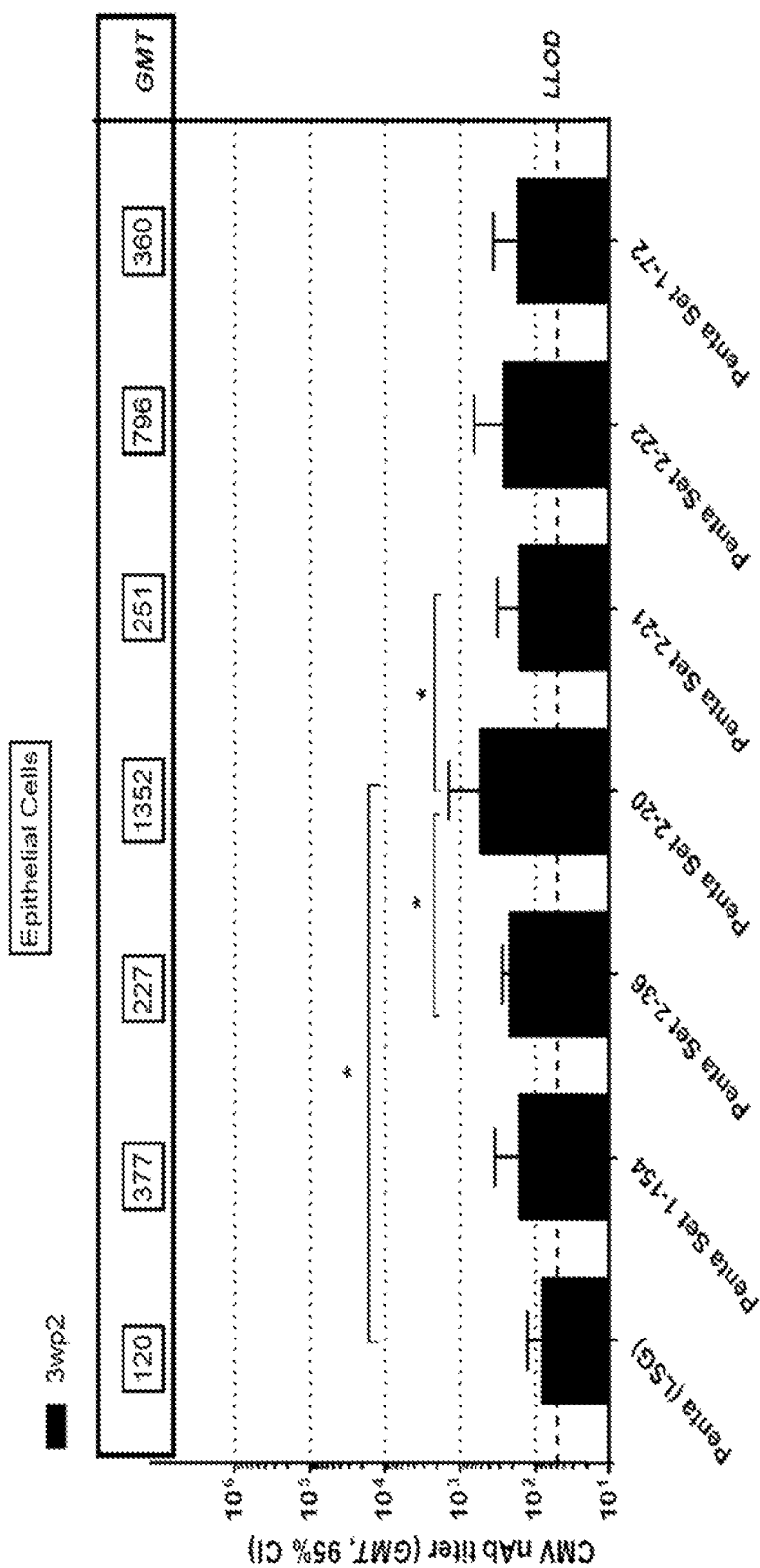
FIG. 8 provides the results of a neutralizing antibody assay using epithelial cells.

Serum samples taken three weeks after the second dose was administered (3wp2) were tested with complement in a neutralization assay performed according to known methods and utilizing ARPE-19 epithelial cells, TB40 virus strain, and Cederlane Guinea Pig complement. Using Geometric Mean Titer (GMT) as endpoint, the neutralization assay confirmed the immunogenicity of all seven HCMV pentamer complexes (FIG. 8). In particular, the results showed that all samples from mice that were immunized with one of the six mutant HCMV pentamer complexes had neutralizing antibody (nAb) titers above titers from mice that were immunized with control pentamer (FIG. 8).

Samples taken three weeks after the third dose was administered are expected to reveal similar trends in results under the same neutralization assay protocol.

EXPLANATION OF SEQUENCES

Amino acid sequences written in N-terminus to C-terminus direction, nucleic acid sequences written in 5'- to 3' direction:

SEQ ID NO: 1—Amino acid sequence of full length gH polypeptide from the HCMV Merlin strain (expected signal sequence residues 1-23) (NCBI GI No.:52139248; NCBI Accession No. YP_081523.1).

SEQ ID NO: 2—Amino acid sequence of gH polypeptide from the HCMV Merlin strain lacking the signal sequence (i.e., the mature gH polypeptide). SEQ ID NO: 2 represents amino acids 24 to 742 of SEQ ID NO: 1.

SEQ ID NO: 3—Amino acid sequence of gH polypeptide from the HCMV Merlin strain lacking the transmembrane (TM) domain and the C-terminal cytoplasmic domain as well as ectodomain residues 716 and 717. SEQ ID NO: 3 consists of amino acids 1 to 715 of SEQ ID NO: 1 (expected signal sequence residues 1-23). See WO 2014/005959 (also published as U.S. Pub. No. 2016/0159864).

SEQ ID NO: 4—Amino acid sequence of the mature gH polypeptide from the HCMV Merlin strain and also lacking the TM domain and the C-terminal cytoplasmic domain. SEQ ID NO: 4 consists of amino acids 24 to 715 of SEQ ID NO: 1.

SEQ ID NO: 5—Amino acid sequence of full length gH polypeptide from the HCMV Towne strain (NCBI GI No.: 138314; NCBI Accession No. P17176.1).

SEQ ID NO: 6—Amino acid sequence of full length gH polypeptide from the HCMV AD169 strain (NCBI GI No.: 138313; NCBI Accession No. P12824.1).

SEQ ID NO: 7—Amino acid sequence of full length gL polypeptide from the HCMV Merlin strain (expected signal sequence residues 1-30) (NCBI GI No.:39842115; NCBI GenBank Accession No. AAR31659.1).

SEQ ID NO: 8—Amino acid sequence of mature gL polypeptide from the HCMV Merlin strain lacking the signal sequence. SEQ ID NO: 8 consists of amino acids 31 to 278 of SEQ ID NO: 7.

SEQ ID NO: 9—Amino acid sequence of full length gL polypeptide from the HCMV Merlin strain comprising a mutation of what is believed to be a protease recognition site (expected signal sequence residues 1-30). SEQ ID NO: 9 consists of SEQ ID NO: 7 and the clipping mutations A96L, N97S, and S98G. See WO2016/116904.

SEQ ID NO: 10—Amino acid sequence of mature gL polypeptide from the HCMV Merlin strain comprising a mutation of what is believed to be a protease recognition site. SEQ ID NO: 10 consists of residues 31-278 of SEQ ID NO: 9. See WO2016/116904.

SEQ ID NO: 11—Amino acid sequence of full length gL polypeptide from the HCMV Towne strain (NCBI GI No.: 239909463; NCBI GenBank Accession No. ACS32410.1).

SEQ ID NO: 12—Amino acid sequence of full length gL polypeptide from the HCMV AD169 strain (NCBI GI No.: 2506510; NCBI Accession No. P16832.2).

SEQ ID NO: 13—Amino acid sequence of full length pUL128 polypeptide from the HCMV Merlin strain (expected signal sequence residues 1-27) (NCBI GI No.: 39842124; NCBI GenBank Accession No. AAR31668.1).

SEQ ID NO: 14—Amino acid sequence of mature pUL128 polypeptide from the HCMV Merlin strain lacking the signal sequence. SEQ ID NO: 14 consists of amino acids 28 to 171 of SEQ ID NO: 13.

SEQ ID NO: 15—Amino acid sequence of full length pUL128 polypeptide from the HCMV Towne strain (NCBI GI No.:39841882; NCBI GenBank Accession No. AAR31451.1).

SEQ ID NO: 16—Amino acid sequence of full length pUL128 polypeptide from the HCMV AD169 strain (NCBI GI No.:59803078; NCBI Accession No. P16837.2).

SEQ ID NO: 17—Amino acid sequence of full length pUL130 polypeptide from the HCMV Merlin strain (expected signal sequence residues 1-25) (NCBI GI No.: 39842125; NCBI Accession No. AAR31669.1).

SEQ ID NO: 18—Amino acid sequence of mature pUL130 polypeptide from the HCMV Merlin strain lacking the signal sequence. SEQ ID NO: 18 consists of amino acids 26-214 of SEQ ID NO: 17.

SEQ ID NO: 19—Amino acid sequence of full length pUL130 polypeptide from the HCMV Towne strain (expected signal sequence residues 1-25) (NCBI GI No.: 239909473; NCBI Accession No. ACS32420.1).

SEQ ID NO: 20—Amino acid sequence of full length pUL130 polypeptide from the HCMV AD169 strain (expected signal sequence residues 1-25). (NCBI UniProtKB Accession No. P16772.1)

SEQ ID NO: 21—Amino acid sequence of full length pUL131A polypeptide from the HCMV Merlin strain (expected signal sequence residues 1-18) (NCBI GI No.: 39842126; NCBI Accession No. AAR31670.1).

SEQ ID NO: 22—Amino acid sequence of mature pUL131A polypeptide from the HCMV Merlin strain. SEQ ID NO: 22 consists of amino acids 19-129 of SEQ ID NO: 21.

SEQ ID NO: 23—Amino acid sequence of full length pUL131A polypeptide from the HCMV Towne strain (expected signal sequence residues 1-18) (NCBI GI No.: 239909474; NCBI Accession No. ACS32421.1).

SEQ ID NO: 24—Amino acid sequence of full length pUL131A polypeptide from the HCMV AD169 strain (expected signal sequence residues 1-18). (NCBI GI No.: 219879712; NCBI GenBank Accession No. DAA06452.1).

SEQ ID NO: 25—Amino acid sequence of full length gO polypeptide from the HCMV Merlin strain (expected signal sequence residues 1-30). (NCBI GI No.:39842082; NCBI GenBank Accession No. AAR31626.1).

SEQ ID NO: 26—Amino acid sequence of mature gO polypeptide from the HCMV Merlin strain. SEQ ID NO: 26 consists of amino acids 31-472 of SEQ ID NO: 25.

SEQ ID NO: 27—Amino acid sequence of full length gO polypeptide from the HCMV Towne strain (expected signal sequence residues 1-30). (NCBI GI No.:239909431; NCBI Accession No. ACS32378.1).

SEQ ID NO: 28—Amino acid sequence of full length gO polypeptide from the HCMV AD169 strain (expected signal sequence residues 1-30). (NCBI GI No.:136968; NCBI UniProtKB Accession No. P16750.1).

SEQ ID NO: 29—Amino acid sequence of full length gL polypeptide from the HCMV Merlin strain comprising a mutation of what is believed to be a protease recognition site (expected signal sequence residues 1-30). SEQ ID NO: 29 consists of SEQ ID NO: 7 and the clipping mutations A96I, N97D, and S98G (which are also underlined). See WO2016/116904.

SEQ ID NO: 30—Amino acid sequence of mature gL polypeptide from the HCMV Merlin strain comprising a mutation of what is believed to be a protease recognition site. SEQ ID NO: 30 consists of residues 31-278 of SEQ ID NO: 29 (includes IDG mutant clipping residues). See WO2016/116904.

SEQ ID NO: 31—A nucleic acid sequence encoding full length gH amino acid sequence SEQ ID NO: 1 (sequence corresponds to base pairs 109224-111452 of NCBI GenBank Accession No. AY446894.2 (encoded in the 3' to 5' direction)).

SEQ ID NO: 32—A nucleic acid sequence encoding gH amino acid sequence SEQ ID NO: 3 (codon optimized for mammalian expression)

SEQ ID NO: 33—A nucleic acid sequence encoding full-length gL amino acid sequence SEQ ID NO: 7.

SEQ ID NO: 34—A nucleic acid sequence encoding full-length LSG gL amino acid sequence SEQ ID NO: 9.

SEQ ID NO: 35—A nucleic acid sequence encoding full-length IDG gL amino acid sequence SEQ ID NO: 29.

SEQ ID NO: 36—A nucleic acid sequence encoding full-length pUL128 amino acid sequence SEQ ID NO: 13.

SEQ ID NO: 37—A nucleic acid sequence encoding full-length pUL130 amino acid sequence SEQ ID NO: 17.

SEQ ID NO: 38—A nucleic acid sequence encoding full-length pUL131A amino acid sequence SEQ ID NO: 21.

SEQ ID NO: 39—A nucleic acid sequence encoding full-length gO amino acid sequence SEQ ID NO: (corresponding to base pairs 108848-107454 of GenBank Accession No. AY446894.2).

SEQ ID NO: 40—corresponds to the HCMV Merlin strain gH amino acid sequence SEQ ID NO: 3 further comprising a G358R mutation (underlined). Expected signal sequence residues 1-23.

SEQ ID NO: 41—corresponds to the HCMV Merlin strain gH amino acid sequence SEQ ID NO: 4 further comprising a G358R mutation.

SEQ ID NO: 42—corresponds to the HCMV Merlin strain gL amino acid sequence SEQ ID NO: 9 further comprising an N74Q mutation. Expected signal sequence residues 1-30.

SEQ ID NO: 43—corresponds to the HCMV Merlin strain gL amino acid sequence SEQ ID NO: 10 further comprising an N74Q mutation.

SEQ ID NO: 44—corresponds to the HCMV Merlin strain gL amino acid sequence SEQ ID NO: 9 further comprising a G140F mutation. Expected signal sequence residues 1-30.

SEQ ID NO: 45—corresponds to the HCMV Merlin strain gL amino acid sequence SEQ ID NO: 10 further comprising a G140F mutation.

SEQ ID NO: 46—corresponds to the HCMV Merlin strain gL amino acid sequence SEQ ID NO: 9 further comprising a G145L mutation. Expected signal sequence residues 1-30 are also underlined.

SEQ ID NO: 47—corresponds to the HCMV Merlin strain gL amino acid sequence SEQ ID NO: 10 further comprising a G145L mutation.

SEQ ID NO: 48—corresponds to the HCMV Merlin strain gL amino acid sequence SEQ ID NO: 9 further comprising an A150C mutation. Expected signal sequence residues 1-30 are also underlined.

SEQ ID NO: 49—corresponds to the HCMV Merlin strain gL amino acid sequence SEQ ID NO: 10 further comprising an A150C mutation.

SEQ ID NO: 50—corresponds to the HCMV Merlin strain gL amino acid sequence SEQ ID NO: 9 further comprising an R160C mutation. Expected signal sequence residues 1-30 are also underlined.

SEQ ID NO: 51—corresponds to the HCMV Merlin strain gL amino acid sequence SEQ ID NO: 10 further comprising an R160C mutation.

SEQ ID NO: 52—corresponds to the HCMV Merlin strain gL amino acid sequence SEQ ID NO: 9 further comprising an R166C mutation. Expected signal sequence residues 1-30 are also underlined.

SEQ ID NO: 53—corresponds to the HCMV Merlin strain gL amino acid sequence SEQ ID NO: 10 further comprising an R166C mutation.

SEQ ID NO: 54—corresponds to the HCMV Merlin strain gL amino acid sequence SEQ ID NO: 9 further comprising a C233V mutation. Expected signal sequence residues 1-30.

SEQ ID NO: 55—corresponds to the HCMV Merlin strain gL amino acid sequence SEQ ID NO: 10 further comprising a C233V mutation.

SEQ ID NO: 56—corresponds to the HCMV Merlin strain pUL128 amino acid sequence SEQ ID NO: 13 further comprising M48C and G107C mutations. Expected signal sequence residues 1-27. This signal sequence differs from the signal sequence of SEQ ID NO: 13 at residue 12.

SEQ ID NO: 57—corresponds to the HCMV Merlin strain pUL128 amino acid sequence SEQ ID NO: 14 further comprising M48C and G107C mutations.

SEQ ID NO: 58—corresponds to the HCMV Merlin strain pUL128 amino acid sequence SEQ ID NO: 13 further comprising a V77I mutation. Expected signal sequence residues 1-27. This signal sequence differs from the signal sequence of SEQ ID NO: 13 at residue 12.

SEQ ID NO: 59—corresponds to the HCMV Merlin strain pUL128 amino acid sequence SEQ ID NO: 14 further comprising a V77I mutation.

SEQ ID NO: 60—corresponds to the HCMV Merlin strain pUL128 amino acid sequence SEQ ID NO: 13 further comprising an S83C mutation. Expected signal sequence residues 1-27. This signal sequence differs from the signal sequence of SEQ ID NO: 13 at residue 12.

SEQ ID NO: 61—corresponds to the HCMV Merlin strain pUL128 amino acid sequence SEQ ID NO: 14 further comprising an S83C mutation.

SEQ ID NO: 62—corresponds to the HCMV Merlin strain pUL128 amino acid sequence SEQ ID NO: 13 further comprising a Y98C mutation. Expected signal sequence residues 1-27. This signal sequence differs from the signal sequence of SEQ ID NO: 13 at residue 12.

SEQ ID NO: 63—corresponds to the HCMV Merlin strain pUL128 amino acid sequence SEQ ID NO: 14 further comprising a Y98C mutation.

SEQ ID NO: 64—corresponds to the HCMV Merlin strain pUL128 amino acid sequence SEQ ID NO: 13 further comprising an L103I mutation. Expected signal sequence residues 1-27. This signal sequence differs from the signal sequence of SEQ ID NO: 13 at residue 12.

SEQ ID NO: 65—corresponds to the HCMV Merlin strain pUL128 amino acid sequence SEQ ID NO: 14 further comprising an L103I mutation.

SEQ ID NO: 66—corresponds to the HCMV Merlin strain pUL128 amino acid sequence SEQ ID NO: 13 further comprising an R142C mutation. Expected signal sequence residues 1-27. This signal sequence differs from the signal sequence of SEQ ID NO: 13 at residue 12.

SEQ ID NO: 67—corresponds to the HCMV Merlin strain pUL128 amino acid sequence SEQ ID NO: 14 further comprising an R142C mutation.

SEQ ID NO: 68—corresponds to the HCMV Merlin strain pUL130 amino acid sequence SEQ ID NO: 17 further comprising a Y56C mutation. Expected signal sequence residues 1-25.

SEQ ID NO: 69—corresponds to the HCMV Merlin strain pUL130 amino acid sequence SEQ ID NO: 18 further comprising a Y56C mutation.

SEQ ID NO: 70—corresponds to the HCMV Merlin strain pUL130 amino acid sequence SEQ ID NO: 17 further comprising a P62C mutation. Expected signal sequence residues 1-25.

SEQ ID NO: 71—corresponds to the HCMV Merlin strain pUL130 amino acid sequence SEQ ID NO: 18 further comprising a P62C mutation.

SEQ ID NO: 72—corresponds to the HCMV Merlin strain pUL130 amino acid sequence SEQ ID NO: 17 further comprising a P64C mutation. Expected signal sequence residues 1-25.

SEQ ID NO: 73—corresponds to the HCMV Merlin strain pUL130 amino acid sequence SEQ ID NO: 18 further comprising a P64C mutation.

SEQ ID NO: 74—corresponds to the HCMV Merlin strain pUL130 amino acid sequence SEQ ID NO: 17 further comprising an E95C mutation. Expected signal sequence residues 1-25.

SEQ ID NO: 75—corresponds to the HCMV Merlin strain pUL130 amino acid sequence SEQ ID NO: 18 further comprising an E95C mutation.

SEQ ID NO: 76—corresponds to the HCMV Merlin strain pUL130 amino acid sequence SEQ ID NO: 17 further comprising a T167C mutation. Expected signal sequence residues 1-25.

SEQ ID NO: 77—corresponds to the HCMV Merlin strain pUL130 amino acid sequence SEQ ID NO: 18 further comprising a T167C mutation.

SEQ ID NO: 78—corresponds to the HCMV Merlin strain pUL130 amino acid sequence SEQ ID NO: 17 further comprising a Y204C mutation. Expected signal sequence residues 1-25.

SEQ ID NO: 79—corresponds to the HCMV Merlin strain pUL130 amino acid sequence SEQ ID NO: 18 further comprising a Y204C mutation.

SEQ ID NO: 80—corresponds to the HCMV Merlin strain pUL131A amino acid sequence SEQ ID NO: 21 further comprising Y52F and A67V mutations. Expected signal sequence residues 1-18.

SEQ ID NO: 81—corresponds to the HCMV Merlin strain pUL131A amino acid sequence SEQ ID NO: 22 further comprising Y52F and A67V mutations.

SEQ ID NO: 82—corresponds to the HCMV Merlin strain pUL131A amino acid sequence SEQ ID NO: 21 further comprising an S86F mutation. Expected signal sequence residues 1-18.

SEQ ID NO: 83—corresponds to the HCMV Merlin strain pUL131A amino acid sequence SEQ ID NO: 22 further comprising an S86F mutation.

All patents and publications referred to herein are expressly incorporated by reference in their entireties.

The invention claimed is:

1. A complex comprising one or more mutant Human Cytomegalovirus (HCMV) polypeptides, wherein the one or more mutant HCMV polypeptides are:

(a) a pUL128 polypeptide, or complex-forming fragment thereof, that has cysteine (C) at residue 142, numbered with respect to SEQ ID NO: 13;
a gL polypeptide, or complex-forming fragment thereof, that has a cavity filling mutant at residue 140, numbered with respect to the wild-type Sequence of SEQ ID NO: 7, and has a cysteine (C) at residue 150, numbered with respect to SEQ ID NO: 7; and
a pUL130 polypeptide, or complex-forming fragment thereof, that has a cysteine (C) at residue 64, numbered with respect to SEQ ID NO: 17, and a cysteine (C) at residue 95, numbered with respect to SEQ ID NO: 17;

(b) a pUL128 polypeptide, or complex-forming fragment thereof, that has cysteine (C) at residue 142, numbered with respect to SEQ ID NO: 13;
a gL polypeptide, or complex-forming fragment thereof, that has a cysteine (C) at residue 150, numbered with respect to SEQ ID NO: 7; and
a pUL130 polypeptide, or complex-forming fragment thereof, that has a cysteine (C) at residue 64, numbered with respect to SEQ ID NO: 17, and a cysteine (C) at residue 95, numbered with respect to SEQ ID NO: 17;

(c) a pUL128 polypeptide, or complex-forming fragment thereof, that has cysteine (C) at residue 142, numbered with respect to SEQ ID NO: 13;
a gL polypeptide, or complex-forming fragment thereof, that has a cavity filling mutant at residue 145, numbered with respect to the wild-type Sequence of SEQ ID NO: 7, and has a cysteine (C) at residue 150, numbered with respect to SEQ ID NO: 7; and a pUL130 polypeptide, or complex-forming fragment thereof, that has a cysteine (C) at residue 64, numbered with respect to SEQ ID NO: 17, and a cysteine (C) at residue 95, numbered with respect to SEQ ID NO: 17;

(d) a pUL128 polypeptide, or complex-forming fragment thereof, that has cysteine
(C) at residue 142, numbered with respect to SEQ ID NO: 13;
a gL polypeptide, or complex-forming fragment thereof, that has a cavity filling mutant at residue 224, numbered with respect to the wild-type Sequence of SEQ ID NO: 7, and has a cysteine (C) at residue 150, numbered with respect to SEQ ID NO: 7; and
a pUL130 polypeptide, or complex-forming fragment thereof, that has a cysteine (C) at residue 64, numbered with respect to SEQ ID NO: 17, and a cysteine (C) at residue 95, numbered with respect to SEQ ID NO: 17;

(e) a pUL128 polypeptide, or complex-forming fragment thereof, that has cysteine
(C) at residue 142, numbered with respect to SEQ ID NO: 13;
a gL polypeptide, or complex-forming fragment thereof, that has a cavity filling mutant at residue 224, numbered with respect to the wild-type Sequence of SEQ ID NO: 7; and
a pUL130 polypeptide, or complex-forming fragment thereof, that has a cysteine (C) at residue 95, numbered with respect to SEQ ID NO: 17;

(f) a pUL128 polypeptide, or complex-forming fragment thereof, that has a cavity filling mutant at residue 77, numbered with respect to the wild-type Sequence of SEQ ID NO: 13, and has a cavity filling mutant at residue 103, numbered with respect to the wild-type Sequence of SEQ ID NO: 13; and
a gL polypeptide, or complex-forming fragment thereof, that has a cavity filling mutant at residue 140, numbered with respect to the wild-type Sequence of SEQ ID NO: 7, and has a cavity filling mutant at residue 145, numbered with respect to the wild-type Sequence of SEQ ID NO: 7;

(g) a pUL128 polypeptide, or complex-forming fragment thereof, that has a cavity filling mutant at residue 77, numbered with respect to the wild-type Sequence of SEQ ID NO: 13, and has a cavity filling mutant at residue 103, numbered with respect to the wild-type Sequence of SEQ ID NO: 13; and
a gL polypeptide, or complex-forming fragment thereof, that has a cavity filling mutant at residue 140, numbered with respect to the wild-type Sequence of SEQ ID NO: 7, has a cavity filling mutant at residue 145, numbered with respect to the wild-type Sequence of SEQ ID NO: 7, and has a cavity filling mutant at residue 224, numbered with respect to the wild-type Sequence of SEQ ID NO: 7;

(h) a gL polypeptide, or complex-forming fragment thereof, that has a cavity filling mutant at residue 140, numbered with respect to the wild-type Sequence of SEQ ID NO: 7; and
a pUL131 polypeptide, or complex-forming fragment thereof, that has a repacking hydrophobic mutant at residue 52, numbered with respect to the wild-type Sequence of SEQ ID NO: 21, and has a repacking hydrophobic mutant at residue 67, numbered with respect to the wild-type Sequence of SEQ ID NO: 21;

(i) a pUL131 polypeptide, or complex-forming fragment thereof, that has a cavity filling mutant at residue 86, numbered with respect to the wild-type Sequence of SEQ ID NO: 21; or (j) a pUL128 polypeptide, or complex-forming fragment thereof, that has a cysteine
(C) at residue 83, numbered with respect to SEQ ID NO: 13; and
a pUL130 polypeptide, or complex-forming fragment thereof, that has a cysteine
(C) at residue 167, numbered with respect to SEQ ID NO: 17.

2. The complex of claim 1, wherein the cavity filling mutant at residue 140, numbered with respect to the wild-type Sequence of SEQ ID NO: 7, is tryptophan (W), phenylalanine (F), tyrosine (Y), valine (V), isoleucine (I), or leucine (L).

3. The complex of claim 1, wherein the cavity filling mutant at residue 145, numbered with respect to the wild-type Sequence of SEQ ID NO: 7, is tryptophan (W), phenylalanine (F), tyrosine (Y), valine (V), isoleucine (I), or leucine (L).

4. The complex of claim 1, wherein the cavity filling mutant at residue 224, numbered with respect to the wild-type Sequence of SEQ ID NO: 7, is tryptophan (W), phenylalanine (F), tyrosine (Y), valine (V), isoleucine (I), or leucine (L).

5. The complex of claim 1, wherein the cavity filling mutant at residue 77, numbered with respect to the wild-type Sequence of SEQ ID NO: 13, is tryptophan (W), phenylalanine (F), tyrosine (Y), isoleucine (I), or leucine (L).

6. The complex of claim 1, wherein the cavity filling mutant at residue 103, numbered with respect to the wild-type Sequence of SEQ ID NO: 13, is tryptophan (W), phenylalanine (F), tyrosine (Y), valine (V), or isoleucine (I).

7. The complex of claim 1, wherein the repacking hydrophobic mutant at residue 52, numbered with respect to the wild-type Sequence of SEQ ID NO: 21, is tryptophan (W), phenylalanine (F), methionine (M), cysteine (C), alanine (A), leucine (L), isoleucine (I), valine (V) or proline (P).

8. The complex of claim 1, wherein the repacking hydrophobic mutant at residue 67, numbered with respect to the wild-type Sequence of SEQ ID NO: 21, is tryptophan (W), phenylalanine (F), methionine (M), cysteine (C), leucine (L), isoleucine (I), valine (V) or proline (P).

9. The complex of claim 1, wherein the cavity filling mutant at residue 86, numbered with respect to the wild-type Sequence of SEQ ID NO: 21, is tryptophan (W), phenylalanine (F), tyrosine (Y), valine (V), isoleucine (I), or leucine (L).

10. The complex of claim 1, wherein the complex has an increased thermostability as compared to a control complex in the same conditions.

11. The complex of claim 1, wherein the complex is an HCMV pentamer complex comprising one or more mutant HCMV polypeptides.

12. An immunogenic composition comprising the complex of claim 1.

13. An isolated nucleic acid molecule comprising one or more operably linked polynucleotide sequences that encode the complex of claim 1.

14. An expression vector comprising the isolated nucleic acid molecule of claim 13.

15. An isolated host cell comprising the isolated nucleic acid molecule of claim 13.

16. An isolated host cell comprising the expression vector of claim 14.

17. A method of inducing an immune response against Human Cytomegalovirus (HCMV), comprising administering to a subject an immunologically effective amount of the immunogenic composition of claim 12.

18. A method of inhibiting Human Cytomegalovirus (HCMV) entry into a cell, comprising contacting the cell with a complex according to claim 1.

* * * * *